United States Patent [19]
Adams et al.

[11] Patent Number: 6,090,836
[45] Date of Patent: Jul. 18, 2000

[54] BENZISOXAZOLE-DERIVED ANTIDIABETIC COMPOUNDS

[75] Inventors: Alan D. Adams, Cranford; Joel P. Berger, Hoboken, both of N.J.; Gregory D. Berger, Stonington, Conn.; Kenneth J. Fitch, Cranford, N.J.; Donald W. Graham, Mountainside, N.J.; Anthony B. Jones, Scotch Plains, N.J.; Derek von Langen, Fanwood, N.J.; Mark D. Leibowitz, Millburn, N.J.; David E. Moller, Bedminster, N.J.; Arthur A. Patchett, Westfield, N.J.; Conrad Santini, Warren, N.J.; Soumya P. Sahoo, Old Bridge, N.J.; Richard L. Tolman, Warren, N.J.; Richard B. Toupence, Scotch Plains, N.J.; Thomas F. Walsh, Watchung, N.J.

[73] Assignee: Merck & Co., Inc., Rahway, N.J.

[21] Appl. No.: 08/791,211

[22] Filed: Jan. 31, 1997

Related U.S. Application Data

[60] Provisional application No. 60/011,080, Feb. 2, 1996, and provisional application No. 60/034,434, Dec. 23, 1996.

[51] Int. Cl.[7] .......................... A61K 31/42; A61K 31/41; C07D 261/20; C07D 413/12
[52] U.S. Cl. ............................. 514/379; 548/241
[58] Field of Search ............................. 548/241; 514/379

[56] References Cited

U.S. PATENT DOCUMENTS

| | | | |
|---|---|---|---|
| 4,820,867 | 4/1989 | Belanger et al. | 562/478 |
| 5,002,953 | 3/1991 | Hindley | 514/275 |
| 5,232,925 | 8/1993 | Hindley | 514/272 |
| 5,453,443 | 9/1995 | Perrier et al. | 514/570 |
| 5,480,910 | 1/1996 | Holloway et al. | 514/567 |

FOREIGN PATENT DOCUMENTS

| | | |
|---|---|---|
| 0 039 913 | 11/1981 | European Pat. Off. |
| 0 061 800 | 10/1982 | European Pat. Off. |
| 0 123 541 | 10/1984 | European Pat. Off. |
| 0 579 412 A1 | 1/1994 | European Pat. Off. |
| 0 611 003 A1 | 8/1994 | European Pat. Off. |
| 0 617 001 A1 | 9/1994 | European Pat. Off. |
| 2 058 785 | 5/1979 | United Kingdom. |
| WO 93/21166 | 10/1993 | WIPO. |
| WO 94/01420 | 1/1994 | WIPO. |
| WO 94/12461 | 6/1994 | WIPO. |
| WO 94/29285 | 12/1994 | WIPO. |
| WO 95/03288 | 2/1995 | WIPO. |
| WO 95/17183 | 6/1995 | WIPO. |

OTHER PUBLICATIONS

Merck Manual, 16th Ed.: pp. 1039–1040 (1992).
Gordon, et al., *Am. J. Med.*, 62: pp. 707–714 (1977).
Stampfer, et a., *New England J. Med.*: 325, pp. 373–381 (1991).
Kannel, et al., *Ann. Internal Med.*, 90: pp. 85–91 (1979).
Elbrecht, et al., *BBRC*, 224: pp. 431–437 (1996).
A. Schmidt et al., *Molecular Endocrinology*, 6: pp. 1634–1641 (1992).
National Cholesterol Educ. Prog., *JAMA*, 269: pp. 3015–3023 (1993).
T. Sher et al., *Biochem.*, 32: pp. 5598–5604 (1993).
R.J. Havel et al., *Metabolic Basis of Inherited Disease*, 6th Ed.: pp. 1129–1138, (1989).

*Primary Examiner*—Laura L. Stockton
*Attorney, Agent, or Firm*—James L. McGinnis; David L. Rose

[57] ABSTRACT

The instant invention is concerned with acetylphenols which are useful as antiobesity and antidiabetic compounds. Compositions and methods for the use of the compounds in the treatment of diabetes and obesity and for lowering or modulating triglyceride levels and cholesterol levels or raising high density lipoprotein levels or for increasing gut motility or for treating atherosclerosis are also disclosed.

16 Claims, No Drawings

BENZISOXAZOLE-DERIVED ANTIDIABETIC COMPOUNDS

This application is a continuation-in part and claims priority from each of the following U.S provisional applications: U.S. provisional application No. 60/011,080 filed Feb. 2, 1996 (Merck attorney docket no. 19632PV); and U.S. provisional application No. 60/034,434 filed Dec. 23, 1996 (Merck attorney docket no. 19632PV2); each of which are herein incorporated by reference in their entirety.

This application is related to the following U.S. non-provisional applications: U.S. Ser. No. 08/797,650, filed Jan. 31, 1997, now abandoned filed Jan. 31,1997 (Merck attorney docket no. 19869Y) which is herein incorporated by reference in its entirety.

BACKGROUND OF THE INVENTION

Diabetes refers to a disease process derived from multiple causative factors and characterized by elevated levels of plasma glucose or hyperglycemia. Uncontrolled hyperglycemia is associated with increased and premature mortality due to an increased risk for microvascular and macrovascular diseases, including nephropathy, neuropathy, retinopathy, hypertension, stroke, and heart disease. Therefore, control of glucose homeostasis is a critically important approach for the treatment of diabetes.

Type I diabetes (IDDM) is the result of an absolute deficiency of insulin, the hormone which regulates glucose utilization. Type II, noninsulin dependent diabetes mellitus (NIDDM) is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver.

The several treatments for NIDDM, which has not changed substantially in many years, are all with limitations. While physical exercise and reductions in dietary intake of calories will dramatically improve the diabetic condition, compliance with this treatment is very poor because of well-entrenched sedentary lifestyles and excess food consumption, especially high fat-containing food. Increasing the plasma level of insulin by administration of sulfonylureas (e.g. tolbutamide, glipizide) which stimulate the pancreatic β-cells to secrete more insulin or by injection of insulin after the response to sulfonylureas fails, will result in high enough insulin concentrations to stimulate the very insulin-resistant tissues. However, dangerously low levels of plasma glucose can result from these last two treatments and increasing insulin resistance due to the even higher plasma insulin levels could theoretically occur. The biguanides increase insulin sensitivity resulting in some correction of hyperglycemia. However, the two biguanides, phenformin and metformin, can induce lactic acidosis and nausea/diarrhea, respectively.

Thiazolidinediones (glitazones) are a recently disclosed class of compounds that are suggested to ameliorate many symptoms of NIDDM. These agents increase insulin sensitivity in muscle, liver and adipose tissue in several animal models of NIDDM resulting in complete correction of the elevated plasma levels of glucose, triglycerides and nonesterified free fatty acids without any occurrence of hypoglycemia. However, serious undesirable effects have occurred in animal and/or human studies including cardiac hypertrophy, hemadilution and liver toxicity resulting in few glitazones progressing to advanced human trials.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. See the *Merck Manual*, 16th Ed. 1992 (see for example pp. 1039–1040) and "Structure and Metabolism of Plasma Lipoproteins" in *Metabolic Basis of Inherited Disease*, 6th Ed. 1989, pp. 1129–1138. One form of hyperlipidemia is hypercholesterolemia, characterized by the existence of elevated LDL cholesterol levels. The initial treatment for hypercholesterolemia is often to modify the diet to one low in fat and cholesterol, coupled with appropriate physical exercise, followed by drug therapy when LDL-lowering goals are not met by diet and exercise alone. LDL is commonly known as the "bad" cholesterol, while HDL is the "good" cholesterol. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, but the quantities needed to achieve HDL raising are associated with undesirable effects, such as flushing.

It is suggested that thiazolidinedione compounds exert their effects by binding to the peroxisome proliferator activated receptor (PPAR) family of receptors, controlling certain transcription elements having to do with the biological entities listed above. See Hulin et al., Current Pharm. Design (1996) 2, 85–102. Three sub-types of PPARs have been discovered and described; they are PPARα, PPARγ and PPARδ. PPARα is activated by a number of medium and long-chain fatty acids, and it is involved in stimulating β-oxidation of fatty acids. PPARα is also involved with the activity of fibrates in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in LDL cholesterol, and they are used particularly for the treatment of hypertriglyceridemia.

The PPARγ receptor subtypes are involved in activating the program of adipocyte differentiation and are not involved in stimulating peroxisome proliferation in the liver. The DNA sequences for the PPARγ receptors are described in Elbrecht, et al., BBRC 224;431–437 (1996). Although peroxisome proliferators, including the fibrates and fatty acids, activate the transcriptional activity of PPAR's, only prostaglandin $J_2$ derivatives have been identified as natural ligands of the PPARγ subtype, which also binds thiazolidinedione antidiabetic agents with high affinity. The glitazones have been shown to bind exclusively to the PPARγ subtype.

The human nuclear receptor gene PPARδ (hPPARδ) has been cloned from a human osteosarcoma cell cDNA library and is fully described in A. Schmidt et al., *Molecular Endocrinology*, 6 :1634–1641 (1992), herein incorporated by reference. It should be noted that PPARδ is also referred to in the literature as PPARβ and as NUC1, and each of these names refers to the same receptor; in Schmidt et al, the receptor is referred to as NUC1.

SUMMARY OF THE INVENTION

This invention is concerned with the compounds of formula I below and its analogs, pharmaceutically acceptable salts thereof, and bioprecursors thereof, which differ from the thiazolidinediones in that they lack the thiazolidinedione moiety and they do not lead to the array of toxicity's associated with the thiazolidinediones. The instant compounds are effective in treating diabetes, atherosclerosis, hyperglycemia, hyperlipidemia and/or obesity because they lower one or more of the following biological entities in mammals; glucose, insulin, triglycerides, fatty acids, cholesterol and the like. Thus, it is an object of this invention to describe such compounds. It is a further object to describe the specific preferred stereoisomers of the substituted compounds. A still further object is to describe processes for the preparation of such compounds. Another object is to describe methods and compositions which use the compounds as the active ingredient thereof. Further objects will become apparent from reading the following description.

DESCRIPTION OF THE INVENTION

The present invention is directed to a compound represented by formula I:

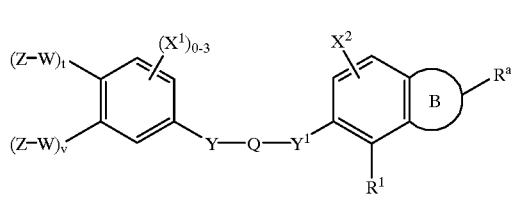

or a pharmaceutically acceptable salt thereof, wherein:

R is selected from the group consisting of H, $C_{1-6}$ alkyl, $C_{5-10}$ aryl, and $C_{5-10}$ heteroaryl, said alkyl, aryl and heteroaryl optionally substituted with 1 to 3 groups of $R^a$;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, $C_{5-10}$ heteroaryl said alkyl, cycloalkyl, alkenyl, alkynyl, aryl and heteroaryl optionally substituted with 1 to 3 groups of $R^a$;

(Z—W—) is Z—$CR^6R^7$—, Z—CH=CH—, or

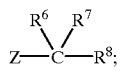

$R^8$ is selected from the group consisting of $CR^6R^7$, O, $NR^6$, and $S(O)_p$;

$R^6$ and $R^7$ are independently selected from the group consisting of H, $C_{1-6}$ alkyl;

B is a 5 or 6 membered heterocycle containing 0 to 2 double bonds, and 2 heteroatoms independently selected from the group consisting of O, N and S, said heteroatoms are optionally substituted at any position on the five or six membered heterocycle, the heterocycle being optionally unsubstituted or substituted with 1 to 3 groups of $R^a$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, $C_{5-10}$ heteroaryl and $C_{1-10}$ acyl, said alkyl, alkenyl, alkynyl, aryl and heteroaryl optionally substituted with 1 to 3 groups of $R^a$;

$R^a$ represents a member selected from the group consisting of: halo, acyl, aryl, heteroaryl, $CF_3$, $OCF_3$, CN, $NO_2$, $R^3$, $OR^3$; $SR^3$, $S(O)R^3$, =N(OR), $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, $OCON(R^3)_2$ said aryl and heteroaryl optionally substituted with 1 to 3 groups of halo or $C_{1-6}$ alkyl;

Y is selected from the group consisting of: $S(O)_p$, —$CH_2$—, —C(O)—, —C(O)NH—, —NR—, —O—, —$SO_2NH$, —$NHSO_2$;

$Y^1$ is selected from the group consisting of: O and C;

Z is selected from the group consisting of: $CO_2R^3$, $CONHSO_2R$, $CONH_2$ and 5-(1H-tetrazole);

t and v are independently 0 or 1 such that t+v=1;

Q is a saturated or unsaturated straight chain hydrocarbon containing 2–4 carbon atoms and p is 0–2.

Included in the invention is a pharmaceutical composition which is comprised of a compound of formula I in combination with a pharmaceutically acceptable carrier.

Also included in the invention is a pharmaceutical composition which is comprised of a compound of formula I in combination with one or more known sulfonylureas, biguanides, α-glucosidase inhibitors, other insulin secretogogues as well as insulin.

Also included in the invention is a method for raising high densisty lipoprotein (HDL) plasma levels in a mammal in need of such treatment comprising administering an effective amount of a compound of formula I.

Also included in the invention is a method for preventing, halting or slowing the progression of atherosclerotic cardiovascular diseases and related conditions and disease events in a mammal in need of such treatment comprising administering an effective amount of a compound of formula I.

Also included in the invention is a method for preventing, halting or slowing the progression of atherosclerotic cardiovascular diseases and related conditions and disease events in a mammal in need of such treatment comprising administering an effective amount of a compound of formula I in combination with one or more active agents such as antihyperlipidemic agents, HMG-CoA synthase inhibitors, squalene epoxidase inhibitors and the like.

Also included in the invention is a method of treating or controlling diabetes, which comprises administering to a diabetic patient an effective amount of a compound of formula I.

Also included in the invention is a method of treating or controlling diabetes, which comprises administering a compound of formula I in combination with one or more known sulfonylureas, biguanides, α-glucosidase inhibitors, other insulin secretogogues as well as insulin.

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

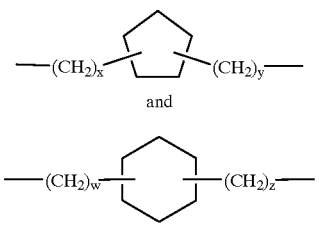

wherein: x and y=from 0–10; and w and z=from 0–9.

The alkylene and monovalent alkyl portion(s) of the alkyl group can be attached at any available point of attachment to the cycloalkylene portion.

When substituted akyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated carbon length in either a straight or branched configuration attached through an oxygen linkage and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term halo as used herein, represents fluoro, chloro, bromo or iodo.

Aryl refers to aromatic rings e.g., phenyl, substituted phenyl and like groups as well as rings which are fused, e.g., naphthyl and the like. Aryl thus contains at least one ring having at least 5 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 0–3 groups selected from $R^a$. The preferred aryl groups are phenyl and naphthyl. Aryl groups may likewise be substituted as defined below. Preferred substituted aryls include phenyl and naphthyl substituted with zero or three groups of $R^a$.

Heteroaryl is a group containing from 5 to 10 atoms, 1–4 of which are heteroatoms, 0–4 of which heteroatoms are N and 0–1 of which are O or S, said heteroaryl group being unsubstituted or substituted with 0–3 $R^a$ groups; examples of heteroaryls are pyridyl, quinolyl, purinyl, imidazolyl, imidazopyridyl and pyrimidinyl.

One embodiment of the novel compounds of the instant invention is realized when:

Y is O and all other variables are described as above.

Another embodiment of the novel compounds of the instant invention is realized when:

Y is $S(O)_p$, p is 0–2 and all other variables are described as above.

Still another embodiment of the novel compounds of the instant invention is realized when:

Y is —CH$_2$— and all other variables are described as above.

Yet another embodiment of the novel compounds of the instant invention is realized when:

Y is CO and all other variables are described as above.

A further embodiment of the novel compounds of the instant invention is realized when:

Y is NR and all other variables are described as above.

Another embodiment of the novel compounds of the instant invention is realized when:

Y is NHSO$_2$ or SO$_2$NH and all other variables are described as above.

Another embodiment of the novel compounds of the instant invention is realized when:

Y is —C(O)NH— and all other variables are described as above.

Another embodiment of the novel compounds of the instant invention is realized when:

B is a 5 or 6 membered heterocycle containing 0 to 2 double bonds, and 2 heteroatoms G and J, which are substituted at any position on the five or six membered heterocycle, the heterocycle being optionally unsubstituted or substituted with 1 to 3 groups of $R^a$ and all other variables are described as above.

Another embodiment of the novel compounds of the instant invention is realized when:

(Z—W—) is Z—CR$^6$R$^7$—, Z—CH═CH—, or

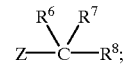

and all other variables are described as above and all other variables are described as above.

Still another embodiment of the novel compounds of the instant invention is realized when:

(Z—W—) is Z—CR$^6$R$^7$— or Z—C(R$^6$)(R$^7$)—R$^8$—;

and all other variables are described as above and all other variables are described as above.

Another embodiment of the novel compounds of the instant invention is realized when: $R^a$ is selected from the group consisting of $C_{1-6}$ alkyl, $CF_3$, aryl, halo, acyl, $OCF_3$, —NO$_2$, OR$^3$; COR$^3$, CO$_2$R$^3$, CON(R$^3$)$_2$, and SO$_2$N(R$^3$)$_2$; and X1 is selected from the group consisting of H, OH, $C_{1-6}$ alkyl, $C_{2-15}$ alkenyl, halo and OR$^3$ and all other variables are described as above.

Another preferred embodiment of the novel compounds of the instant invention is realized when:

R is $C_{1-6}$ alkyl or $C_{5-10}$ aryl, said alkylor aryl optionally substituted with 1 to 3 groups of $R^a$;

$R^1$ is $C_{1-15}$ alkyl;

$X^1$ & $X^2$ are independently H, $C_{1-6}$ alkyl or halo;

Y is O, NH or S;
Y¹ is O;

(Z—W—) is Z—CR⁶R⁷—  or  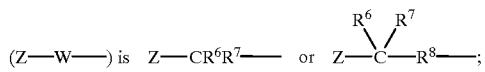

R$^a$ is a member selected from the group consisting of:
halo, acyl, aryl, heteroaryl, CF$_3$, OCF$_3$, —O—, CN, NO$_2$, R$^3$, OR$^3$; SR$^3$, S(O)R$^3$, SO$_2$R$^3$, NR$^3$COR$^3$, COR$^3$, CON(R$^3$)$_2$, SO$_2$N(R$^3$)$_2$, said aryl and heteroaryl optionally substituted with 1 to 3 groups of halo or C$_{1-6}$ alkyl; and Z is CO$_2$R$^3$, CONHSO$_2$R, CONH$_2$ or 5-(1H-tetrazole).

Examples of the compounds of the instant invention are:

Methyl 3-chloro-4-(3-(3-ethyl-7-propyl-6-benz-[4,5]-isoxazoloxy)propylthio)phenylacetate;
3-chloro-4-(3-(3-ethyl-7-propyl-6-benz-[4,5]-isoxazoloxy)propylthio)phenylacetic acid;
Methyl 3-chloro-4-(3-(3-methoxy-7-propyl-6-benz-[4,5]-isoxazoloxy)propylthio)phenylacetate;
3-chloro-4-(3-(3-methoxy-7-propyl-6-benz-[4,5]-isoxazoloxy)propylthio)-phenylacetic acid;
Methyl 3-chloro-4-(3-(3-ethyl-7-propyl-6-benz-[4,5]-isothiazoloxy)propylthio)phenyl acetate;
3-chloro-4-(3-(3-ethyl-7-propyl-6-benz-[4,5]-isothiazole)oxy)propylthio phenylacetic acid;
Methyl 3-chloro-4-(3-(3-methyl-7-propyl-6-benz-[4,5]-isoxazoloxy)propylthio)phenylacetate;
3-chloro-4-(3-(3-methyl-7-propyl-6-benz-[4,5]-isoxazoloxy)propylthio)phenylacetic acid;
Methyl 3-chloro-4-(3-(3,7-dipropyl-6-benz-[4,5]-isoxazoloxy)propylthio)-phenylacetate;
3-chloro-4-(3-(3,7-dipropyl-6-benz-[4,5]-isoxazoloxy)propylthio)phenyl-acetic acid;
Methyl 3-chloro-4-(3-(3-ethyl-7-propyl-6-benz-[4,5]-isoxazoloxy)propylthio)phenylacetate S-oxide;
3-chloro-4-(3-(3-ethyl-7-propyl-6-benz-[4,5]-isoxazoloxy)propylthio)phenylacetic acid S-oxide;
Methyl 3-chloro-4-(3-(3-ethyl-7-propyl-6-benz-[4,5]-isoxazoloxy) propyl-thio)phenylacetate S,S-dioxide;
3-Chloro-4-(3-(3-ethyl-7-propyl-6-benz-[4 ,5]-isoxazole)oxy)-propylthio phenylacetic acid S,S-dioxide;
tert-Butyl 3-chloro-4-(3-(3-ethyl-7-propyl-6-benz-[4,5]-isoxazoloxy)propylthio)phenyl acetate;
2-methyl-2-(3-chloro-4-(3-(3-phenyl-7-propylbenz[4,5]isoxazol-6-oxy)propyl)thio)phenyl propionic acid;
Methyl 3-chloro-4-(3-(3-(2,2-dimethylpropyl)-7-propyl-6-benz-[4,5]-isoxazoloxy)-propylamino)phenylacetate;
3-Chloro-4-(3-(3-(2,2-dimethylpropyl)-7-propyl-6-benz-[4, 5]-isoxazoloxy)-propylamino)phenylacetic acid;
3-Chloro-4-(3-(2-phenyl-6-propyl-5-benz-[4,7]-oxazoloxy) propylthio)phenylacetic acid;
Methyl 3-propyl-4-(3-(3-trifluoromethyl-7-propyl-6-benz-[4,5]-isoxazoloxy)-propylthio)phenylacetate;
3-propyl-4-(3-(3-trifluoromethyl-7-propyl-6-benz-[4,5]-isoxazoloxy)propylthio)phenylacetic acid;
3-chloro-4-(3-(2-propyl-3-trifluoromethyl-6-benz-[4,5]-isoxazoloxy)propylthio)phenylacetic acid;
3-chloro-4-(3-(3-phenyl-7-cyclopropylmethyl-6-benz-[4,5]-isoxazoloxy)-butyloxy)phenylacetic acid;
4-(3-(3-Phenyl-7-propylbenzisoxazol-6-yloxy)propylthio)-phenyl(2,2-dimethyl)acetic acid;
3-(3-(3-Phenyl-7-propylbenz[c]pyrazol-6-yloxy)-propylamino)-phenyl(2,2-dimethyl)acetic acid;
4-(3-(3-Phenyl-7-propylbenz[c]pyrazol-6-yloxy) propylamino)-phenyl(2,2-dimethyl)acetic acid;
4-(3-(3-Phenyl-7-propylbenzisoxazol-6-yloxy)propyloxy)-phenylpropan-3-oic acid;
4-(4-(3-Phenyl-7-propylbenz[c]pyrazol-6-yloxy) butylamino)-phenylpropan-3-oic acid;
3-(3-(3-Phenyl-7-propylbenzisoxazol-6-yloxy)propylthio) phenoxyacetic acid;
4-(3-(3-Phenyl-7-propylbenzisoxazol-6-yloxy)propylthio) phenoxyacetic acid;
4-(4-(1-Phenyl-4-propylbenz[d]triazol-5-yloxy)butyloxy)-phenoxyacetic acid;
N-[4-(3-(3-Phenyl-7-propylbenzisoxazol-6-yloxy)propylamino)phenyl]glycine;
N-[3-(4-(4-Phenyl-8-propylquinazolin-7-yloxy)butyloxy) phenyl]glycine;
N-[4-(4-(4-Phenyl-8-propylquinazolin-7-yloxy)butyloxy) phenyl]glycine;
4-(3-(3-Phenyl-7-propylbenzisoxazol-6-yloxy) propylamino)phenylacetic acid;
4-(3-(4-Phenyl-8-propylquinazolin-7-yloxy)propylthio)-phenylacetic acid;
3-(3-(2-Phenyl-6-propylbenzoxazol-5-yloxy)propylamino)-3-chlorophenylacetic acid;
4-(3-(2-Phenyl-6-propylbenzoxazol-5-yloxy)propylamino)-3-chlorophenylacetic acid;
4-(3-(2-Phenyl-6-propylbenzoxazol-5-yloxy)propylamino)-phenylacetic acid;
3-(3-(2-Phenyl-5-propylbenzisoxazol-6-yloxy) propylamino)-3-chlorophenylacetic acid;
4-(3-(1-Phenyl-4-propylbenz[d]triazol-5-yloxy) propylamino)-3-chlorophenylacetic acid;
3-(3-(3-Phenyl-7-propylbenz[c]pyrazol-6-yloxy) propylamino)-3-chlorophenylacetic acid;
4-(3-(3-Phenyl-7-propylbenzisoxazol-6-yloxy) propylamino)-3-chlorophenylacetic acid;
4-(4-(3-Phenyl-7-prop-2-enylbenzisoxazol-6-yloxy) butyloxy)-3-chlorophenylacetic acid;
4-(3-(3-Phenyl-7-propylbenzisoxazol-6-yloxy) propylamino)phenoxyacetic acid;
3-(3-(3-Phenyl-7-butylbenzisoxazol-6-yloxy)propylthio)-phenylpropan-3-oic acid;
4-(3-(3-Phenyl-7-butylbenzisoxazol-6-yloxy)propylthio)-phenylpropan-3-oic acid;
4-(3-(3-Phenyl-7-propylbenzisoxazol-6-yloxy)propyloxy)-2-phenyl-2,2-dimethylacetic acid;
4-(4-(3-Phenyl-7-(cyclopropylmethyl)benzisoxazol-6-yloxy)butylamino)-phenoxy-2,2-dimethylacetic acid;
3-(3-(3-Neopentyl-7-propylbenzisoxazol-6-yloxy) propylthio)-3-methylphenylacetic acid
4-(3-(3-(2-Phenyl-2,2-dimethyl)-7-propylbenzisoxazol-6-yloxy)propyloxy)-3-butylphenylacetic acid;
4-(3-(3-Chloro-7-propylbenzisoxazol-6-yloxy) propylamino)-2-propylphenylacetic acid;
3-(3-(3-Chloro-7-propylbenzisoxazol-6-yloxy) propylamino)-2-propylphenylacetic acid;
4-(4-(3-Butoxy-7-propylbenzisoxazol-6-yloxy)butylthio)-2-fluorophenylacetic acid;
4-(3-(3-Phenyl-7-propylbenzisoxazol-6-yloxy) propylamino)phenoxyacetic acid;
3-(3-(3-(3-Butylphenyl)-7-butylbenzisoxazol-6-yloxy) propylthio)phenylpropan-3-oic acid;
4-(3-(3-(2-Tolyl)-7-butylbenzisoxazol-6-yloxy)propylthio) phenylpropan-3-oic acid;
4-(3-(3-(4-Fluorophenyl)-7-propylbenzisoxazol-6-yloxy) propyloxy)-2-phenyl-2,2-dimethylacetic acid;
4-(3-(3-Phenyl-7-propylbenzisoxazol-6-yloxy)propyloxy)-phenoxy-2-spiro-cyclopropylacetic acid;
3-(3-(3-Phenyl-7-propylbenzisoxazol-6-yloxy)propyloxy)-phenoxy-2-spirocyclopropylacetic acid;

5-(4-(3-(3-Phenyl-7-propylbenz[c]pyrazol-6-yloxy) propylamino)phenyl-2-(2,2-dimethyl)-ethyl)-tetrazole;

5-(4-(3-(3-Phenyl-7-propylbenzisoxazol-6-yloxy) propyloxy)phenyl-3-propyl)-tetrazole;

5-(4-(4-(1-Phenyl-4-propylbenz[d]triazol-5-yloxy) butylamino)phenyl-3-propyl)-tetrazole;

5-(3-(3-Phenyl-7-propylbenzisoxazol-6-yloxy) propylthio)phenoxy-2-ethyl)-tetrazole;

5-(4-(3-(3-Phenyl-7-propylbenzisoxazol-6-yloxy) propylthio)phenoxy-2-ethyl)-tetrazole;

3-chloro-4-(3-(3-ethyl-7-propyl-6-benz-[4,5]-isoxazoloxy)-but-2-en-thio)phenylacetic acid;

4-(3-(3-ethyl-7-propyl-6-benz[4,5]isoxazole)oxy)propyloxy phenoxy acetic acid;

N-Methylsulfonyl 3-chloro-4-(3-(3-ethyl-7-propyl-6-benz[4,5]isoxazole)oxy)propylthio phenyl acetamide;

3,5-dirnethoxy-4-(3-(3-(Ethyl)-7-(propyl)-6-benz-[4,5]-isoxazoloxy)propyloxy)phenyl acetic acid;

3,5-dichloro-4-(3-(3-(Ethyl)-7-(propyl)-6-benz-[4,5]-isoxazoloxy)propyloxy)phenyl acetic acid;

3,5-dimethyl-4-(3-(3-(Ethyl)-7-(propyl)-6-benz-[4,5]-isoxazoloxy)propyloxy)phenyl acetic acid;

4-(3-(3-(Ethyl)-7-(propyl)-6-benz-[4,5]-isoxazoloxy)-propyloxy)-phenyl propionic acid;

3-chloro-4-(3-phenylmethyl-7-(n-propyl)-6-benz[4,5] isoxazoloxy)propyl-thio)phenylacetic acid;

3-chloro-4-(3-(2,2-dimethylpropyl)-7-(n-propyl)-6-benz[4,5]isoxazoloxy)-propylthio)phenylacetic acid;

2-methyl-4-(3-(3-(Ethyl)-7-(propyl)-6-benz-[4,5]-isoxazoloxy)propyloxy)-phenyl propionic acid;

3-Propyl-4-(3-(3-ethyl-7-propyl-6-benz-[4,5]-isoxazoloxy) propyloxy)phenylacetic acid;

4-(3-(3-(Ethyl)-7-propyl-6-benz-[4,5]-isoxazoloxy)butyl) phenylacetate;

3-chloro-4-(7-(n-propyl)-3-(3,3,3-trifluoropropyl)-6-benz [4,5]isoxazoloxy)propylthio)phenylacetic acid;

3-chloro-4-(3-(4-chlorophenylmethyl)-7-(n-propyl)-6-benz [4,5]isoxazol-oxy)propylthio)phenylacetic acid;

3-Chloro-4-(3-(3-(2,2-dimethylpropyl)-7-propyl-6-benz-[4,5]-isoxazoloxy)propyl-N-methylamino)phenylacetate;

3,5-Dipropyl-4-(3-(3-ethyl-7-propyl-6-benz-[4,5]-isoxazoloxy)propyloxy)phenylacetic acid;

3-fluoro-4-(3-(7-propyl-3-trifluoromethyl-6-benz-[4,5] isoxazoloxy)propyloxy)phenylacetic acid;

3-chloro-4-(3-(3-trifluoromethyl-7-propyl-6-benz-[4,5]-isoxazoloxy)propylamino)phenylacetic acid;

3-Isobutyl-4-(3-(3-neo-pental-7-propyl-6-benz-[4,5]-isoxazoloxy)propyloxy)phenylacetic acid;

3-Propyl-4-(3-(3-neo-pental-7-propyl-6-benz-[4,5]-isoxazoloxy) propylthio)phenylacetic acid S,S-dioxide;

3-Chloro-4-(3-(3-phenyl-7-propyl-6-benz-[4,5]-isoxazoloxy)-propylsulfoxy)phenylacetic acid;

3-fluoro-4-(4-(3-phenyl-7-propyl-6-benz-[4,5]-isoxazoloxy)butyloxy)phenylacetic acid;

3-chloro-4-(3-(7-propyl-3-trifluoromethyl-6-benz-[4,5]-isoxazoloxy)propyl-thio)phenylacetic acid S, S-dioxide;

3-chloro-4-(3-(7-propyl-3-trifluoromethyl-6-benz-[4,5]-isoxazoloxy)propyl-thio)phenylacetic acid S-oxide;

3-chloro-4-(3-(2-phenylethyl)-7-propyl-6-benz[4,5] isoxazoloxy)propylthio)phenylacetic acid;

3-Chloro-4-(3-(3-(4-fluorophenyl)-7-propyl-6-benz-[4,5]-isoxazoloxy)propylthio)phenylacetic acid;

3-Chloro-4-(3-(3-(4-fluorophenyl)-7-propyl-6-benz-[4,5]-isoxazoloxy)propylsulfinyl)phenylacetic acid;

3-Chloro-4-(3-(3-(4-fluorophenyl)-7-propyl-6-benz-[4,5]-isoxazoloxy)propylsulfonyl)) phenylacetic acid;

2,3-Dichloro-4-(3-(3-neo-pental-7-propyl-6-benz-[4,5]-isoxazoloxy)propylthio)phenylacetic acid;

2-Trifloroethoxy-4-(3-(3-neo-pental-7-propyl-6-benz-[4,5]-isoxazoloxy)propyloxy)phenylacetic acid;

3-Chloro-4-(3-(3-cyclopropyl)-7-propyl-6-benz-[4,5]-isoxazoloxy)propylamino)phenylacetate;

2-(3-chloro-4-(3-(3-ethyl-7-propyl-6-benz-[4,5]-isoxazoloxy)propylthio)) phenylpropionic acid;

3-(4-(3-(3-phenyl-7-propyl-6-benz-[4,5]-isoxazoloxy) propyloxy)) phenylpropionic acid;

3-Chloro-4-(3-(3-(3-fluorophenyl)-7-propyl-6-benz-[4,5]-isoxazoloxy)propylthio)phenylacetic acid;

3-Chloro-4-(3-(3-neo-pental-7-propyl-6-benz-[4,5]-isoxazoloxy)propyloxy)phenoxylacetic acid;

4-(3-(3-phenyl-7-propyl-6-benz[4,5]isoxazole)oxy) propyloxy phenoxy acetic acid;

(3-(4-(3-phenyl-7-propyl-6-benz-[4,5]-isoxazoloxy) butyloxy)) phenylacetic acid;

3-(4-(4-(3-phenyl-7-propyl-6-benz-[4,5]-isoxazoloxy) butyloxy)) phenylpropionic acid;

3-chloro-4-(3-(2-methyl-2-phenylpropyl)-7-(n-propyl)-6-benz[4,5]isoxazoloxy)propylthio)phenylacetic acid;

3-Methoxy-4-(3-(2,2-dimethylpropyl)-7-propyl-6-benz-[4,5]-isoxazoloxy)propyloxy)phenylacetate;

3-(4-(2-(3-phenyl-7-propyl-6-benz-[4,5]-isoxazoloxy) ethyloxy)) phenylpropionic acid;

(3-(4-(3-phenyl-7-propyl-6-benz-[4 ,5]-isoxazoloxy) butyloxy)) phenoxyacetic acid;

E-(4-(3-(3-phenyl-7-propyl-6-benz[4,5]isoxazole)oxy) propyloxy) cinnamic acid;

E-(3-(3-(3-phenyl-7-propyl-6-benz[4,5]isoxazole)oxy) propyloxy) cinnamic acid;

3-(3-(3-phenyl-7-propyl-6-benz[4,5]isoxazole)oxy) propyloxy) phenylpropionic acid;

N-((4-carbomethoxymethyl)benzoyl)-3(3-phenyl-7-propyl-6-benz-[4,7]-isooxazolyloxy) propylamine 2-(4-(3-(3-phenyl-7-propyl-6-benz-[4,5]-isoxazoloxy) propyloxy)) phenoxypropionic acid;

2-(4-(4-(3-phenyl-7-propyl-6-benz-[4,5]-isoxazoloxy) butyloxy)) phenoxypropionic acid;

3-chloro-4-(3-(7-cyclopropylmethyl-3-phenyl-6-benz-[4,5]-isoxazoloxy)propyl-thio)phenylacetic acid;

1-(3-chloro-4-(3-(3-(2,2-dimethylpropyl)-7-propyl-6-benz [4,5]isoxazole)oxy)propylthio) phenyl cyclopropane carboxylic acid;

4-(3-(3-(Ethyl)-7-(phenyl)-6-benz-[4,5]-isoxazoloxy) propyloxy)-3-chloro-α, α-dimethyl-phenyl propionic acid;

3-Ethoxy-4-(3-(3-(2,2-dimethylpropyl)-7-propyl-6-benz-[4,5]-isoxazoloxy)propyloxy)phenylacetate; and 3-chloro-4-(3-(3-phenyl-6-propyl-5-benz-[4,7]-isoxazolyloxy)propylthio) phenylacetic acid.

Preferred examples of the compounds of the instant invention are:

Methyl 3-chloro-4-(3-(3-ethyl-7-propyl-6-benz-[4,5]-isoxazoloxy)propylthio)phenylacetate;

3-chloro-4-(3-(3-ethyl-7-propyl-6-benz-[4,5]-isoxazoloxy) propylthio)phenylacetic acid;

Methyl 3-chloro-4-(3-(3-methoxy-7-propyl-6-benz-[4,5]-isoxazoloxy)propylthio)phenylacetate;

3-chloro-4-(3-(3-methoxy-7-propyl-6-benz-[4,5]-isoxazoloxy) propylthio)-phenylacetic acid;

Methyl 3-chloro-4-(3-(3-ethyl-7-propyl-6-benz-[4,5]-isothiazoloxy)propylthio)phenyl acetate;

3-chloro-4-(3-(3-ethyl-7-propyl-6-benz-[4,5]-isothiazole) oxy)propylthio phenylacetic acid;

Methyl 3-chloro-4-(3-(3-methyl-7-propyl-6-benz-[4,5]-isoxazoloxy)propylthio)phenylacetate;

3-chloro-4-(3-(3-methyl-7-propyl-6-benz-[4,5]-isoxazoloxy)propylthio)phenylacetic acid;

Methyl 3-chloro-4-(3-(3,7-dipropyl-6-benz-[4,5]-isoxazoloxy) propylthio)-phenylacetate;

3-chloro-4-(3-(3,7-dipropyl-6-benz-[4,5]-isoxazoloxy) propylthio) phenyl-acetic acid;

Methyl 3-chloro-4-(3-(3-ethyl-7-propyl-6-benz-[4,5]-isoxazoloxy)propylthio)phenylacetate S-oxide;

3-chloro-4-(3-(3-ethyl-7-propyl-6-benz-[4,5]-isoxazoloxy) propylthio)phenylacetic acid S-oxide;

Methyl 3-chloro-4-(3-(3-ethyl-7-propyl-6-benz-[4,5]-isoxazoloxy) propyl-thio)phenylacetate S,S-dioxide;

3-Chloro-4-(3-(3-ethyl-7-propyl-6-benz-[4,5]-isoxazole) oxy)-propylthio phenyl acetic acid S,S-dioxide;

tert-Butyl 3-chloro-4-(3-(3-ethyl-7-propyl-6-benz-[4,5]-isoxazoloxy)propylthio)phenyl acetate;

2-methyl-2-(3-chloro-4-(3-(3-phenyl-7-propylbenz[4,5] isoxazol-6-oxy)propyl)thio)phenyl propionic acid;

Methyl 3-chloro-4-(3-(3-(2,2-dimethylpropyl)-7-propyl-6-benz-[4,5]-isoxazoloxy)-propylamino)phenylacetate;

3-Chloro-4-(3-(3-(2,2-dimethylpropyl)-7-propyl-6-benz-[4,5]-isoxazoloxy)-propylamino)phenylacetic acid;

3-Chloro-4-(3-(2-phenyl-6-propyl-5-benz-[4,7]-oxazoloxy) propylthio)phenylacetic acid;

Methyl 3-propyl-4-(3-(3-trifluoromethyl-7-propyl-6-benz-[4,5]-isoxazoloxy)-propylthio)phenylacetate;

3-propyl-4-(3-(3-trifluoromethyl-7-propyl-6-benz-[4,5]-isoxazoloxy)propylthio)phenylacetic acid;

3-chloro-4-(3-(2-propyl-3-trifluoromethyl-6-benz-[4,5]-isoxazoloxy)propylthio)phenylacetic acid;

3-chloro-4-(3-(3-phenyl-7-cyclopropylmethyl-6-benz-[4,5]-isoxazoloxy)-butyloxy)phenylacetic acid;

4-(3-(3-Phenyl-7-propylbenzisoxazol-6-yloxy)propyloxy)-phenylacetic acid;

4-(3-(3-Phenyl-7-propylbenz[c]pyrazol-6-yloxy)propyloxy) phenylacetic acid;

3-(4-(3-Phenyl-7-propylbenzisoxazol-6-yloxy)butyloxy)-phenylacetic acid;

3-(4-(3-Phenyl-7-propylbenz[c]pyrazol-6-yloxy)butyloxy)-phenylacetic acid;

4-(3-(3-Phenyl-7-propylbenzisoxazol-6-yloxy)propyloxy)-phenoxyacetic acid;

4-(3-(3-Phenyl-7-propylbenz [c]pyrazol-6-yloxy) propyloxy)-phenoxyacetic acid;

4-(3-(3-Phenyl-7-propylbenzisoxazol-6-yloxy)propylthio)-3-propylphenylacetic acid;

4-(4-(3-Phenyl-7-propylbenz[c]pyrazol-6-yloxy)butylthio)-3-chlorophenylacetic acid;

4-(4-(1-Phenyl-4-propylbenz[c]pyrazol-5-yloxy)butylthio)-3-chlorophenylacetic acid;

4-(3-(3-Phenyl-7-propylbenzisoxazol-6-yloxy) propylsulfono)-3-propylphenylacetic acid;

4-(3-(3-Phenyl-7-propylbenz[c]pyrazol-6-yloxy) propylsulfono)-3-chlorophenylacetic acid;

4-(4-(3-Phenyl-7-propylbenzisoxazol-6-yloxy)butylthio)-3-propylbenzyl-tetrazole;

4-(4-(3-Phenyl-7-propylindol-6-yloxy)butylthio)-3-chlorobenzyltetrazole;

4-(4-(1-Phenyl-4-propylindol-5-yloxy)butylthio)-3-chlorobenzyltetrazole;

4-(3-(3-Phenyl-7-propylbenzisoxazol-6-yloxy) propylamino)phenylacetic acid;

4-(3-(3-Phenyl-7-propylbenz[c]pyrazol-6-yloxy) propylamino)phenylacetic acid;

3-(4-(3-Phenyl-7-propylbenzisoxazol-6-yloxy) butyloxy)-phenylacetic acid;

3-(4-(3-Phenyl-7-propylbenz [c]pyrazol-6-yloxy) butyloxy)phenylacetic acid;

3-chloro-4-(3-(2,2-dimethylpropyl)-7-(n-propyl)-6-benz[4,5]isoxazoloxy)-propylthio)phenylacetic acid;

3-Propyl-4-(3-(3-ethyl-7-propyl-6-benz-[4,5-isoxazoloxy) propyloxy)phenylacetic acid;

4-(3-(3-(Ethyl)-7-propyl-6-benz-[4,5]-isoxazoloxy)butyl) phenylacetate;

3-chloro-4-(7-(n-propyl)-3-(3,3,3-trifluoropropyl)-6-benz [4,5]isoxazoloxy)propylthio)phenylacetic acid;

3-chloro-4-(3-(3-trifluoromethyl-7-propyl-6-benz-[4,5]-isoxazoloxy)propylamino)phenylacetic acid;

3-Chloro-4-(3-(3-phenyl-7-propyl-6-benz-[4,5]-isoxazoloxy)-propylsulfoxy)phenylacetic acid;

3-fluoro-4-(4-(3-phenyl-7-propyl-6-benz-[4,5]-isoxazoloxy)butyloxy)phenylacetic acid;

3-chloro-4-(3-(2-phenylethyl)-7-propyl-6-benz[4,5] isoxazoloxy)propylthio)phenylacetic acid;

3-Chloro-4-(3-(3-(4-fluorophenyl)-7-propyl-6-benz-[4,5]-isoxazoloxy)propylthio)phenylacetic acid;

3-Chloro-4-(3-(3-(4-fluorophenyl)-7-propyl-6-benz-[4,5]-isoxazoloxy)propylsulfonyl)) phenylacetic acid;

2,3-Dichloro-4-(3-(3-neo -pental-7-propyl-6-benz-[4,5]-isoxazoloxy)propylthio)phenylacetic acid;

2-(3-chloro-4-(3-(3-ethyl-7-propyl-6-benz-[4,5]-isoxazoloxy)propylthio)) phenylpropionic acid;

3-(4-(3-(3-phenyl-7-propyl-6-benz-[4,5]-isoxazoloxy) propyloxy)) phenylpropionic acid;

3-Chloro-4-(3-(3-(3-fluorophenyl)-7-propyl-6-benz-[4,5]-isoxazoloxy)propylthio)phenylacetic acid;

4-(3-(3-phenyl-7-propyl-6-benz[4,5]isoxazole)oxy) propyloxy phenoxy acetic acid;

(3-(4-(3-phenyl-7-propyl-6-benz-[4,5]-isoxazoloxy) butyloxy)) phenylacetic acid;

3-(4-(4-(3-phenyl-7-propyl-6-benz-[4,5]-isoxazoloxy) butyloxy)) phenylpropionic acid;

3-chloro-4-(3-(2-methyl-2-phenylpropyl)-7-(n-propyl)-6-benz[4,5]isoxazoloxy)propylthio)phenylacetic acid;

3-(4-(2-(3-phenyl-7-propyl-6-benz-[4,5]-isoxazoloxy) ethyloxy)) phenylpropionic acid;

(3-(4-(3-phenyl-7-propyl-6-benz-[4,5]-isoxazoloxy) butyloxy)) phenoxyacetic acid;

E-(4-(3-(3-phenyl-7-propyl-6-benz[4,5]isoxazole)oxy) propyloxy) cinnamic acid;

3-(3-(3-phenyl-7-propyl-6-benz[4,5]isoxazole)oxy) propyloxy) phenylpropionic acid;

2-(4-(3-(3-phenyl-7-propyl-6-benz-[4,5]-isoxazoloxy) propyloxy)) phenoxypropionic acid;

2-(4-(4-(3-phenyl-7-propyl-6-benz-[4,5]-isoxazoloxy) butyloxy)) phenoxypropionic acid;

3-chloro-4-(3-(7-cyclopropylmethyl-3-phenyl-6-benz-[4,5]-isoxazoloxy)propyl-thio)phenylacetic acid;

1-(3-chloro-4-(3-(3-(2,2-dimethylpropyl)-7-propyl-6-benz [4,5]isoxazole)oxy)propylthio) phenyl cyclopropane carboxylic acid; and 4-(3-(3-(Ethyl)-7-(phenyl)-6-benz-[4,5]-isoxazoloxy) propyloxy)-3-chloro-α, α-dimethyl-phenyl propionic acid.

The compounds of the present invention may have asymmetric centers and occur as racemates, racemic mixtures, and as individual diastereomers, with all possible isomers, including optical isomers, being included in the present invention.

Compounds of the general Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

As previously indicated, the compounds of the present invention have valuable pharmacological properties. They are useful in treating or preventing diabetes, treating obesity, lowering triglyceride levels and prevention of vascular restenosis. They are useful in treating other disorders where insulin resistance is a component including ovarian hyperandrogenism (polycyctic ovarian syndrome). They are also useful in raising high density lipoprotein levels, preventing, halting or slowing the progression of atherosclerotic cardiovascular diseases and related conditions and disease events.

The present invention also provides a compound of the general Formula I or a pharmaceutically acceptable salt thereof for use as an active therapeutic substance.

The present invention further provides a compound of the general Formula I, or a pharmaceutically acceptable ester thereof; or pharmaceutically acceptable salt thereof, for use in the treatment of hyperglycemia (diabetes) in human or non-human animals.

The present invention further provides a compound of the general Formula I, or a pharmaceutically acceptable ester thereof; or pharmaceutically acceptable salt thereof, in combination with known sulfonylureas, other insulin secretogogues as well as insulin for use in the treatment of diabetes treating obesity, lowering triglyceride levels, prevention of vascular restenosis, treating other disorders where insulin resistance is a component including ovarian hyperandrogenism (polycyctic ovarian syndrome), raising high density lipoprotein levels, and preventing, halting or slowing the progression of atherosclerotic cardiovascular diseases and related conditions and disease events.and hypertension in human or non-human animals.

In one aspect, the present invention provides a compound of the general Formula I for use in the treatment of obesity in human or non-human animals. Said compound can be effectively used in combination with other known or proposed strategies for the treatment of obesity or obesity-related disorders; for example, fenfluramine, dexfenfluramine, phentiramine and $\beta_3$ adrenergic receptor agonist agents.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies. The instant compounds can be effectively used in combination with known therapies for diabetes including insulin, sulfonylureas, biguanides (such as metformin), α-glucosidase inhibitors (such as acarbose) and others.

Two major forms of diabetes mellitus are now recognized. Type I diabetes, or insulin-dependent diabetes, is the result of an absolute deficiency of insulin, the hormone which regulates glucose utilization. Type II diabetes, or non-insulin-independent diabetes, often occurs in the face of normal, or even elevated levels of insulin and appears to be the result of the inability of tissues to respond appropriately to insulin. Most of the Type II diabetics are also obese. Accordingly, in another aspect the present invention provides a method of lowering triglyceride levels which comprises administering, to an animal in need thereof, a therapeutically effective amount of a compound of the formula I or pharmaceutically acceptable salt or ester thereof.

In addition the compounds of the present invention lower or modulate triglyceride levels and/or cholesterol levels and raise HDL plasma levels and are therefore of use in combating medical conditions wherein such lowering (and raising) is thought to be beneficial. Thus they may be used in the treatment of hypertension, obesity, atherosclerotic disease events, diabetes and related conditions by administering to an animal in need thereof, a therapeutically effective amount of a compound of the formula (I) or pharmaceutically acceptable salt thereof. The compositions are formulated and administered in the same general manner as detailed below. They may also contain other active ingredients known for use in the treatment of atherosclerotic disease events, diabetes, hypertension, obesity and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA-:cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; and thyromimetics.

In particular the invention provides methods for preventing or reducing the risk of developing atherosclerosis, comprising the administration of a prophylactically effective amount of a compound of formula I alone or in combination with one or more additional pharmaceutically active agents, to a mammal, particularly human, who is at risk of developing atherosclerosis.

Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease."

The instant invention further provides methods for preventing or reducing the risk of a first or subsequent (where the potential exists for recurrence) atherosclerotic disease event, comprising the administration of a prophylactically effective amount, or more particularly an HDL-raising amount, of a compound of formula I alone or in combination with one or more additional pharmaceutically active agents, to a mammal, particularly human, who is at risk for having an atherosclerotic disease event. The term "atherosclerotic disease event" as used herein is intended to encompass coronary heart disease events, cerebrovascular events, and intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. It is intended that persons who have previously experienced one or more non-fatal atherosclerotic disease event are those for whom the potential for recurrence of such an event exists.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein cholesterol, high levels of low density lipoprotein cholesterol, and a family history of atherosclerotic cardiovascular disease. Published guidelines for determining those who are at risk of developing atherosclerotic disease can be found in: National Cholesterol Education Program, Second report of the Expert Panel on *Detection, Evaluation, and Treatment of High Blood Cholesterol in Adults* (*Adult Treatment Panel II*), National Institute of Health, National Heart Lung and Blood Institute, NIH Publication No. 93–3095, September 1993; abbreviated version: Expert Panel on Detection, Evaluation, and Treatment of High Blood Cholesterol in Adults, *Summary of the second report of the national cholesterol education program (NCEP) Expert Panel on Detection, Evaluation, and Treatment of High Blood Cholesterol in Adults* (*Adult Treatment Panel II*), *JAMA*, 1993, 269, pp. 3015–23. People identified as having one or more of the above-noted risk factors, as well as people who already have atherosclerosis, are intended to be included within the group of people considered to be at risk for having an atherosclerotic disease event.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating or preventing diabetes mellitus and/or hyperglycemia or hypertriglyceridemia, or obesity, or when treating, preventing or slowing the progression of atherosclerosis generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

The compositions are formulated and administered in the same general manner as detailed below. The compounds of the instant invention may be used effectively alone or in combination with one or more additional active agents depending on the desired target therapy. Combination therapy includes administration of a single pharmaceutical dosage formulation which contains a compound of formula I and one or more additional active agents, as well as administration of a compound of formula I and each active agent in its own separate pharmaceutical dosage formulation. For example, a compound of formula I and an HMG-CoA reductase inhibitor can be administered to the patient together in a single oral dosage composition such as a tablet or capsule, or each agent administered in separate oral dosage formulations. Where separate dosage formulations are used, a compound of formual I and one or more additional active agents can be administered at essentially the same time, i.e., concurrently, or at separately staggered times, i.e, sequentially; combination therapy is understood to include all these regimens.

An example of combination treatment or prevention of atherosclerosis may be wherein a compound of formula I is administered in combination with one or more of the following active agents:an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor such as melinamide; probucol; nicotinic acid and the salts thereof and niacinamide; a cholesterol absorption inhibitor such as beta-sitosterol; a bile acid sequestrant anion exchange resin such as cholestyramine, colestipol or dialkylaminoalkyl derivatives of a cross-linked dextran; an LDL (low density lipoprotein) receptor inducer; fibrates such as clofibrate, bezafibrate, fenofibrate, and gemfibrizol; vitamin $B_6$ (also known as pyridoxine) and the pharmaceutically acceptable salts thereof such as the HCl salt; vitamin $B_{12}$ (also known as cyanocobalamin); antioxidant vitamins such as vitamin C and E and beta carotene; a beta-blocker; an angiotensin II antagonist; an angiotensin converting enzyme inhibitor; and a platelet aggregation inhibitor such as fibrinogen receptor antagonists (i.e., glycoprotein IIb/IIIa fibrinogen receptor antagonists) and aspirin. As noted above, the compounds of formula I can be administered in combination with more than one additional active agent, for example, a combination of a compound of formula I with an HMG-CoA reductase inhibitor (e.g. lovastatin, simvastatin and pravastatin) and aspirin, or a compound of formula I with an HMG-CoA reductase inhibitor and a beta blocker.

Another example of combination therapy can be seen in treating obesity or obesity-related disorders, wherein the compounds of formula I may be effectively used in combination with for example, fenfluramine, dexfenfluramine, phentiramine and $β_3$ adrenergic receptor agonist agents.

Still another example of combination therapy can be seen in treating diabetes and related disorders wherein the compounds of formula I can be effectively used in combination with for example sulfonylureas, biguanides, α-glucosidase inhibitors, other insulin secretogogues, insulin as well as the active agents discussed above for treating atherosclerosis.

In accordance with this invention, a pharmaceutically effective amount of a compound of formula I can be used for the preparation of a medicament useful for treating diabetes, treating obesity, lowering tryglyeride levels, raising the plasma level of high density lipoprotein, and for treating, preventing or reducing the risk of developing atherosclerosis, and for preventing or reducing the risk of having a first or subsequent atherosclerotic disease event in mammals, particularly in humans.

Additionally, an effective amount of a compound of formula I and a therapeutically effective amount of one or more active agents selected from the group consisting of: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozol; vitamin $B_6$ and the pharmaceutically acceptable salts thereof; vitamin $B_{12}$; an antioxidant vitamin; a beta-blocker; an angiotensin II antagonist; an angiotensin converting enzyme inhibitor; a platelet aggregation inhibitor; a fibrinogen receptor antagonist; aspirin; fenfluramines, dexfenfluramines, phentiramines, $\beta_3$ adrenergic receptor agonists; sulfonylureas, biguanides, $\alpha$-glucosidase inhibitors, other insulin secretogogues, and insulin can be used together for the preparation of a medicament useful for the above-described treatments.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Specific examples of formula I may require the use of protecting groups to enable their successful elaboration into the desired structure. Protecting groups may be chosen with reference to Greene, T. W., et al., *Protective Groups in Organic Synthesis*, John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butldiphenylsilyl, 2-(trimethylsilyl)ethyl, phenacyl, p-methoxybenzyl, acetonyl, p-methoxyphenyl, 4-pyridylmethyl and t-butyl.

The process for making the compounds of the instant invention is generally depicted in Scheme 1 below:

SCHEME 1

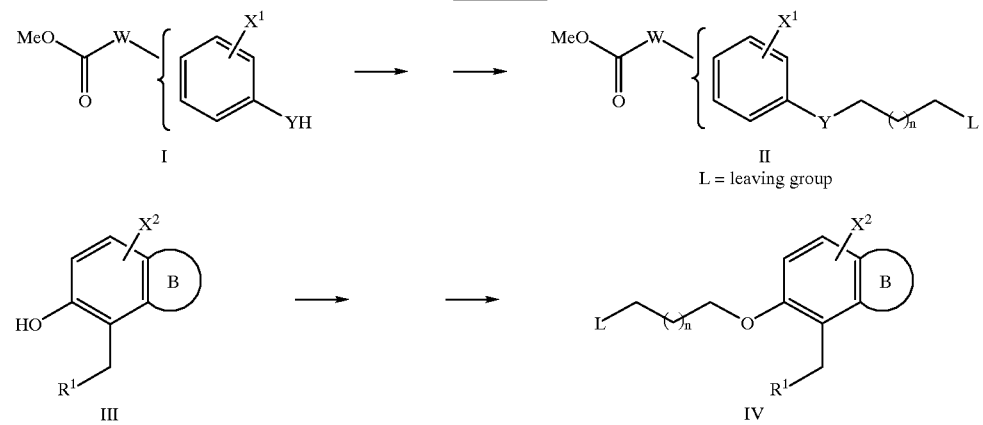

I + IV →

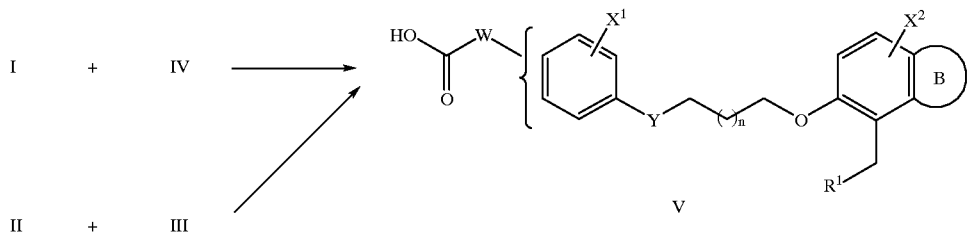

II + III ↗

L is a leaving group such as halo, preferably bromide, or sulfonyloxy, preferably mesyloxy or tosyloxy.

The following examples are provided so that the invention might be more fully understood. They should not be construed as limiting the invention in any way.

EXAMPLE 1

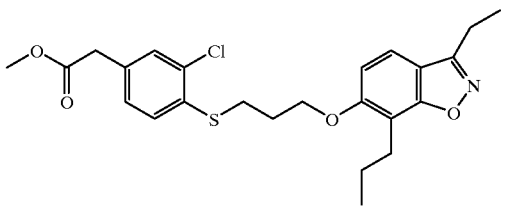

Methyl 3-chloro-4-(3-(3-ethyl-7-propyl-6-benz-[4,5]-isoxazoloxy)-propylthio)phenylacetate Step A: Preparation of 1-bromo-3-(2-hydroxy-3-propyl-4-propionyl)-phenoxy)propane A solution of 2,4-dihydroxy-3-propylphenyl ethyl ketone (25.545 grams) in 2-butanone (300 mL) was treated with 1,3-dibromopropane (48.79 mL) and potassium carbonate (50.859 grams). The mixture was refluxed for 4 hours. The reaction mixture was partitioned between isopropyl acetate and pH 4 buffer. The organic was washed once with water, then dried over magnesium sulfate. The organic was filtered and evaporated to an oil which was chromatographed over silica gel with hexane/methylene chloride (2:1) to afford the title compound.

NMR (CDCl$_3$) δ 7.62 (d, 1H, J=8.8 Hz), 6.43 (d, 1H, J=8.8 Hz), 4.16 (t, 2H, J=5.8 Hz), 3.60 (t, 2H, J=6.4 Hz), 2.94 (quart, 2H, J =7.3 Hz), 2.61 (bt, 2H, J=7.5 Hz).

Step B: Preparation of methyl 3-chloro-4-(3-(2-propyl-3-hydroxy-4-propionylphenoxy)propylthio)phenylacetate A solution of 3-chloro-4-dimethylcarbamoylthiophenylacetic acid methyl ester (33.038 grams) in dry methanol (350 mL) was treated with a solution of sodium methoxide in methanol (25 wt %; 34.15 mL). The solution was refluxed for 2 hours. HPLC analysis showed the disappearance of the carbamate. The solution was allowed to cool to 50° C. 1-bromo-3-(2-hydroxy-3-propyl- 4-propionyl)-phenoxy)propane (Step A; 31.500 grams) was added and the solution stirred for 1 hour. The reaction was partitioned between isopropyl acetate and pH 4 buffer. The organic was washed once more with pH 4 buffer, then water. The organic was dried over magnesium sulfate, filtered and concentrated to an oil. The oil was applied to a silica gel column packed with hexane/methylene chloride (2:1). The column was eluted with this mobile phase until the product began to appear in the eluant. The mobile phase was switched to 100% methylene chloride and elution continued until all the title compound was recovered.

NMR (Acetone) δ 7.81 (d, 1H, J=9.1 Hz), 7.25 (dd, 1H, J=8.1, 1.8 Hz), 6.62 (d, 1H, J=9.1 Hz), 4.27 (t, 2H, J=5.9 Hz), 3.64 (s, 3H), 3.25 (t, 2H, J=7.5 Hz), 3.04 (quart, 2H, J=7.3 Hz), 2.65 (bt, 2H, J=7.6 Hz).

Step C: Preparation of methyl 3-chloro-4-(3-(2-propyl-3-hydroxy-4-(1-hydroxyiminopropyl)phenoxy)propylthio) phenylacetate A solution of methyl 3-chloro-4-(3-(2-propyl-3-hydroxy-4-propionylphenoxy)propylthio)phenylacetate (Step B; 25.655 grams) in dry methanol (260 mL) was treated with hydroxylamine hydrochloride (3.833 grams). Anhydrous sodium acetate (4.524 grams) was added and the mixture refluxed for 4 hours. The reaction mixture was partitioned between isopropyl acetate and pH 7 buffer. The organic phase was washed once with water and dried over magnesium sulfate, filtered and evaporated to an oil. The title compound was used without further purification.

NMR (CDCl$_3$) δ 7.11 (dd, 1H, J=8.1, 1.8 Hz), 6.42 (d, 1H, J=8.9 Hz), 4.09 (t, 2H, J=5.7 Hz), 3.68 (s, 3H), 3.14 (t, 2H, J=7.2 Hz), 2.83 (quart, 2H, J=7.7 Hz), 2.66 (bt, 2H, J=7.7 Hz).

Step D: Preparation of methyl 3-chloro-4-(3-(2-propyl-3-hydroxy-4-(1-acetoxyiminopropyl)phenoxy)propylthio) phenylacetate A solution of methyl 3-chloro-4-(3-(2-propyl-3-hydroxy-4-(1-hydroxyiminopropyl)phenoxy)propylthio)phenyl acetate (Step C; 5.96 grams) in acetic anhydride (50 mL) was stirred for 16 hours. The solvent was removed in vacuo. The remaining residue was dissolved in isopropyl acetate and washed with pH 7 buffer. The organic phase was dried over magnesium sulfate, filtered and evaporated. The title compound was used without further purification.

NMR (CDCl$_3$) δ 7.11 (dd, 1H, J=8.0, 1.9 Hz), 6.44 (d, 1H, J=8.8 Hz), 4.10 (t, 2H, J=5.7 Hz), 3.68 (s, 3H), 3.13 (t, 2H, J=7.2 Hz), 2.86 (quart, 2H, J=7.6 Hz), 2.67 (bt, 2H, J=7.6 Hz), 2.22 (s, 3H).

Step E: Preparation of methyl 3-chloro-4-(3-(3-ethyl-7-propyl-6-benz-[4,5]-isoxazoloxy)propylthio)phenylacetate A solution of methyl 3-chloro-4-(3-(2-propyl-3-hydroxy-4-(1-acetoxyiminopropyl)phenoxy)propylthio) phenylacetate (Step D; 6.19 grams) in dry pyridine (65 mL) was refluxed for 3 hours. The solvent was removed in vacuo and the residue partitioned between isopropyl acetate and 0.1N HCl. The organic was washed once more with 0.1N HCl. The organic was dried over magnesium sulfate, filtered and evaporated to an oil. The crude product was placed on a slica gel column and eluted with hexane/CH$_2$Cl$_2$ (1:1) until the product appeared in the eluant. The mobile phase was changed to 100% CH$_2$Cl$_2$ and elution continued until all the title compound was recovered.

NMR (CDCl$_3$) δ 7.38 (d, 1H, J=8.6 Hz), 7.10 (dd, 1H, J=8.1, 1.8 Hz), 6.87 (d, 1H, J=8.6 Hz), 4.17 (t, 2H, J=5.8 Hz), 3.68 (s, 3H), 3.16 (t, 2H, J=7.1 Hz), 2.94 (quart, 2H, J=7.6 Hz), 2.85 (bt, 2H, J=7.5 Hz).

EXAMPLE 2

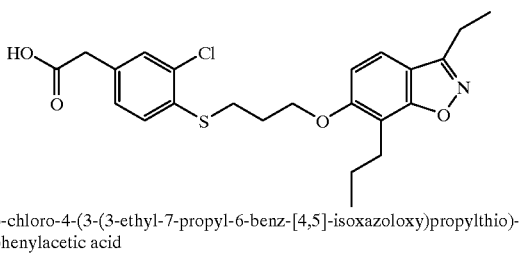

3-chloro-4-(3-(3-ethyl-7-propyl-6-benz-[4,5]-isoxazoloxy)propylthio)-phenylacetic acid A solution of methyl 3-chloro-4-(3-(3-ethyl-7-propyl-6-benz-[4,5]-isoxazoloxy)propylthio)phenylacetate (4.95 grams) in methanol (95 mL) was treated with a solution of LiOH in water (1.299 M; 16.50 mL). The solution was refluxed for 1 hour. The solution was partitioned between isopropyl acetate and 0.1N HCl. The organic layer was dried over magnesium sulfate, filtered and evaporated to a solid. The solid was suspended in methylene chloride (18 mL) and heated to reflux. Cyclohexane (1 8 mL) was added dropwise while refluxing. The solution was cooled to 0° C. and the title compound isolated by filtration.

NMR (CDCl$_3$) δ 7.38 (d, 1H, J=8.7 Hz), 7.10 (dd, 1H, J=8.1, 1.8 Hz), 6.87 (d, 1H, J=8.7 Hz), 4.17 (t, 2H, J=5.8 Hz), 3.57 (s, 2H), 3.16 (t, 2H, J=7.1 Hz), 2.94 (quart, 2H, J=7.6 Hz), 2.85 (bt, 2H, J=7.5 Hz).

EXAMPLE 3

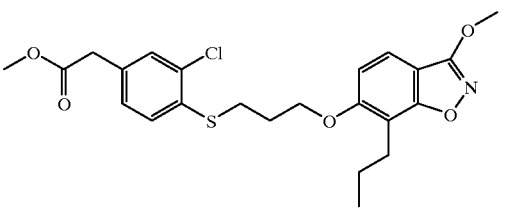

Methyl 3-chloro-4-(3-(3-methoxy-7-propyl-6-benz-[4,5]-isoxazoloxy)propylthio)phenylacetate Step A: Preparation of methyl 2-hydroxy-3-propyl-4-benzyloxybenzoate A solution of methyl 2,4-dihydroxy-3-propylbenzoate (3.00 grams) in 2-butanone (30 mL) was treated with benzyl bromide (1.70 mL) and potassium carbonate (1.972 grams). The mixture was refluxed for 4 hours. The reaction mixture was partitioned between isopropyl acetate and pH 4 buffer. The organic was washed once with water, then dried over magnesium sulfate. The organic was filtered and evaporated to an oil which was chromatographed over silica gel to afford the title compound.

NMR (CDCl$_3$) δ 7.67 (d, 1H, J=8.9 Hz), 7.42–7.29 (m, 5H), 6.48 (d, 1H, J=8.9 Hz), 5.12 (bs, 2H), 3.89 (s, 3H), 2.69 (bt, 2H, J=7.4 Hz).

Step B: Preparation of 2-hydroxy-3-propyl-4-benzyloxyphenyl hydroxamic acid

A solution of methyl 2-hydroxy-3-propyl-4-benzyloxy benzoate (Step A; 0.863 grams) in dry methanol (8 mL) was treated with hydroxylamine hydrochloride (0.299 grams) and a solution of methanolic sodium methoxide (25 wt %; 0.986 mL). The solution was refluxed for 8 hours. The reaction was partitioned between isopropyl acetate and pH 4 buffer. The organic was dried over magnesium sulfate, filtered and concentrated to a solid. The title compound was used without further purification.

NMR (CD$_3$OD) δ 7.45–7.26 (m, 6H), 6.54 (d, 1H, J=8.8 Hz), 5.12 (bs, 2H), 2.67 (bt, 2H, J=7.4 Hz).

Step C: Preparation of 3-hydroxy-6-benzyloxy-7-propylbenz-[4,5]-isoxazole

A solution of 2-hydroxy-3-propyl-4-benzyloxyphenyl hydroxamic acid (Step B; 0.477 grams) in dry THF (5 mL) was treated with carbonyl di-imidazole (0.513 grams). The solution was stirred at 50° for 14 hours. The reaction was partitioned between isopropyl acetate and pH 4 buffer. The organic was dried over magnesium sulfate, filtered and evaporated to a solid which was digested in refluxing tert-butyl methyl ether. The mixture was allowed to cool to 25° C. and the product recovered by filtration. The title compound was used without further purification.

NMR (CD$_3$OD) δ 7.89 (d, 1H, J=8.8 Hz), 7.47–7.31 (m, 5H), 7.18 (d, 1H, J=8.8 Hz), 5.25 (bs, 2H), 2.80 (bt, 2H, J=7.4 Hz).

Step D: Preparation of 3-methoxy-6-benzyloxy-7-propylbenz-[4,5]-isoxazole

A solution of 3-hydroxy-6-benzyloxy-7-propylbenz-[4,5]-isoxazole (Step C; 195 mg) in acetone (3 mL) was treated with methyl iodide (0.067 mL) and potassium carbonate (100 mg). The mixture was refluxed for 8 hours. The reaction was partitioned between isopropyl acetate and pH 4 buffer. The organic was dried over magnesium sulfate, filtered and concentrated to a solid, which was chromatographed over silica gel to afford the title compound.

NMR (CD$_3$OD) δ 7.89 (vbd, 1H, J=8.8 Hz), 7.47–7.31 (m, 5H), 7.16 (vbd, 1H, J=8.8 Hz), 5.23 (bs, 2H), 3.97 (s, 3H), 2.79 (vbt, J=7.3 Hz).

Step E: Preparation of 3-methoxy-6-hydroxy-7-propylbenz-[4,5]-isoxazole

A solution of 3-methoxy-6-benzyloxy-7-propyl-(4,5)-isoxazole (Step E; 181 mg) in ethyl acetate (4 mL) was treated with 10% palladium on carbon catalyst (25 mg). The mixture was shaken under a hydrogen atmosphere (40 psi) for 3 hours. The mixture was filtered through Celite and concentrated to a solid. The title compound was used without further purification.

NMR (CD$_3$OD) δ 7.70 (d, 1H, J=8.9 Hz), 6.80 (d, 1H, J=8.9 Hz), 3.93 (s, 3H), 2.69 (bt, 2H, J=7.6 Hz).

Step F: Preparation of 3-methoxy-6-(3-bromopropyl)oxy-7-propyl-benz-[4,5]-isoxazole Using the method of Example 1, Step A, substituting 3-methoxy-6-hydroxy-7-propylbenz-(4,5)-isoxazole (Step E) as the starting material, the title compound was obtained.

NMR (CDCl$_3$) δ 7.92 (d, 1H, J=8.9 Hz), 6.90 (d, 1H, J=8.8 Hz), 4.22 (t, 2H, J=5.8 Hz), 4.04 (s, 3H), 3.60 (t, 2H, J=6.3 Hz), 2.72 (bt, 2H, J=7.5 Hz).

Step G: Preparation of methyl 3-chloro-4-(3-(3-methoxy-7-propyl-6-benz-4,5]-isoxazoloxy)propylthio)phenylacetate Using the method of Example 1, Step B, substituting 3-methoxy-6-(3-bromopropyl)oxy-7-propyl-benz-[4,5]-isoxazole as the starting material, the title compound was obtained.

NMR (CDCl$_3$) δ 7.66 (d, 1H, J=8.9 Hz), 7.10 (dd, 1H, J=8.1, 1.8 Hz), 6.40 (d, 1H, J=8.9 Hz), 4.14 (t, 2H, J=5.7 Hz), 3.89 (s, 3H), 3.68 (s, 3H), 3.13 (t, 2H, J=7.2 Hz), 2.65 (bt, 2H, J=7.6 Hz).

EXAMPLE 4

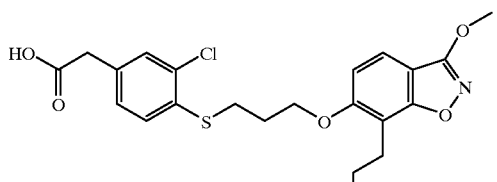

3-chloro-4-(3-(3-methoxy-7-propyl-6-benz-[4,5]-isoxazoloxy)-propylthio)-phenylacetic acid

1. 2-hydroxy-3-propyl-4-benzyloxyphenyl hydroxamic acid

A solution of 2-hydroxy-3-propyl-4-benzyloxy benzoic acid methyl ester (0.863 grams) in dry methanol (8 mL) was treated with hydroxylamine hydrochloride (0.299 grams) and a solution of methanolic sodium methoxide (25 wt %; 0.986 mL). The solution was refluxed for 8 hours. The reaction was partitioned between isopropyl acetate and pH 4 buffer. The organic was dried over magnesium sulfate, filtered and concentrated to a solid. The product was used without further purification.

NMR (CD$_3$OD) d 7.45–7.26 (m, 6H), 6.54 (d, 1H, J=8.8 Hz), 5.12 (bs, 2H), 2.67 (bt, 2H, J=7.4 Hz).

2. 3-hydroxy-6-benzyloxy-7-propyl-benz[4,5] isoxazole

A solution of 2-hydroxy-3-propyl-4-benzyloxyphenyl hydroxamic acid (0.477 grams) in dry THF (5 mL) was treated with carbonyl di-imidazole (0.513 grams). The solution was stirred at 50° for 14 hours. The reaction was partitioned between isopropyl acetate and pH 4 buffer. The organic was dried over magnesium sulfate, filtered and evaporated to a solid which was digested in refluxing tert-butyl methyl ether. The mixture was allowed to cool to 25° C. and the product recovered by filtration. The product was used without further purification.

NMR (CD$_3$OD) d 7.89 (d, 1H, J=8.8 Hz), 7.47–7.31 (m, 5H), 7.18 (d, 1H, J=8.8 Hz), 5.25 (bs, 2H), 2.80 (bt, 2H, J=7.4 Hz).

3. 3-methoxy-6-benzyloxy-7-propyl-benz[4,5] isoxazole

A solution of 3-hydroxy-6-benzyloxy-7-propyl benz[4,5] isoxazole (195 mg) in acetone (3 mL) was treated with methyl iodide (0.067 mL) and potassium carbonate (100 mg). The mixture was refluxed for 8 hours. The reaction was partitioned between isopropyl acetate and pH 4 buffer. The organic was dried over magnesium sulfate, filtered and concentrated to a solid, which was chromatographed over silica gel to afford the product.

NMR (CD$_3$OD) d 7.89 (vbd, 1H, J=8.8 Hz), 7.47–7.31 (m, 5H), 7.16 (vbd, 1H, J=8.8 Hz), 5.23 (bs, 2H), 3.97 (s, 3H), 2.79 (vbt, J=7.3 Hz).

4. 3-methoxy-6-hydroxy-7-propyl-benz[4,5] isoxazole

A solution of 3-methoxy-6-benzyloxy-7-propyl benz-(4, 5)-isoxazole (181 mg) in ethyl acetate (4 mL) was treated with 10% palladium on carbon catalyst (25 mg). The mixture was shaken under a hydrogen atmosphere (40 psi) for 3 hours. The mixture was filtered through Celite and concentrated to a solid. The product was used without further purification.

NMR (CD$_3$OD) d 7.70 (d, 1H, J=8.9 Hz), 6.80 (d, 1H, J=8.9 Hz), 3.93 (s, 3H), 2.69 (bt, 2H, J=7.6 Hz).

5. 1-bromo-3-(3-methoxy-7-propyl-6-benz[4,5] isoxazole)oxy propane

A solution of 3-methoxy-6-hydroxy-7-propylbenz[4,5] isoxazole (0.112 grams) in 2-butanone (1.5 mL) was treated with 1,3-dibromopropane (0.215 mL) and potassium carbonate (0.078 grams). The mixture was stirred at 60° C. for 16 hours. The reaction was partitioned between isopropyl acetate and pH 4 phosphate buffer. The organic was dried over magnesium sulfate, filtered and evaporated to a residue. The product was purified by silica gel chromatography.

NMR (CDCl$_3$) d 7.92 (d, 1H, J=8.9 Hz), 6.90 (d, 1H, J=8.9 Hz), 4.12 (t, 2H, J=5.6 Hz), 4.03 (s, 3H), 3.60 (t, 2H, J=6.5 Hz), 2.72 (bt, 2H, J=7.5 Hz).

6. Methyl 3-chloro-4-(3-(3-methoxy-7-propyl-6-benz[4,5]isoxazole) oxy)propylthio phenyl acetate A solution of 3-chloro-4-dimethylcarbamoylthiophenyl acetic acid methyl ester (0.109 grams; 0.380 mmol) in dry methanol (2 mL) was treated with a solution of sodium methoxide in methanol (25 wt %; 0.122 mL). The solution was refluxed for 2 hours. LC analysis showed the disappearance of the carbamate. The solution was allowed to cool to ambient temperature. 1-bromo-3-(3-methoxy-7-propyl-6-benz[4,5]isoxazole)oxy propane (0.104 grams; 0.317 mmol) was added and the solution stirred for 1 hour. The reaction was partitioned between isopropyl acetate and pH 4 buffer. The organic was dried over magnesium sulfate, filtered and concentrated to an oil. The oil was chromatographed over silica gel to afford the title compound.

NMR (CDCl$_3$): 7.66 (d, 1H, J=8.9 Hz); 7.11 (dd, 1H, J=8.1, 1.9 Hz); 6.39 (d, 1H, J=8.9 Hz); 4.12 (t, 2H, J=5.7 Hz); 3.89 (s, 3H); 3.68 (s, 3H); 3.58 (s, 2H); 3.13 (t, 2H, J=7.1 Hz); 2.63 (bt, 2H, J=7.6 Hz).

7. 3-chloro-4-(3-(3-methoxy-7-propyl-6-benz[4,5] isoxazole)oxy) propylthio phenyl acetic acid A solution of methyl 3-chloro-4-(3-(3-methoxy-7-propyl-6-benz[4,5]isoxazole)oxy)propylthio phenyl acetate (0.130 grams; 0.280 mmol) in methanol (2 mL) was treated with a solution of LiOH in water (1.084 M; 0.387 mL). The solution was refluxed for 1 hour. The solution was partitioned between isopropyl acetate and 0.1N HCl. The organic layer was dried over magnesium sulfate, filtered and evaporated to a solid. The solid was suspended in methylene chloride (1 mL) and heated to reflux. Cyclohexane (2 mL) was added dropwise while refluxing. The solution was cooled to 0° C. and the product isolated by filtration.

NMR (CDCl$_3$): 7.66 (d, 1H, J=8.9 Hz), 7.11 (dd, 1H, J=8.1, 1.9 Hz), 6.39 (d, 1H, J=8.9 Hz), 4.12 (t, 2H, J=5.7 Hz), 3.89 (s, 3H), 3.58 (s, 2H), 3.13 (t, 2H, J=7.1 Hz), 2.63 (bt, 2H, J=7.6 Hz).

EXAMPLE 5

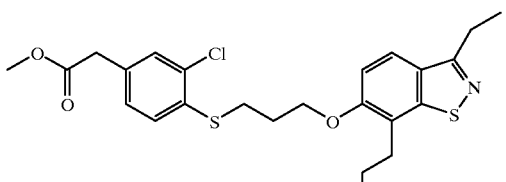

Methyl 3-chloro-4-(3-(3-ethyl-7-propyl-6-benz-[4,5]-isothiazoloxy)-propylthio)phenyl acetate Step A: Preparation of 2-chloro-3-(3-propenyl)-4-hydroxybenzaldehyde A solution of 2-chloro-4-(3-propenyl)oxybenzaldehyde (6.62 grams) in ortho-dichlorobenzene (40 mL) was refluxed for 22 hours. The solvent was removed in vacuo and the derived solid was chromatographed over silica gel to afford the title compound.

NMR (CD$_3$OD) d 10.28 (s, 1H), 7.79 (d, 1H, J=8.9 Hz), 6.84 (d, 1H, J=8.9 Hz), 5.90 (m, 1H), 5.03–4.95 (two overlapping dd, 2H), 3.68 (d, 2H, J=4.7 Hz).

Step B: Preparation of 2-chloro-3-propyl-4-hydroxybenzaldehyde

A solution of 2-chloro-3-(3-propenyl)-4-hydroxybenzaldehyde (Step A; 0.923 grams) in methyl tert-butyl ether (10 mL) was treated with 5% rhodium on alumina (140 mg). The mixture was shaken under a hydrogen atmosphere (21 psi) for 2 hours. The mixture was filtered through Celite and evaporated to a solid. The title compound was used without further purification.

NMR (CD$_3$OD) δ 10.27 (s, 1H), 7.64 (d, 1H, J=8.8 Hz), 6.81 (d, 1H, J=8.7 Hz), 2.79 (bt, 2H, J=7.6 Hz).

Step C: Preparation of 2-chloro-3-propyl-4-benzyloxybenzaldehyde

Using the method of Example 3, Step A, substituting 2-chloro-3-(3-propenyl)-4-hydroxybenzaldehyde (Step B) as the starting material, the title compound was obtained.

NMR (acetone) δ 10.35 (s, 1H), 7.79 (d, 1H, J=8.8 Hz), 7.22 (d, 1H, J=8.8 Hz), 5.31 (bs, 2H), 2.88 (bt, 2H, J=7.4 Hz).

Step D: Preparation of 2-methylthio-3-propyl-4-benzyloxybenzaldehyde

A solution of 2-chloro-3-propyl-4-benzyloxybenzaldehyde (Step C; 0.683 grams) in dry DMF (7 mL) was treated with sodium methanethiolate (0.166 grams). The solution was stirred at 50° C. for 3 hours. The reaction mixture was partitioned between isopropyl acetate and pH 7 buffer. The organic was washed 3 times with water, then dried over magnesium sulfate. Filtration and concentration afforded an oil which was chromatographed over silica gel to afford the title compound.

NMR (acetone) δ 10.61 (s, 1H), 7.79 (d, 1H, J=8.8 Hz), 7.52–7.45 (m, 5H), 7.24 (d, 1H, J=8.8 Hz), 5.29 (bs, 2H), 3.05 (bt, 2H, J=7.6 Hz), 2.38 (s, 3H).

Step E. Preparation of 1-(2-methylthio-3-propyl-4-benzyloxy)phenyl-1-propanol

A solution of 2-methylthio-3-propyl-4-benzyloxybenzaldehyde (Step D; 324 mg) in dry diethyl ether (3 mL) was added dropwise to a −78° C. solution of 1M ethyl magnesium bromide in diethyl ether (2.5 mL). The reaction was stirred for 15 minutes, then allowed to warm to −10° C. The solution was treated with saturated aqueous ammonium chloride (2 mL), then allowed to warm to 25° C. The reaction was partitioned between isopropyl acetate and water. The organic was dried over magnesium sulfate, filtered and evaporated to an oil which was chromatographed over silica gel to afford the desired product.

NMR (acetone) δ 7.09 (d, 1H, J=8.9 Hz), 5.31 (vbm, 1H), 5.13 (bs, 2H), 4.00 (vbs, 1H), 3.02 (bm, 2H), 2.24 (s, 3H).

Step F: Preparation of 2-methylthio-3-propyl-4-benzyloxypropiophenone

A −55° C. solution of trifluoroacetic anhydride (0.291 mL) in dry methylene chloride (2 mL) was treated dropwise with a solution of dry DMSO (0.292 mL) in methylene chloride (1 mL). The reaction was stirred for 15 minutes, then treated with a solution of 1-(2-methylthio-3-propyl-4-benzyloxy)phenyl-1-propanol (Step E; 136 mg) in methylene chloride (2 mL). The solution was stirred for 30 minutes, then treated dropwise with dry triethylamine (1.15 mL). The mixture was stirred for 1 hour as it was allowed to warm to 25° C. The reaction was partitioned between isopropyl acetate and pH 7 buffer. The organic layer was dried over magnesium sulfate, filtered and concentrated to an oil which was chromatographed over silica gel to afford the title compound.

NMR (acetone) d 7.16 (d, 1H, J=8.8 Hz), 7.11 (d, 1H, J=8.8 Hz), 5.20 (bs, 2H), 3.00 (bt, 2H, J=7.4 Hz), 2.88 (quart, 2H, J=7.2 Hz), 2.27 (s, 3H).

Step G: Preparation of 2-methylthio-3-propyl-4-benzyloxypropiophenone oxime

Using the method of Example 1, Step C, substituting 2-methylthio-3-propyl-4-benzyloxypropiophenone (Step F) as the starting material, the title compound was obtained.

NMR (major isomer, acetone) δ 9.91 (vbs, 1H), 7.07 (d, 1H, J=8.7 Hz), 7.03 (d, 1H, J=8.7 Hz), 5.16 (bs, 2H), 3.02 (bt, 2H, J=7.6 Hz), 2.79 (quart, 2H, J=7.4 Hz), 2.22 (s, 3H).

Step H: Preparation of 3-ethyl-6-benzyloxy-7-propylbenz-[4,5]-isothiazole

A solution of 2-methylthio-3-propyl-4-benzyloxypropiophenone oxime (Step G; 86 mg) in dry pyridine (2 mL) was treated with acetic anhydride (0.050 mL). The solution was refluxed for 4 hours. Three-quarters of the solvent was removed in vacuo. The remaining reaction mixture was partitioned between isopropyl acetate and 0.1N HCl. The organic was washed 3 times more with 0.1N HCl, then once with water. The organic was dried over magnesium sulfate, filtered and concentrated to an oil. Silica gel chromatography afforded the title compound.

NMR (acetone) δ 7.88 (bd, 1H, J=8.9 Hz), 7.54–7.30 (m, 6H), 5.30 (bs, 2H), 3.04 (b quart, 2H, J=7.3 Hz), 2.86 (bt, 2H, J=7.5 Hz).

Step J: Preparation of 3-ethyl-6-hydroxy-7-propyl-benz-[4,5]-isothiazole

Using the method of Example 3, Step E, substituting 3-ethyl-6-benzyloxy-7-propylbenz-[4,5]-isothiazole (Step H) as the starting material, the title compound was obtained.

NMR (acetone) δ 8.93 (vbs, 1H), 7.72 (d, 1H, J=8.8 Hz), 7.08 (d, 1H, J=8.8 Hz), 3.03 (quart, 2H, J=7.4 Hz), 2.80 (bt, 2H, J=7.7 Hz).

Step K: Preparation of 3-ethyl-6-(3-bromopropyloxy)-7-propylbenz-[4,5]-isothiazole Using the method of Example 1, Step A, substituting 3-ethyl-6-hydroxy-7-propylbenz-[4,5]-isothiazole (Step J) as the starting material, the title compound was obtained.

NMR (acetone) δ 7.90 (d, 1H, J=8.9 Hz), 7.28 (d, 1H, J=8.9 Hz), 4.31 (t, 2H, J=5.6 Hz), 3.75 (t, 2H, J=6.5 Hz), 3.04 (quart, 2H, J=7.3 Hz), 2.82 (bt, 2H, J=7.5 Hz).

Step L: Preparation of methyl 3-chloro-4-(3-(3-ethyl-7-propyl-6-benz-[4,5]-isothiazoloxy)propylthio)phenylacetate Using the method of Example 1, Step B, substituting 3-ethyl-6-(3-bromopropyloxy)-7-propylbenz-[4,5]-isothiazole (Step K) as the starting material, the title compound was obtained.

NMR (acetone) δ 7.90 (d, 1H, J=8.8 Hz), 7.25 (overlapping d and dd, 2H, Jd=8.8 Hz), 4.33 (t, 2H, J=5.7 Hz), 3.63 (two overlapping s, 5H), 3.29 (t, 2H, J=7.4 Hz), 3.04 (quart, 2H, J=7.6 Hz), 2.83 (bt, 2H, J =7.5 Hz).

EXAMPLE 6

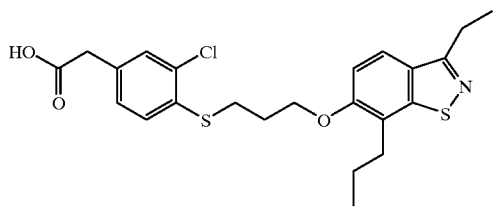

3-chloro-4-(3-(3-ethyl-7-propyl-6-benz-[4,5]-isothiazole)oxy)propyl-thio phenylacetic acid Using the method of Example 2, substituting methyl 3-chloro-4-(3-(3-ethyl-7-propyl-6-benz[4,5]isothiazoloxy) propylthio)phenylacetate (Example 5) as the starting material, the title compound was obtained.

NMR (acetone) δ 7.90 (d, 1H, J=8.8 Hz), 7.26 (overlapping d and dd, 2H, Jd=8.8 Hz), 4.33 (t, 2H, J=5.7 Hz), 3.63 (s, 2H), 3.29 (t, 2H, J=7.4 Hz), 3.05 (quart, 2H, J=7.6 Hz), 2.83 (bt, 2H, J=7.5 Hz).

EXAMPLE 7

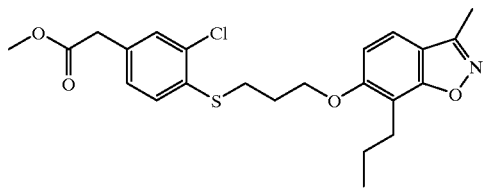

Methyl 3-chloro-4-(3-(3-methyl-7-propyl-6-benz-[4,5]-isoxazoloxy)-propylthio)phenylacetate Step A: Preparation of 3-methyl-6-hydroxy-7-propylbenz-[4,5]-isoxazole A solution of 2,4-dihydroxy-3-propylacetophenone (1.008 grams) in dry methanol (10 mL) was treated with hydroxylamine hydrochloride (1.803 grams) and anhydrous sodium acetate (2.127 grams). The mixture was refluxed 4 hours. HPLC analysis indicated the complete disappearance of starting material. The reaction was partitioned between isopropyl acetate and pH 7 buffer. The organic was dried over magnesium sulfate, filtered and evaporated to a solid. Acetic anhydride (11 mL) was added and the solution stirred at ambient temperature for 14 hours. The solvent was removed in vacuo and the residue partitioned between isopropyl acetate and pH 7 buffer. The organic was dried over magnesium sulfate, filtered and concentrated to a residue. Pyridine (12 mL) was added and the solution refluxed for 3 hours. The solvent was removed in vacuo and the residue partitioned between isopropyl acetate and 0.1 N HCl. The organic was washed with 0.1 N HCl and dried over magnesium sulfate. The organic was filtered and concentrated to a residue which was chromatographed over silica gel to afford the title compound.

NMR (CDCl$_3$) δ 7.28 (d, 1H, J=8.8 Hz), 6.80 (d, 1H, J=8.8 Hz), 5.33 (vbs, 1H), 2.83 (bt, 2H, J=7.6 Hz), 2.50 (s, 3H).

Step B: Preparation of 3-methyl-6-(3-bromopropyl)oxy-7-propyl-benz-[4,5]-isoxazole Using the method of Example 1, step A, substituting 3-methyl-6-hydroxy-7-propylbenz-[4,5]-isoxazole (Step A) as the starting material, the title compound was obtained.

NMR (CDCl$_3$) δ 7.38 (d, 1H, J=9.0 Hz), 6.92 (d, 1H, J=9.0 Hz), 4.20 (t, 2H, J=5.7 Hz), 3.64 (t, 2H, J=6.4 Hz), 2.87 (bt, 2H, J=7.6 Hz), 2.51 (s, 3H).

Step C: Preparation of methyl 3-chloro-4-(3-(3-methyl-7-propyl-6-benz-[4,5]-isoxazoloxy)propylthio)phenylacetate Using the method of Example 1, step B, substituting 3-methyl-6-(3-bromopropyl)oxy-7-propyl-benz-[4,5]-isoxazole (Step C) as the starting material, the title compound was obtained.

NMR (CDCl$_3$) δ 7.35 (d, 1H, J=8.6 Hz), 7.10 (dd, 1H, J=8.1, 1.8 Hz), 6.89 (d, 1H, J=8.6 Hz), 4.17 (t, 2H, J=5.8 Hz), 3.68 (s, 3H), 3.16 (t, 2H, J=7.1 Hz), 2.50 (s, 3H), 2.85 (bt, 2H, J=7.5 Hz).

EXAMPLE 8

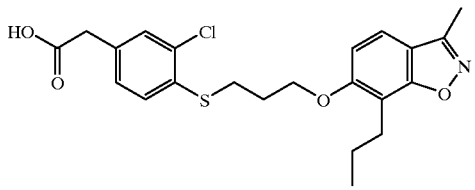

3-chloro-4-(3-(3-methyl-7-propyl-6-benz-[4,5]-isoxazoloxy)propylthio)-phenylacetic acid Using the method of Example 2, substituting methyl 3-chloro-4-(3-(3-methyl-7-propyl-6-benz-[4,5]-isoxazoloxy)propylthio)phenylacetate (Example 7) as the starting material, the title compound was obtained.

NMR (CDCl$_3$) δ 7.34 (d, 1H, J=8.7 Hz), 7.10 (dd, 1H, J=8.1, 1.8 Hz), 6.89 (d, 1H, J=8.7 Hz), 4.17 (t, 2H, J=5.8 Hz), 3.58 (s, 2H), 3.17 (t, 2H, J=7.2 Hz), 2.84 (bt, 2H, J=7.5 Hz), 2.50 (s, 3H).

EXAMPLE 9

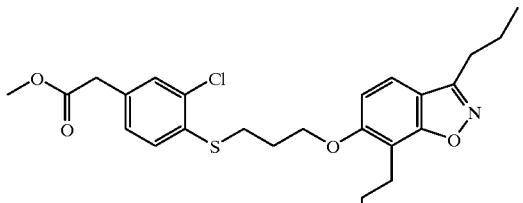

Methyl 3-chloro-4-(3-(3,7-dipropyl-6-benz-[4,5]-isoxazole)oxy)-propylthio phenyl acetate Step A: Preparation of 2-hydroxy-3-propyl-4-(3-bromopropyloxy)phenyl propyl ketone Using the method of Example 1, step A, substituting 2,4-dihydroxy-3-propylphenyl propyl ketone as the starting material, the title compound was obtained.

NMR (CDCl$_3$) δ 7.61 (d, 1H, J=8.8 Hz), 6.43 (d, 1H, J=8.8 Hz), 4.16 (t, 2H, J=5.7 Hz), 3.60 (t, 2H, J=6.4 Hz), 2.87 (t, 2H, J=7.4 Hz), 2.61 (bt, 2H, J=7.5 Hz).

Step B: Preparation of methyl 3-chloro-4-(3-(2-propyl-3-hydroxy-4-butyrophenoxy)propylthio)phenylacetate Using the method of Example 1, step B, substituting 2-hydroxy-3-propyl-4-(3-bromopropyloxy)phenyl propyl ketone as the starting material, the title compound was obtained.

NMR (CDCl$_3$) δ 7.61 (d, 1H, J=9.0 Hz), 7.11 (dd, 1H, J=8.1, 1.8 Hz), 6.41 (d, 1H, J=8.9 Hz), 4.14 (t, 2H, J=5.8 Hz), 3.68 (s,3H), 3.13 (t, 2H, J=7.6 Hz), 2.87 (t, 2H, J=7.1 Hz), 2.60 (bt, 2H, J=7.4 Hz).

Step C: Preparation of methyl 3-chloro-4-(3-(2-propyl-3-hydroxy-4-(1-hydroxyliminobutyl)phenoxy)propylthio) phenylacetate Using the method of Example 1, step C, substituting methyl 3-chloro-4-(3-(2-propyl-3-hydroxy-4-butyrophenoxy)propylthio)phenyl-acetate as the starting material, the title compound was obtained.

NMR (CDCl$_3$) δ 7.12 (dd, 1H, J=8.0, 1.8 Hz), 6.43 (d, 1H, J=8.9 Hz), 4.09 (t, 2H, J=5.7 Hz), 3.69 (s, 3H), 3.13 (t, 2H, J=7.3 Hz), 2.79 (bt, 2H, J=7.9 Hz), 2.65 (bt, 2H, J=7.6 Hz).

Step D: Preparation of methyl 3-chloro-4-(3-(2-propyl-3-hydroxy-4-(1-acetoxyiminobutyl))phenoxy)propylthio phenyl acetate Using the method of Example 1, step D, substituting methyl 3-chloro-4-(3-(2-propyl-3-hydroxy-4-(1-hydroxyliminobutyl)phenoxy)-propylthio)phenylacetate as the starting material, the title compound was obtained.

NMR (CDCl$_3$) δ 7.11 (dd, 1H, J-7.9, 1.8 Hz), 6.43 (d,1H, J=8.8 Hz), 4.09 (t, 2H, J=5.8 Hz), 3.69 (s, 3H), 3.13 (t, 2H, J=7.2 Hz), 2.82 (bt, 2H, J=7.8 Hz), 2.68 (bt, 2H, J=7.7 Hz).

Step E: Preparation of methyl 3-chloro-4-(3-(3,7-dipropyl-6-benz-[4,5]-isoxazoloxy)propylthio)phenyl acetate Using the method of Example 1, step E, substituting methyl 3-chloro-4-(3-(2-propyl-3-hydroxy-4-(1-acetoxyiminobutyl)phenoxy) propylthio)phenylacetate as the starting material, the title compound was obtained.

NMR (CDCl$_3$) δ 7.37 (d, 1H, J=8.7 Hz), 7.10 (dd, 1H, J=8.1, 1.8 Hz), 6.88 (d, 1H, J=8.7 Hz), 4.17 (t, 2H, J=5.9 Hz), 3.68 (s, 3H), 3.15 (t, 2H, J=7.2 Hz), 2.90–2.81 (2 overlapping t, 4H).

EXAMPLE 10

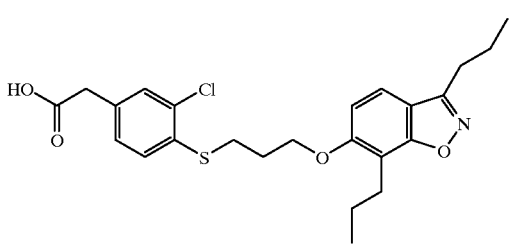

3-chloro-4-(3-(3,7-dipropyl-6-benz-[4,5]-isoxazoloxy)propylthio) phenyl-acetic acid Using the method of Example 2, substituting methyl 3-chloro-4-(3-(3,7-dipropyl-6-benz-[4,5]-isoxazoloxy) propylthiophenylacetate as the starting material, the title compound was obtained.

NMR (CDCl$_3$) δ 7.38 (d, 1H, J=8.8 Hz), 7.10 (dd, 1H, J=8.1, 1.8 Hz), 6.87 (d, 1H, J=8.8 Hz), 4.17 (t, 2H, J=5.8 Hz), 3.57 (s, 2H), 3.16 (t, 2H, J=7.1 Hz) 2.91–2.81 (2 overlapping t, 4H).

EXAMPLE 11

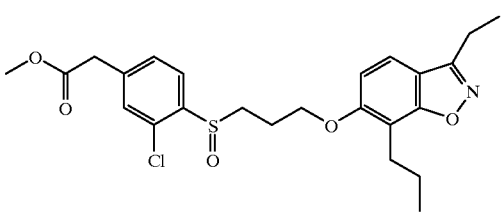

Methyl 3-chloro-4-(3-(3-ethyl-7-propyl-6-benz-[4,5]-isoxazoloxy)-propylthio)phenylacetate S-oxide A 25° C. solution of methyl 3-chloro-4-(3-(3-ethyl-7-propyl-6-benz-[4,5]-isoxazoloxy)propylthio)phenylacetate (Example 1; 57 mg) in methanol (2 mL) was treated with 80% magnesium monoperoxyphtalate hexahydrate (49 mg). The mixture was stirred for 1 hour. The reaction was partitioned between isopropyl acetate and pH 7 buffer. The organic was washed once with water and dried over magnesium sulfate. Filtration and concentration afforded a solid which was purified by chromatography over silica gel to afford the title compound.

NMR (CDCl$_3$) δ 7.83 (d, 1H, J=8.8 Hz), 7.41 (dd, 1H, J=8.1, 1.8 Hz), 6.82 (d, 1H, J=8.8 Hz), 4.16 (dtt, 2H), 3.70 (s, 3H), 3.35 (ddd, 1H), 2.98 (ddd, 1H), 2.92 (quart, 2H, J=7.5 Hz), 2.79 (bt, 2H, J=7.6 Hz).

EXAMPLE 12

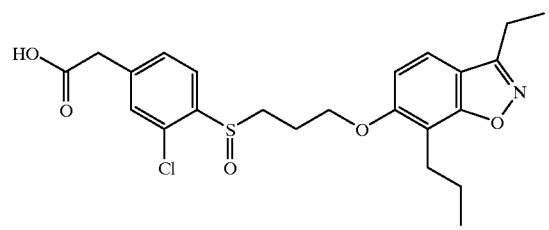

3-chloro-4-(3-(3-ethyl-7-propyl-6-benz-[4,5]-isoxazoloxy)propylthio)-phenylacetic acid S-oxide Using the method of Example 2, substituting methyl 3-chloro-4-(3-(3-ethyl-7-propyl-6-benz-[4,5]-isoxazoloxy) propylthio)phenylacetate S-oxide (Example 11) as the starting material, the title compound was obtained.

NMR (acetone) δ 7.81 (d, 1H, J=8.9 Hz), 7.59 (dd, 1H, J=8.1, 1.8 Hz), 7.04 (d, 1H, J=9.0 Hz), 4.27 (tt, J=5.7, 1.1, 1.1 Hz), 3.78 (s, 2H), 3.39 (ddd, 1H), 3.03 (ddd, 1H), 2.94 (quart, 2H, J=7.8 Hz), 2.82 (bt, 2H, J=7.9 Hz).

EXAMPLE 13

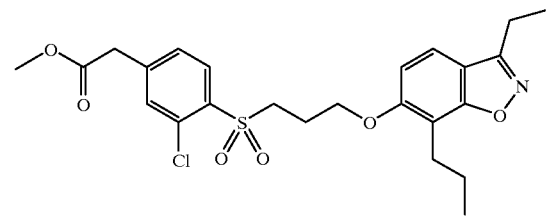

Methyl 3-chloro-4-(3-(3-ethyl-7-propyl-6-benz-[4,5]-isoxazoloxy) propyl-thio)phenylacetate S,S-dioxide A solution of methyl 3-chloro-4-(3-(3-ethyl-7-propyl-6-benz-[4,5]-isoxazoloxy)propylthio)phenylacetate S-oxide (Example 11; 34 mg) in methanol (1 mL) was treated with 80% magnesium monoperoxyphtalate hexahydrate (33 mg). The solution was stirred at 25° C. for 16 hours. The reaction was partitioned between isopropyl acetate and pH 7 buffer. The organic was washed once with water, then dried over magnesium sulfate. Filtration and evaporation afforded a solid which was chromatographed over silica gel to give the title compound.

NMR (CDCl$_3$) δ 8.05 (d, 1H, J=8.9 Hz), 7.36 (dd, 1H, J=8.1, 1.9 Hz), 6.77 (d, 1H, J=8.9 Hz), 4.12 (t, 2H J=5.7 Hz), 3.71 (s, 3H), 3.67 (bt, 2H, J=7.3 Hz), 2.92 (quart, 2H, J=7.4 Hz), 2.80 (bt, J=7.6 Hz).

EXAMPLE 14

3-Chloro-4-(3-(3-ethyl-7-propyl-6-benz-[4,5]-isoxazole)oxy)-propylthio phenylacetic acid S,S-dioxide Using the method of Example 2, substituting methyl 3-chloro-4-(3-(3-ethyl-7-propyl-6-benz-[4,5]-isoxazoloxy) propylthio)phenylacetate S,S-dioxide (Example 13) as the starting material, the title compound was obtained.

NMR (CDCl$_3$) δ 8.09 (d, 1H, J=8.8 Hz), 7.38 (dd, 1H, J=8.1, 1.9 Hz), 6.80 (d, 1H, J=8.8 Hz), 4.13 (t, 2H J=5.6 Hz), 3.69 (s, 2H), 3.65 (bt, 2H, J=7.2 Hz), 2.93 (quart, 2H, J=7.5 Hz), 2.80 (bt, J=7.6 Hz).

EXAMPLE 15 tert-Butyl 3-chloro-4-(3-(3-ethyl-7-propyl-6-benz-[4,5]-isoxazoloxy)-propylthio) phenyl acetate A solution of 3-chloro-4-(3-(3-ethyl-7-propyl-6-benz-[4,5]-isoxazoloxy)propylthio)phenylacetic acid (Example 2; 0.073 grams) in dry toluene (1.0 mL) was treated with dimethylformamide bis-tert-butyl acetal (0.780 mL). The solution was heated at 70° C. for 24 hours. The reaction was partitioned between isopropyl acetate and pH 4 buffer. The organic layer was dried over magnesium sulfate and filtered. Concentration afforded a solid which was chromatographed over silica gel to afford the title compound.

NMR (CDCl$_3$) δ 7.38 (d, 1H, J=8.8 Hz), 7.10 (dd, 1H, J=8.1, 1.8 Hz), 6.87 (d, 1H, J=8.8 Hz), 4.17 (t, 2H, J=5.8 Hz), 3.43 (s, 2H), 3.16 (t, 2H, J=7.1 Hz), 2.94 (quart, 2H, J=7.6 Hz), 2.85 (bt, 2H, J=7.5 Hz), 1.40 (s overlapping with downfield peak of t, 12H total).

EXAMPLE 16

3-Chloro-4-(3-(3-phenyl-7-propyl-6-benz-[4,5]-isoxazoloxy)-propylthio)phenylacetic acid Step 1A A solution of 3-chloro-4-dimethylcarbamoylthiophenyl acetic acid methyl ester (10.028 grams; 34.848 mmol) in dry MeOH (90 mL) was treated with a solution of sodium methoxide (4.37 M; 11.16 mL; 48.788 mmol). The reaction was refluxed for 2 hours. The reaction mixture was cooled to $_{20}$° C. and transferred to a dropping funnel. The dropping funnel was placed atop a flask containing a solution of dibromopropane (14.15 mL; 139.392 mmol) in dry MeOH (50 mL). The contents of the dropping funnel were added to the flask dropwise, and the solution stirred for 2 hours. The reaction mixture was partitioned between isopropyl acetate and pH 4 buffer. The layers were separated and the organic washed once with water. The organic was dried over magnesium sulfate, filtered and concentrated. Silica gel chromatography afforded 3-chloro-4-(3-bromopropyl)thiophenyl acetic acid methyl ester.

Step 1

Commercially available 4-allyloxy-2-hydroxybenzophenone (15 g) was rearranged by heating under reflux in ortho-dichlorobenzene (60 mL) for 26 hours. The product was isolated by dilution of the reaction mixture with 5 volumes hexanes to give a crystalline product as fine needles.

Characteristic NMR Resonances; $^1$H NMR 400 MHz (CDCl$_3$); 7.62–7.59 (m, 2H), 7.56–7.52 (m, 2H), 7.49–7.44 (m, 2H), 7.40 (d, 1H, J=8.9 Hz), 6.34 (d, 1H, J=8.8 Hz), 6.02 (ddt, 1H, J=17.21, 10.1, 6.2 Hz), 5.72 (s, 1H, phenol OH), 5.14–5.24 (m, 2H), 3.53 (d with fine splitting, 2H, J=6.2 Hz).

Step 2

A solution of 2,4-dihydroxy-3-(2-propenyl) benzophenone (3 g) was reduced under ~1 atm H$_2$ in ethyl acetate (100 mL) over 10% Pd/C catalyst (0.3 grams) for 3 hours. The product was purified by crystallization from methanol/water. The product is obtained as small yellow plates.

Characteristic NMR Resonances; $^1$H NMR 400 MHz (CDCl$_3$); 7.61–7.59 (m, 2H), 7.55–7.51 (m, 1H), 7.48–7.44

(m, 2H), 7.33 (d, 1H, J=8.8 Hz), 6.29 (d, 1H, J=8.8 Hz), 5.51 (s, 1H, phenol OH), 2.66 (dd, 2H, J=7.6, 9.3 Hz), 1.61 (sext, 2H, J=7.7 Hz), 0.99 (t, 3H, J=7.3 Hz).

Step 3

The 2,4-dihydroxy-3-propylbenzophenone (2.5 g, 1.0 Eq, 9.8 mmol) was converted to the oxime with NH$_2$OH—HCl (2.7 g, 4.0 Eq, 39 mmol) and NaOAc (3.21 g, 4.0 Eq, 39 mmol) as in Example 7 Step A. The oxime was purified by elution from a silica gel column (180 g E. Merck 40–63μ) with 97:3 Toluene: EtOAc. The product oxime (1.82 g) was further treated as in Example 7 Step A with acetic anhydride (15 ml) and subsequent reflux in pyridine (15 ml). The cooled reaction mixture was poured into 2 N Hcl and EtOAc. The aqueous phase was extracted with EtOAc and washed with sat'd aq NaHCO$_3$, followed by sat'd aq NaCl. The EtOAc extracts were dried over Na$_2$SO$_4$ and reduced i. vac. The residue was taken up in refluxing toluene (50 ml). The product benzisoxazole is obtained as colorless crystals upon cooling to RT.

Characteristic NMR Resonances; $^1$H NMR 400 MHz (CDCl$_3$); 7.92–7.89 (m, 2H), 7.57 (d, 1H, J=8.5 Hz), 7.55–7.49 (m, 3H), 6.86 (d, 1H, J=8.6 Hz), 5.14 (s, 1H, phenol OH), 2.90 (dd, 2H, J=8.9, 7.6 Hz), 1.76 (sext, 2H, J=7.5 Hz), 1.01 (t, 3H, J=7.3 Hz). MS CI NH$_3$ M+1 254.1

Step 4

The hydroxy-3-phenylbenzisoxazole (50 mg, 1.0 Eq, 0.195 mmol) was dissolved in DMF (0.4 ml) with the bromide (73 mg, 1.1 Eq, 0.22 mmol) and CsCO$_3$ (62 mg, 1.0 Eq, 0.195 mmol). The suspension was stirred 3 Hrs at RT. The mixture was poured into 0.2 N HCl and EtOAc. The aqueous phase was extracted with EtOAc and the EtOAc extracts washed with sat'd aq NaCl. The extracts were dried over MgSO$_4$ and reduced i. vac. The product was purified by elution from a silica gel column (4 g E. Merck 40–63μ) with toluene:hexanes EtOAc 60:37:3.

Characteristic NMR Resonances; $^1$H NMR 400 MHz (CDCl$_3$); 7.91–7.93 (m, 2H), 7.64 (d, 2H, J=8.7 Hz), 7.51–7.53 (m, 3H), 7.30 (d, 1H, 1.8 Hz), 7.28 (d, 1H, J=8.1 Hz), 7.12 (dd, 1H), 6.96 (d, 1H, J=8.8), 4.21 (t, 2H, J=5.9 Hz), 3.68 (s, 3H), 3.54 (s, 2H), 3.17 (t, 2H, J=7.1 Hz), 2.92 (dd, 2H), 2.20 (pent, 2H), 1.72 (sext, 2H, J=7.5 Hz), 0.97 (t, 3H, J=7.3 Hz). MS ESI M+1 510.1.

Step 5

The ester (43.8 mg, 1 Eq, 0.086 mmol) was dissolved in approximately 1 ml 2:1 dioxane: H$_2$O. 1.5 M Aqueous LiOH (120 l, 2.0 Eq, 0.180 mmol) was added dropwise at RT and the mixture stirred ¾ Hr. The reaction mixture was diluted into 0.2 N HCl and EtOAc. The aqueous phase was extracted with EtOAc and the EtOAc extracts washed with sat'd aq NaCl. The extracts were dried over MgSO$_4$ and reduced i. vac. The crude acid can be purified by crystallization from methanol.

Characteristic NMR Resonances; $^1$H NMR 400 MHz (CDCl$_3$);); 7.92 (m, 2H), 7.64 (d, 1H, J=8.8 Hz), 7.52 (m, 3H), 7.3 (m, 2H), 7.13 (dd, 1H, J=1.9, 8.1 Hz), 6.96 (d, 1H, J=8.8 Hz), 4.21 (t, 2H, J=5.8 Hz), 3.58 (s, 2H), 3.18 (t, 2H, J=7.2 Hz), 2.91 (dd, 2H, J=6.5, 7.7 Hz), 2.2 (pent, 2H, J=5.8 Hz), 1.71 (sext, 2H, J=7.5 Hz), 0.97 (t, 3H, J=7.4Hz). MS ESI M+1 496.1.

EXAMPLE 17

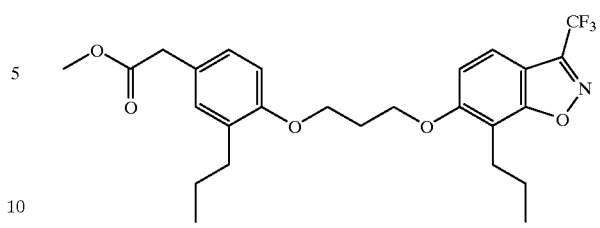

Methyl 3-propyl-4-(3-(3-trifluoromethyl-7-propyl-6-benz-[4,5]-isoxazoloxy)-propylthio)-phenylacetate Step A: Preparation of methyl 4-alloxyphenylacetate A solution of methyl 4-hydroxyphenylacetate (3.2 grams) in 2-butanone (70 mL) was treated with allyl bromide (2.0 mL) and potassium carbonate (3.5 grams). The mixture was refluxed overnight. The reaction mixture was cooled to room temperature and partitioned between isopropyl acetate and pH 4 buffer. The organic layer was separated, washed with water, dried over MgSO$_4$, and concentrated. Column Chromatography (silica gel 60, 50% methylene chloride in hexane) gave the tittle compound.

$^1$H NMR(400 MHz, CDCl$_3$): δ 7.16 (d, 2H, J=8.7 Hz), 6.85 (d, 2H, J=8.7 Hz), 6.04 (m, 1H), 5.4–5.2 (m, 2H), 4.5 (m, 2H), 3.66 (s, 3H), 3.54 (s, 2H).

Step B: Preparation of methyl 3-allyl-4-hydroxyphenylacetate

A solution of methyl 4-alloxyphenylacetate (3.1 grams) in dry ortho-dichlorobenzene (50 mL) was refluxed for 25 hours. The solvent was removed under reduced pressure, and the residue was purified by chromatography (silica gel, 50% methylene chloride in hexane) to afford the tittle compound.

$^1$H NMR(400 MHz, CDCl$_3$): δ 7.01 (m, 2H), 6.71 (d, 1H, J=7.4 Hz), 5.27 (s, 1H), 5.12 (m, 2H), 3.67 (s, 3H), 3.52 (s, 2H), 3.35 (m, 2H).

Step C: Preparation of methyl 3-propyl-4-hydroxyphenylacetate

A solution of methyl 3-propyl-4-hydroxyphenylacetate (1.71 grams) and palladium (10 wt. % on activated carbon) (0.27 grams) in ethyl acetate (30 mL) was hydrogenated at 50 PSI for 2 hours. The reaction mixture was filtered and concentrated to afford the tittle compound.

$^1$H NMR(400 MHz, CDCl$_3$): δ 6.99 (d, 1H, J=2.2 Hz), 6.95 (dd, 1H, J=8.1, 2.2 Hz), 6.67 (d, 1H, J=8.1 Hz), 4.83 (s, 1H), 3.66 (s, 3H), 3.51 (s, 2H), 2.53 (t, 2H, J=7.6 Hz), 1.61 (hex, 2H, J=7.5 Hz), 0.95 (t, 3H, J=7.3 Hz).

Step D: Preparation of methyl 3-propyl-4-(3-(3-trifluoromethyl-7-propyl-6-benz-[4,5]-isoxazoloxy)-propylthio)phenylacetate A solution of methyl 3-propyl-4-hydroxyphenylacetate (0.10 grams), 1-bromo-3-(3-trifluoromethyl-7-propyl-6-benz-[4,5]-isoxazoloxy)phenoxypropane (0.21 grams) and potassium carbonate (0.07 grams) in 2-butanone (4 mL). The mixture was refluxed overnight. The reaction mixture was cooled to room temperature and partitioned between isopropyl acetate and pH 4 buffer. The organic layer was separated, washed with water, dried over MgSO4, and concentrated. Column Chromatography (silica gel 60, 50% methylene chloride in hexane) gave the tittle compound.

$^1$H NMR(400 MHz, CDCl$_3$): δ 7.53 (d, 1H, J=8.8 Hz), 7.03 (d, 1H, J=8.9 Hz), 7.01 (m, 2H), 6.78 (d, 1H, J=8.3 Hz), 4.30 (t, 2H, J=6.1 Hz), 4.16 (t, 2H, J=6.0 Hz), 3.65 (s, 3H), 3.52 (s, 2H), 2.87 (t, 2H, J=7.5 Hz), 2.53 (t, 2H, J=7.6 Hz), 2.32 (quint, 2H, J=6.1 Hz), 1.66 (hex, 2H, J=7.6 Hz), 1.55 (hex, 2H, J=7.5 Hz), 0.91 (t, 3H, J=7.3 Hz), 0.87 (t, 3H, J=7.3 Hz).

EXAMPLE 18

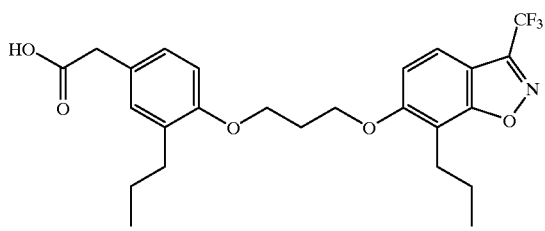

3-propyl-4-(3-(3-trifluoromethyl-7-propyl-6-benz-[4,5]-isoxazoloxy)-propylthio)phenylacetic acid A solution of methyl 3-propyl-4-(3-(3-trifluoromethyl-7-propyl-6-benz-[4,5]-isoxazoloxy)-propylthio)phenylacetate (0.08 grams) in methanol (3 mL) was treated with a solution of LiOH in water (1.0 M, 0.32 mL). The solution was refluxed for 1 hour. The solution was partitioned between isopropyl acetate and 0.2 N HCl. The organic layer was separated, washed with water, dried over MgSO4, and concentrated to afford the tittle compound.

$^1$H NMR(400 MHz, CDCl$_3$): δ 7.53 (d, 1H, J=8.8 Hz), 7.05 (d, 1H, J=8.8 Hz), 7.02 (m, 2H), 6.79 (d, 1H, J=8.3 Hz), 4.29 (t, 2H, J=6.1 Hz), 4.16 (t, 2H, J=6.0 Hz), 3.54 (s, 2H), 2.88 (t, 2H, J=7.5 Hz), 2.52 (t, 2H, J=7.6 Hz), 2.33 (quint, 2H, J=6.1 Hz), 1.67 (hex, 2H, J=7.6 Hz), 1.54 (hex, 2H, J=7.5 Hz), 0.90 (t, 3H, J=7.3 Hz), 0.86 (t, 3H, J=7.3 Hz).

EXAMPLE 19

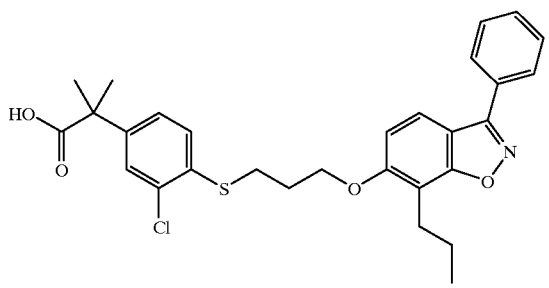

2-methyl-2-(3-chloro-4-(3-(3-phenyl-7-propylbenz[4,5]isoxazol-6-oxy)propyl)thio)phenyl propionic acid

1. 2-methyl-2-(3-chloro-4-dimethyl carbamoylthio)phenyl propionic acid methyl ester A -78° C. solution 2-(3-chloro-4-dimethylcarbamoylthio)-phenyl propionic acid methyl ester (0.378 grams; 1.25 mmol) in dry THF (2 mL) was treated with a solution of lithium bis(trimethylsilyl)amide (1.0M; 1.50 mL; 1.50 mmol). The reaction was stirred for 1 hour at -78° C., then allowed to warm to -10° C. and stirred for 30 minutes. The solution was re-cooled to -78° C. and treated dropwise with a solution of methyl iodide (0.094 mL; 1.50 mmol) in dry THF (0.5 mL). The reaction was stirred at -78° C. for 30 minutes, then warmed to -10° C. and stirred for an additional 30 minutes. The reaction mixture was partitioned between isopropyl acetate and pH 4 buffer. The layers were separated and the organic washed once with water. The organic was dried over magnesium sulfate, filtered and concentrated to an oil. Silica gel chromatography afforded 2-methyl-2-(3-chloro-4-dimethyl carbamoylthio)phenyl propionic acid methyl ester.

NMR (CDCl$_3$): 7.54 (d, 1H, J=8.2 Hz): 7.48 (d, 1H, J=2.1 Hz); 7.24 (dd, 1H, J=8.1, 2.0 Hz); 3.65 (s, 3H); 3.12 (vbs, 3H); 3.04 (vbs, 3H); 1.56 (s, 6H).

2. 2-methyl-2-(3-chloro-4-(3-bromopropyl)thio)phenyl propionic acid methyl ester A solution of 2-methyl-2-(3-chloro-4-dimethylcarbamoylthio)-phenyl propionic acid methyl ester (0.403 grams; 1.27 mmol) in dry MeOH (4 mL) was treated with a solution of sodium methoxide (4.37 M; 0.407 mL; 1.78 mmol). The reaction was refluxed for 2 hours. The reaction mixture was cooled to 20° C. and transferred to a dropping funnel. The dropping funnel was placed atop a flask containing a solution of dibromopropane (0.516 mL; 5.08 mmol) in dry MeOH (2 mL). The contents of the dropping funnel were added to the flask dropwise, and the solution stirred for 2 hours. The reaction mixture was partitioned between isopropyl acetate and pH 4 buffer. The layers were separated and the organic washed once with water. The organic was dried over magnesium sulfate, filtered and concentrated. Silica gel chromatography afforded 2-methyl-2-(3-chloro-4-(3-bromopropyl)thio) phenyl propionic acid methyl ester.

NMR (CDCl$_3$); 7.36 (d, 1H, J=2.1 Hz); 7.26 (d, 1H, J=8.3 Hz); 7.19 (dd, 1H, J=8.2, 2.0 Hz); 3.66 (s, 3H); 3.55 (t, 2H, J=6.3 Hz); 3.09 (t, 2H, J=7.0 Hz); 2.18 (pent, 2H, J=6.6 Hz).

3. 2-methyl-2-(3-chloro-4-(3-(3-phenyl-7-propyl-6-benz[4,5]isoxazole)oxypropyl)thio)phenyl propionic acid methyl ester A solution of 2-methyl-2-(3-chloro-4-(3-bromopropyl)thio)phenyl propionic acid methyl ester (0.053 grams; 0.145 mmol) in dry DMF (1 mL) was treated with 3-phenyl-6-hydroxy-7-propylbenz[4,5]isoxazole (0.044 grams; 0.174 mmol). Cesium carbonate (0.057 grams; 0.174 mmol) was added and the reaction was stirred for 7 hours. The reaction mixture was partitioned between isopropyl acetate and pH 4 buffer. The layers were separated and the organic washed twice with water. The organic was dried over magnesium sulfate, filtered and concentrated. Silica gel chromatography afforded 2-methyl-2-(3-chloro-4-(3-(3-phenyl-7-propyl-6-benz[4,5]isoxazole)oxypropyl)thio)phenyl propionic acid methyl ester.

NMR (CDCl$_3$): 7.92 (dd, 2H, J=7.8, 2.6 Hz); 7.63 (d, 1H, J=8.8 Hz); 7.55–7.48 (mult, 4H); 7.39 (d, 1H, J=2.1 Hz); 7.28 (d, 1H, J=8.4 Hz); 7.23 (dd, 1H, J=8.7, 2.1 Hz); 6.95 (d, 1H, J=8.6 Hz); 4.20 (t, 2H, J=5.7 Hz); 3.18 (t, 2H, J=7.1 Hz); 2.92 (bt, 2H, J=7.5 Hz); 0.96 (t, 3H, J=7.4 Hz).

4. 2-methyl-2-(3-chloro-4-(3-(3-phenyl-7-propylbenz[4,5]isoxazol-6-oxy)propyl)thio)phenyl propionic acid A solution of 2-methyl-2-(3-chloro-4-(3-(3-phenyl-7-propylbenz[4,5]isoxazol-6-oxy)propyl)thio)phenyl propionic acid methyl ester (0.038 grams; 0.071 mmol) in isopropanol (1 mL) was refluxed. A solution of potassium hydroxide (1.00 M; 0.212 mL; 0.212 mmol) in water was added dropwise and refluxing continued for 4 hours. The reaction mixture was partitioned between isopropyl acetate and 0.1N HCl. The layers were separated and the organic was dried over magnesium sulfate, filtered and concentrated. Trituration with cyclohexane/methylene chloride (3:1) afforded 2-methyl-2-(3-chloro-4-(3-(3-phenyl-7-propyl-6-benz[4,5]isoxazole) oxypropyl)thio)phenyl propionic acid NMR (CDCl$_3$): 7.91 (dd, 2H, J=7.8, 2.6 Hz); 7.63 (d, 1H, J=8.8 Hz); 7.53–7.47 (mult, 4H); 7.40 (d, 1H, J=2.1 Hz); 7.28 (d, 1H, J=8.4 Hz); 7.21 (dd, 1H, J=8.7, 2.1 Hz); 6.95 (d, 1H, J=8.6 Hz); 3.63 (s, 3H); 4.21 (t, 2H, J=5.7 Hz); 3.18 (t, 2H, J=7.1 Hz); 2.90 (bt, 2H, J=7.5 Hz); 0.98 (t, 3H, J=7.4 Hz).

EXAMPLE 20

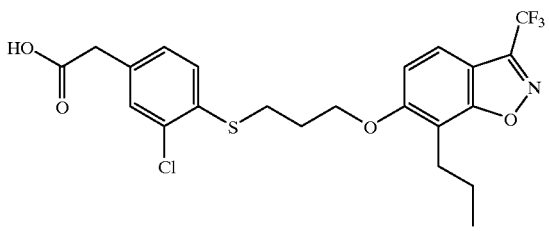

3-chloro-4-(3-(2-propyl-3-trifluoromethyl-6-benz-[4,5]-isoxazoloxy)propylthio)phenylacetic acid Step A: Preparation of 2,4-dihydroxy-3-propyltrifluoroacetophenone A solution of 2-propylresorcinol (5.0 grams) and trifluoroacetic anhydride (9.6 mL) in 1,2-dichloroethane (30.0 mL) was treated with aluminum chloride(4.38 grams). This mixture was stirred overnight. The reaction mixture was partitioned between methylene choride and water. The organic phase was dried over sodium sulfate and filtered. The solvent was evaporated and the resulting solid was recrystalized using methylene chloride and cyclohexane (1:1) to give the titled compound.

NMR (CDCl$_3$) δ 7.59 (d, 1H), 6.24 (d, 1H), 5.92 (s, 1H), 2.63 (t, 2H), 1.74 (s, 1H), 1.58 (m, 2H), 0.98 (t, 3H).

STEP B: Preparation of 3-trifluoromethyl-7-propyl-6-hydroxybenzisoxazole

A mixture of 2,4-dihydroxy-3-propyltrifluoroacetophenone(2.5 grams), sodium acetate (4.18 grams), hydroxylamine hydrochloride (3.59 grams) and methanol (80 mL) was refluxed overnight. The solvent was then evaporated and the resulting solid was partitioned in ethyl acetate and pH 7 buffer. The organic phase was seperated and washed with brine. The organic phase was dried over sodium sulfate and the solvent was evaporated to give a oil. The oil was then dissolved in acetic anhydride. The solution was stirred for two hours, then the acetic anhydride was evaporated in vacuo. The residue was partitioned between ethyl acetate and pH 7 buffer and the organic phase was dried over sodium sulfate. The organic phase was evaporated to give an oil. This was dissolved in pyridine and refluxed overnight. The solvent was evaporated in vacuo to give an oil which was chromatographed on silica gel using ethyl acetate and hexane (1:4) to give the titled compound.

NMR (CDCl$_3$) δ 7.46 (d, 1H), 6.92 (d, 1H), 5.42 (bs, 1H), 2.89 (t, 2H), 1.74 (m, 2H), 0.98 (t, 3H).

STEP C: Preparation of methyl 3-chloro-4-(3-(7-propyl-3-trifluoromethyl-6-benz-[4,5]-isoxazoloxy)propylthio) phenylacetic acid A solution of 3-trifluoromethyl-7-propyl-6-hydroxybenzisoxazole (2.5 grams) in 2-butanone (30 mL) was treated with 1,3-dibromopropane (4.8 mL) and potassium carbonate (5.0 grams). The mixture was refluxed for 4 hours. The reaction mixture was partitioned between isopropyl acetate and pH 4 buffer. The organic was washed once with water, then dried over magnesium sulfate. The organic was filtered and evaporated to an oil which was flitered through a silica gel plug using methylene chloride and hexane (1:2) to give 3-trifluoromethyl-7-propyl-6-(3-bromopropyloxy)-benzisoxazole. A solution of 3-chloro-4-dimethylcarbamoylthio-phenylacetic acid methyl ester (0.33 grams) in dry methanol (3.5 mL) was treated with a solution of sodium methoxide in methanol (25 wt %; 0.341 mL). The solution was refluxed for 2 hours. HPLC analysis showed the disappearance of the carbamate. The solution was allowed to cool to 50° C. 3-trifluoromethyl-7-propyl-6-(3-bromopropyloxy)-benzisoxazole (0.31 grams) was added and the solution stirred for 1 hour. The reaction was partitioned between isopropyl acetate and pH 4 buffer. The organic was washed once more with pH 4 buffer, then water. The organic was dried over magnesium sulfate, filtered and concentrated to an oil. The oil was applied to a silica gel column packed with hexane/methylene chloride (2:1). The column was eluted with this mobile phase until the product began to appear in the eluant. The mobile phase was switched to 100% methylene chloride and elution continued until all the product was recovered.

NMR (CDCl$_3$) δ 7.52 (d, 2H), 7.30 (d, 1H), 7.27 (d, 1H), 7.12 (d, 1H), 7.08 (d, 1H), 4.21 (t, 2H), 3.68 (s, 3H), 3.54 (s, 2H), 3.15 (t, 2H), 2.89 (t, 2H), 2.19 (m, 2H), 1.68 (m, 2H), 0.94 (t, 3H).

Step D: Preparation of 3-chloro-4-(3-(2-propyl-3-trifluoromethyl-6-benz-[4,5]-isoxazoloxy)propylthio) phenylacetic acid A solution of methyl 3-chloro-4-(3-(2-propyl-3-trifluoromethyl-6-benz-[4,5]-isoxazoloxy)propylthio) phenylacetic acid (0.113 grams) in methanol (1.5 mL) was treated with a solution of lithium hydroxide in water (1.01 M; 0.362 mL). The reaction was refluxed 1 hour. The reaction mixture was partitioned between isopropyl acetate and 0.1N HCl. The organic was dried over magnesium sulfate, filtered and concentrated to a solid. The solid was suspended in methylene chloride/cyclohexane (1:1; 2 mL). The mixture was refluxed briefly and cooled to 0° C. The title compound was isolated by filtration.

NMR (CDCl$_3$) δ 7.53(d, 2H), 7.31 (d, 1H), 7.27 (d, 1H), 7.12 (d, 1H), 7.02 (d, 1H), 4.21 (t, 2H), 3.57 (s, 2H), 3.16 (t, 2H), 2.89 (t, 2H), 2.19 (m, 2H), 1.67 (m, 2H), 0.93 (t, 3H). ESI-MS: m/e=488 (m+1).

EXAMPLE 21

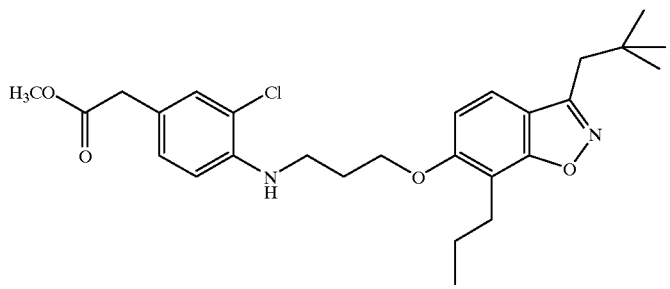

Methyl 3-chloro-4-(3-(3-(2,2-dimethylpropyl)-7-propyl-6-benz-[4,5]-isoxazoloxy)-propylamino)phenylacetate Step A: Preparation of 3-chloro-4-acetamidophenylacetic acid Acetic anhydride (152 mL, 1.6 moles) was added dropwise to a rapidly stirring mixture of 4-aminophenylacetic acid (195 grams, 1.3 moles) in acetic acid (600 mL) and water (250 mL) at room temperature. After a slight exotherm, the dark brown solution was stirred for one hour at room temperature. The solution was diluted with ethanol (500 mL) and water (250 mL), and a suspension of Calcium hypochlorite (340 grams, 2.3 moles) in water (1 L plus 500 mL rinse) was added portionwise. The temperature rose to 50° C. and the mixture was stirred for 16 hours at room temperature. The mixture was poured into ice-water (8 L) and extracted with ethyl acetate (3×2 L). The combined extracts were washed with saturated brine, dried over magnesium sulfate and concentrated in vacuo to a small volume. Hexane was added and the resulting precipitate filtered, washed with hexane and dried to give the title compound (180 grams) as a brown solid NMR (CDCl$_3$+10% CD$_3$OD): δ 2.12 (s, 3H); 3.45 (s, 2H); 7.10 (dd, 2H)); 8.02 (dd, 1H).

Step B: Preparation of methyl 3-chloro-4-aminophenylacetate.HCl

A solution of 3-chloro-4-acetamidophenylacetic acid (180 grams, 0.79 moles) in methanol (2 L), was treated with concentrated HCl (200 mL) and the resulting solution refluxed for 6 hours and then stirred at room temperature for 16 hours. The mixture was concentrated in vacuo to about one-half its volume and ether (4 L) was added. The resulting precipitate was filtered, washed with ether and dried to give the title compound (173 grams) as a tan solid NMR, (CD$_3$OD): δ 3.70 (s, 2H); 3.73 (s, 3H); 7.35 (d, 1H); 7.43 (d, 1H); 7.56 (s, 1H).

Step C: Preparation of methyl 3-chloro-4-(3-bromopropylamino)phenylacetate

Magnesium oxide (10 grams, 250 mmoles), was added to a solution of 1,3-dibromopropane (139 grams, 70 mL, 700 mmoles) in dimethylacetamide (150 mL). A solution of methyl 3-chloro-4-aminophenylacetate.HCl (23.6 grams, 100 mmoles) in dimethylacetmide (200 mL) was added dropwise over 30 minutes and the mixture stirred at 80° C. for 6 hours. The cooled mixture was partitioned with methylene chloride and water. The aqueous phase was extracted with methylene choride and the combined organic phases washed with brine, dried over magnesium sulfate and concentrated in vacuo to an oil. The crude product was chromatographed on a silica gel column eluting with hexane-:ethyl acetate (9:1). The product was further purified by a second silica gel chromatography in methylene chloride-:hexane (2:3) to give the title compound as an oil. NMR, (CDCl$_3$): δ 2.15 (qnt, 2H); 3.35 (q, 2H); 3.47 (s,2H); 3.49 (t, 2H); 3.67 (s, 3H); 6.63 (d, 1H); 7.03 (dd, 1H); 7.17 (d, 1H).

Step D: Preparation of 3-chloro-4-(3-(3-(2,2-dimethylpropyl)-7-propyl-6-benz-[4,5]-isoxazoloxy)-propylamino)-phenylacetate A solution of methyl 3-chloro-4-(3-bromopropylamino)-phenylacetate (4.55grams, 14.19 mmoles) and 3-(2,2-dimethylpropyl)-6-hydroxy-7-propylbenz-[4,5]-isoxazole (3.51 grams, 14.19 mmoles) in 2-butanone (50 mL) was treated with potassium carbonate (2.35 grams, 17.0 mmoles). The mixture was refluxed for 8 hours, stirred at room temperature for 16 hours and filtered. Evaporation in vacuo followed by flash chromatography on silica gel in hexane:ethyl acetate (9:1) afforded the title compound as a white solid. NMR, (CD$_3$OD): δ 0.94 (t, 3H); 1.04 (s, 9H); 1.70 (m, 2H); 2.15 (m, 2H); 2.83 (s, 2H); 2.90 (t, 2H); 3.45 (t, 2H); 3.48 (s, 2H); 3.66 (s, 3H); 4.22 (t, 2H); 6.71 (d, 1H); 6.99 (d, 1H); 7.07 (d, 1H); 7.15 (d, 1H); 7.52 (d, 1H).

EXAMPLE 22

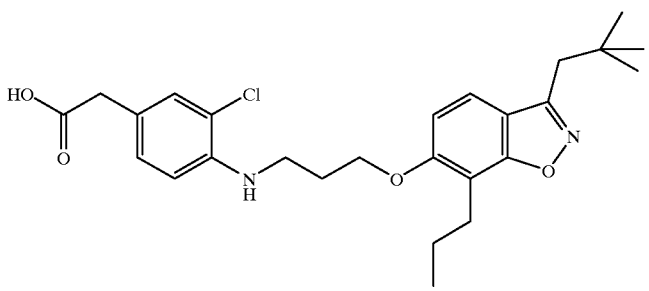

3-Chloro-4-(3-(3-(2,2-dimethylpropyl)-7-propyl-6-benz-[4,5]-isoxazoloxy)-propylamino)phenylacetic acid To a solution of methyl 3-chloro-4-(3-(3-(2,2-dimethylpropyl)-7-propyl-6-benz-[4,5]-isoxazoloxy)-propylamino)phenylacetate (4.24 grams, 8.71 mmoles) in methanol (90 mL) was added a solution of lithium hydroxide (1M, 17.42 mL, 17.42 mmoles), and the resulting mixture stirred at 60° C. for 2.5 hours. The solution was evaporated in vacuo and the residue diluted with water and ethyl acetate. The pH was brought to 5.0 with 1M hydrochloric acid and organic phase separated. The aqueous phase was extracted 3 times with ethyl acetate and the combined organic extracts dried over magnesium sulfate and evaporated in vacuo to give the title compound as a white crystalline solid.(mp= 115–116° C.; Mass spec=473, 475, calc=473) NMR, ($CD_3OD$); δ 0.96 (t, 3H); 1.03 (s, 9H); 1.71 (m, 2H); 2.15 (m, 2H); 2.83 (s, 2H); 2.90 (t 2H); 3.44 (s, 2H); 3.45 (t, 2H); 4.22 (t, 2H); 6.72 (d, 1H); 7.01 (d, 1H); 7.03 (d, 1H); 7.07 (d, 1H); 7.16 (d, 1H); 7.50 (d, 1H).

EXAMPLE 23

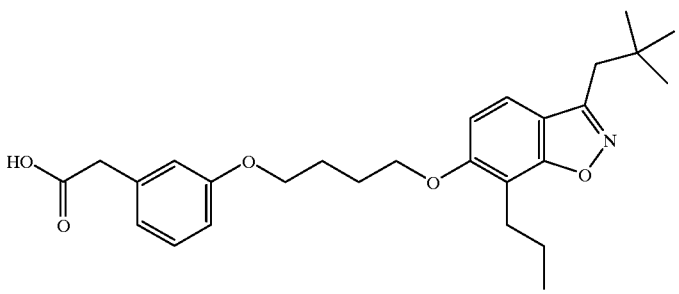

3-(4-(3-(2,2-dimethylpropyl)-7-propyl-6-benz-[4,5]-isoxazoloxy)-butoxy)phenylacetic acid Step 1A A solution of 2,4-dihydroxy-3-propylphenyl ethyl ketone (25.545 grams) in 2-butanone (300 mL) was treated with 1,3-dibromopropane (48.79 mL) and potassium carbonate (50.859 grams). The mixture was refluxed for 4 hours. The reaction mixture was partitioned between isopropyl acetate and pH 4 buffer. The organic was washed once with water, then dried over magnesium sulfate. The organic was filtered and evaporated to an oil which was chromatographed over silica gel with hexane/methylene chloride (2:1) to afford the title compound.

Step 1

The ester was obtained from the Fischer esterification of the commercially available acid in methanol. The 3-hydroxyphenylacetic acid (25 g) was dissolved in methanol (100 ml) with approximately 0.4 ml $H_2SO_4$ conc. The mixture was heated 16 Hrs under reflux. The mixture was cooled and reduced i. vac. The residue was taken up in ethyl acetate and washed with sat'd aq $NaHCO_3$, followed by sat'd aq NaCl. The EtOAc extracts were dried over $MgSO_4$ and reduced i. vac. The ester was used without further purification. Characteristic NMR Resonances; $^1H$ NMR 400 MHz ($CDCl_3$); 7.15 (t, 1H, J=7.7 Hz), 6.80 (t, 1H, J=8.1 Hz), 6.75 (brd s, 1H), 6.72 (dd, 1H, J=2.6, 8.1 Hz), 3.68 (s, 3H), 3.56 (s, 2H).

Step 2

The ester (4.0 g, 1 Eq, 0.024 mol) was dissolved in DMF (30 ml) with 1,4-dibromobutane (14.4 ml, 5 Eq, 0.121 mol) and $CsCO_3$ (8.3 g, 1.05 Eq, 0.025 mol). The suspension was stirred 1.5 Hrs at RT. The mixture was poured into 0.2 N HCl and EtOAc. The aqueous phase was extracted with EtOAc and the EtOAc extracts washed three times with water, followed by sat'd aq NaCl. The extracts were dried over $MgSO_4$ and reduced i. vac. The product was purified by elution from a silica gel column (150 g E. Merck 40–63μ) with 9:1 Hexanes: EtOAc. The bromide is obtained as an oil.

Characteristic NMR Resonances; $^1H$ NMR 400 MHz ($CDCl_3$); 7.21 (t, 1H, J=7.9 Hz), 6.86–6.76 (m, 3H), 3.97 (t, 2H, J=6.0 Hz), 3.67 (s, 3H), 3.58 (s, 2H), 3.47 (t, 2H, J=6.6 Hz), 2.02–2.09 (complex m, 2H), 1.89–1.96 (complex m, 2H).

Step 3

The hydroxybenzisoxazole (41 mg, 1.0 Eq, 0.165 mmol) was dissolved in DMF (0.5 ml) with the bromide (52 mg, 1.05 Eq, 0.174 mmol) and $CsCO_3$ (59 mg, 1.1 Eq, 0.182 mmol). The suspension was stirred 16 Hrs at RT. The mixture was poured into 0.2 N HCl and EtOAc. The aqueous phase was extracted with EtOAc and the EtOAc extracts washed with sat'd aq NaCl. The extracts were dried over $Na_2SO_4$ and reduced i. vac. The product was purified by elution from a silica gel column (10 g E. Merck 40–63μ) with 98:2 toluene EtOAc. The product is obtained as an oil.

Characteristic NMR Resonances; $^1H$ NMR 400 MHz ($CDCl_3$); 7.34 (d, 1H, J=8.7 Hz), 7.21 (t, 1H, J=7.9 Hz), 6.88 (d, 1H, J=8.7 Hz), 6.85–6.78 (m, 3H), 4.11 (t, 2H, J=5.7 Hz), 4.03 (t, 2H, J=5.7 Hz), 3.67 (s, 3H), 3.57 (s, 2H), 2.86 (dd, 2H, J=8.9, 7.5 Hz), 2.79 (s, 2H), 1.99 (m, 4H), 1.69 (sext, 2H, J=7.5 Hz), 1.03 (s, 9H), 0.95 (t, 3H, J=7.4 Hz). MS ESI $CH_3CN/NH_4CO_2$ aq. M+1 468.5.

Step 4

The ester (60 mg, 1 Eq, 0.13 mmol) was dissolved in approximately 3 ml 2:1 dioxane: $H_2O$. 1.5 M Aqueous LiOH (170 ml, 2.0 Eq, 0.25 mmol) was added dropwise at RT and the mixture stirred 1 Hr. The reaction mixture was diluted into 0.2 N HCl and EtOAc. The aqueous phase was extracted with EtOAc and the EtOAc extracts washed with sat'd aq NaCl. The extracts were dried over $Na_2SO_4$ and reduced i. vac. The product is obtained as an oil.

Characteristic NMR Resonances; $^1H$ NMR 400 MHz ($CDCl_3$); 7.34 (d, 1H, J=8.6 Hz), 7.24 (t, 1H, J=7.7 Hz), 6.88 (d, 1H, J=8.7 Hz), 6.85–6.79 (m, 3H), 4.10 (t, 2H, J=5.7 Hz), 4.03 (t, 2H, J=5.7 Hz), 3.59 (s, 2H), 2.85 (dd, 2H, J=8.9, 7.5 Hz), 2.79 (s, 2H), 1.99 (m, 4H), 1.67 (sext, 2H, J=7.5), 0.94 (t, 3H, J=7.4 Hz). MS ESI $CH_3CN/NH_4CO_2$ aq. M+1 454.5.

EXAMPLE 24

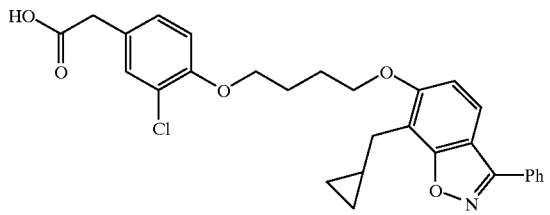

3-chloro-4-(3-(3-phenyl-7-cyclopropylmethyl-6-benz-[4,5]-isoxazoloxy)-butyloxy)phenylacetic acid Step A: Preparation of 7-cyclopropylmethyl-3-phenyl-6-hydroxybenz-[4,5]-isoxazole A solution of 2,4-dihydrobezophenone (2.14 grams) in DMF (20 mL) was treated with potassium carbonate (1.45 grams). This mixture was heated to 40° C. and stirred for 0.5 hours. To this mixture was added allyl bromide (3.6 grams), then the reaction was stirred overnight. The mixture was diluted with ethyl acetate and washed with 1 M HCl solution and brine. The organic phase was dried over sodium sulfate and filtered. The solvent was removed in vacuo and the resulting oil was filtered through a plug of silica gel using methylene chloride and hexane (1:2) to give 4-allyloxy-2-hydroxybenzophenone. This was then dissolved in 1,2-dichlorobenzene and refluxed for 24 hours. The solvent was evaporated in vacuo and the resulting oil was filtered through a plug of silica gel using methylene chloride and hexane (1:1) to give 3-allyl-2,4-dihydrobezophenone. 3-allyl-2,4-dihydrobezophenone (1.0 grams) was dissolved in methanol (20 mL) and treated with hydroxylamine hydrochloride (1.35 grams) and sodium acetate (1.6 grams) and refluxed overnight. The solvent was evaporated in vacuo and the resulting solid was partitioned in ethyl acetate and pH 7 buffer. The organic phase was dried over sodium sulfate and filtered. The solvent was removed to give a solid. This was stirred in acetic anhydride for 2 hours and then the solvent was remove in vacuo to give an oil. The oil was dissolved in pyridine and refluxed overnight. The solvent was evaporated in vacuo and the residue was filtered through a pad of siliga gel using methylene chloride and hexane (1:1) to give 7-allyl-3-phenyl-6-hydroxybenz-[4,5]-isoxazole. To a solution of 7-allyl-3-phenyl-6-hydroxybenz-[4,5]-isoxazole (0.5 grams) in 2 mL of ethyl ether was added diazomethane (15 mL of a 0.70M soln. in $Et_2O$) under nitrogen followed by the addition of palladium acetate (cat., 2 mg). The reaction mixture was stirred at ambient temperature for 30 min until gas evolution had ceased. The ether was evaporated in vacuo, and the residue was purified on a silica gel flash chromatography column eluted with 10% EtOAc:hexane. Evaporation of the purified fractions and solvent removal in vacuo afforded the product.

NMR ($CDCl_3$) δ 7.91 (d, 2H), 7.58 (d, 1H), 7.53 (m, 3H), 6.89 (d, 1H), 5.64 (s, 1H), 2.91 (d, 2H), 1.24 (m, 1H), 0.54 (m, 2H), 0.37 (d, 2H).

STEP B: Preparation of 3-chloro-4-(3-(3-phenyl-7-cyclopropylmethyl-6-benz-[4,5]-isoxazoloxy)-butyloxy) phenylacetic acid A solution of 7-cyclopropylmethyl-3-phenyl-6-hydroxybenz-[4,5]-isoxazole (0.25 grams) in 2-butanone (3.0 mL) was treated with 1,3-dibromopropane (0.48 mL) and potassium carbonate (0.50 grams). The mixture was refluxed for 4 hours. The reaction mixture was partitioned between isopropyl acetate and pH 4 buffer. The organic was washed once with water, then dried over magnesium sulfate. The organic was filtered and evaporated to an oil which was flitered through a silica gel plug using methylene chloride and hexane (1:2) to give 7-cyclopropylmethyl-3-phenyl-6-(3-bromopropyloxy)benz-[4,5]-isoxazole. A solution of 3-chloro-4-hydroxyphenylacetic acid methyl ester (42.0 mg) in DMF (1.0 mL) was treated with potassium carbonate (26 mg) and this mixture was stirred for 0.5 hours. Then 7-cyclopropylmethyl-3-phenyl-6-(3-bromopropyloxy)benz-[4,5]-isoxazole was added and the mixture was stirred over night. The reaction mixture was partitioned between ethyl acetate and 1 M HCl solution. The organic was dried over sodium sulfate and filtered. The solvent was removed in vacuo and the residue was chromatographed on silica gel using methlene chloride and hexane (1:1) to give an oil. A solution of methyl 3-chloro-4-(3-(3-phenyl-7-cyclopropylmethyl-6-benz-[4,5]-isoxazoloxy)-butyloxy) phenylacetic acid (0.04 grams) in methanol (1.5 mL) was treated with a solution of lithium hydroxide in water (1.01 M; 0.1 mL). The reaction was refluxed 1 hour. The reaction mixture was partitioned between isopropyl acetate and 0.1N HCl. The organic was dried over magnesium sulfate, filtered and concentrated to a solid. The solid was suspended in methylene chloride/cyclohexane (1:1; 2 mL). The mixture was refluxed briefly and cooled to 0° C. The title compound was isolated by filtration.

NMR ($CDCl_3$) δ 7.93(d, 2H), 7.65 (d, 1H), 7.53 (m, 3H), 7.28 (s, 1H), 7.01 (d, 1H), 6.98 (d,1H), 6.87 (d, 1H), 4.18 (t, 2H), 4.08 (t, 2H), 3.55 (s, 2H), 2.88 (d, 2H), 2.08 (m, 4H), 0.41 (m, 2H), 0.30 (m, 2H). ESI-MS: m/e=506 (m+1).

EXAMPLE 25

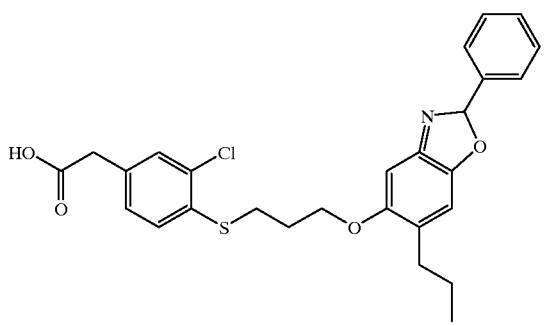

3-chloro-4-(3-(2-phenyl-6-propyl-5-benz-[4,7]-oxazoloxy)
propylthio)phenylacetic acid Step A: Preparation of 1-propenyloxy-4-benzyloxy benzene:
5.0 grams (25.0 mmole, 1.0 eq.) of 4-benzyloxyphenol was dissolved in 100 ml of N,N-dimethylformamide. 10.4 grams (75.0 mmole, 3.0 eq.) of potassium carbonate and 3.25 ml (37.5 mmole, 1.5 eq.) of allyl bromide were added to the reaction and it was stirred at 80° C. for 3 hours and at room temperature for another 136 hours. The reaction mixture was diluted with water and extracted 3× with 60 ml of ethyl acetate. The combined organics were dried over sodium sulfate, filtered, evaporated and pumped on high vacuum overnight. The title compound (4.3 grams, 72% yield) was isolated by recrystallization from methanol.
NMR (400 MHz, CDCl$_3$) δ 7.36 (m, 5H), 6.88 (m, 4H), 6.04 (m, 1H), 5.39 (d, 1H), 5.24 (d, 1H), 5.01 (s, 2H), 4.44 (d, 2H).

Step B: Preparation of 2-propenyl-4-benzyloxyphenol:
7.5 grams (31.3 mmole, 1.0 eq.) of product from step A was dissolved in 35 ml of 1,2-dichloroethane and heated to reflux for 24 hours. The reaction mixture was directly chromatographed after cooling to give 6.8 grams (91% yield) of the title compound.
NMR (300 MHz, CDCl$_3$) δ 7.36 (m, 5H), 6.77 (d, 1H), 6.74 (m, 2H), 6.00 (m, 1H), 5.18 (dm, 2H), 4.99 (s, 2H), 4.58 (s, 1H), 3.39 (dd, 2H).

Step C Preparation of 2-propylhydroquinone:
6.8 grams (28.4 mmole, 1.0 eq.) of product from step B was dissolved in 60 ml of methanol. 680 mg of 10% palladium on carbon (0.64 mmole, 0.023 eq.) was added and the stirring suspension was evacuated and charged with hydrogen. After 16 hours the catalyst was filtered over celite and the filtrate evaporated. The title compound (4.3 grams) was recovered by recrystallization from dichloromethane/hexanes.
NMR (400 MHz, CD$_3$OD) δ 6.56 (d, 1H), 6.51 (d, 1H), 6.43 (dd, 1H), 2.48 (t, 2H), 1.58 (m, 2H), 0.96 (t, 3H).

Step D: Preparation of 1,4-dimethoxy-2-propyl benzene:
1.0 gram (6.6 mmole, 1.0 eq.) of product from step C was dissloved in 30 ml of freshly distilled THF. The solution was cooled to 0° C. and 0.65 gram of 61% sodium hydride (16.5 mmole, 2.5 eq) and 1.25 ml (20.1 mmole, 3.0 eq.) of iodomethane were added. The reaction was stirred at 0° C. for 16 hours under nitrogen atmosphere. The reaction was quenched with saturated aqueous ammonium chloride and extracted 3× with dichloromethane. The organic was dried over sodium sulfate, filtered and evaporated. The recovered crude material was chromatographed to give 0.96 gram of the title compound as a clear liquid.
NMR (400 MHz, CDCl$_3$) δ 6.74 (d, 1H), 6.71 (d, 1H), 6.66 (dd, 1H), 3.76 (s, 3H), 3.74 (s, 3H), 2.55 (t, 2H), 1.60 (m, 2H), 0.96 (t, 3H).

Step E: Preparation of 2,5-dimethoxy-4-propyl benzophenone:
0.254 gram (1.4 mmole, 1.0 eq.) of product from step D was dissolved in 7 ml of 1,2-dichloroethane, after which 0.20 ml of benzoyl chloride and 0.225 gram aluminum (III) chloride (1.7 mmole, 1.2 eq. each) were added. Stirred at room temperature under nitrogen atmosphere for 75 minutes, then quenched with aqueous potassium carbonate. Diluted further with water and extracted 3× with dichloromethane. The combined organics were dried over sodium sulfate, filtered and evaporated. The resulting crude material was chromatographed to give 0.38 gram (95% yield) of the title compound.
NMR (400 MHz, CDCl$_3$) δ 7.80 (dd, 2H), 7.53 (dt, 1H), 7.42 (t, 2H), 6.88 (s, 1H), 6.78 (s, 1H), 3.77 (s, 3H), 3.62 (s, 3H), 2.62 (t, 2H), 1.64 (m, 2H), 0.97 (t, 3H).

Step F: Preparation of 2,5-dihydroxy-4-propyl benzophenone:
0.37 gram (1.3 mmole, 1.0 eq.) of product from step E was dissolved in 5 ml of dichloromethane. The solution was stirred under nitrogen atmosphere at −78° C. and 3.2 ml of 1.0 M boron tribromide solution in hexanes (3.2 mmole, 2.5 eq.) was added dropwise over a 5–8 minute span. The reaction was allowed to slowly warm, and after 3 hours ice was added to the reaction mixture. After an additional 30 minutes some water was added and the mixture was diluted with dichloromethane. The layers were separated and the organic was washed twice more with water, dried over sodium sulfate, filtered and evaporated to give the title compound (0.33 gram, 100% yield) without further purification.
NMR (400 MHz, CDCl$_3$) δ 11.65 (s, 1H), 7.65 (dd, 2H), 7.55 (dt, 1H), 7.46 (t, 2H), 6.92 (s, 1H), 6.84 (s, 1H), 4.34 (s, 1H), 2.59 (t, 2H), 1.67 (m, 2H), 0.98 (t, 3H).

Step G: Preparation of 2,5-dihydroxy-4-propyl benzoxime:
0.22 gram (0.88 mmole, 1.0 eq.) of product from step F was dissolved in 2.5 ml of 100% ethanol. 0.61 gram of hydroxylamine hydrochloride and 0.72 gram of sodium acetate (8.8 mmole, 10 eq. each) were then added and the reaction was heated to reflux under nitrogen atmosphere for 16 hours. The reaction was cooled to room temperature and diluted with water and ethyl acetate. The layers were separated and the organic layer was washed twice more with water, then dried over sodium sulfate, filtered and evaporated to give 0.23 gram (97% yield) of the title compound without further purification.
NMR (400 MHz, CDCl$_3$) δ 7.40 (m, 5H), 6.88 (s, 0.25H), 6.78 (s, 0.75H), 6.37 (s, 0.25H), 6.19 (s, 0.75H), 2.58 (t, 0.5H), 2.50 (t, 1.5H), 1.62 (m, 2H), 0.99 (t, 0.75H), 0.98 (t, 2.25H).

Step H: Preparation of 2-phenyl-5-hydroxy-6-propyl benz-[4,7]-oxazole:
0.23 gram (0.83 mmole, 1.0 eq.) of product from step G was dissolved in 0.75 ml of acetonitrile and 0.25 ml of N,N-dimethylacetamide. Under a nitrogen atmosphere 0.085 ml (0.91 mmole, 1.1 eq.) of phosphorus oxychloride was added and the reaction stirred for 30 minutes. Water and ethyl acetate were added, as was solid sodium acetate (ca. 0.3 gram). The layers were separated and the organic was washed with saturated aqueous sodium chloride solution, then dried over sodium sulfate, filtered and evaporated. The crude was purified by column chromatography to give 0.12 gram (57% yield) of the title compound. Structure confirmed by NMR, MS, and NOE difference spectroscopy.
NMR (500 MHz, DMSO-d6) δ 9.39 (s, 1H), 8.11 (m, 2H), 7.56 (m, 3H), 7.42 (s, 1H), 7.10 (s, 1H), 2.62 (t, 2H), 1.61 (m, 2H), 0.91 (t, 3H). MS[ESI]: m/e 254.1 (M+1).

Step 1: Preparation of methyl 3-chloro-4-(3-bromopropylthio) phenyl acetate:

10.0 grams (34.7 mmole, 1.0 eq.) of 3-chloro-4-dimethylcarbamoylthio-phenylacetic acid methyl ester was dissolved in 15 ml anhydrous methanol, then 8.3 ml of 25% w/w (38.2 mmole, 1.1 eq.) sodium methoxide in methanol was added and the reaction heated to reflux for one hour. In a separate flask, 14.1 ml (139 mmole, 4.0 eq.) of 1,3-dibromopropane was dissolved in 15 ml of anhydrous methanol, which was then cooled by an ice bath. The sodium thiolate solution was cooled to room temperature, then added dropwise via cannula to the stirring dibromopropane. After 30 minutes at 0° C. and one hour at room temperature, the reaction was quenched by adding saturated aqueous ammonium chloride followed by water. The aqueous was extracted twice with ethyl acetate. The combined organics were washed with water (2x) and saturated sodium chloride (1x). The organic layer was dried over sodium sulfate, filtered and evaporated. The recovered crude material was purified by silica gel chromatography to give 8.1 gram (71% yield) of the title compound.

NMR (500 MHz, CDCl$_3$) δ 7.34 (d, 1H), 7.30 (d, 1H), 7.17 (dd, 1H), 3.72 (s, 3H), 3.59 (s, 2H), 3.57 (t, 2H), 3.10 (t, 2H), 2.20 (quint, 2H).

Step J: Preparation of methyl 3-chloro-4-(3-(2-phenyl-6-propyl-5-benz-[4,7]-oxazoloxy) propylthio) phenyl acetate:

20.0 mg of product from step H (79 μmole, 1.0 eq.) was dissolved in 0.75 ml of N,N-dimethylformamide. 27.0 mg of cesium carbonate (83 μmole, 1.05 eq.) and 26.7 mg (79 μmole, 1.0 eq.) of product from step I were then added, and the reaction stirred at 65° C. for 2 hours. The reaction mixture was diluted with water, acidified with dilute aqueous HCl and extracted with ethyl acetate. The organic was dried over sodium sulfate, filtered and evaporated, then purified by silica gel chromatography to give 26.5 mg (66% yield) of the title compound.

NMR (500 MHz, CDCl$_3$) δ 8.23 (m, 2H), 7.52 (m, 3H), 7.37–7.30 (m, 3H), 7.20 (s, 1H), 7.15 (dd, 1H), 4.34 (t, 2H), 3.72 (s, 3H), 3.58 (s, 2H), 3.21 (t, 2H), 2.74 (t, 2H), 2.23 (m, 2H), 1.70 (m, 2H), 1.00 (t, 3H).

Step K: Preparation of 3-chloro-4-(3-(2-phenyl-6-propyl-5-benz-[4,7]-oxazoloxy)propylthio) phenylacetic acid:

24.6 mg (48.2 μmole, 1.0 eq.) of the product from step J was dissolved in 0.6 ml of a 1:1 mixture of tetrahydrfuran and methanol. Then 0.35 ml of 0.25N lithium hydroxide (87.5 μmole, 1.8 eq.) was added and the reaction stirred for 16 hours. Then the reaction was heated to 80° C. for 20 minutes, but this failed to push the reaction to completion. The reaction mixture was diluted with water, acidified with dilute HCl, and extracted with ethyl acetate. The organic was dried over sodium sulfate, filtered and evaporated. The recovered crude was purified by silica gel chromatography that utilized an acetic acid modified mobile phase, giving 16.4 mg (69% yield) of the title compound.

NMR (500 MHz, CDCl$_3$) δ 8.24 (m, 2H), 7.54 (m, 3H), 7.46 (d, 1H), 7.42 (d, 1H), 7.33 (s, 1H), 7.24 (dd, 1H), 6.81 (s, 1H), 3.85 (t, 2H), 3.64 (s, 2H), 3.23 (t, 2H), 2.70 (t, 2H), 2.29 (m, 2H), 1.66 (m, 2H), 0.97 (t, 3H). MS[ESI]: m/e 496.2 (M+1).

EXAMPLE 26

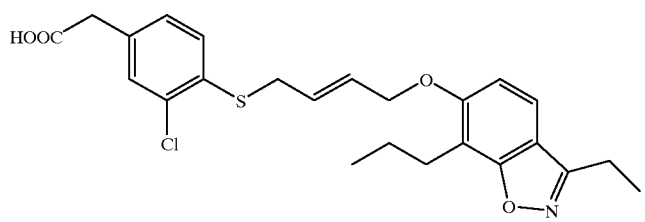

3-chloro-4-(3-(3-ethyl-7-propyl-6-benz-[4,5]-isoxazoloxy)-but-2-en-thio)phenylacetic acid STEP A: Preperation of 1-bromo-4-(3-ethyl-7-propyl-6-benz-[4,5]-isoxazoloxy)but-2-ene Using the method found in example 1 step A, substituting 2-hydroxy-3-ethyl-7-propyl-6-benz-[4,5]-isoxazoloxy as the starting material and substituting 1,4-dibromobut-2-ene in place of 1,3-dibromopropane, the titled compound was obtained. This compound purified by filtering it through a plug of silica gel, using 100% hexane and then 20% ethyl acetate/hexane to remove the excess 1,4-dibromobut-2-ene.

NMR (CDCl$_3$) δ 7.37 (d, 1H, J=8.7 Hz); 6.85 (d, 1H, J=8.7 Hz); 6.03 (m, 2H); 4.63 (d, 2H, J=5.78 Hz); 3.99 (d, 2H, J=7.2 Hz); 2.93 (q, 2H, J=7.65 Hz); 2.86 (t, 2H, J=6.27 Hz); 1.67 (m, 2H); 1.40 (t, 3H, J=7.61 Hz); 0.948 (t, 3H, J=7.4 Hz).

STEP B: Preparation of Methyl 3-chloro-4-(4-(3-ethyl-7-propyl-6-benz-[4,5]-isoxazoloxy)-but-2-en-thio) phenylacetate Using the method in example 1 step B, substituting 1-bromo-4-(3-ethyl-7-propyl-6-benz-[4,5]-isoxazoloxy)but-2-ene as the starting material, the titled compound was obtained. This compound was taken forward without further purification.

STEP C: Preparation of 3-chloro-4-(4-(3-ethyl-7-propyl-6-benz-[4,5]-isoxazoloxy)-but-2-en-thio)phenylacetic acid Using the method in example 2 step A (19632PV2), substituting Methyl 3-chloro-4-(4-(3-ethyl-7-propyl-6-benz-[4,5]-isoxazoloxy)-but-2-en-thio)phenylacetate as the starting material, the titled compound was obtained.

NMR (CDCl$_3$) δ 7.33 (d, 1H, J=8.63 Hz); 7.29 (s, 1H); 7.20 (d, 1H, J=8.13); 7.06 (d, 1H, J=8.09 Hz); 6.80 (d, 1H, J=8.63 Hz); 5.87 (m, 2H); 4.55 (d, 2H, J=4.4 Hz); 3.60 (d, 2H, J=5.62 Hz); 3.56 (s, 2H); 2.93 (q, 2H, J=7.6 Hz); 2.81 (t, 2H, J=7.4 Hz); 1.64 (m, 2H, J=7.49 Hz); 1.41 (t, 3H, J=7.61 Hz); 0.91 (t, 3H, J=7.41 Hz). ESI: Mass spec: m/e=460 (M+1).

EXAMPLE 27

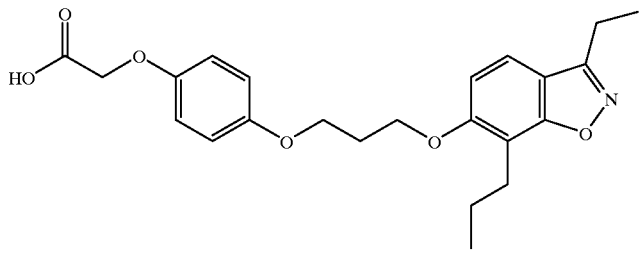

4-(3-(3-ethyl-7-propyl-6-benz[4,5]isoxazole)oxy)propyloxy phenoxy acetic acid

1. Methyl p-Hydroxyphenoxy acetate

A solution of p-hydroxyphenyl acetic acid (4.602 grams; 27.368 mmol) in dry methanol (80 mL) was treated with con. $H_2SO_4$ (0.50 mL). The solution was stirred at 55° C. for 2 hours. The reaction was partitioned between isopropyl acetate and aqueous sodium bicarbonate solution. The organic was dried over magnesium sulfate, filtered and evaporated to afford the title compound as a solid.

NMR (acetone): 6.75 (apparent quart, 4H, J=9.5 Hz); 4.60 (s, 2H); 3.71 (s, 3H).

2. Methyl 4-(3-(3-ethyl-7-propyl-6-benz[4,5]isoxazole)oxy) propyloxy phenoxy acetate A solution of methyl p-hydroxyphenoxy acetate (0.530 grams; 2.909 mmol) in dry methyl ethyl ketone (6 mL) was treated with 3-ethyl-6-(3-bromopropyl)oxy-7-propylbenz[4,5]isoxazole (0.790 grams; 2.424 mmol) and potassium carbonate (0.422 grams; 3.055 mmol). The mixture was refluxed for 12 hours. The reaction mixture was cooled to ambient and partitioned between isopropyl acetate and pH 4 buffer. The organic was washed with water, then dried over magnesium sulfate, filtered and evaporated in vacuo to an oil. Silica gel chromatograhy afforded the title compound.

NMR (CDCl$_3$): 7.38 (d, 1H, J=8.6 Hz); 6.90 (d, 1H, J=8.5 Hz); 6.83 (apparent s, 4H); 4.57 (s, 2H); 4.21 (t, 2H, J=5.9 Hz); 4.12 (t, 2H, J=5.8 Hz); 3.78 (s, 3H); 2.94 (quart, 2H, J=7.4 Hz); 2.84 (bt, 2H, J=7.9 Hz).

3. 4-(3-(3-ethyl-7-propyl-6-benz[4,5]isoxazole)oxy) propyloxy phenoxy acetic acid A solution of methyl 4-(3-(3-ethyl-7-propyl-6-benz[4,5]isoxazole) oxy)propyloxy phenoxy acetate (0.358 grams; 0.837 mmol) in methanol (4 mL) was treated with a solution of LiOH in water (1.299 M; 0.770 mL; 1.00 mmol). The solution was refluxed for 2 hours. The reaction was partitioned between isopropyl acetate and 0.1 N HCl. The organic was dried over magnesium sulfate, filtered and evaporated to an oil which was digested in cyclohexane/methylene chloride (1:1; 3 mL). Removal of volatiles under high vacuum afforded the title compound as a glass.

NMR (acetone): 7.68 (d, 1H, J=8.6 Hz); 7.12 (d, 1H, J=8.7 Hz); 6.88 (AB dd, 4H); 4.62 (s, 2H); 4.32 (t, 2H, J=5.6 Hz); 4.20 (t, 2H, J=5.6 Hz); 2.94 (quart, 2H, J=7.5 Hz); 2.85 (bt, 2H, J=7.5 Hz).

EXAMPLE 28

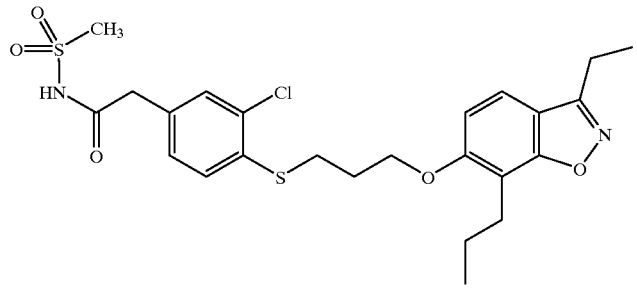

N-Methylsulfonyl 3-chloro-4-(3-(3-ethyl-7-propyl-6-benz[4,5]isoxazole)oxy) propylthio phenyl acetamide

1. 3-chloro-4-(3-(3-ethyl-7-propyl-6-benz[4,5]isoxazole)oxy) propylthio phenyl acetamide A solution of 3-chloro-4-(3-(3-ethyl-7-propyl-6-benz[4,5]isoxazole) oxy)propylthio phenyl acetic acid (L-165,461) (0.204 grams; 0.455 mmol) in dry methylene chloride (3 mL) was treated with dry DMF (5 μL). Oxalyl chloride (0.048 mL; 0.546 mmol) was added dropwise and the solution stirred for 14 hours. All volatiles were removed in vacuo and the derived residue dissolved in dry THF (10 mL). Concentrated ammonia (1 mL) was added dropwise and the mixture stirred for 3 hours. The reaction was partitioned between isopropyl acetate and water. The organic was washed once more with water, then dried over magnesium sulfate. Filtration and evaporation afforded the title compound as a solid.

NMR (CDCl$_3$): 7.59 (d, 1H, J=8.7 Hz); 7.40 (two overlapping d, 2H, J=8.0, 1.9 Hz); 7.15 (dd, 1H, J=8.1, 1.8 Hz);

7.09 (d, 1H, J=8.8 Hz); 6.91 (vbs, 1H); 6.29 (vbs, 1H); 4.20 (t, 2H, J=5.9 Hz); 3.48 (s, 2H); 3.27 (t, 2H, J=7.2 Hz); 2.95 (quart, 2H, J=7.4 Hz);

2. N-Methylsulfonyl 3-chloro-4-(3-(3-ethyl-7-propyl-6-benz[4,5]isoxazole)oxy)propylthio phenyl acetamide A solution of 3-chloro-4-(3-(3-ethyl-7-propyl-6-benz[4,5] isoxazole) oxy)propylthio phenyl acetamide (L-783,573) (0.069 grams; 0.154 mmol) in dry toluene (2 mL) was treated with methanesulfonyl chloride (0.013 mL; 0.162 mmol) and 80% sodium hydride (0.005 grams; 0.162 mmol). The mixture was stirred at 80° C. for 14 hours. The reaction mixture was partitioned between isopropyl acetate and 0.1 N HCl. The organic was dried over magnesium sulfate, filtered and concentrated to an oil which was chromatographed over silica gel to afford the title compound.

NMR (CDCl$_3$): 7.59 (d, 1H, J=8.6 Hz); 7.43 (d, 1H, J=8.1 Hz); 7.41 (d, 1H, J=1.9 Hz); 7.27 (dd, 1H, J=8.0, 2.0 Hz); 7.09 (d, 1H, J=8.5 Hz); 4.30 (t, 2H, J=5.8 Hz); 3.72 (s, 2H); 3.27 (t, 2H, J=7.0 Hz); 3.22 (s, 3H); 2.94 (quart, 2H, J=7.2 Hz); 2.88 (bt, 2H, J=7.6 Hz).

EXAMPLE 29

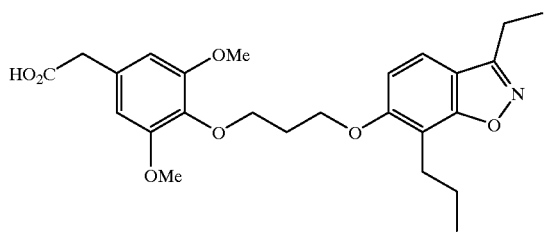

3,5-dimethoxy-4-(3-(3-(Ethyl)-7-(propyl)-6-benz-[4,5]-isoxazoloxy) propyloxy)phenyl acetic acid Step A: Preparation of Methyl-3,5-dimethoxy-4-hydroxyphenyl acetate A solution of 3,5-dimethoxy-4-hydroxyphenyl acetic acid (424 mg) in methanol (2 mL) was treated with excess trimethylsilyldiazomethane (2M in hexanes) at room temperature for 30 min. The reaction was then treated with solid magnesium sulfate filtered and concentrated to yield the title compound (450 mg). NMR (CDCl$_3$); δ 8.20 (s,1H), 6.49 (s,2H), 3.72 (s,6H), 3.59 (s,3H), 3.52 (s,2H).

Step B: Preparation of Methyl-3,5-dimethoxy-4-(3-(3-(Ethyl)-7-(propyl)-6-benz-[4,5]-isoxazoloxy)propyloxy) phenyl acetate The procedure from Example 76 Step C was followed using methyl-3,5-dimethoxy-4-hydroxyphenyl acetate (108 mg) and 3-bromo-1-(3-(Ethyl)-7-(propyl)-6-benz-[4,5]-isoxazoloxy)propane (156 mg) to afford a colorless oil (88 mg). NMR (CDCl$_3$); δ 7.41 (d,2H), 6.99 (d,2H), 6.45 (s,2H), 3.76 (s,6H), 3.71 (s,3H), 3.55 (s,3H), 1.43 (t,3H), 0.92 (t,3H).

Step C: Preparation of 3,5-dimethoxy-4-(3-(3-(Ethyl)-7-(propyl)-6-benz-[4,5]-isoxazoloxy)propyloxy)phenyl acetic acid Methyl-3,5-dimethoxy-4-(3-(3-(Ethyl)-7-(propyl)-6-benz-[4,5]-isoxazoloxy)propyloxy)phenyl acetate (80 mg) was hydrolyzed according to the procedure found in Example 30 Step B to give the desired compound (68 mg) as a colorless solid. NMR (CDCl$_3$); δ 7.41 (d,2H), 6.98 (d,2H), 6.45 (s,2H), 3.76 (s,6H), 3.58 (s,3H), 1.43 (t,3H), 0.92 (t,3H).

EXAMPLE 30

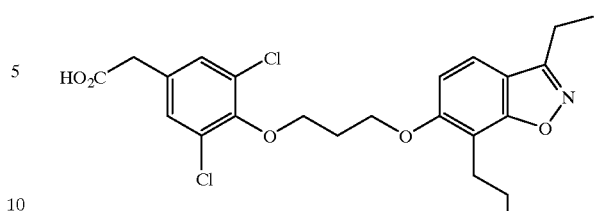

3,5-dichloro-4-(3-(3-(Ethyl)-7-(propyl)-6-benz-[4,5]-isoxazoloxy) propyloxy)phenyl acetic acid Step A: Preparation of Methyl 3,5-dichloro-4-hydroxy benzoate A solution of 2,4-dichloro-4-hydroxybenzoic acid (414 mg) in ether (2 mL) was trated with excess trimethylsilyl diazomethane (2M in hexanes). After 1 hour at room temperature the reaction was concentrated to yield an amber oil. The oil was chromatographed on silica gel to yield the title compound (220 mg). NMR (CDCl$_3$); δ 7.80 (s,2H), 3.85 (s,3H).

Step B: Preparation of Methyl-3,5-dichloro-4-(3-(3-(Ethyl)-7-(propyl)-6-benz-[4,5]-isoxazoloxy)propyloxy)benzoate The title compound was prepared according to Example 76 Step C using methyl 2,4-dichloro-4-hydroxy benzoate (112 mg) and 3-bromo-1-(3-(Ethyl)-7-(propyl)-6-benz-[4,5]-isoxazoloxy)propane (165 mg) to afford a slightly pink colored solid (220 mg). NMR (CDCl$_3$); 8.0 (s,2H), 7.42 (d2H), 6.96 (d,2H), 3.91 (s,3H), 1.42 (t,3H), 0.94 (t,3H).

Step C: Preparation of 3,5-dichloro-4-(3-(3-(Ethyl)-7-(propyl)-6-benz-[4,5]-isoxazoloxy)propyloxy)-benzoic acid Methyl-2,5-dichloro-4-(3-(3-(Ethyl)-7-(propyl)-6-benz-[4,5]-isoxazoloxy)propyloxy)-benzoate (281 mg) was hydrolyzed to give the title compound following the procedure of example 32 Step D as a colorless solid (227 mg). NMR (CDCl$_3$); δ 790 (s,2H), 7.42 (d,2H), 6.95 (d,2H), 3.90 (s,3H), 1.41 (t,3H), 0.94 (t,3H).

Step D: Preparation of Methyl-3,5-dichloro-4-(3-(3-(Ethyl)-7-(propyl)-6-benz-[4,5]-isoxazoloxy)propyloxy)phenyl acetate The title compound was prepared from 2,5-dichloro-4-(3-(3-(Ethyl)-7-(propyl)-6-benz-[4,5]-isoxazoloxy) propyloxy)-benzoic acid (202 mg) following the procedure from Example 77, Step C, to give a clorless solid (177 mg). NMR (CDCl$_3$); δ 7.42 (d,2H), 7.21 (s,2H), 6.96 (d,2H), 3.76 (s,3H), 3.54 (s,2H), 1.42 (t,3H), 0.97 (t,3H).

Step E: Preparation of 3,5-dichloro-4-(3-(3-(Ethyl)-7-(propyl)-6-benz-[4,5]-isoxazoloxy)propyloxy)phenyl acetic acid Methyl-2,5-dichloro-4-(3-(3-(Ethyl)-7-(propyl)-6-benz-[4,5]-isoxazoloxy)propyloxy)phenyl acetate (37 mg) was hydrolyzed according to the procedure found in Example 30 Step B to give a colorless solid (30 mg). NMR (CDCl$_3$); δ 7.41 (d,2H), 7.20 (s,2H), 6.95 (d,2HO, 3.59 (s,2HO, 1.42 (t,3H), 0.95 (t, 3H).

EXAMPLE 31

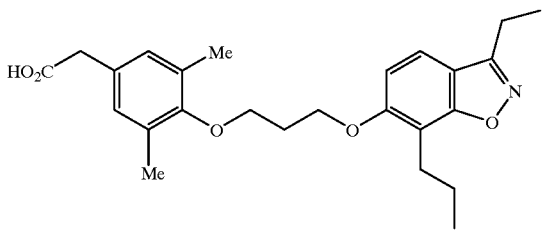

3,5-dimethyl-4-(3-(3-(Ethyl)-7-(propyl)-6-benz-[4,5]-isoxazoloxy)
propyloxy)phenyl acetic acid Step A: Preparation of Methyl-3,5-dimethylbenzoate A solution of 3,5-dimethyl-4-hydroxybenzoic acid (1.0 g) in ether (5 mL) and methanol(5 mL) was treated with excess trimethylsilyldiazomethane. After stirring 30 min at room temperature the reaction was treated with magnesium sulfate, filtered and concentrated to a brown solid. The title compound was obtained by purification on silica gel to give a colorless solid (670 mg). NMR (CDCl$_3$); δ 7.75 (s,2H), 3.85 (s,3H), 2.30 (s,6H).

Step B: Preparation of Methyl-3,5-dimethyl-4-(3-(3-(Ethyl)-7-(propyl)-6-benz-[4,5]-isoxazoloxy)propyloxy)benzoate The title compound was prepared following the procedure for example 17, Step D, using methyl-3,5-dimethylbenzoate (500 mg) and 3-bromo-1-(3-(Ethyl)-7-(propyl)-6-benz-[4,5]-isoxazoloxy)propane (890 mg) as starting materials to give after silicagel chromatography 1.1 g of a waxy solid. NMR (CDCl$_3$); δ 7.80 (s,2H), 7.42 (d,2H), 6.95 (d,2H), 3.85 (s,3H), 2.26 (s,3H),1.40 (t,3H), 0.96 (t,3H).

Step C: Preparation of Methyl-3,5-dimethyl-4-(3-(3-(Ethyl)-7-(propyl)-6-benz-[4,5]-isoxazoloxy)propyloxy)phenyl acetate Methyl-3,5-dimethyl-4-(3-(3-(Ethyl)-7-(propyl)-6-benz-[4,5]-isoxazoloxy)propyloxy)benzoate (200 mg) was hydrolyzed according to the procedure found in Example 77, Step C to give a waxy colorless solid (180 mg). This material was then treated according to Example 77, Step C to give a colorless oil (88 mg). NMR (CDCl$_3$); δ 7.41 (d,2H), 7.20 (s,2H), 6.94 (d,2H), 3.80 (s,3H), 3.52 (s,3H), 1.41 (t,3H), 0.95 (t,3H).

Step D: Preparation of 3,5-dimethyl-4-(3-(3-(Ethyl)-7-(propyl)-6-benz-[4,5]-isoxazoloxy)propyloxy)phenyl acetic acid 3,5-dimethyl-4-(3-(3-(Ethyl)-7-(propyl)-6-benz-[4,5]-isoxazoloxy)propyloxy)phenyl acetate (77 mg) was hydrolyzed according to Example 30 Step B to give the desired compound (53 mg).

NMR (CDCl$_3$); δ 7.41 (d,2H), 7.22 (s,2H), 6.94 (d,2H), 3.51 (s,3H), 1.42 (t,3H), 0.96 (t,3H).

EXAMPLE 32

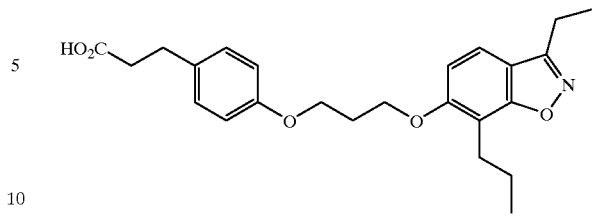

4-(3-(3-(Ethyl)-7-(propyl)-6-benz-[4,5]-isoxazoloxy)-propyloxy)-
phenyl propionic acid Step A: Preparation of 3-(4-hydroxyphenyl)propionate:

In a 0° C. ice bath, 3-(4-hydroxyphenyl)propionic acid (313.3 mg; 1.9 mmol), was dissolved in 3 ml of ether. Added to this solution was about 6 mL of diazomethane dissolved in ether (0.32 mmoL/mL). Allowed to stir for 5 minutes, vented the excess diazomethane with nitrogen to a colorless solution and concentrated in vacuo to afford a light yellow oil. Isolated 340.0 mg of the title compound and used without further purification. NMR: δ 7.07 (d,2H); 6.76 (d,2H); 3.68 (s,3H); 2.89 (t,2H); 2.62 (t,2H);

Step B: Preparation of 3-ethyl-6-hydroxy-7-propylbenz-[4,5]-isoxazole

The title compound was prepared by following the procedures from Example 7 Step A substituting commercially available 2,4-dihydroxy-3-propylpropiophenone, as a colorless solid. NMR 7.42 (d,2H), 6.98 (d,2H), 2.95 (q,2H), 2.84 (t,2H), 1.76 (m,2H), 1.42 (t,3H), 1.0 (t,3H).

Step C: Preparation of 3-ethyl-6-(3-bromopropyl)oxy-7-propylbenz-[4,5]-isoxazole Following the procedure of Example 7 Step B and substituting 3-ethyl-6-hydroxy-7-propylbenz-[4,5]-isoxazole, the title compound was prepared as a colorless solid. NMR: δ 7.40 (d,1H); 6.92 (d, 1H); 4.22 (t,2H); 3.69 (t,2H); 2.99 (q,2H); 2.84 (t,2H); 2.38 (m,2H); 1.41 (t,3H); 0.95 (t,3H)

Step D: Preparation of Methyl 4-(3-(3-(Ethyl)-7-(propyl)-6-benz-[4,5]-isoxazoloxy)propyloxy)-phenyl propionate A mixture of 3-(4-hydroxyphenyl)propionate (73.7 mg; 0.409 mmol), (3-(3-(Ethyl)-7-(propyl)-6-benz-[4,5]-isoxazoloxy bromide (146.7 mg; 0.45 mmol), cesium carbonate (139.7 mg; 0.43 mmol) and about 2.0 ml dry dimethylformamide was stirred and heated for 16 hours. It was concentrated in vacuo, diluted with water and extracted with ethyl acetate. The organic layer was washed with water, dried (Na$_2$SO$_4$), concentrated and chromatographed (silica gel, 30% ethyl acetate in hexane) to yield 118.7 mg of the title compound as a light yellow oil. NMR: δ 7.20 (d,1H); 7.12 (d,2H); 6.92 (d,1H); 6.83 (d,2H); 4.28 (t,2H); 3.99 (t,2H); 3.69 (s,3H); 2.98 (q,2H); 2.90 (m,4H); 2.61 (m,2H); 2.32 (m,2H); 1.70 (m,2H); 1.43 (t,3H); 0.93 (t,3H)

Step E: Preparation of 4-(3-(3-(Ethyl)-7-(propyl)-6-benz-[4,5]-isoxazoloxy)-propyloxy)-phenyl propionic acid A solution of 4-(3-(3-(Ethyl)-7-(propyl)-6-benz-[4,5]-isoxazoloxy)propyloxy)-phenyl (32.3 mg; 0.071 mmol), 1M LiOH (aq) (124 μL)and methanol (2.0 mL) was heated at 60° C. for 16 hours. The mixture was diluted with ethyl acetate and acidified to pH 5–6 with 1 M HCl, washed with water (2 times), brine (1 time) and dried over sodium sulfate and concentrated to afford 29.4 mg of the title compound. MS 412 (M+H), NMR: δ 7.41 (d,1H); 7.13 (d,2H); 6.94 (d,1H); 6.87 (d,2H); 4.28 (t,2H); 4.20 (t,2H); 2.93 (m,6H); 2.66 (m,2H); 2.33 (m,2H); 1.68 (m,2H); 1.44 (t,3H); 0.95 (t,3H)

EXAMPLE 33

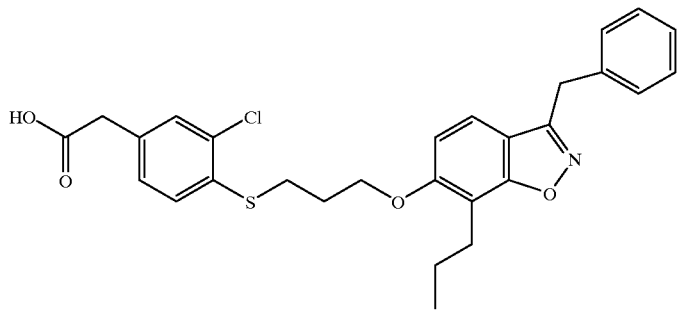

3-chloro-4-(3-phenylmethyl-7-(n-propyl)-6-benz[4,5]isoxazoloxy)propyl-thio)phenylacetic acid Step A Preparation of 1,3-dihydroxy-4-phenylacetyl-2-(n-propyl)-benzene Using the procedure in Example 51, step 1, phenylacetic acid and 2-(n-propyl)resorcinol were condensed in triflic acid to form 1,3-dihydroxy-4-phenylacetyl-2-(n-propyl) benzene.

NMR (CDCl$_3$): d 7.64 (d, 1H); 7.24–7.38 (m, 5H); 6.35 (d, 1H); 5.36 (s, 1H); 4.23 (s, 2H); 2.61 (t, 2H); 1.56 (m, 2H); 0.98 (t, 3H).

Step B Preparation of 6-hydroxy-3-phenylmethyl-7-(n-propyl)-benz[4,5]isoxazole

Using the procedures in Example 51. steps 2 and 3, 1,3-dihydroxy-4-phenylacetyl-2-(n-propyl)benzene was converted into 6-hydroxy-3-phenylmethyl-7-(n-propyl)benz [4,5]isoxazole.

NMR (CDCl$_3$): d 7.21–7.37 (m, 5H); 7.03 (d, 1H); 6.68 (d, 1H); 5.2 (bs, 1H); 4.26 (s, 2H); 2.85(t, 2H); 1.72 (m, 2H); 1.00 (t, 3H).

Step C Preparation of methyl 3-chloro-4-(3-phenylmethyl-7-(n-propyl)-6-benz[4,5]isoxazoloxy)propylthio) phenylacetate Using the procedure in Example 16, step 4, 6-hydroxy-3-phenylmethyl-7-(n-propyl)benz[4,5]isoxazole and methyl 3-chloro-4-(3-bromopropylthio)phenylacetate were heated in DMF with Cs$_2$CO$_3$ to prepare methyl 3-chloro-4-(3-phenylmethyl-7-(n-propyl)-6-benz[4,5]-isoxazoloxy) propylthio)phenylacetate NMR (CDCl$_3$): d 7.22–7.35 (m, 5H); 7.12 (m, 2H); 6.79 (d, 1H); 4.29 (s, 2H); 4.13 (t, 2H); 3.71 (s, 3H); 3.55 (s, 2H); 3.15 (t, 2H); 2.86 (t, 2H); 2.16 (m, 2H); 1.69 (m, 2H); 0.95 (t, 3H).

Step D Preparation of 3-chloro-4-(3-phenylmethyl-7-(n-propyl)-6-benz[4,5]isoxazoloxy)propylthio)phenylacetic acid Using the procedure in Example 2, methyl 3-chloro-4-(3-phenylmethyl-7-(n-propyl)-6-benz[4,5]isoxazoloxy) propylthio)phenyl acetate was saponified with LiOH to form 3-chloro-4-(3-phenylmethyl-7-(n-propyl)-6-benz[4,5] isoxazoloxy)propylthio)phenylacetic acid NMR (DMSOd$_6$): d 7.43 (d, 1H); 7.20–7.39 (m, 4H); 7.13 (dd, 1H); 7.04 (d, 1H); 4.30 (s, 2H); 4.16 (t, 2H); 3.30 (s, 2H); 3.12 (t, 2H); 2.77 (t, 2H); 2.04 (m, 2H); 1.59 (m, 2H); 0.87 (t, 3H).

EXAMPLE 34

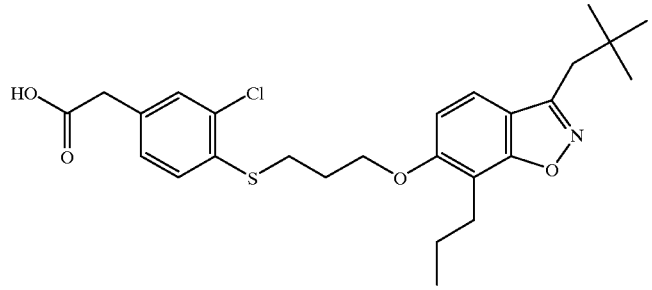

3-chloro-4-(3-(2,2-dimethylpropyl)-7-(n-propyl)-6-benz[4,5]isoxazoloxy)-propylthio)phenylacetic acid Step A Preparation of 1,3-dihydroxy-4-(3,3-dimethylbutyryl)-2-(n-propyl)benzene Using the procedure in Example 51, step 1, 3,3-dimethylbutyric acid and 2-(n-propyl)resorcinol were condensed in triflic acid to form 1,3-dihydroxy-4-(3,3-dimethylbutyryl)-2-(n-propyl)benzene NMR (CDCl$_3$): d 7.53 (d, 1H); 6.32 (d, 1H); 2.86 (s, 2H); 2.62 (t, 2H); 1.59 (m, 2H); 1.06 (s, 9H); 0.98 (t, 3H).

Step B Preparation of 3-(2,2-dimethylpropyl)-6-hydroxy-7-(n-propyl)benz[4,5]isoxazole Using the procedures in Example 51, steps 2 and 3, 1,3-dihydroxy-4-(3,3-dimethylbutyryl)-2-(n-propyl) benzene was converted into 3-(2,2-dimethylpropyl)-6-hydroxy-7-(n-propyl)benz[4,5]isoxazole NMR (CDCl$_3$): d 7.29 (d, 1H); 6.80 (d, 1H); 5.30 (vbs, 1H); 2.87 (t, 2H); 2.80 (s, 2H); 1.75 (m, 2H); 1.04 (s, 9H); 1.00 (t, 3H).

Step C Preparation of methyl 3-chloro-4-(3-(2,2-dimethylpropyl)-7-(n-propyl)-6-benz[4,5]isoxazoloxy) propylthio)-phenylacetate Using the procedure in Example 16, step 4, 3-(2,2-dimethyl-propyl)-6-hydroxy-7-(n-propyl)benz[4,5] isoxazole and methyl 3-chloro-4-(3-bromopropylthio) phenylacetate were heated in DMF with $Cs_2CO_3$ to prepare methyl 3-chloro-4-(3-(2,2-dimethylpropyl)-7-(n-propyl)-6-benz[4,5]isoxazoloxy)propylthio)phenylacetate NMR (CDCl$_3$): d 7.37 (d, 1H); 7.25–7.33 (m, 2H); 7.12 (dd, 1H); 6.90 (d, 1H); 4.19 (t, 2H); 3.70 (s, 3H); 3.55 (s, 2H); 3.18 (t, 2H); 2.89 (t, 2H); 2.81 (s, 2H); 2.20 (m, 2H); 1.71 (m, 2H); 1.05 (s, 9H); 0.96 (t, 3H).

Step D Preparation of 3-chloro-4-(3-(2,2-dimethylpropyl)-7-(n-propyl)-6-benz[4,5]isoxazoloxy)propylthio) phenylacetic acid Using the procedure in Example 2, methyl 3-chloro-4-(3-(2,2-dimethylpropyl)-7-(n-propyl)-6-benz[4,5]isoxazoloxy) propylthio)phenyl acetate was saponified with LiOH to form 3-chloro-4-(3-(2,2-dimethyl-propyl)-7-(n-propyl)-6-benz[4,5]isoxazoloxy)propylthio)phenylacetic acid NMR (CDCl$_3$): d 7.36 (d, 1H); 7.26–7.35 (m, 2H); 7.13 (dd, 1H); 6.89 (d, 1H); 4.19 (t, 2H); 3.60 (s, 2H); 3.17 (t, 2H); 2.86 (t, 2H); 2.81 (s, 2H); 2.19 (m, 2H); 1.70 (m, 2H); 1.04 (s, 9H); 0.95 (t, 3H).

EXAMPLE 35

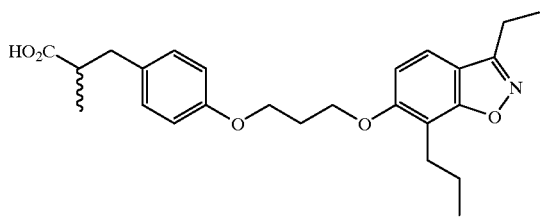

2-methyl-4-(3-(3-(Ethyl)-7-(propyl)-6-benz-[4,5]-isoxazoloxy)-propyloxy)-phenyl propionic acid Step A: Preparation of Preparation of Methyl-2-methyl-4-(3-(3-(Ethyl)-7-(propyl)-6-benz-[4,5]-isoxazoloxy) propyloxy)-phenyl propionate A solution of Methyl 4-(3-(3-(Ethyl)-7-(propyl)-6-benz-[4,5]-isoxazoloxy)propyloxy)-phenyl propionate from Example 32 Step C (16.5 mg, 0.36 mmoL) in THF (0.5 mL) at −78° C., under nitrogen was trated with KHMDS (0.08 mL, 0.5 M in toluene)and stirred for 30 min. Excess methyl iodide was then added and the reaction stirred 30 min longer then warmed to RT. After 45 min the reaction was treated with 1M ammonium chloride and extracted with ethyl acetate (×2), dried over anhydrous sodium sulfate, filtered and concentrated. The title compound was obtained after purification by silica gel chromatography to give a colorless oil (12 mg, 76%) NMR (CDCl$_3$); δ 7.41 (d,2H), 7.09 (d, 2H), 6.95 (d, 2H), 6.83 (d,2H), 3.65 (s,3H), 1.43 (t,3H), 1.16 (d,2H), 0.90 (t,3H).

Step B: Preparation of 2-methyl-4-(3-(3-(Ethyl)-7-(propyl)-6-benz-[4,5]-isoxazoloxy)propyloxy)-phenyl propionic acid A solution of methyl-2-methyl-4-(3-(3-(Ethyl)-7-(propyl)-6-benz-[4,5]-isoxazoloxy)propyloxy)-phenyl propionate (11.5 mg, Step A) was dissolved in MeOH (0.5 mL)and 1M LiOH (0.10 mL) was added. The resulting solution was warmed to 50° C. for 2 hours, cooled and concentrated. The residue was partitioned between ethyl acetate and 1 M Hcl. The organic fraction was removed, dried and concentrated to give the title compound as a colorless oil (10.7 mg) NMR (CDCl$_3$); δ 7.40 (d,2H), 7.11 (d,2H), 6.95 (d,2H), 6.85 (d,2H), 1.43 (t,3H), 1.18 (d,2H), 0.95 (t,3H).

EXAMPLE 36

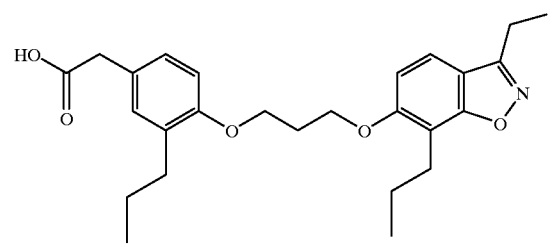

3-Propyl-4-(3-(3-ethyl-7-propyl-6-benz-[4,5]-isoxazoloxy)-propyloxy) phenylacetic acid Step A: Preparation of methyl 3-propyl-4-(3-(3-ethyl-7-propyl-6-benz-[4,5]-isoxazoloxy)-propyloxy)phenylacetate Using the method of Example 17, Step D, 1-bromo-3-(3-ethyl-7-propyl-6-benz-[4,5]-isoxazoloxy)phenoxypropane as the starting material, the title compound was obtained.

$^1$H NMR(400 MHz, CDCl$_3$): δ 7.37 (d, 1H, J=8.6 Hz), 7.01 (m, 2H), 6.90 (d, 1H, J=8.5 Hz), 6.78 (d, 1H, J=8.3 Hz), 4.24 (t, 2H, J=6.1 Hz), 4.15 (t, 2H, J=6.0 Hz), 3.65 (s, 3H), 3.52 (s, 2H), 2.94 (quart, 2H, J=7.6 Hz), 2.82 (t, 2H, J=7.7 Hz), 2.53 (t, 2H, J=7.7 Hz), 2.29 (quint, 2H, J=6.0 Hz), 1.66 (hex, 2H, J=7.5 Hz), 1.57 (hex, 2H, J=7.6 Hz), 1.41 (t, 3H, J=7.6 Hz), 0.89 (m, 6H).

Step B: Preparation of 3-propyl-4-(3-(3-ethyl-7-propyl-6-benz-[4,5]-isoxazoloxy)-propyloxy)phenylacetic acid Using the method of Example 18, methyl 3-propyl-4-(3-(3-ethyl-7-propyl-6-benz-[4,5]-isoxazoloxy)-propyloxy) phenylacetate as the starting material, the title compound was obtained.

$^1$H NMR(400 MHz, CDCl$_3$): δ 7.37 (d, 1H, J=8.6 Hz), 7.01 (m, 2H), 6.90 (d, 1H, J=8.5 Hz), 6.78 (d, 1H, J=8.3 Hz), 4.24 (t, 2H, J=6.1 Hz), 4.15 (t, 2H, J=6.0 Hz), 3.52 (s, 2H), 2.94 (quart, 2H, J=7.6 Hz), 2.82 (t, 2H, J=7.7 Hz), 2.53 (t, 2H, J=7.7 Hz), 2.29 (quint, 2H, J=6.0 Hz), 1.66 (hex, 2H, J=7.5 Hz), 1.57 (hex, 2H, J=7.6 Hz), 1.41 (t, 3H, J=7.6 Hz), 0.89 (m, 6H). ESI: MS m/e=440 (M+1)

EXAMPLE 37

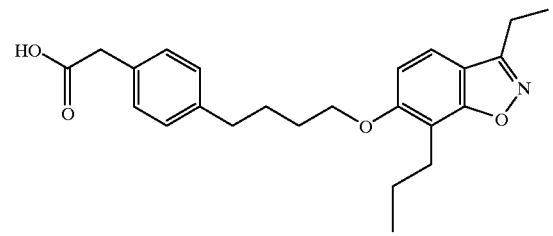

4-(3-(3-(Ethyl-7-propyl-6-benz-[4,5]-isoxazoloxy)butyl)phenylacetate

Step A: Preparation of methyl 4-(4-hydroxybutyn-1-yl) phenylacetate

To a solution of methyl 4-bromophenylacetate (229 mg, 1.0 mmole) and 3-butyn-1-ol (151 μL, 2.0 mmole) in triethylamine (4.0 mL) was added cuprous bromide (18 mg, 0.12 mmole) and tetra(triphenylphosphine)palladium (46 mg, 0.04 mmole), and the mixture refluxed under a nitrogen atmosphere for 1 hr 20 min. The mixture was evaporated in vacuo and the residue partitioned with water and ether. The organic phase was washed with brine, dried over magnesium sulfate and concentrated in vacuo to an oil. Flash chromatography on silica gel in 7:3 hexane:ethyl acetate afforded the title compound (175 mg) as an oil NMR (CDCl$_3$): δ 1.69

(s, 1H); 2.71 (t, 2H); 3.63 (s, 2H); 3.71 (s, 3H); 3.83 (t, 2H); 7.22 (d, 2H); 7.38 (d, 2H).

Step B: Preparation of methyl 4-(4-hydroxybutyl) phenylacetate

A solution of methyl 4-(4-hydroxybutyn-1-yl) phenylacetate (178 mg, 0.82 mmole) and 10% palladium on carbon (30 mg) in ethanol (2 mL) were stirred under a balloon of hydrogen for 3 days at room temperature. The mixture was filtered and the filtrate concentrated in vacuo to give the title compound (181 mg) as an oil. NMR (CDCl$_3$): δ 1.52 (s, 1H); 1.64 (m, 2H); 1.71 (m, 2H); 2.65 (t, 2H); 3.61 (s, 2H); 3.68 (t, 2H); 3.71 (s, 3H); 7.15 (d, 2H); 7.21 (d, 2H).

Step C: Preparation of methyl 4-(4-methansulfonyloxybutyl)-phenylacetate

To a solution of methyl 4-(4-hydroxybutyl)phenylacetate (170 mg, 0.77 mmole) in methylene chloride (2 mL) was added methansulfonyl anhydride (146 mg, 1.06 mmole), pyridine (187 μL, 2.31 mmole) and 4-dimethylaminopyridine (5 mg, 0.04 mmole) and the mixture stirred at room temperature for 2 hours. The mixture was concentrated in vacuo and the residue dissolved in ethyl acetate and washed with 1N HCl, water, brine, dried over magnesium sulfate and concentrated in vacuo to give the title compound (187 mg) as an oil.

NMR (CDCl$_3$): δ 1.77 (m, 4H); 2.66 (t, 2H); 3.00 (s, 3H); 3.62 (s, 2H); 3.71 (s, 3H); 4.25 (t, 2H); 7.15 (d, 2H); 7.22 (d, 2H).

Step D: Preparation of methyl 4-(3-(3-(ethyl)-7-propyl-6-benz-[4,5]-isoxazoloxy)butyl)phenylacetate A suspension of sodium hydride (15 mg, 0.36 mmole) in DMF (1.5 mL) was treated with 3-ethyl-6-hydroxy-7-propylbenz-[4,5]-isoxazole (68 mg, 0.33 mmole) and the mixture stirred at room temperature for 10 minutes under a nitrogen atmosphere. A solution of methyl 4-(4-methansulfonyloxybutyl)phenylacetate (100 mg, 0.33 mmole) in DMF (0.5 mL) was added and the mixture stirred at 80° C. for 5 hours. The cooled reaction mix was dissolved in ethyl acetate and washed with water (twice), brine, dried over magnesium sulfate and concentrated in vacuo to an oil. The crude product was purified by thin layer chromatography on silica gel eluting with hexane:ethyl acetate (4:1) to give the title compound (80 mg) as an oil. NMR (CDCl$_3$): δ 0.97 (t, 3H); 1.44 (t, 3H); 1.71 (m, 2H); 1.87 (m, 4H); 2.71 (t, 2H); 2.88 (t, 2H); 2.97 (q, 2H); 3.62 (s, 2H); 3.71 (s, 3H); 6.89 (d, 1H); 7.18 (d, 2H); 7.22 (d, 2H); 7.39 (d, 1H).

Step E: Preparation of 4-(3-(3-(ethyl)-7-propyl-6-benz-[4,5]-isoxazoloxy)butyl)phenylacetate To a solution of methyl 4-(3-(3-(ethyl)-7-propyl-6-benz-[4,5]-isoxazoloxy)butyl)phenylacetate (80 mg, 0.195 mmole) in methanol (2 mL) was added a solution of lithium hydroxide (1M, 390 μL), and the resulting solution stirred at 60° C. for 2 hours. The solution was concentrated in vacuo and the residue partitioned with ethyl acetate and 1NHCl. The aqueous phase was washed with ethyl acetate and the combined organic extracts washed with water, brine, dried over magnesium sulfate and concentrated in vacuo to afford the title compound (76 mg) as an oil. NMR (CDCl$_3$): δ 0.968 (t, 3H); 1.44 (t, 3H); 1.71 (m, 2H); 1.87 (m, 4H); 2.71 (t, 2H); 2.88 (t, 2H); 2.97 (q, 2H); 3.65 (s, 2H); 4.07 (t, 2H); 6.89 (d, 1H); 7.19 (d, 2H); 7.23 (d, 2H); 7.39 (d, 1H). Mass spec, m/e=396 (m+1).

EXAMPLE 38

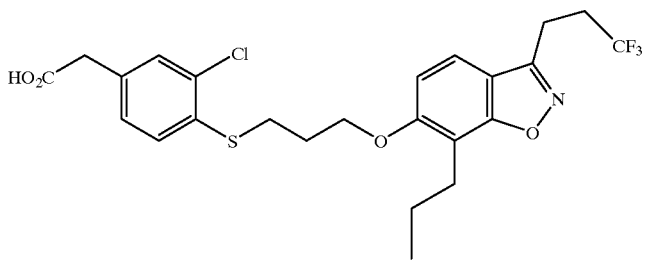

3-chloro-4-(7-(n-propyl)-3-(3,3,3-trifluoropropyl)-6-benz[4,5]isoxazol-oxy)propylthio) phenylacetic acid Step A Preparation of 1,3-dihydroxy-2-(n-propyl)-4-(4,4,4-trifluoro-butyryl)benzene Using the procedure in Example 51, step 1, 4,4,4-trifluoro-butyric acid and 2-(n-propyl)resorcinol were condensed in triflic acid to form 1,3-dihydroxy-2-(n-propyl)-4-(4,4,4-trifluorobutyryl)benzene NMR (CDCl$_3$): d 7.52 (d, 1H); 6.38 (d, 1H); 5.42 (s, 1H); 3.22 (t, 2H); 2.62 (t, 2H); 2.59 (m, 2H); 1.58 (m, 2H); 0.98 (t, 3H).

Step B Preparation of 6-hydroxy-7-(n-propyl)-3-(3,3,3-trifluoropropyl)benz[4,5]isoxazole Using the procedures in Example 51, steps 2 and 3, 1,3-dihydroxy-2-(n-propyl)-4-(4,4,4-trifluorobutyryl) benzene was converted into 6-hydroxy-7-(n-propyl)-3-(3,3,3-trifluoropropyl)benz[4,5]isoxazole NMR (CDCl$_3$): d 7.31 (d, 1H); 6.84 (d, 1H); 5.31 (vbs, 1H); 3.18 (m, 2H); 2.86 (t, 2H); 2.70 (m, 2H); 1.74 (m, 2H); 0.99 (t, 3H).

Step C Preparation of methyl 3-chloro-4-(7-(n-propyl)-3-(3,3,3-trifluoropropyl)-6-benz[4,5]isoxazoloxy)propylthio)-phenylacetate Using the procedure in Example 16, step 4, 6-hydroxy-7-(n-propyl)-3-(3,3,3-trifluoropropyl)benz[4,5]isoxazole and methyl 3-chloro-4-(3-bromopropylthio)phenylacetate were heated in DMF with Cs$_2$CO$_3$ to prepare methyl 3-chloro-4-(7-(n-propyl)-3-(3,3,3-trifluoropropyl)-6-benz [4,5]isoxazoloxy)propylthio)phenylacetate NMR (CDCl$_3$): d 7.38 (d, 1H); 7.25–7.33 (m, 2H); 7.13 (dd, 1H); 6.93 (d, 1H); 4.21 (t, 2H); 3.71 (s, 3H); 3.56 (s, 2H); 3.19 (m, 4 H); 2.89 (t, 2H); 2.72 (m, 2H); 2.21 (m, 2H); 1.70 (m, 2H); 0.95 (t, 3H).

Step D Preparation of 3-chloro-4-(7-(n-propyl)-3-(3,3,3-trifluoropropyl)-6-benz[4,5]isoxazoloxy)propylthio) phenylacetic acid Using the procedure in Example 2, methyl 3-chloro-4-(7-(n-propyl)-3-(3,3,3-trifluoropropyl)-6-benz[4,5] isoxazoloxy)propylthio)-phenylacetate was saponified with LiOH to form 3-chloro-4-(7-(n-propyl)-3-(3,3,3-trifluoropropyl)-6-benz[4,5]isoxazoloxy)propylthio) phenylacetic acid.

NMR (CDCl$_3$): d 7.39 (d, 1H); 7.26–7.34 (m, 2H); 7.13 (dd, 1H); 6.92 (d, 1H); 4.20 (t, 1H); 3.60 (s, 2H); 3.19 (m, 2H); 2.87 (t, 2H); 2.71 (m, 2H); 2.20 (m, 2H); 1.69 (m, 2H); 0.95 (t, 3H).

EXAMPLE 39

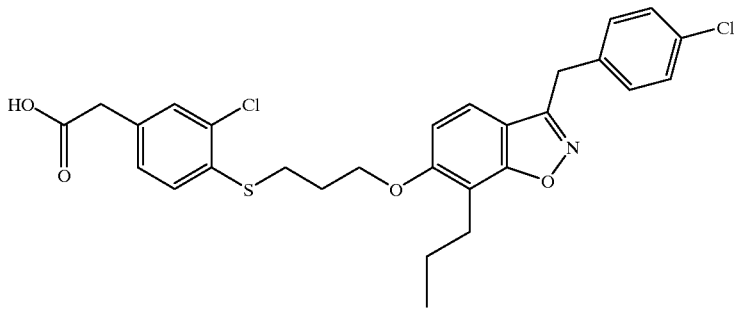

3-chloro-4-(3-(4-chlorophenylmethyl)-7-(n-propyl)-6-benz[4,5]isoxazol-oxy)propylthio) phenylacetic acid Step A Preparation of 4-(4-chlorophenylacetyl)-1,3-dihydroxy-2-(n-propyl)benzene Using the procedure in Example 51, step 1, 4-chlorophenyl-acetic acid and 2-(n-propyl)resorcinol were condensed in triflic acid to form 4-(4-chlorophenylacetyl)-1,3-dihydroxy-2-(n-propyl)benzene.

NMR (CDCl$_3$): d 7.60 (d, 1H); 7.31 (d, 2H); 7.20 (d, 2H); 6.35 (d, 1H); 4.19 (s, 2H); 2.61 (t, 2H); 1.59 (m, 2H); 0.96 (t, 3H).

Step B Preparation of 3-(4-chlorophenylmethyl)-6-hydroxy-7-(n-propyl)benz[4,5]isoxazole Using the procedure in Example 51, step 4-(4-chlorophenyl-acetyl)-1,3-dihydroxy-2-(n-propyl) benzene.was converted into 3-(4-chlorophenylmethyl)-6-hydroxy-7-(n-propyl)benz[4,5]isoxazole NMR (CDCl$_3$): d 7.27 (q, 4H); 7.03 (d, 1H); 6.71 (d, 1H); 5.14 (bs, 1H); 4.24 (s, 2H); 2.85 (t, 2H); 1.73 (m, 2H); 1.00 (t, 3H).

Step C Preparation of methyl 3-chloro-4-(3-(4-chlorophenylmethyl)-7-(n-propyl)-6-benz[4,5]isoxazoloxy) propylthio)phenylacetate Using the procedure in Example 16, step 4, 6-hydroxy-3-(4-chlorophenylmethyl)-7-(n-propyl)benz[4,5]isoxazole and methyl 3-chloro-4-(3-bromopropylthio)phenylacetate were heated in DMF with Cs$_2$CO$_3$ to prepare methyl 3-chloro-4-(3-(4-chlorophenylmethyl)-7-(n-propyl)-6-benz [4,5]-isoxazoloxy)propylthio)phenyl acetate NMR (CDCl$_3$): d 7.23–7.32 (m, 6H); 7.12 (dd, 1H); 7.10 (d, 1H); 6.71 (d, 1H); 4.25 (s, 2H); 4.15 (t, 2H); 3.71 (s, 3H); 3.54 (s, 2H); 3.15 (t, 2H); 2.86 (t, 2H); 2.17 (m, 2H); 1.69 (m, 2H); 0.95 (t, 3 H).

Step D Preparation of 3-chloro-4-(3-(4-chlorophenylmethyl)-7-(n-propyl)-6-benz[4,5]isoxazoloxy) propylthio)phenylacetic acid Using the procedure in Example 2, methyl 3-chloro-4-(3-(4-chlorophenylmethyl)-7-(n-propyl)-6-benz[4,5] isoxazoloxy)propylthio)-phenyl acetate was saponified with LiOH to form 3-chloro-4-(3-(4-chlorophenylmethyl)-7-(n-propyl)-6-benz[4,5]isoxazoloxy)propyl-thio)phenylacetic acid NMR (DMSOd$_6$)): d 7.46 (d, 1H); 7.34–7.41 (q, 4H); 7.27–7.34 (m, 2H); 7.13 (dd, 1H); 7.04 (d, 1H); 4.31 (s, 2H); 4.17 (t, 2H); 3.29 (s, 2H); 3.14 (t, 2H); 2.78 (t, 2H); 2.04 (m, 2H); 1.59 (m, 2H); 0.86 (t, 3 H).

EXAMPLE 40

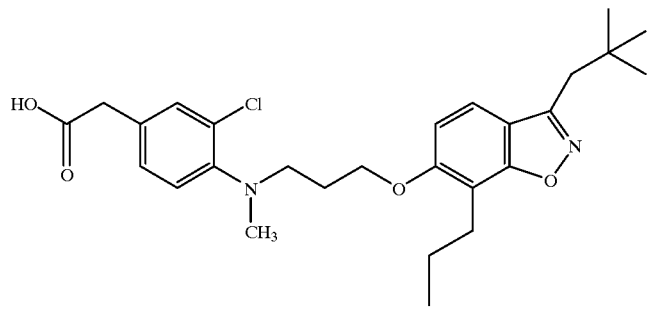

3-Chloro-4-(3-(3-(2,2-dimethylpropyl)-7-propyl-6-benz-[4,5]-isoxazoloxy)propyl-N-methylamino)phenylacetate Step A: Preparation of Methyl 3-Chloro-4-(3-(3-(2,2-dimethylpropyl)-7-propyl-6-benz-[4,5]-isoxazoloxy) propyl-N-methylamino)phenylacetate Sodium cyanoborohydride (10.5 mg, 0.16 mmole) was added in portions to a solution of methyl 3-chloro-4-(3-(3-(2,2-dimethylpropyl)-7-propyl-6-benz-[4,5]-isoxazoloxy) propylamino)phenylacetate (obtained as the product in Example 21, 50 mg, 0.102 mmole), 37% formaldehyde (92 µL, 1.02 mmole) and bromocresol green solution (0.04%, 1 drop) in acetonitrile (1 mL) at room temperature. The mixture was stirred for 1 hour during which time acetic acid was added to maintain an acid pH (yellow indicator color). The mixture was diluted with ethyl acetate and washed with ice-cold 2.5M sodium hydroxide (2×), water (2×), brine, dried over magnesium hydroxide and concentrated in vacuo to give the title compound (51 mg) as gum. NMR (CD$_3$OD); δ 0.904 (t, 3H); 1.03 (s, 9H); 1.63 (m, 2H); 2.07 (m, 2H); 2.77 (s, 2H); 2.82 (t, 2H); 2.82 (s, 3H); 3.27 (t, 2H); 3.57 (s, 2H); 3.67 (s, 3H); 4.17 (t, 2H); 7.01 (d, 1H); 7.14 (m, 2H); 7.27 (s, 1H); 7.49 (d, 1H).

Step B: Preparation of 3-Chloro-4-(3-(3-(2,2-dimethylpropyl)-7-propyl-6-benz-[4,5]-isoxazoloxy) propyl-N-methylamino(phenylacetate)

Using the method of Example 22, substituting methyl 3-chloro-4-(3-(3-(2,2-dimethylpropyl)-7-propyl-6-benz-[4,5]-isoxazoloxy)propyl-N-methylamino)phenylacetate as starting material, the title compound was obtained. NMR (CD$_3$OD); δ 0.91 (t, 3H); 1.03 (s, 9H); 1.64 (m, 2H); 2.06 (m, 2H); 2.77 (s, 2H); 2.82 (t, 2H); 2.82 (s, 3H); 3.26 (t, 2H); 3.52 (s, 2H); 4.17 (t, 2H); 7.01 (d, 1H); 7.15 (s, 2H); 7.29 (s, 1H); 7.49 (d, 1H). Mass spec, m/e=488 (m +1).

EXAMPLE 41

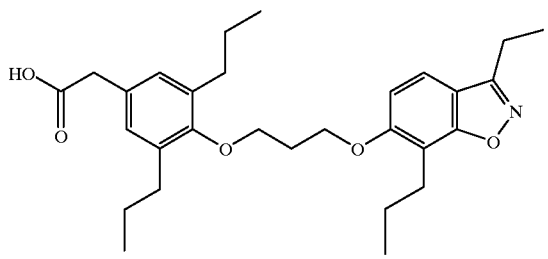

3,5-Dipropyl-4-(3-(3-ethyl-7-propyl-6-benz-[4,5]-isoxazoloxy)-propyloxy)phenylacetic acid Step A: Preparation of methyl 3-allyl-4-allyloxyphenylacetate A solution of methyl 3-allyl-4-hydroxyphenylacetate (4.10 g)(Example 17, Step B), allyl bromide (2.30 mL) and potassium carbonate (3.95 g) in 2-butanone (40 mL) was refluxed for four hours. The mixture was partioned between 0.2N HCl and ethyl acetate. The organic layer was dried over magnesium sulfate, filted, concentrated in vacuo. Column Chromatography (silica gel 60, 50% methylene chloride in hexane) gave the tittle compound.

$^1$H NMR(400 MHz, CDCl$_3$): δ 7.04 (m, 2H), 6.76 (d, 1H, J=8.2 Hz), 6.08–5.92 (m, 2H), 5.41–5.01 (m, 4H), 4.49 (m, 2H), 3.66 (s, 3H), 3.52 (s, 2H), 3.37 (d, 2H, J=6.7 Hz).

Step B: Preparation of methyl 3,5-diallyl-4-hydroxyphenylacetate

Using the method of Example 17, Step B, methyl 3-allyl-4-allyloxyphenylacetate as the starting material, the title compound was obtained.

$^1$H NMR(400 Mhz, CDCl$_3$): δ 6.90 (s, 2H), 5.98–5.94 (m, 2H), 5.14 (m, 5H), 3.66 (s, 3H), 3.49 (s, 2H), 3.37 (d, 4H, J=6.5 Hz)

Step C: Preparation of methyl 3,5-dipropyl-4-hydroxyphenylacetate

Using the method of Example 17, Step C, methyl 3,5-diallyl-4-hydroxyphenylacetate as the starting material, the title compound was obtained.

$^1$H NMR(400 MHz, CD3COCD3): δ 6.88 (s, 2H), 4.62 (s,1H), 3.68 (s, 3H), 3.51 (s, 2H), 2.54 (t, 4H, J=7.6 Hz), 1.62 (hex, 4H, J=7.5 Hz), 0.98 (t, 6H, J=7.4 Hz).

Step D: Preparation of methyl 3,5-dipropyl-4-(3-(3-ethyl-7-propyl-6-benz-[4,5]-isoxazoloxy)-propyloxy)phenylacetate Using the method of Example 17, Step D, methyl 3,5-dipropyl-4-hydroxyphenylacetate and 1-bromo-3-(3-ethyl-7-propyl-6-benz-[4,5]-isoxazoloxy)phenoxypropane as the starting material, the title compound was obtained.

$^1$H NMR(400 MHz, CDCl$_3$): δ 7.39 (d,1H, J=8.5 Hz), 6.94 (d, 1H, J=8.6 Hz), 6.90 (m, 2H), 4.31 (t, 2H, J=5.9 Hz), 3.94 (t, 2H, J=5.9 Hz), 3.66 (s, 3H), 3.51 (s, 2H), 2.95 (quart, 2H, J=7.5 Hz), 2.85 (t, 2H, J=7.3 Hz), 2.52 (m, 4H), 2.28 (quint, J=6.5 Hz), 1.71–1.52 (m, 6H), 1.40 (t, 3H, J=7.3 Hz), 0.94 (t, 3H, J=7.3 Hz), 0.84 (t, 6H, J=7.4 Hz).

Step E: Preparation of 3,5-dipropyl-4-(3-(3-ethyl-7-propyl-6-benz-[4,5]-isoxazolox y)-propyloxy)phenylacetic acid Using the method of Example 18, methyl 3,5-dipropyl-4-(3-(3-ethyl-7-propyl-6-benz-[4,5]-isoxazoloxy)-propyloxy)phenylacetate as the starting material, the title compound was obtained.

$^1$H NMR(400 MHz, CDCl$_3$): δ 7.39 (d,1H, J=8.5 Hz), 6.94 (d, 1H, J=8.6 Hz), 6.90 (m, 2H), 4.31 (t, 2H, J=5.9 Hz), 3.94 (t, 2H, J=5.9 Hz), 3.51 (s, 2H), 2.95 (quart, 2H, J=7.5 Hz), 2.85 (t, 2H, J=7.3 Hz), 2.52 (m, 4H), 2.28 (quint, J=6.5 Hz), 1.71–1.52 (m, 6H), 1.40 (t, 3H, J=7.3 Hz), 0.94 (t, 3H, J=7.3 Hz), 0.84 (t, 6H, J=7.4 Hz). ESI: MS m/e=482 (M+1)

EXAMPLE 42

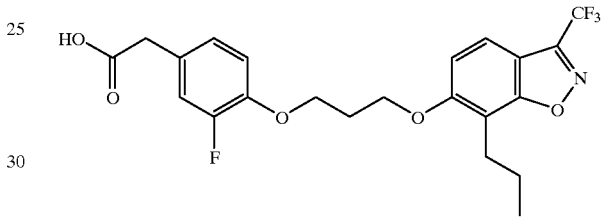

3-fluoro-4-(3-(7-propyl-3-trifluoromethyl-6-benz-[4, 5]isoxazoloxy)-propyloxy)phenylacetic acid STEP A: Preparation of Methyl 3-fluoro-4-(3-bromopropyloxy)-phenylacetate A solution of methyl 3-fluoro-4-hydroxyphenylacetate (25.545 grams) in 2-butanone (300 mL) was treated with 1,3-dibromopropane (48.79 mL) and potassium carbonate (50.859 grams). The mixture was refluxed for 4 hours. The reaction mixture was partitioned between isopropyl acetate and pH 4 buffer. The organic was washed once with water, then dried over magnesium sulfate. The organic was filtered and evaporated to an oil which was chromatographed over silica gel with hexane/methylene chloride (2:1) to afford the title compound. This compound was taken forward without further purification.

STEP B: Preparation of 3-trifluoromethyl-7-propyl-6-hydroxybenz-[4,5]-isoxazole

Using the method and materials in example 20 steps A and B the titled compound was obtained.

STEP C: Preparation of Methyl 3-fluoro-4-(3-(7-propyl-3-trifluoromethyl-6-benz-[4,5]-isoxazoloxy)propyloxy) phenylacetate Using the method in example 17 step D substituting methyl 3-fluoro-4-(3-bromopropyloxy)phenylacetate and 3-trifluoromethyl-7-propyl-6-hydroxybez-[4,5]-isoxazole as the starting materials, the titled compound was obtained.

NMR (CDCl$_3$) δ 7.54 (d,1H, J=8.79 Hz); 7.07 (d, 1H, J=8.83 Hz); 7.02 (d, 1H, J=10.25 Hz); 6.92 (m, 2H); 4.29 (t, 2H, J=5.97 Hz); 4.23 (t, 2H, J=5.98 Hz); 3.67 (s, 1H); 3.53 (s, 2H); 2.88 (t, 2H, J=7.49 Hz); 2.33 (m, 2H, J=6.03 Hz); 1.65 (m, 2H); 0.91 (t, 3H, J=7.41 Hz).

STEP D: Preparation of 3-fluoro-4-(3-(7-propyl-3-trifluoromethyl-6-benz-[4,5]-isoxazoloxy)propyloxy) phenylacetic acid Using the method in example 2 step A, substituting Methyl 3-fluoro-4-(3-(7-propyl-3-trifluoromethyl-6-benz-[4,5]-isoxazoloxy)propyloxy)phenylacetate as the starting material, the titled compound was obtained.

NMR (CDCl₃) δ 7.53 (d,1H, J=8.42 Hz); 7.07 (d, 1H, J=8.82 Hz); 7.01 (d, 1H, J=10.18 Hz); 6.93 (m, 2H); 4.29 (t, 2H, J=5.94 Hz); 4.23 (t, 2H, J=6.06 Hz); 3.56 (s, 2H); 2.87 (t, 2H, J=7.40 Hz); 2.33 (m, 2H, J=5.98 Hz); 1.66 (m, 2H); 0.91 (t, 3H, J=7.41 Hz). ESI: Mass spec: m/e=456 (M+1).

EXAMPLE 43

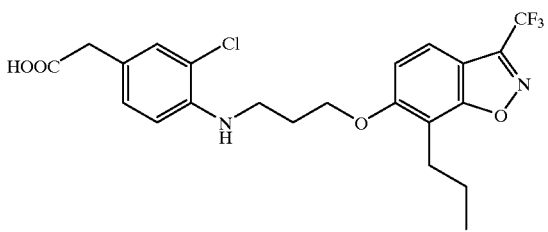

3-chloro-4-(3-(3-trifluoromethyl-7-propyl-6-benz-[4,5]-isoxazoloxy)propylamino)phenylacetic acid STEP A: Preparation of 3-trifluoromethyl-7-propyl-6-hydroxybenz-[4,5]-isoxazole Using the method and materials in example 20 steps A and B the titled compound was obtained.

STEP B: Preparation of Methyl 3-chloro-4-(3-bromopropylamino)-phenylacetate

Magnesium oxide (10 grams, 250 mmoles), was added to a solution of 1,3-dibromopropane (139 grams, 70 mL, 700 mmoles) in dimethylacetamide (150 mL). A solution of methyl 3-chloro-4-aminophenylacetate.HCl (23.6 grams, 100 mmoles) in dimethylacetmide (200 mL) was added dropwise over 30 minutes and the mixture stirred at 80° C. for 6 hours. The cooled mixture was partitioned with methylene chloride and water. The aqueous phase was extracted with methylene choride and the combined organic phases washed with brine, dried over magnesium sulfate and concentrated in vacuo to an oil. The crude product was chromatographed on a silica gel column eluting with hexane-:ethyl acetate (9:1). The product was further purified by a second silica gel chromatography in methylene chloride-:hexane (2:3) to give the title compound as an oil. NMR, (CDCl₃): δ 2.15 (qnt, 2H); 3.35 (q, 2H); 3.47 (s,2H); 3.49 (t, 2H); 3.67 (s, 3H); 6.63 (d, 1H); 7.03 (dd, 1H); 7.17 (d, 1H).

STEP C: Methyl 3-chloro-4-(3-(3-trifluoromethyl-7-propyl-6-benz-[4,5]-isoxazoloxy)propylamino)phenylacetate Using the method in example 17 step D substituting Methyl 3-chloro-4-(3-bromopropylamino)phenylacetate and 3-trifluoromethyl-7-propyl-6-hydroxybenz-[4,5]-isoxazole as the starting materials, the titled compound was obtained.

NMR (CDCl₃) δ 7.54 (d,1H, J=8.10 Hz); 7.18 (s, 1H); 7.03 (m, 2H); 6.64 (d, 1H, J=8.34 Hz); 4.39 (bs, 1H); 4.20 (t, 2H, J=5.86 Hz); 3.66 (s, 3H); 3.47 (s, 2H); 3.42 (t, 2H, J=6.83 Hz); 2.92 (t, 2H, J=7.58 Hz); 2.18 (m, 2H); 1.69 (m, 2H); 0.95 (t, 3H, J=7.41 Hz).

STEP D: 3-chloro-4-(3-(3-trifluoromethyl-7-propyl-6-benz-[4,5]-isoxazoloxy)propylamino)phenylacetic acid A solution of Methyl 3-chloro-4-(3-(3-trifluoromethyl-7-propyl-6-benz-[4,5]-isoxazoloxy)propylamino)-phenylacetate (Step C, 0.113 grams) in methanol (1.5 mL) was treated with a solution of lithium hydroxide in water (1.01 M; 0.362 mL). The reaction was refluxed 1 hour. The reaction mixture was partitioned between isopropyl acetate and 0.1N HCl. The organic was dried over magnesium sulfate, filtered and concentrated to a solid. The solid was suspended in methylene chloride/cyclohexane (1:1; 2 mL). The mixture was refluxed briefly and cooled to 0° C. The title compound was isolated by filtration.

NMR (CDCl₃) δ 7.54 (d,1H, J=8.10 Hz); 7.18 (s, 1H); 7.03 (m, 2H); 6.64 (d, 1H, J=8.34 Hz); 4.19(t, 2H, J=5.86 Hz); 3.50 (s, 2H); 3.43 (t, 2H, J=6.83 Hz); 2.92 (t, 2H, J=7.58 Hz); 2.18 (m, 2H); 1.69 (m, 2H); 0.95 (t, 3H, J=7.41 Hz). ESI: Mass spec: m/e=471 (M+1).

EXAMPLE 44

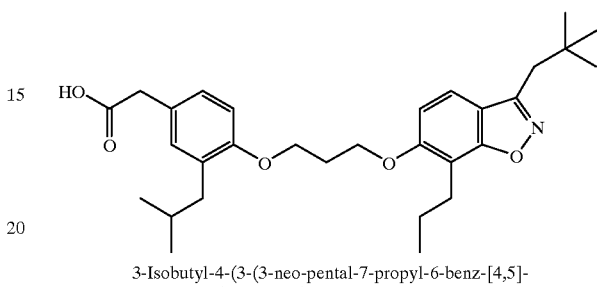

3-Isobutyl-4-(3-(3-neo-pental-7-propyl-6-benz-[4,5]-isoxazoloxy)-proploxy)phenylacetic acid Step A: Preparation of methyl 4-methallyloxyphenylacetate Using the method of Example 17, step A, methallyl bromide as the starting material, the title compound was obtained.

¹H NMR(400 MHz, CDCl₃): δ 7.16 (d, 2H, J=8.5 Hz), 6.86 (dd, 2H, J=8.6, 2.1 Hz), 5.06 (s, 1H), 4.97 (s, 1H), 4.39 (s, 2H), 3.66 (s, 3H), 3.54 (s, 2H), 1.80 (s, 3H).

Step B: Preparation of methyl 4-hydroxy-3-methallylphenylacetate

Using the method of Example 17, step B, methyl 4-methallyloxyphenylacetate as the starting material, the title compound was obtained.

¹H NMR(400 MHz, CDCl₃): δ 7.03 (dd, 1H, J=8.1, 2.2 Hz), 6.98 (d, 1H, J=2.5 Hz), 6.98 (d, 1H, J=8.2 Hz), 5.18 (s, 1H), 4.90 (s, 1H), 4.82 (s, 1H), 3.66 (s, 3H), 3.52 (s, 2H), 3.33 (s, 2H).

Step C: Preparation of methyl 4-hydroxy-3-isobutylphenylacetate

Using the method of Example 17, step C, methallyl bromide as the starting material, the title compound was obtained.

¹H NMR(400 MHz, CDCl₃): δ 6.95 (m, 2H), 6.66 (d, 2H, J=8.2 Hz), 3.70 (s, 3H), 3.54 (s, 2H), 2.43 (d, 2H, J=7.5 Hz), 1.91 (m, 1H), 0.92 (d, 6H, J=7.6 Hz).

Step D: Preparation of methyl 3-isobutyl-4-(3-(3-neo-pental-7-propyl-6-benz-[4,5]-isoxazoloxy)-propyloxy) phenylacetate Using the method of Example 17, step D, methyl 4-hydroxy-3-isobutylphenylacetate and 1-bromo-3-(3-neo-pental-7-propyl-6-benz-[4,5]-isoxazoloxy)phenoxypropane as the starting material, the title compound was obtained.

¹H NMR(400 MHz, CDCl₃): δ 7.34 (d, 1H, J=8.7 Hz), 7.04 (dd, 1H, J=8.3, 2.2 Hz), 6.97 (d,1H, J=2.2 Hz), 6.90 (d, 1H, J=8.7 Hz), 6.78 (d, 1H, J=8.2 Hz), 4.24 (t, 2H, J=6.1 Hz), 4.14 (t, 2H, J=5.9 Hz), 3.66 (s, 3H), 3.51 (s, 2H), 2.83 (t, 2H, J=7.4 Hz), 2.78 (s, 2H), 2.42 (d, 2H, J=7.0 Hz), 2.30 (quint, 2H, J=6.0 Hz), 1.83 (m, 1H), 1.64 (m, 2H), 1.02 (s, 9H), 0.91 (t, 3H, J=7.4 Hz), 0.82 (d, 6H, J=6.7 Hz).

Step E: Preparation of 3-isobutyl-4-(3-(3-neo-pental-7-propyl-6-benz-[4,5]-isoxazoloxy)-propyloxy)phenylacetic acid Using the method of Example 18, the product of step D was saponified to give the title compound.

¹H NMR(400 MHz, CDCl₃): δ 7.34 (d, 1 H, J=8.7 Hz), 7.04 (dd, 1H, J=8.3, 2.2 Hz), 6.97 (d,1H, J=2.2 Hz), 6.90 (d, 1H, J=8.7 Hz), 6.78 (d, 1H, J=8.2 Hz), 4.24 (t, 2H, J=6.1 Hz), 4.14 (t, 2H, J=5.9 Hz), 3.51 (s, 2H), 2.83 (t, 2H, J=7.4 Hz), 2.78 (s, 2H), 2.42 (d, 2H, J=7.0 Hz), 2.30 (quint, 2H, J=6.0 Hz), 1.83 (m, 1H), 1.64 (m, 2H), 1.02 (s, 9H), 0.91 (t, 3H, J=7.4 Hz), 0.82 (d, 6H, J=6.7 Hz). ESI: MS m/e=496 (M+1)

EXAMPLE 45

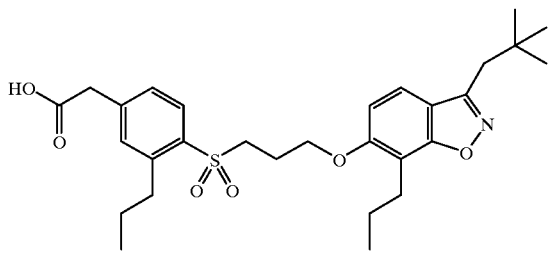

3-Propyl-4-(3-(3-neo-pental-7-propyl-6-benz-[4,5]-isoxazoloxy) propylthio)phenylacetic acid S,S-dioxide Step A: Preparation of methyl 3-propyl-4-(3-(3-neo-pental-7-propyl-6-benz-[4,5]-isoxazoloxy)propylthio) phenylacetate S,S-dioxide Using the method of Example 13, methyl 3-propyl-4-(3-(3-neo-pental-7-propyl-6-benz-[4,5]-isoxazoloxy) propylthio)phenylacetate as the starting material, the title compound was obtained.

¹H NMR(400 MHz, CDCl₃): δ 7.96 (d, 1H, J=8.6 Hz), 7.33 (d, 1H, J=8.6 Hz), 7.32 (m, 2H), 6.92 (d, 1H, J=8.7 Hz), 4.12 (t, 2H, J=5.9 Hz), 3.69 (s, 3H), 3.66 (s, 2H), 3.35 (t, 2H, J=7.5 Hz), 2.94 (t, 2H, J=7.9 Hz), 2.78 (2H, J=8.0 Hz), 2.27 (m, 2H), 1.74–1.58 (m, 4H), 1.02 (s, 9H), 0.98 (t, 3H, J=7.4 Hz), 0.98 (t, 3H, J=7.3 Hz)

Step B: Preparation of 3-propyl-4-(3-(3-neo-pental-7-propyl-6-benz-[4,5]-isoxazoloxy)propylthio)phenylacetic acid S,S-dioxide Using the method of Example 14, methyl 3-propyl-4-(3-(3-neo-pental-7-propyl-6-benz-[4,5]-isoxazoloxy) propylthio)phenylacetate S,S-dioxide as the starting material, the title compound was obtained. ¹H NMR(400 MHz, CDCl₃): δ 7.96 (d, 1H, J=8.6 Hz), 7.33 (d, 1H, J=8.6 Hz), 7.32 (m, 2H), 6.92 (d, 1H, J=8.7 Hz), 4.12 (t, 2H, J=5.9 Hz), 3.66 (s, 2H), 3.35 (t, 2H, J=7.5 Hz), 2.94 (t, 2H, J=7.9 Hz), 2.78 (2H, J=8.0 Hz), 2.27 (m, 2H), 1.74–1.58 (m, 4H), 1.02 (s, 9H), 0.98 (t, 3H, J=7.4 Hz), 0.98 (t, 3H, J=7.3 Hz) ESI: MS m/e=530 (M+1)

EXAMPLE 46

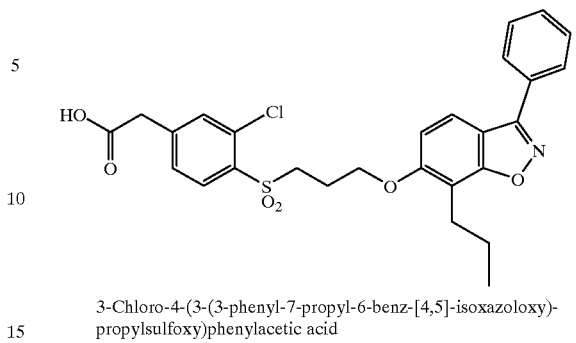

3-Chloro-4-(3-(3-phenyl-7-propyl-6-benz-[4,5]-isoxazoloxy)-propylsulfoxy)phenylacetic acid Step 1

The acid prepared in Example 16 Step 5 (19.2 mg, 1.0 Eq, 0.04 mmol) was dissolved in methylene chloride (0.3 ml) with mCPBA (85%, 18.2 mg, 2.3 Eq, 0.11 mmol). At 1 ¼ Hr the mixture was diluted with EtOAc and sodium bisulfite 10% aq. The EtOAc extract was washed again with sodium bisulfite 10% aq, followed by NaCl sat'd aq. The EtOAc extracts were dried over MgSO₄ and reduced to an oil i. vac. The product was purified by elution from a reversed phase RP-8 col (E. Merck 40–63µ) with 65:35 CH₃CN:H₂O 0.1% TFA. The ester is obtained as a glass.

Analytical HPLC 75:25 CH₃CN:H₂O 0.1% TFA, E. Merck RP-8 5µ 4×250 mm, 1 ml/min. UV 210, RT 7.73 min. Characteristic NMR Resonances; ¹H NMR 400 MHz (CDCl₃); 8.09 (d, 1H, J=8.1 Hz), 7.90 (m, 1H), 7.62 (d, 1H, J=8.7 Hz), 7.52 (m, 4H), 7.38 (dd, 1H, J=8.2, 1.6 Hz), 6.89 (d, 1H, J=8.8 Hz), 4.17 (t, 2H, J=5.8 Hz), 3.70 (s, 2H), 3.67 (m, 2H), 2.87 (t, 2H, J=7.4 Hz), 2.28 (m, 2H), 1.67 (sext, 2 H, 7.5 Hz), 0.93 (t, 3H, J=7.36 Hz). MS ESI M+1=528.3. MW=527.1

EXAMPLE 47

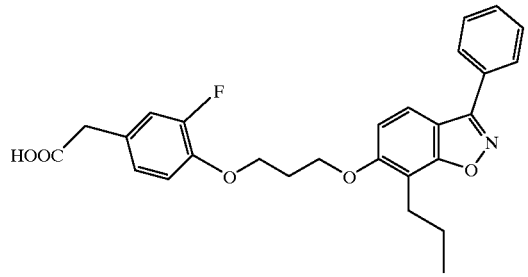

3-fluoro-4-(4-(3-phenyl-7-propyl-6-benz-[4, 5]-isoxazoloxy)-butyloxy)phenylacetic acid STEP A: Preparation of Methyl 3-fluoro-4-(4-bromobutyloxy)-phenylacetate A solution of methyl 3-fluoro-4-hydroxyphenylacetate and 1,4-dibromobutane (Step A; 0.552 grams) in 2-butanone (6 mL) was treated with 3-propyl-2,4-dihydroxypropiophenone (0.299 grams). Potassium carbonate (0.217 grams) was added and the mixture refluxed for 4 hours. The reaction was partitioned between isopropyl acetate and pH 4 phosphate buffer. The organic was dried over magnesium sulfate, filtered and evaporated to a residue which was chromatographed over silica gel to give the product.

NMR (CDCl$_3$) δ 7.08 (d, 1H); 6.91 (m, 2H); 4.05 (t, 2H); 3.69 (s, 3H);3.52 (s, 2H); 3.48 (t, 2H); 2.06 (m, 2H); 1.97 (m, 2H).

STEP B: Preparation of 3-phenyl-7-propyl-6-hydroxybenz-[4,5]-isoxazole

Using the method and materials in example 16 steps 1A, 1, 2, and 3 the titled compound was obtained.

STEP C: Preparation of Methyl 3-fluoro-4-(4-(3-phenyl-7-propyl-6-benz-[4,5]-isoxazoloxy)butyloxy)phenylacetate Using the method in example 23 step 3 substituting Methyl 3-fluoro-4-(4-bromobutyloxy)phenylacetate as the starting material, the titled compound was obtained.

NMR (CDCl$_3$) δ 7.92 (m, 2H); 7.64 (d, 1H, J=8.70 Hz); 7.51 (m, 3H); 6.97 (m, 4H); 4.12 (m, 4H); 3.67 (s, 3H);3.53 (s, 2H); 2.90 (t, 2H, J=7.35 Hz); 2.02 (m, 4H); 1.71 (m, 2H); 0.96 (t, 3H, J=7.36 Hz).

STEP D: Preparation of 3-fluoro-4-(4-(3-phenyl-7-propyl-6-benz-[4,5]-isoxazoloxy)butyloxy)phenylacetic acid Using the method in example 23 step 4 substituting Methyl 3-fluoro-4-(4-(3-phenyl-7-propyl-6-benz-[4,5]-isoxazoloxy)butyloxy)-phenylacetate as the starting material, the titled compound was obtained.

NMR (CDCl$_3$) δ 7.93 (m, 2H); 7.65 (d, 1H, J=8.70 Hz); 7.51 (m, 3H); 6.98 (m, 4H); 4.12 (m, 4H); 3.58(s, 2H); 2.90 (t, 2H, J=7.35 Hz); 2.02 (m, 4H); 1.71 (m, 2H); 0.99 (t, 3H, J=7.36 Hz). ESI: Mass spec: m/e=479 (M+1).

EXAMPLE 48

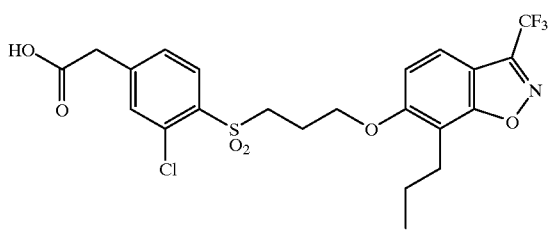

3-chloro-4-(3-(7-propyl-3-trifluoromethyl-6-benz-[4, 5]-isoxazoloxy)propyl-thio)phenylacetic acid S,S-dioxide STEP A: Preparation of Methyl 3-chloro-4-(3-(7-propyl-3-trifluoromethyl-6-benz-[4,5]-isoxazoloxy)propyl-thio) phenylacetate Using the method and materials in example 20 step A, B and C the titled compound was obtained.

STEP B: Preparation of Methyl 3-chloro-4-(3-(7-propyl-3-trifluoromethyl-6-benz-[4,5]-isoxazoloxy)propyl-thio) phenylacetate S, S-dioxide Using the method in example 13 substituting Methyl 3-chloro-4-(3-(7-propyl-3-trifluoromethyl-6-benz-[4,5]-isoxazoloxy)propyl-thio)phenylacetate as the starting material and using 2 equivalents of the oxidating agent, the titled compound was obtained. This compound was filtered through a pad of silica gel using ethyl ether and hexane (1:1) as the mobile phase, and taken forward without further purification.

STEP C: Preparation of 3-chloro-4-(3-(7-propyl-3-trifluoromethyl-6-benz-[4,5]-isoxazoloxy)propyl-thio) phenylacetic acid S, S-dioxide Using the method in example 2 step A, substituting Methyl 3-chloro-4-(3-(7-propyl-3-trifluoromethyl-6-benz-[4,5]-isoxazoloxy)propyl-thio)phenylacetate S, S-dioxide as the starting material, the titled compound was obtained.

NMR (CDCl$_3$) δ 8.09 (d, 1H, J=8.15 Hz); 7.51 (m, 2H); 7.39 (d, 1H, J=5.38 Hz); 6.97 (d, 1H, J=8.87 Hz); 4.18 (t, 2H, J=5.86 Hz); 3.71 (s, 2H); 3.64 (t, 2H, J=7.49 Hz); 2.85 (t, 2H, J=7.41 Hz); 2.30 (m, 2H); 1.64 (m, 2H); 0.91 (t, 3H, J=7.36 Hz). ESI: Mass spec: m/e=520 (M+1).

EXAMPLE 49

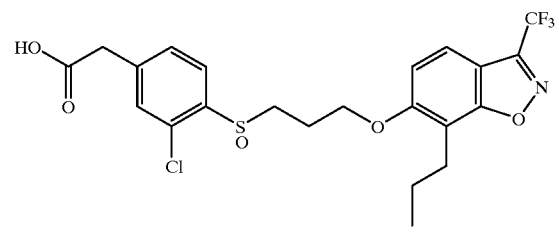

3-chloro-4-(3-(7-propyl-3-trifluoromethyl-6-benz-[4, 5]-isoxazoloxy)propyl-thio)phenylacetic acid S-oxide STEP A: Preparation of Methyl 3-chloro-4-(3-(7-propyl-3-trifluoromethyl-6-benz-[4,5]-isoxazoloxy)propyl-thio) phenylacetate S-oxide Using the method in example 11 substituting Methyl 3-chloro-4-(3-(7-propyl-3-trifluoromethyl-6-benz-[4,5]-isoxazoloxy)propyl-thio)phenylacetate as the starting material, (Example 20, step C) the titled compound was obtained. This compound was filtered through a pad of silica gel using ethyl ether and hexane (1:1) as the mobile phase, and taken forward without further purification.

STEP B: Preparation of 3-chloro-4-(3-(7-propyl-3-trifluoromethyl-6-benz-[4,5]-isoxazoloxy)propyl-thio) phenylacetic acid S-oxide Using the method in example 2 substituting Methyl 3-chloro-4-(3-(7-propyl-3-trifluoromethyl-6-benz-[4,5]-isoxazoloxy)propyl-thio)phenylacetate S-oxide as the starting material, the titled compound was obtained.

NMR (CDCl$_3$) δ 7.85 (d, 1H, J=8.02 Hz); 7.52 (d, 2H, J=8.79 Hz); 7.43 (d, 1H, J=6.43 Hz); 7.35 (s, 1H); 6.99 (d, 1H, J=8.87 Hz); 4.18 (m, 2H); 3.68 (s, 2H); 3.38 (m, 1H); 3.02 (m, 1H); 2.84 (t, 2H, J=7.49 Hz); 2.44 (m, 1H); 2.18 (m, 1H); 1.63 (m, 2H); 0.91 (m, 3H). ESI: Mass spec: m/e=504 (M+1).

EXAMPLE 50

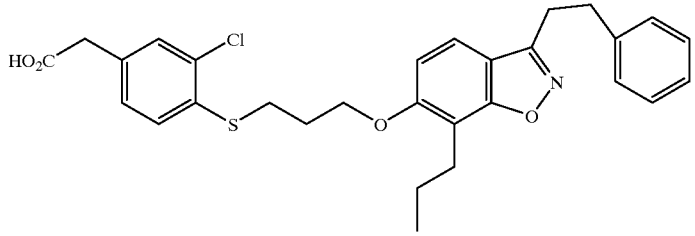

3-chloro-4-(3-(2-phenylethyl-7-propyl-6-benz[4,5]isoxazoloxy)propyl-thio) phenylacetic acid Step A Preparation of 1,3-dihydroxy-4-(3-phenylpropionyl)-2-(n-propyl)benzene Using the procedure in Example 51, step 1, 3-phenylpropionic acid and 2-(n-propyl)resorcinol were condensed in triflic acid to form 1,3-dihydroxy-4-(3-phenylpropionyl)-2-(n-propyl)benzene.

NMR (CDCl$_3$): d 7.20 (d, 1H); 7.19–7.33 (m, 5H); 6.33 (d, 1H); 5.28 (s, 1H); 3.24 (t, 2H); 3.04 (t, 2H); 2.63 (t, 2H); 1.57 (m, 2H); 0.99 (t, 3H).

Step B Preparation of 6-hydroxy-3-(2-phenylethyl)-7-(n-propyl)benz-[4,5]isoxazole Using the procedures in Example 51, steps 2 and 3, 1,3-dihydroxy-4-(3-phenylpropionyl)-2-(n-propyl)benzene was converted into 6-hydroxy-3-(2-phenylethyl)-7-(n-propyl)benz[4,5]isoxazole.

NMR (CDCl$_3$): d 7.21–7.32 (m, 5H); 7.18 (d, 1H); 6.77 (d, 1H); 5.32 (vbs, 1H); 3.22 (m, 2H); 3.14 (m, 2H); 2.77 (t, 2H); 1.74 (m, 2H); 1.00 (t, 3H).

Step C Preparation of methyl 3-chloro-4-(3-(2-phenylethyl)-7-propyl-6-benz[4,5]isoxazoloxy)propylthio)phenylacetate Using the procedure in Example 16, step 4, 6-hydroxy-3-(2-phenylethyl)-7-(n-propyl)benz [4,5]isoxazole and methyl 3-chloro-4-(3-bromopropylthio)phenylacetate were heated in DMF with Cs$_2$CO$_3$ to prepare methyl 3-chloro-4-(3-(2-phenylethyl)-7-propyl-6-benz[4,5]-isoxazoloxy) propylthio)phenylacetate.

NMR (CDCl$_3$): d 7.21–7.35 (m, 8H); 7.13 (dd, 1H); 6.87 (d, 1H); 4.19 (t, 2H); 3.71 (s, 3H); 3.57 (s, 2H); 3.12–3.27 (m, 6H); 2.88 (t, 2H); 2.20 (m, 2H), 1.70 (m, 2H); 0.95 (t, 3H).

Step D Preparation of 3-chloro-4-(3-(2-phenylethyl)-7-propyl-6-benz [4,5]isoxazoloxy)propylthio)phenylacetic acid Using the procedure in Example 2, methyl 3-chloro-4-(3-(2-phenylethyl)-7-propyl-6-benz[4,5]isoxazoloxy) propylthio)-phenylacetate was saponified with LiOH to form 3-chloro-4-(3-(2-phenylethyl)- 7-propyl-6-benz[4,5] isoxazoloxy)propylthio)phenylacetic acid.

NMR (CDCl$_3$): d 7.21–7.35 (m, 8H); 7.13 (dd, 1H); 6.87 (d, 1H); 4.19 (t, 2H); 3.60 (s, 2H); 3.12–3.26 (m, 6H); 2.88 (t, 2H); 2.20 (m, 2H); 1.69 (m, 2H); 0.95 (t, 3H)

EXAMPLE 51

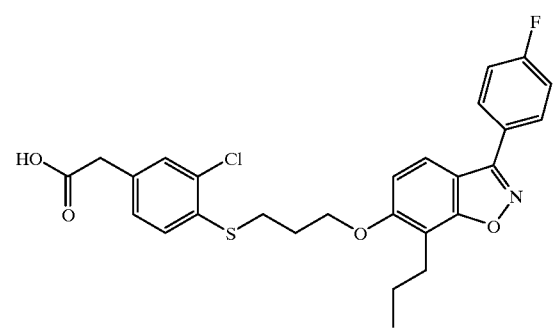

3-chloro-4-(3-(3-(4-fluorophenyl)-7-propyl-6-benz-[4,5]-isoxazoloxy)-propylthio)phenylacetic acid Step 1

Commercially available 2-propylresorcinol (3.0 g, 1.0 Eq, 0.019 mol) and p-fluorobenzoic acid (3.2 g, 1.15 Eq, 0.023 mol) were dissolved in trifluoromethanesulfonic acid (10 ml) at RT. The mixture was heated to 85° C. under N$_2$. At 2 ½ hrs, the reaction was cooled to RT and poured into H$_2$O. The mixture was extracted with EtOAc. The extracts were washed with NaHCO$_3$ sat'd. aq., washed with NaCl aq sat'd, and dried over MgSO$_4$. The EtOAc solution was reduced i. vac The product was purified by elution from a silica gel column (20 g E. Merck 40–63μ) with toluene: EtOAc 98:2.

Characteristic NMR Resonances; $^1$H NMR 400 MHz (CDCl$_3$); 7.64 (m, 2H), 7.30 (d, 1H, J=8.8 Hz), 7.15 (m, 2H), 6.31 (d, 2H, J=8.8 Hz), 5.47 (s, 1H), 2.66 (dd, 2H, J=9.3, 7.6 Hz), 1.60 (m, 2H), 0.99 (t, 3H). MS ESI M+1=275.1. MW=274.1

Step 2

The ketone of Example 52 step 1 (2.5 g, 1.0 Eq, 9.1 mmol) was converted to the oxime with NH$_2$OH—HCl (2.54 g, 4.0 Eq, 37 mmol) as for the procedure of Example 7 Step A.The product was purified by recrystallization from toluene to provide one isomer.

Characteristic NMR Resonances; $^1$H NMR 400 MHz (CDCl$_3$); 7.27 (m, 2H), 7.17 (m, 2H), 6.50 (d, 1H, J=8.7 Hz), 6.21 (d, 1H, J=8.7 Hz), 2.66 (dd, 2H, J=9.3, 7.6 Hz), 1.61 (sext, 2H, J=7.7 Hz), 0.99 (t, 3H, J=7.4 Hz). MS ESI M+1=290. MW=289.

Step 3

The oxime of Example 51 step 2 (1.45 g, 5 mmol) was converted to the 3-(p-fluorophenyl)-6-hydroxy-7-propylbenzisoxazole as for Example 7 Step A. The product was purified by recrystallization from toluene.

Characteristic NMR Resonances; $^1$H NMR 400 MHz (CDCl$_3$); 7.90 (m, 2H), 7.52 (d, 2H, J=8.5 Hz), 7.2 (m, 2H), 6.86 (d, 1H, J=8.6 Hz), 5.14 (s, 1H), 2.90 (dd, 2H, J unresolved), 1.75 (sext, 2H, J=7.5 Hz), 1.01 (t, 3H, J=7.3 Hz). MS ESI M+1=272.0. MW=271.1

Step 4

The 3-(p-fluorophenyl)-6-hydroxy-7-propylbenzisoxazole of Example 51 Step 3 (285 mg, 1.0 Eq, 1 mmol) was coupled with the bromide of Example 16 Step 1A (390 mg, 1.1 Eq, 1.1 mmol) as for Example 16 Step 4. The product was purified by elution from a silica gel column (40 g E. Merck 40–63µ) with toluene: hexanes: EtOAc 70:26:4.

Characteristic NMR Resonances; $^1$H NMR 400 MHz (CDCl$_3$); 7.91 (m, 2H), 7.60 (d, 1H, J=8.7 Hz), 7.26 (m, 4H), 7.11 (dd, 1H, J=8.1, 1.8 Hz), 6.96 (d, 1H, 8.8 Hz), 4.21 (t, 2H, J=5.8 Hz), 3.68 (s, 2H), 3.54 (s, 2H), 3.17 (t, 2H, J=7.1 Hz), 2.91 (dd, 2H, J unresolved), 2.19 (pent, 2H, J=5.9 Hz), 1.71 (sext, 2H, J=7.5 Hz), 0.96 (t, 3H, J=7.4 Hz). MS ESI M+1=528.3. MW=527.1

Step 5

The ester of Example 51 Step 4 (344 mg, 1.0 Eq, 0.65 mmol) was hydrolyzed with LiOH (869 µL, 1.5 N, 2.0 Eq, 1.3 mmol) as described in Example 16 Step 5.The product is purified by recrystallization from MeOH.

Characteristic NMR Resonances; $^1$H NMR 400 MHz (CDCl$_3$); 7.89–7.94 (m, 2H), 7.59 (d, 1H, J=8.8 Hz), 7.2–7.5 (m, 4H), 7.11 (dd, 1H, J=8.1, 1.9 Hz), 6.96 (d, 1H, 8.8 Hz), 4.20 (t, 2H, J=5.8 Hz), 3.58 (s, 2H), 3.17 (t, 2H, J=7.1 Hz), 2.91 (t, 2H, J=7.6 Hz), 2.20 (pent, 2H, J=6.1 Hz), 1.70 (sext, 2H, J=7.5 Hz), 0.96 (t, 3H, J=7.4 Hz). HPLC; 60:40 to 85:15 CH$_3$CN:H$_2$O 0.1% TFA 25 min linear gradient. E. Merck 5µ RP-8 4×250 mm. RT 16.2 min. UV 210 nM. MS ESI M+1=514.2. MW=513.1

EXAMPLE 52

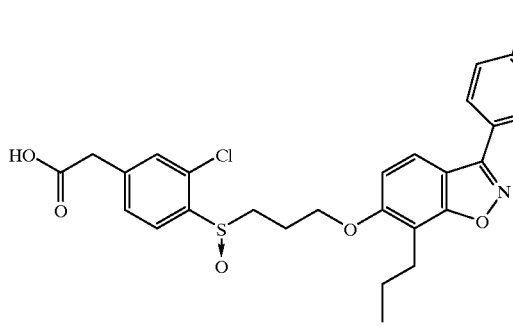

3-Chloro-4-(3-(3-(4-fluorophenyl)-7-propyl-6-benz-[4,5]-isoxazoloxy)-propylsulfinyl)phenylactic acid Step 1

The ester of Example 51 Step 4 (60 mg, 1.0 Eq, 0.114 mmol) was combined with mCPBA (85%, 33.4 mg, 1.5 Eq, 0.165 mmol) in methylene chloride (0.5 ml) at 0° C. The mixture was stirred at 0° C. for 2 Hrs, followed by stirring at RT for 1 ½ Hrs. The mixture was diluted with EtOAc and sodium thiosulfate ~10% aq. The EtOAc extract was washed again with sodium thiosulfate ~10% aq, followed by NaHCO$_3$ sat'd. aq. and NaCl sat'd aq. The EtOAc extracts were dried over MgSO$_4$ and reduced to an oil i. vac. Two products were recovered by elution from a silica gel column (2.5 g E. Merck 40–63µ) with toluene: EtOAc 91:9

Sulfoxide:

Characteristic NMR Resonances; $^1$H NMR 400 MHz (CDCl$_3$); 7.8–7.9 (m, 2H), 7.85 (d, 1H, J=8.1 Hz), 7.59 (d, 1H, J=8.8 Hz), 7.42 (dd, 1H, J=8.1, 1.8 Hz), 7.34 (d, 1H, J=1.7 Hz), 7.2 (m, 2H), 6.93 (d, 1H, J=8.8 Hz), 4.15–4.26 (complex m, 2H), 3.70 (s, 3H), 3.65 (s, 2H), 3.33–3.64 (complex m, 1H), 2.97–3.04 (complex m, 1H), 2.86 (dd, 2H, J=8.8, 7.5 Hz), 2.40–2.47 (complex m, 1 H), 2.12–2.22 (complex m, 1H), 1.68 (sext, 2H, J=7.5 Hz), 0.933 (t, 3H, J=7.4 Hz). MS ESI M+1=544. MW=543.5

Sulfone:

Characteristic NMR Resonances; $^1$H NMR 400 MHz (CDCl$_3$); 8.09 (d, 1H, J=8.1 Hz), 7.9 (m, 2H), 7.58 (d, 1H, J=8.7 Hz), 7.49 (d, 1H, J=1.7 Hz), 7.38 (dd, 1H, J=8.1, 1.7 Hz), 7.14–7.24 (m, 2H), 6.90 (d, 1H, J=8.8 Hz), 4.18 (t, 2H, J=5.8 Hz), 3.71 (s, 3H), 3.67 (s, 2H), 3.66 (t, 2H, J obscured), 2.87 (dd, 2H, J=8.6, 7.4 Hz), 2.30 (m, 2H), 1.67 (sext, 2H, J=7.4 Hz), 0.94 (t, 3H, J=7.4 Hz). MS ESI M+1=560.4. MW=559.5

Step 2

The sulfoxide of Example 52 step 1(45 mg, 1.0 Eq, 0.083 mmol) was hydrolyzed with LiOH (110 µL, 1.5 N, 2.0 Eq, 0.166 mmol) as described in Example 16 Step 5.

Characteristic NMR Resonances; $^1$H NMR 400 MHz (CDCl$_3$); 7.88–7.92 (m, 2H), 7.85 (d, 1H, J=8.1 Hz), 7.58 (d, 1H, J=8.7 Hz), 7.42 (d, 1H, J=8.1 Hz), 7.35 (s, 1H), 7.21 (m, 2H), 6.91 (d, 1H, J=8.7 Hz), 4.1–4.25 (complex m, 2H), 3.67 (s, 2H), 3.35–3.42 (complex m, 1H), 2.99–3.06 (complex m, 1H), 2.85 (t, 2H, J=7.4 Hz), 2.38–2.45 (complex m, 1H), 2.1–2.2 (complex m, 1H), 1.65 (sext, 2H, J=7.4 Hz), 0.916 (t, 3H, J=7.3 Hz). HPLC; 65:35 CH$_3$CN:H$_2$O 0.1% TFA isocratic. E. Merck 5µ RP-8 4×250 mm. RT 7.4 min. UV 210 nM. MS ESI M+1=530.3. MW=529.1

EXAMPLE 53

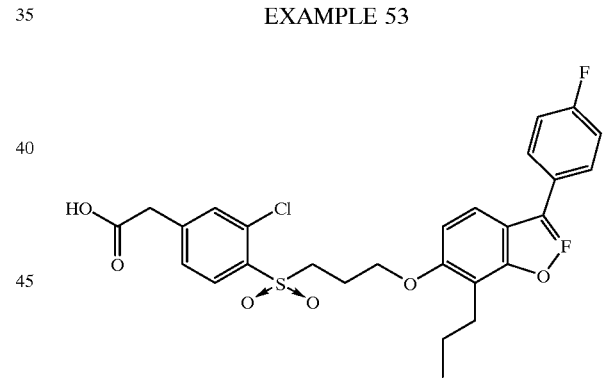

3-Chloro-4-(3-(3-(4-fluorophenyl)-7-propyl-6-benz-[4,5]-isoxazoloxy)-propylsulfonyl))phenylacetic acid Step 1

The sulfone of Example 52 step 1(13 mg, 1.0 Eq, 0.023 mmol) was hydrolyzed with LiOH (31 µL, 1.5 N, 2.0 Eq, 0.046 mmol) as described in Example 16 Step 5.

Characteristic NMR Resonances; $^1$H NMR 400 MHz (CDCl$_3$); 8.08 (d, 1H, J=8.1 Hz), 7.89 (m, 2H), 7.58 (d, 1H, J=8.7 Hz), 7.49 (d, 1H, J=1.5 Hz), 7.37 (dd, 1H, J=8.1, 1.5 Hz), 7.20 (m, 2H), 6.89 (d, 1H, J=8.8 Hz), 4.17 (t, 2H, J=5.8 Hz), 3.69 (s, 2H), 3.66 (dd, 2H, J obscured), 2.86 (dd, 2H, J unresolved), 2.25–2.31 (m, 2H), 1.66 (sext, 2H, J=7.5 Hz), 0.924 (t, 3H, J=7.4 Hz). HPLC; 65:35 CH$_3$CN:H$_2$O 0.1% TFA isocratic. E. Merck 5µ RP-8 4×250 mm. RT 8.1 min. UV 210 nM. MS ESI M+1=546.3. MW=545.1

EXAMPLE 54

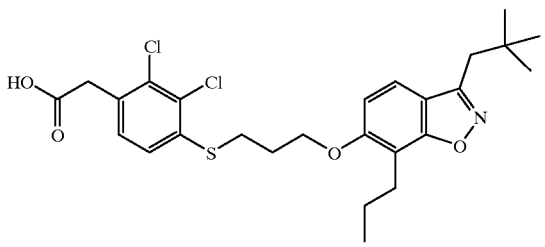

2,3-Dichloro-4-(3-(3-neo-pental-7-propyl-6-benz-[4,5]-isoxazoloxy)-propylthio)phenylacetic acid Step A: Preparation of methyl 2,3-dichloro-4-dimethylcarbamoylthiophenylacetate A solution of methyl 2,3-dichloro-4-dimethylthiocarbamoyloxyphenylacetate (5.0 g) andin tetramethylene sulfone (65 mL) was heated to reflux for 20 minutes. After 20 minutes, the reaction was cooled as rapidly as possible with a stream of air. The mixture was partitioned between water and ether. The combined organics were washed with water and brine, dried over magnessium sulfate, poured onto a column of silica gel and eluted with ethyl acetate/hexane (20/80) to give the title compound.

$^1$H NMR(400 MHz, CDCl$_3$): δ 7.49 (d, 1H, J=8.3 Hz), 7.20 (d, 1H, J=8.2 Hz), 3.81 (s, 2H), 3.69 (s, 3H), 3.12 (broad s, 3H), 3.00 (broad s, 3H).

Step B: Preparation of methyl 2,3-dichloro-4-(3-(3-neo-pental-7-propyl-6-benz-[4,5]-isoxazoloxy)propylthio)phenylacetate Using the method of Example 20, step C, 1-bromo-3-(3-neo-pental-7-propyl-6-benz-[4,5]-isoxazoloxy)phenoxypropane as the starting material, the title compound was obtained.

$^1$H NMR(300 MHz, CDCl$_3$): δ 7.36 (d, 1H, J=8.7 Hz), 7.17 (d, 1H, J=8.3 Hz), 7.13 (d, 1H, J=8.2 Hz), 6.89 (d, 1H, J=8.7 Hz), 4.19 (t, 2H, J=5.8 Hz), 3.76 (s, 2H), 3.71 (s, 3H), 3.19 (t, 2H, J=7.2 Hz), 2.88 (t, 2H, J=7.5 Hz), 2.81 (s, 2H), 2.22 (quint, 2H, J=7.1 Hz), 1.71 (hex, 2H, J=7.3 Hz), 1.05 (s, 9H), 0.96 (t, 3H, J=7.3 Hz)

Step C: Preparation of 2,3-dichloro-4-(3-(3-neo-pental-7-propyl-6-benz-[4,5]-isoxazoloxy)propylthio)phenylacetatic acid Using the method of Example 20, step D, methyl 2,3-dichloro-4-(3-(3-neo-pental-7-propyl-6-benz-[4,5]-isoxazoloxy)propylthio)-phenylacetate as the starting material, the title compound was obtained.

$^1$H NMR(300 MHz, CDCl$_3$): δ 7.36 (d, 1H, J=8.7 Hz), 7.17 (d, 1H, J=8.3 Hz), 7.13 (d, 1H, J=8.2 Hz), 6.89 (d, 1H, J=8.7 Hz), 4.19 (t, 2H, J=5.8 Hz), 3.76 (s, 2H), 3.19 (t, 2H, J=7.2 Hz), 2.88 (t, 2H, J=7.5 Hz), 2.81 (s, 2H), 2.22 (quint, 2H, J=7.1 Hz), 1.71 (hex, 2H, J=7.3 Hz), 1.05 (s, 9H), 0.96 (t, 3H, J=7.3 Hz) ESI: MS m/e=524 (M+1)

EXAMPLE 55

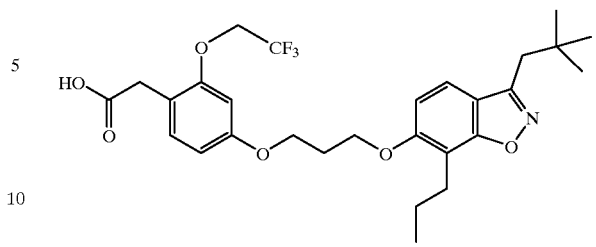

2-Trifloroethoxy-4-(3-(3-neo-pental-7-propyl-6-benz-[4,5]-isoxazoloxy)propyloxy)phenylacetic acid Step A: Preparation of methyl 2-trifluoroethoxy-4-(3-(3-neo-pental-7-propyl-6-benz-[4,5]-isoxazoloxy)propyloxy)phenylacetate Using the method of Example 20, step C, 1-bromo-3-(3-neo-pental-7-propyl-6-benz-[4,5]-isoxazoloxy)phenoxypropane and methyl 2-trifluoroethoxy-4-hydroxyphenylacetate as the starting material, the title compound was obtained.

$^1$H NMR(300 MHz, CDCl$_3$): δ 7.34 (d, 1H, J=8.7 Hz), 7.08 (d, 1H, J=8.3 Hz), 6.92 (d, 1H, J=8.7 Hz), 6.52 (d, 1H, J=2.4 Hz), 6.42 (dd, 1H, J=8.4, 2.5 Hz), 4.30 (2H, J=8.2 Hz), 4.21 (t, 2H, J=6.1 Hz), 4.16 (t, 2H, J=5.9 Hz), 3.55 (s, 3H), 3.53 (s, 2H), 2.83 (t, 2H, J=7.5 Hz), 2.78 (s, 2H), 2.27 (quint, 2H, J=6.5 Hz), 1.65 (hex, 2H, J=7.5 Hz), 1.02 (s, 9H), 0.92 (t, 3H, J=7.3 Hz)

Step B: Preparation of 2-trifluoroethoxy-4-(3-(3-neo-pental-7-propyl-6-benz-[4,5]-isoxazoloxy)propyloxy)phenylacetic acid Using the method of Example 20, step D, methyl 2-trifluoroethoxy-4-(3-(3-neo-pental-7-propyl-6-benz-[4,5]-isoxazoloxy)-propylthio)phenylacetate as the starting material, the title compound was obtained.

$^1$H NMR(300 MHz, CDCl$_3$): δ 7.34 (d, 1H, J=8.7 Hz), 7.08 (d, 1H, J=8.3 Hz), 6.92 (d, 1H, J=8.7 Hz), 6.52 (d, 1H, J=2.4 Hz), 6.42 (dd, 1H, J=8.4, 2.5 Hz), 4.30 (2H, J=8.2 Hz), 4.21 (t, 2H, J=6.1 Hz), 4.16 (t, 2H, J=5.9 Hz), 3.53 (s, 2H), 2.83 (t, 2H, J=7.5 Hz), 2.78 (s, 2H), 2.27 (quint, 2H, J=6.5 Hz), 1.65 (hex, 2H, J=7.5 Hz), 1.02 (s, 9H), 0.92 (t, 3H, J=7.3 Hz) ESI: MS m/e=538 (M+1)

EXAMPLE 56

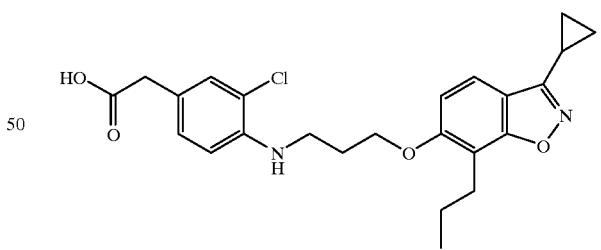

3-Chloro-4-(3-(3-cyclopropyl)-7-propyl-6-benz-[4,5]-isoxazoloxy)propylamino)phenylacetate Step A: Preparation of 4-cyclopropylcarbonyl-2-(n-propyl)resorcinol Using the method of Example 50, Step B, substituting cyclopropylcarboxylic acid as the starting material, the title compound was obtained as a coral-colored solid. NMR (CDCl$_3$); δ 1.00 (t, 3H); 1.05 (m, 2H); 1.27 (m, 2H); 1.60 (m, 2H); 2.62 (m, 1H); 2.65 (t, 2H); 6.40 (d, 1H); 7.76 (d, 1H).

Step B: Preparation of 4-cyclopropylhydroxyimino-2-(n-propyl)resorcinol

A solution of 4-cyclopropylcarbonyl-2-(n-propyl) resorcinol (1.0 g, 4.54 mmole) in methanol (10 mL) was treated with hydroxylamine.HCl (1.58g, 22.7 mmole) and sodium acetate (1.86g, 22.7 mmole) and the mixture refluxed for 7 hours. The cooled mixture was poured into water and extracted 3× with ethyl acetate. The combined extracts were washed with water (2×), 10% sodium bicarbonate, brine, dried over magnesium sulfate and concentrated in vacuo to give a solid. The crude product was chromatographed on silica gel eluting with methylene chloride followed by methanol:methylene chloride (5:95) to afford the title compound. NMR (CDCl$_3$); δ 0.89 (m, 2H); 0.94 (t, 3H); 1.10 (m, 2H); 1.76 (m, 1H); 2.61 (t, 2H); 6.35 (d, 1H); 7.41 (d, 1H).

Step C: Preparation of 3-cyclopropyl-6-hydroxy-7-propylbenz-[4,5]-isoxazole

A solution of 4-cyclopropylhydroxyimino-2-(n-propyl) resorcinol (537 mg, 2.28 mmole) in acetic anhydride (6 mL) was stirred at room temperature for 2 days. The mixture was concentrated in vacuo and the residue partitioned with ethyl acetate and 10% sodium carbonate and stirred for 1 hour. The organic phase was washed with brine, dried over magnesium sulfate and concentrated in vacuo to give a solid. Flash chromatography on silica gel in ethyl acetate:hexane (15:85) afforded the title compound (150 mg) as a solid.

NMR (CDCl$_3$); δ 1.00 (t, 3H); 1.17 (m, 2H); 1.26 (m, 2H); 1.74 (m, 2H); 2.25 (m, 1H); 2.82 (t, 2H); 6.77 (d, 1H); 7.27 (d, 1H).

Step D: Preparation of methyl 3-chloro-4-(3-(3-cyclopropyl)-7-propyl-6-benz-[4,5]-isoxazoloxy) propylamino)phenylacetate To a solution of 3-cyclopropyl-6-hydroxy-7-propylbenz-[4,5]-isoxazole (34 mg, 0.156 mmole) and methyl 3-chloro-4-(3-bromopropylamino)phenylacetate (Example 21, Step C, 50 mg, 0.156 mmole) in DMF (0.70 mL) was added cesium carbonate (54 mg , 0.164 mmole), and the mixture stirred at 80° C. in a nitrogen atmosphere for 2 hours. The cooled mixture was dissolved in ethyl acetate and washed with water, brine, dried over magnesium sulfate and concentrated in vacuo to give an oil. Thin layer chromatography on silica gel eluting with hexane:ethyl acetate (2:1) afforded the title compound (44 mg).

NMR (CDCl$_3$); δ 0.95 (t, 3H); 1.15 (m, 2H); 1.24 (m, 2H); 1.67 (m, 2H); 2.15 (t, 2H); 2.18 (m, 1H); 2.81 (t, 2H); 3.43 (t, 2H); 3.47 (s, 2H); 3.67 (s, 3H); 4.10 (t, 2H); 6.65 (d, 1H); 6.83 (d, 1H); 7.04 (d, 1H); 7.18 (d, 1H); 7.32 (d, 1H).

Step E: Preparation of 3-chloro-4-(3-(3-cyclopropyl)-7-propyl-6-benz-[4,5]-isoxazoloxy)propylamino) phenylacetate Using the method of Example 22, substituting methyl 3-chloro-4-(3-(3-cyclopropyl)-7-propyl-6-benz-[4,5]-isoxazoloxy)propylamino)phenylacetate as starting material, the title compound was obtained. NMR (CD$_3$OD); δ 0.95 (t, 3H); 1.3 (m, 4H);1.69 (m, 2H); 2.13 (m, 2H); 2.2 (m, 1H); 2.85 (t, 2H); 3.42 (t, 2H); 3.43 (s, 2H); 4.13 (m, 2H); 6.72 (d, 1H); 6.98 (d, 1H); 7.03 (dd, 1H); 7.17 (d, 1H); 7.29 (d, 1H).

EXAMPLE 57

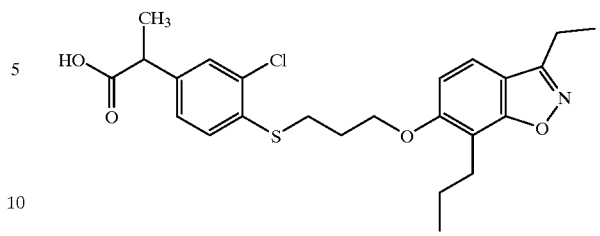

2-(3-chloro-4-(3-(3-ethyl-7-propyl-6-benz-[4,5]-isoxazoloxy)propylthio))phenylpropionic acid 1. 3-ethyl-6-(3-bromopropyl)oxy-7-propylbenz[4,5] isoxazole A solution of 3-ethyl-6-hydroxy-7-propylbenz[4,5] isoxazole (2.00 grams; 9.74 mmol) in dry DMF was treated with dibromopropane (7.17 mL; 38.97 mmol) and cesium carbonate (3.49 grams; 10.71 mmol). The solution was stirred at room temperature for 10 hours, then partioned between isopropyl acetate and pH 4.0 buffer. The organic layer was washed twice with water, dried over magnesium sulfate, filtered and concentrated in vacuo. Silica gel chromatography afforded the title compound (1.74 g).

NMR (CDCl$_3$): 7.39 (d, 1H, J=8.8 Hz); 6.91 (d, 1H, J=8.8 H); 4.18 (t, 2H, J=5.7 Hz); 3.63 (t, 2H, J=6.4 Hz); 2.94 (quart, 2H, J=7.6 Hz); 2.35 (quint, 2H, J=6.0 Hz); 1.40 (t, 3H, J=7.5 Hz); 0.94 (t, 3H, 7.4 Hz).

2. 2-(3-chloro-4-(3-(3-ethyl-7-propyl-6-benz[4,5] isoxazole)oxy) propylthio) phenyl propionic acid methyl ester A solution of 2-(3-chloro-4-dimethylcarbamoylthio) phenyl propionic acid methyl ester (0.106 g; 0.352 mmol) in dry methanol (1.42 mL) was treated with a solution of sodium methoxide in methanol (4.37 M; 0.113 mL; 0.493 mmol). The solution was refluxed for 4 hours and then cooled to room temperature. 3-ethyl-6-(3-bromopropyl)oxy-7-propyl-benz[4,5]isox-azole (0.096 grams; 0.293 mmol) was added and the reaction stirred for 1 hour. The reaction mixture was partitioned between isopropyl acetate and pH 4.0 buffer. The organic layer was dried over magnesium sulfate, filtered and evaporated. Silica gel chromatography afforded the title compound.

NMR (CDCl$_3$): 7.38 (d, 1H, J=8.4Hz); 7.25 (d, 1H, J=5.4 Hz); 7.15 (d, 1H, J=8.1 Hz); 6.87 (d, 1H, J=8.7); 4.17 (t, 2H, J=5.6 Hz); 3.66 (quart, 1H, J=7.0 Hz); 3.60 (s, 3H); 3.15 (t, 2H, J=7.0 Hz); 2.94 (quart, 2H, J=7.6 Hz); 2.85 (t, 2H, J=7.5); 1.66 (quart, 2H, J=7.1 Hz); 1.40 (t, 2H, J=7.5 Hz).

3. 2-(3-chloro-4-(3-(3-ethyl-7-propyl-6-benz[4,5] isoxazole)oxy) propyl thio) phenyl propionic acid A solution of 2-(3-chloro-4-(3-(3-ethyl-7-propyl-6-benz [4,5]isoxazole) oxy)propylthio)phenyl propionic acid methyl ester (0.037 g; 0.076 mmol) in ethanol (1.0 mL) was treated with a solution of potassium hydroxide in water (1.0M; 0.153 mL; 0.153 mmol). The solution was refluxed for 1 hour. The reaction mixture was partitioned between isopropyl acetate and 0.1 N HCl. The organic was dried over magnesium sulfate, filtered and concentrated to afford the title compound.

NMR (CDCl$_3$): 7.38 (d, 1H, J=8.4Hz); 7.25 (d, 1H, J=5.4 Hz); 7.15 (d, 1H, J=8.1 Hz); 6.87 (d, 1H, J=8.7); 4.17 (t, 2H,

J=5.6 Hz); 3.66 (quart, 1H, J=7.0 Hz); 3.15 (t, 2H, J=7.0 Hz); 2.94 (quart, 2H, J=7.6 Hz); 2.85 (t, 2H, J=7.5); 1.66 (quart, 2H, J=7.1 Hz); 1.40 (t, 2H, J=7.5 Hz).

EXAMPLE 58

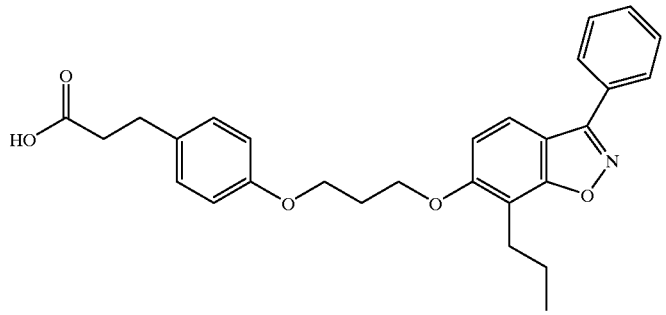

3-(4-(3-(3-phenyl-7-propyl-6-benz-[4,5]-isoxazoloxy)propyloxy))phenylpropionic acid Step 1

The methyl 3-(4-(3-bromoprop-1-oxy)phenyl)propionate can be obtained from commercially available methyl 3-(4-hydroxyphenyl)propionate and 1,3-dibromopropane as described in Example 16 Step 4. The product was purified by elution from a silica gel column (E. Merck 40–63μ) with hexanes: methylene chloride 50:50.

Characteristic NMR Resonances; $^1$H NMR 400 MHz (CDCl$_3$); 6.95 (ABq, 4H), 4.06 (t, 2H, J=5.8 Hz), 3.65 (s, 3H), 3.58 (t, 2H, J=6.4 Hz), 2.87 (t, 2H, J=8.0 Hz), 2.58 (t, 2H, J=6.5 Hz), 2.28 (pent, 2H, J=5.9 Hz).

Step 2

The 3-phenyl-6-hydroxy-7-propylbenzisoxazole of Example 16 Step 3 (37 mg, 1.0 Eq, 0.145 mmol) was coupled with the bromide of Example 59 Step 1 (49 mg, 1.1 Eq, 0.16 mmol) as described in the procedure of Example 16 Step 4.The product was purified by elution from a silica gel column (2.5 g E. Merck 40–63μ) with toluene: hexanes: EtOAc 60:35:5.

Characteristic NMR Resonances; $^1$H NMR 400 MHz (CDCl$_3$); 7.92 (m, 2H), 7.64 (d, 1H, J=8.7 Hz), 7.5–7.3 (m, 2H), 7.09 (d, 1H, J=8.8 Hz), 6.99 (d, 1H, J=8.8 Hz), 6.83 (m, 2H), 4.26 (t, 2H, J=6.1 Hz), 4.17 (t, 2H, J=6.1 Hz), 2.90 (m, 4H), 2.57 (t, 2H, J=8.1 Hz), 2.30 (pent, 2H, J=6.1 Hz), 1.69 (sext, 2H, J=7.5 Hz), 0.946 (t, 3H, J=7.3 Hz). MS ESI M+1=474.3. MW=473.2

Step 3

The ester of Example 58 Step 2 (46 mg, 1.0 Eq, 0.096 mmol) was hydrolyzed with LiOH (150 μL, 1.5 N, 2.3 Eq, 0.255 mmol) as described in Example 16 Step 5.

Characteristic NMR Resonances; $^1$H NMR 400 MHz (CDCl$_3$); 7.9–7.93 (m, 2H), 7.64 (d, 1H, J=8.7 Hz), 7.5–7.55 (m, 3H), 7.10 (d, 1H, J=8.7 Hz), 6.99 (d, 1H, J=8.7 Hz), 6.83 (d, 1H, J=8.7 Hz), 4.26 (t, 2H, J=5.98 Hz), 4.17 (t, 2H, J=6.03 Hz), 2.88 (t, 2H, J=8.4 Hz), 2.90 (t, 2H, J=7.7 Hz), 2.62 (t, 2H, J=8.1 Hz), 2.30 (pent, 2H, J=6.1 Hz), 1.69 (sext, 2H, J=7.5 Hz), 0.945 (t, 3H, J=7.4 Hz). Analytical HPLC 75:25 CH$_3$CN:H$_2$O 0.1% TFA, E. Merck RP-8 5μ 4×250 mm, 1 ml/min. UV 210, RT 6.47 min. MS ESI M+1=460.3. MW=459.2

EXAMPLE 59

3-Chloro-4-(3-(3-(3-fluorophenyl)-7-propyl-6-benz-[4,5]-isoxazoloxy)-propylthio)phenylacetic acid Step 1

Commercially available 2-propylresorcinol (3.0 g, 1.0 Eq, 0.02 mol) and meta-fluorobenzoic acid (3.2 g, 1.15 Eq, 0.023 mol) were condensed as described in Example 51 Step 1. The product was purified by elution from a silica gel column (20 g E. Merck 40–63μ) with toluene: hexanes: EtOAc 60:35:5.

Characteristic NMR Resonances; $^1$H NMR 400 MHz (CDCl$_3$); 7.42–7.47 (m, 1H), 7.36–7.4 (m, 1H), 7.29–7.33 (m, 1H), 7.2–7.26 (m, 1H), 6.31 (d, 1H, J=8.8 Hz), 2.66 (dd, 2H, J=9.3, 7.6 Hz), 1.61 (sext, 2H, J=7.7 Hz), 0.994 (t, 3H, J=7.4 Hz). MS ESI M+1=275.1. MW=274.1

Step 2

The ketone of Example 59 Step 1 (2.6 g, 1.0 Eq, 9.4 mmol) was converted to the oxime with $NH_2OH$—HCl (0.7 g, 1.05 Eq, 9.8 mmol) as described in the procedure of Example 7 Step A. Heating was continued for 72 Hrs. The product was purified by elution from a silica gel column (112 g E. Merck 40–63$\mu$) with toluene: EtOAc 97:3.

Characteristic NMR Resonances; $^1$H NMR 400 MHz (CDCl$_3$); 7.0–7.5 (four 1H multiplets), 6.49 (d, 1H, J=8.7 Hz), 6.21 (d, 1H, J=8.8 Hz), 2.66 (dd, 2H, J=9.3, 7.6 Hz), 1.61 (sext, 2H, J=7.7 Hz), 0.996 (t, 3H, J=7.4 Hz).

Step 3

The oxime of Example 59 step 2 (846 mg, 2.9 mmol) was converted to the 3-(meta-fluorophenyl)-6-hydroxy-7-propylbenzisoxazole as described in Example 7 Step A. The product was purified by recrystallization from toluene.

Characteristic NMR Resonances; $^1$H NMR 400 MHz (CDCl$_3$); 7.69 (m, 1H), 7.61 (m, 1H), 7.55 (d, 1H, J=8.5 Hz), 7.50 (m, 1H), 7.20 (m, 1H), 6.88 (d, 1H, J=8.5 Hz), 5.23 (s, 1H), 2.91 (t, 2H, J=7.5 Hz), 1.75 (sext, 2H, J=7.5 Hz), 1.01 (t, 3H, J=7.3 Hz). MS ESI M+1=272.1. MW=271.1

Step 4

The 3-(meta-fluorophenyl)-6-hydroxy-7-propylbenzisoxazole of Example 59 Step 3 (34 mg, 1.0 Eq, 0.123 mmol) was coupled with the bromide of Example 16 Step 1A (43 mg, 1.05 Eq, 0.128 mmol) as described in Example 16 Step 4. The product was purified by elution from a silica gel column (3 g E. Merck 40–63$\mu$) with toluene: hexanes: EtOAc 60:35:5.

Characteristic NMR Resonances; $^1$H NMR 400 MHz (CDCl$_3$); 7.72 (m, 1H), 7.6 (m, 1H), 7.63 (d, 1H, J=8.8 Hz), 7.51 (dt, 1H), 7.31 (d, 1H, J=~1.5 Hz), 7.27 (d, 1H, J=8.1 Hz), 7.21 (dt, 1H), 7.12 (dd, 1H), 6.97 (d, 1H, J=8.8 Hz), 4.21 (t, 2H, J=5.8 Hz), 3.68 (s, 3H), 3.55 (s, 2H), 3.17 (t, 2H, J=7 Hz), 2.92 (dd, 2H, J unresolved), 2.19 (pent, 2H), 1.71 (sext, 2H, J=7.5 Hz), 0.964 (t, 3H, J=7.4 Hz). MS ESI M+1=528.2. MW=527.1

Step 5

The ester of Example 59 Step 4 (51 mg, 1.0 Eq, 0.097 mmol) was hydrolyzed with LiOH (150 $\mu$L, 1.5 N, 2.3 Eq, 0.225 mmol) as described in Example 16 Step 5. The product was purified by elution from a reversed phase RP-8 col (10 g E. Merck 40–63$\mu$) with 75:25 CH$_3$CN:H$_2$O 0.1% TFA.

Characteristic NMR Resonances; $^1$H NMR 400 MHz (CDCl$_3$); 7.70 (dd, 1H), 7.62 (d, 1H, J=8.7 Hz). 7.62 (m, 1H), 7.50 (dt, 1H), 7.31 (d, 1H, J=1.9 Hz), 7.28 (d, 1H J=8.1 Hz), 7.20 (dt, 1H), 7.12 (dd, 1H), 6.97 (d, 1H, J=8.8 Hz), 4.21 (t, 2H, J=5.8 Hz), 3.69 (s, 2H), 3.18 (t, 2H, J=7.1 Hz), 2.91 (dd, 2H, J=8.8, 7.5 Hz), 2.19 (pent, 2H), 1.71 (sext, 2H, J=7.7 Hz), 0.96 (t, 3H, J=7.4 Hz). Analytical HPLC 75:25 CH$_3$CN:H$_2$O 0.1% TFA, E. Merck RP-8 5$\mu$ 4×250 mm, 1 ml/min. UV 210, RT 7.55 min. MS ESI M+1=514.3. MW=513.1

EXAMPLE 60

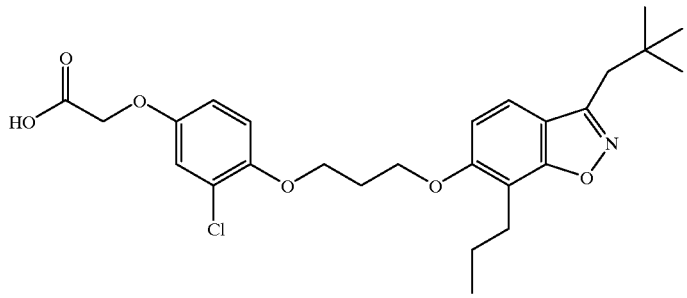

3-Chloro-4-(3-(3-neo-pental-7-propyl-6-benz-[4,5]-isoxazoloxy)-propyloxy)phenoxylacetic acid Step A: Preparation of methyl 3-chloro-4-hydroxyphenoxylacetate A sulotion of chlorohydroxyquinone (5.0 g), ethyl bromoacetate (3.84 mL) and potassium carbonate (4.78 g) was refluxed for five hours. The mixture of reaction was partitioned between water and ether. The combined organics were washed with water and brine, dried over magnesium sulfate, poured onto a column of silica gel and eluted with ethyl acetate/hexane (20/80) to give the title compound.

$^1$H NMR(400 MHz, CDCl$_3$): δ 6.92 (m, 2H), 6.77 (dd, 1H, J=8.8, 3.0 Hz), 5.21 (s, 2H), 4.52 (s, 3H), 4.24 (quart, 2H, J=7.2 Hz), 1.27 (t, 3H, J=7.2 Hz).

Step B: Preparation of methyl 2-trifluoroethoxy-4-(3-(3-neo-pental-7-propyl-6-benz-[4,5]-isoxazoloxy)propyloxy) phenylacetate Using the method of Example 20, step C, 1-bromo-3-(3-neo-pental-7-propyl-6-benz-[4,5]-isoxazoloxy) phenoxypropane and methyl 2-trifluoroethoxy-4-hydroxyphenylacetate as the starting material, the title compound was obtained.

$^1$H NMR(400 MHz, CDCl$_3$): δ 7.34 (d, 1H, J=8.7 Hz), 6.97 (d, 1H, J=3.0 Hz), 6.93 (d, 1H, J=8.7 Hz), 6.87 (d, 1H, J=9.0 Hz), 6.77 (dd, 1H, J=9.0, 3.0 Hz), 4.52 (s, 2H), 4.27 (s, 4H), 4.16 (t, 2H, J=5.9 Hz), 2.82 (t, 2H, J=7.4 Hz), 2.78 (s, 2H), 2.31 (quint, 2H, J=6.0 Hz), 1.65 (hex, 2H, J=7.3 Hz), 1.26 (t, 2H, J=7.1 Hz), 1.02 (s, 9H), 0.90 (t, 3H, J=7.3 Hz)

Step C: Preparation of 2-trifluoroethoxy-4-(3-(3-neo-pental-7-propyl-6-benz-[4,5]-isoxazoloxy)propyloxy)phenylacetic acid Using the method of Example 20, step D, methyl 2-trifluoroethoxy-4-(3-(3-neo-pental-7-propyl-6-benz-[4,5]-isoxazoloxy)propylthio)phenylacetate as the starting material, the title compound was obtained.

$^1$H NMR(400 MHz, CDCl$_3$): δ 7.34 (d, 1H, J=8.7 Hz), 6.97 (d, 1H, J=3.0 Hz), 6.93 (d, 1H, J=8.7 Hz), 6.87 (d, 1H, J=9.0 Hz), 6.77 (dd, 1H, J=9.0, 3.0 Hz), 4.60 (s, 2H), 4.27 (t, 2H, J=5.9 Hz), 4.18 (t, 2H, J=5.9 Hz), 2.82 (t, 2H, J=7.4 Hz), 2.78 (s, 2H), 2.31 (quint, 2H, J=6.0 Hz), 1.65 (hex, 2H, J=7.3 Hz), 1.02 (s, 9H), 0.90 (t, 3H, J=7.3 Hz) ESI: MS m/e=490 (M+1)

EXAMPLE 61

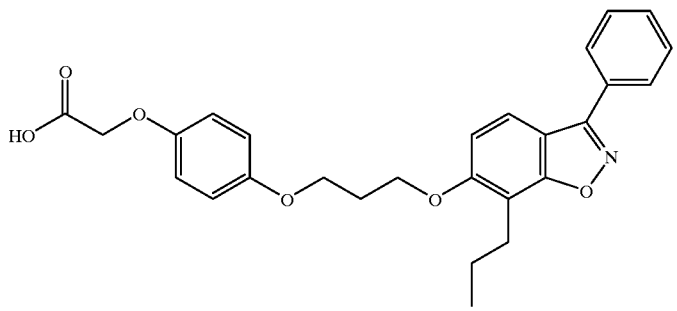

4-(3-(3-phenyl-7-propyl-6-benz[4,5]-isoxazole)oxy)propyloxy phenoxy acetic acid

Step 1

The 6-(3-bromoprop-1-oxy)-3-phenyl-7-propylbenzisoxazole can be prepared as in Example 1 Step A from 6-hydroxy-3-phenyl-7-propylbenzisoxazole (1.5 g, 1.0 Eq, 6 mmol), prepared as described in Example 16 Step 3, and 1,3-dibromopropane (3.0 ml, 5 Eq, 30 mmol). The product was purified by elution from a silica gel column (100 g E. Merck 40–63μ) with toluene: hexanes: EtOAc 30:65:5.

Characteristic NMR Resonances; $^1$H NMR 400 MHz (CDCl$_3$); 7.91 (m, 2H), 7.65 (d, 1H, J=8.7 Hz), 7.5–7.55 (m, 3H), 7.24 (m, 1H), 7.16 (m, 1H), 7.69 (d, 1H, J=8.7 Hz), 4.22 (t, 2H, J=5.7 Hz), 3.65 (t, 2H, J=6.4 Hz), 2.9 (t, 2H, J=7.4 Hz), 2.38 (pent, 2H, J=5.9 Hz), 1.71 (sext, 2H, J=7.4 Hz), 0.977 (t, 3H, J=7.4 Hz). MS ESI M+1=360.0/362. MW=359.1/361.1 (Bromine isotopes).

Step 2

Commercially available 4-hydroxyphenoxyacetic acid (2 g) was esterified as described in Example 23 Step 1. The ester was used without purification further.

Characteristic NMR Resonances; $^1$H NMR 400 MHz (CDCl$_3$); 6.76 (Aromatic ABq, 4H), 4.56 (s, 2H), 3.78 (s, 3H). MS CI NH$_3$ M+NH$_4^+$=200. MW=182.1

Step 3

The 6-(3-bromoprop-1-oxy)-3-phenyl-7-propylbenzisoxazole of Example 62 Step 1 (56.4 mg, 1.0 Eq, 0.15 mmol) was coupled with the methyl 4-hydroxyphenoxyacetate of Example 61 Step 2 (32 mg, 1.15 Eq, 0.176 mmol) as described in the procedure of Example 16 Step 4. The product was purified by elution from a silica gel column (4 g E. Merck 40–63μ) with toluene: hexanes: EtOAc 60:35:5.

Characteristic NMR Resonances; $^1$H NMR 400 MHz (CDCl$_3$); 7.91 (m, 2H), 7.64 (d, 1H, J=8.8 Hz), 7.52 (m, 3H), 6.99 (d, 1H, J=8.8 Hz), 6.84 (s, 4H), 4.57 (s, 2H), 4.26 (t, 2H, J=5.9 Hz), 4.14 (t, 2H, J=6.1 Hz), 3.78 (s, 3H), 2.90 (dd, 2H, J unresolved), 2.29 (pent, 2H, J=6.1 Hz), 1.70 (sext, 2H), 0.946 (t, 3H, J=7.4 Hz). MS ESI M+1=476.2. MW=475.2.

Step 4

The ester of Example 61 Step 3 (44 mg, 1.0 Eq, 0.092 mmol) was hydrolyzed with LiOH (130 μL, 1.5 N, 2 Eq, 0.195 mmol) as described in Example 16 Step 5.

Characteristic NMR Resonances; $^1$H NMR 400 MHz (CDCl$_3$); 7.92 (m, 2H), 7.66 (d, 1H, J=8.7 Hz), 7.52 (m, 3H), 6.99 (d, 1H, J=8.8 Hz), 6.87 (s, 4H), 4.62 (s, 2H), 4.28 (t, 2H, J=5.9 Hz), 4.17 (t, 2H, J=6.0 Hz), 2.92 (dd, 2H, J unresolved), 2.31 (pent, 2H, J=6.1 Hz), 1.71 (sext, 2H, J=7.5 Hz), 0.964 (t, 3H, J=7.3 Hz). Analytical HPLC 75:25 CH$_3$CN:H$_2$O 0.1% TFA, E. Merck RP-8 5μ 4×250 mm, 1 ml/min. UV 210, RT 5.47 min. MS ESI M+1=462.3. MW=461.2

EXAMPLE 62

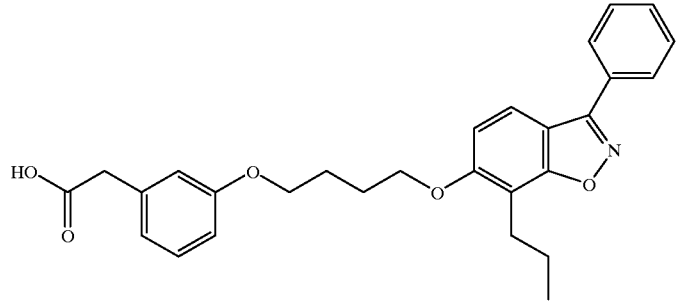

(3-(4-(3-phenyl-7-propyl-6-benz-[4,5]-isoxazoloxy)butyloxy)) phenylacetic acid

Step 1

The 6-(4-bromobut-1-oxy)-3-phenyl-7-propylbenzisoxazole can be prepared as in Example 1 Step A from 6-hydroxy-3-phenyl-7-propylbenzisoxazole (2 g, 1.0 Eq, 7.9 mmol), prepared as described in Example 16 Step 3, and 1,4-dibromobutane (4.8 ml, 5 Eq, 39.5 mmol). The product was purified by elution from a silica gel column (100 g E. Merck 40–63μ) with toluene: hexanes: EtOAc 30:65:5.

Characteristic NMR Resonances; $^1$H NMR 400 MHz (CDCl$_3$); 7.92 (m, 2H), 7.64 (d, 1H, J=8.8 Hz), 7.53 (m, 3H), 6.95 (d, 1H, J=8.8 Hz), 4.11 (t, 2H, J=5.9 Hz), 3.51 (t, 2H, J=6.4 Hz), 2.91 (t, 2H, J=7.5 Hz), 2.12 (complex m, 2H), 2.03 (complex m, 2H), 1.71 (sext, 2H, J=7.5 Hz), 0.977 (t, 3H, J=7.4 Hz). MS ESI M+1=388.2/390.2. MW=387.1/389.1 (Bromine Isotopes).

Step 2

The methyl 3-hydroxyphenylacetic acid from Example 23 Step 1 (26 mg, 1.05 Eq, 0.15 mmol) and the 6-(4-bromobut-1-oxy)-3-phenyl-7-propylbenzisoxazole from Example 62 Step 1 (42 mg, 1.0 Eq, 0.108 mmol) were condensed as described in Example 16 Step 4. The product was purified by elution from a silica gel column (3 g E. Merck 40–63µ) with toluene: hexanes: EtOAc 60:35:5.

Characteristic NMR Resonances; $^1$H NMR 400 MHz (CDCl$_3$); 7.92 (m, 2H), 7.64 (d, 1H, J=8.8 Hz), 7.53 (m, 3H), 7.22 (t, 1H), 6.97 (d, 1H, J=8.8 Hz), 6.83 (m, 3H), 4.14 (t, 2H), 4.04 (t, 2H), 3.67 (s, 3H), 3.58 (s, 2H), 2.92 (dd, 2H, J unresolved), 2.02 (m, 4H), 1.71 (sext, 2H, J=7.5 Hz) 0.968 (t, 3H, J=7.4 Hz). MS ESI M+1=474.4. MW=473

Step 3

The ester of Example 62 Step 2 (46 mg, 1.0 Eq, 0.098 mmol) was hydrolyzed with LiOH (150 µL, 1.5 N, 2.3 Eq, 0.225 mmol) as described in Example 16 Step 5.

Characteristic NMR Resonances; $^1$H NMR 400 MHz (CDCl$_3$); 7.92 (m, 2H), 7.63 (d, 1H, J=8.8 Hz), 7.52 (m, 3H), 7.22 (t, 1H), 6.96 (d, 1H, J=8.8 Hz), 6.83 (m, 3H), 4.14 (t, 2H), 4.04 (t, 2H), 3.59 (s, 2H), 2.91 (dd, 2H, J unresolved), 2.02 (m, 4H), 1.71 (sext, 2H, J=7.5 Hz), 0.963 (t, 3H, J=7.4 Hz). Analytical HPLC 75:25 CH$_3$CN:H$_2$O 0.1% TFA, E. Merck RP-8 5µ 4×250 mm, 1 ml/min. UV 210, RT 6.61 min. MS ESI M+1=460.4. MW=459.2.

The 6-(4-bromobut-1-oxy)-3-phenyl-7-propylbenzisoxazole prepared in Example 62 Step 1 (48 mg, 1.0 Eq 0.124 mmol) and commercially available methyl 3-(4-hydroxyphenyl)propionate (26.3 mg, 1.15 Eq , 0.146 mmol) were condensed as described Example 16 Step 4. The product was purified by elution from a silica gel column (2.5 g E. Merck 40–63µ) with toluene: hexanes: EtOAc 60:35:5.

Characteristic NMR Resonances; $^1$H NMR 400 MHz (CDCl$_3$); 7.92 (m, 2H), 7.64 (d, 1H, J=8.8 Hz), 7.52 (m, 3H), 7.09 (m, 2H), 6.97 (d, 1H, J=8.8 Hz), 6.81 (m, 2H), 4.14 (t, 2H), 4.02 (t, 2H), 3.65 (s, 3H), 2.91 (t, 2H, J=7.5 Hz), 2.89 (t, 2H, J=8.5 Hz), 2.58 (t, 2H, J=7.5 Hz), 2.01 (m, 4H), 1.71 (sext, 2H, J=7.5 Hz), 0.964 (t, 3H, J=7.3 Hz). MS ESI M+1=488.4. MW=487.2

Step 2

The ester of Example 63 Step 1 (49.3 mg, 1.0 Eq, 0.101 mmol) was hydrolyzed with LiOH (160 µL, 1.5 N, 2.3 Eq, 0.240 mmol) as described in Example 16 Step 5.

Characteristic NMR Resonances; $^1$H NMR 400 MHz (CDCl$_3$); 7.91 (m, 2H), 7.64 (d, 1H, J=8.8 Hz), 7.52 (m, 3H), 7.10 (d, 2H, J=8.8 Hz), 6.96 (d, 1H, J=8.8 Hz), 6.81 (m, 2H), 4.14 (t, 2H), 4.02 (t, 2H), 2.89 (2 overlapping t, 4H), 2.65 (t, 2H, 8.1 Hz), 2.01 (m, 4H), 1.71 (sext, 2H), 0.964 (t, 3H, J=7.4 Hz). Analytical HPLC 75:25 CH$_3$CN:H$_2$O 0.1% TFA, E. Merck RP-8 5µ 4×250 mm, 1 ml/min. UV 210, RT 7.22 min. MS ESI M+1=474.4. MW=473.2

EXAMPLE 63

EXAMPLE 64

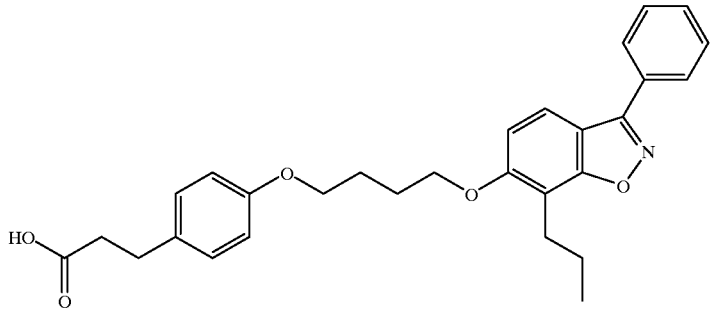

(3-(4-(4-(3-phenyl-7-propyl-6-benz-[4,5]-isoxazoloxy)butyloxy))phenylpropionic acid Step 1

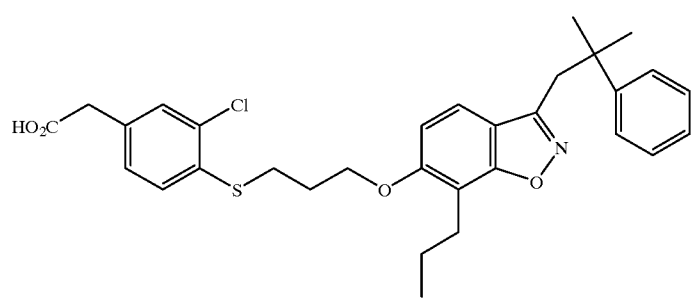

3-chloro-4-(3-(2-methyl-2-phenylpropyl)-7-(n-propyl)-6-benz[4, 5]isoxazoloxy)propylthio)phenylacetic acid Step A Preparation of 1,3-dihydroxy-4-(3-methyl-3-phenylbutyryl)-2-(n-propyl)benzene Using the procedure in Example 51, step 1; 3-methyl-3-phenylbutyric acid and 2-(n-propyl)resorcinol were condensed in triflic acid to form 1,3-dihydroxy-4-(3-methyl-3-phenylbutyryl)-2-(n-propyl)benzene.

NMR (CDCl$_3$): d 7.14–7.41 (m, 6H); 6.24 (d, 1H); 5.30 (bs, 1H); 3.21 (s, 2H); 2.58 (t, 2H); 1.55 (m, 2H); 1.49 (s, 6H); 0.96 (t, 3H).

Step B Preparation of 3-(2-methyl-2-phenylpropyl)-6-hydroxy-7-(n-propyl)benz[4,5]isoxazole Using the procedures in Example 51, steps 2 and 3, 1,3-dihydroxy-4-(3-methyl-3-phenylbutyryl)-2-(n-propyl)-benzene was converted into 3-(2-methyl-2-phenylpropyl)-6-hydroxy-7-(n-propyl)benz-[4,5]isoxazole.

NMR (CDCl$_3$): d 7.18–7.42 (m, 5H); 6.56 (d, 1H); 6.43 (d, 1H); 5.30 (vbs, 1H); 3.19 (s, 2H); 2.82 (t, 2H); 1.71 (m, 2H); 1.46 (s, 6H); 0.98 (t, 3H).

Step C Preparation of methyl 3-chloro-4-(3-(2-methyl-2-phenylpropyl)-7-(n-propyl)-6-benz[4,5]isoxazoloxy) propylthio)-phenylacetate Using the procedure Example 16, step 4, 3-(2-methyl-2-phenylpropyl)-6-hydroxy-7-(n-propyl)benz[4,5]isoxazole. and methyl 3-chloro-4-(3-bromopropylthio)phenylacetate were heated in DMF with Cs$_2$CO$_3$ to prepare methyl 3-chloro-4-(3-(2-methyl-2-phenylpropyl)-7-propyl-6-benz [4,5]isoxazoloxy)propylthio)phenylacetate.

NMR (CDCl$_3$): d 7.10–7.43 (m, 8H); 6.65 (d, 1H); 6.51 (d, 1H); 4.13 (t, 2H); 3.71 (s, 3H); 3.56 (s, 2H); 3.20 (s, 2H); 3.15 (t, 2H); 2.83 (t, 2H); 2.15 (m, 2H); 1.67 (m, 2H); 1.46 (s, 6H); 0.93 (t, 3H).

Step D Preparation of 3-chloro-4-(3-(2-methyl-2-phenylpropyl)-7-(n-propyl)-6-benz[4,5]isoxazoloxy) propylthio)phenylacetic acid Using the procedure in Example 2, methyl 3-chloro-4-(3-(2-methyl-2-phenylpropyl)-7-(n-propyl)- 6-benz[4,5] isoxazoloxy)propylthio)-phenylacetate was saponified with LiOH to form 3-chloro-4-(3-(2-methyl-2-phenylpropyl)-7-propyl-6-benz[4,5]isoxazoloxy)propylthio)phenylacetic acid.

NMR (CDCl$_3$): d 7.12–7.53 (m, 8H); 6.65 (d, 1H); 6.51 (d, 1H); 4.13 (t, 2H); 3.60 (s, 2H); 3.21 (s, 2H); 3.16 (t, 2H); 2.84 (t, 2H); 2.17 (m, 2H); 1.67 (m, 2H); 1.47 (s, 6H); 0.94 (t, 3H).

EXAMPLE 65

1,3-dibromopropane (2.05 mL, 20.2 mmole) in 2-butanone (20 mL) was added potassium carbonate (585 mg, 4.29 mmole) and the resulting mixture refluxed for 18 hours. The cooled mixture was filtered and the filtrate concentrated in vacuo to give an oil. Flash chromatography on silica gel eluting with methyl t-butyl ether:hexane (3:97) afforded the title compound (1.11 g) as a white solid. NMR (CDCl$_3$); δ 0.99 (t, 3H); 1.07 (s, 9H); 1.72 (m, 2H); 2.39 (m, 2H); 2.83 (s, 2H); 2.90 (m, 2H); 3.67 (t, 2H); 4.22 (t, 2H); 6.94 (d, 1H); 7.39 (d, 1H).

Step B: Preparation of methyl 3-methoxy-4-(3-(2,2-dimethylpropyl)-7-propyl-6-benz-[4,5]-isoxazoloxy)-propyloxy)-phenylacetate Using the method of Example 56, Step D, and substituting 3-(2,2-dimethylpropyl)-6-(3-bromopropyloxy)-7-propyl-6-benz-[4,5]-isoxazole and methyl 4-hydroxy-3-methoxyphenylacetate as starting materials, the title compound was obtained as a gum. NMR (CDCl$_3$); δ 0.98 (t, 3H); 1.07 (s, 9H); 1.69 (m, 2H); 2.37 (m, 2H); 2.82 (s, 2H); 2.88 (t, 2H); 3.58 (s, 2H); 3.71 (s, 3H); 3.85 (s, 3H); 4.26 (m, 4H); 6.83 (m, 2H); 6.88 (d, 1H); 6.95 (d, 1H); 7.37 (d, 1H).

Preparation of 3-methoxy-4-(3-(3-(2,2-dimethylpropyl)-7-propyl-6-benz-[4,5]-isoxazoloxy)propyloxy)phenylacetate Using the method of Example 37, Step E and substituting methyl 3-methoxy-4-(3-(3-(2,2-dimethylpropyl)-7-propyl-6-benz-[4,5]-isoxazoloxy)propyloxy)phenylacetate, the title compound was obtained as a gum. NMR (CDCl$_3$) δ 0.959 (t, 3H); 1.07 (s, 9H); 1.69 (m, 2H); 2.37 (m, 2H); 2.82 (s, 2H); 2.87 (t, 2H); 3.61 (s, 2H); 3.85 (s, 3H); 4.27 (m, 4H); 6.83 (m, 2H); 6.94 (d, 1H); 6.95 (d, 1H); 7.37 (d, 1H). Mass spec, m/e=470 (m +1).

EXAMPLE 66

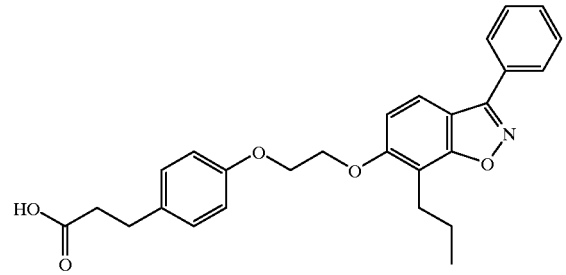

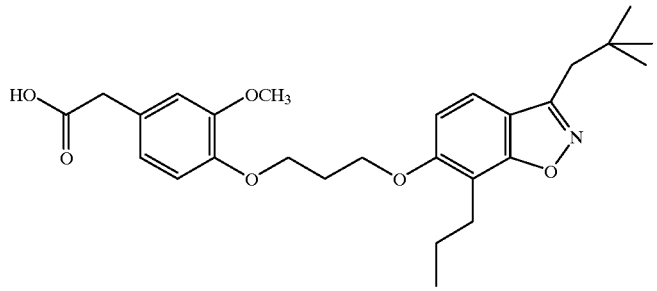

3-Methoxy-4-(3-(3-(2, 2-dimethylpropyl)-7-propyl-6-benz[4, 5]-isoxazoloxy)propyloxy)phenylacetate Step A: Preparation of 3-(2,2-dimethylpropyl)-6-(3-bromopropyloxy)-7-propyl-6-benz-[4,5]-isoxazole To a solution of 3-(2,2-dimethylpropyl)-6-hydroxy-7-propyl-6-benz-[4,5]-isoxazole (1.00 g, 4.04 mmole) and -continued 3-(4-(2-(3-phenyl-7-propyl-6-benz-[4,5]-isoxazoloxy)ethyloxy))phenylpropionic acid Step 1

The 6-(2-bromoeth-1-oxy)-3-phenyl-7-propylbenzisoxazole can be prepared as in Example 1 Step A from 6-hydroxy-3-phenyl-7-propylbenzisoxazole (1 g, 1.0 Eq, 4 mmol), prepared as described in Example 16 Step 3, and 1,2-dibromoethane (1.7 ml, 5 Eq, 20 mmol). The product was purified by elution from a silica gel column (44 g E. Merck 40–63μ) with toluene: hexanes: EtOAc 30:65:5.

Characteristic NMR Resonances; $^1$H NMR 400 MHz (CDCl$_3$); 7.92 (m, 2H), 7.65 (d, 1H, J=8.7 Hz), 7.53 (m, 3H), 6.94 (d, 1H, J=8.7 Hz), 4.39 (t, 2H, J=6.1 Hz), 3.69 (t, 2H, J=6.1 Hz), 2.94 (dd, 2H, J=8.9, 7.5 Hz), 1.74 (sext, 2H, J=7.5 Hz), 0.983 (t, 3H, J=7.3 Hz). MS ESI M+1=360/362.0. MW=359.1/361.1

Step 2

The 6-(2-bromoeth-1-oxy)-3-phenyl-7-propylbenzisoxazole of example 67 Step 1 (47 mg, 1.0 Eq, 0.13 mmol) and commercially available methyl 3-(4-hydroxyphenyl)propionate (30 mg, 1.3 Eq, 0.16 mmol) were condensed as described in Example 16 Step 4. The product was purified by elution from a silica gel column (44 g E. Merck 40–63μ) with toluene: hexanes: EtOAc 60:35:5.

Characteristic NMR Resonances; $^1$H NMR 400 MHz (CDCl$_3$); 7.92 (m, 2H), 7.66 (d, 1H, J=8.7 Hz), 7.52 (m, 3H), 7.12 (d, 2H, J=8.8 Hz & fine cplg), 7.02 (d, 1H, J=8.8 Hz), 6.87 (d, 2H, J=8.7 Hz & fine cplg.), 4.41 (complex m, 2H), 4.34 (complex m, 2H), 3.65 (s, 3H), 2.91 (t, 2H, J=8.7 Hz), 2.89 (t, 2H, J=8.1 Hz), 2.59 (dd, 2H, J=8.1, 7.0 Hz), 1.71 (sext, 2H, 8.5 Hz), 0.939 (t, 3H, J=7.4 Hz). MS ESI M+1=460.3. MW=459.2

Step 3

The ester of Example 66 Step 2 (34 mg, 1.0 Eq, 0.074 mmol) was hydrolyzed with LiOH (120 μL, 1.5 N, 2.3 Eq, 0.240 mmol) as described in Example 16 Step 5.

Characteristic NMR Resonances; $^1$H NMR 400 MHz (CDCl$_3$); 7.91 (m, 2H), 7.66 (d, 1H, J=8.8 Hz), 7.51 (m, 3H), 7.14 (d, 2H, J=8.8 Hz & fine spltg.), 7.02 (d, 1H, J=8.8 Hz), 6.88 (d, 2H, J=8.7 Hz & fine spltg.), 4.41 (m, 2H), 4.34 (m, 2H), 2.90 (m, 4H), 2.64 (t, 2H, J=8.0 Hz), 1.71 (sext, 2H, J=7.4 Hz), 0.938 (t, 3H, J=7.4 Hz). Analytical HPLC 75:25 CH$_3$CN:H$_2$O 0.1% TFA, E. Merck RP-8 5μ 4×250 mm, 1 ml/min. UV 210, RT 5.42 min. MS ESI M+1=446.3. MW=445.2.

EXAMPLE 67

Step 1

Resorcinol (11 g, 4.0 Eq, 0.1 mol) and methyl α-bromoacetate (2.37 ml, 1.0 Eq, 0.025 mol) were combined in DMF (50 ml) with CsCO$_3$ (8.96 g, 1.1 Eq, 0.0275 mol). The mixture was stirred at RT 16 Hrs. The mixture was poured into 2 N HCl and EtOAc. The aqueous phase was extracted with EtOAc and the extracts washed with NaHCO$_3$ sat'd. aq. The extracts were dried over Na$_2$SO$_4$ and reduced i. vac. The product was purified by elution from a silica gel column (220 g E. Merck 40–63μ) with toluene: EtOAc 82:18.

Characteristic NMR Resonances; $^1$H NMR 400 MHz (CDCl$_3$); 7.12 (t, 1H), 6.4–6.46 (m, 2H), 4.60 (s, 2H), 3.79 (s, 3H).

Step 2

The 6-(4-bromobut-1-oxy)-3-phenyl-7-propylbenzisoxazole of Example 62 Step 1 (123 mg, 1.05 Eq, 0.316 mmol) and methyl 3-hydroxyphenoxyacetate of Example 67 Step 1 (50 mg, 1.0 Eq , 0.301 mmol) were condensed as described in Example 16 Step 4. The product was purified by elution from a silica gel column (10 g E. Merck 40–63μ) with toluene: hexanes: EtOAc 50:45:5.

Characteristic NMR Resonances; $^1$H NMR 400 MHz (CDCl$_3$); 7.92 (m, 2H), 7.64 (d, 1H, J=8.7Hz), 7.52 (m, 3H), 7.16 (t, 1H, J=8.2 Hz), 6.97 (d, 1 H, J=8.8 Hz), 6.54 (dd, 1 H, J=8.3, 2.3 Hz), 6.46 (m , 2H), 4.60 (s, 2H), 4.14 (t, 2H, J=5.8 Hz), 4.03 (t, 2H, J=5.8 Hz), 3.78 (s, 3H), 2.91 (dd, 2H, J=8.7, 7.5 Hz), 2.01 (m, 4H), 1.71 (sext, 2H, J=7.5 Hz), 0.968 (t, 3H, J=7.4 Hz). MS ESI M+1=490.3. MW=489.22.

Step 3

The ester of Example 67 Step 2 (110 mg, 1.0 Eq, 0.225 mmol) was hydrolyzed with LiOH (299 μL, 1.5 N, 2.0 Eq, 0.45 mmol) as described in Example 16 Step 5.

Characteristic NMR Resonances; $^1$H NMR 400 MHz (CDCl$_3$); 7.91 (m, 2H), 7.63 (d, 1H, J=8.8 Hz), 7.51 (m, 3H), 7.18 (t, 2H, J=8.1 Hz), 6.96 (d, 1H, J=8.8 Hz), 6.57 (dd, 1H, J=7.5, 2.0 Hz), 6.48 (m, 2H), 4.64 (s, 2H), 4.14 (t, 2H, J=5.6 Hz), 4.02 (t, 2H, J=5.6 Hz), 2.91 (dd, 2H, J unresolved), 2.02 (m, 4H), 1.71 (sext, 2H, J=7.5 Hz), 0.964 (t, 3H, J=7.4 Hz). MS ESI M+1=476.3. MW=475.2

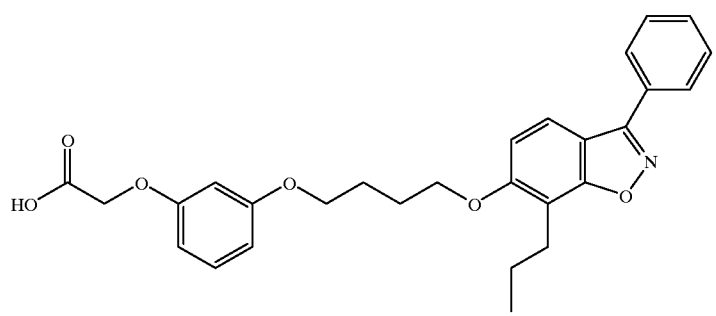

(3-(4-(3-phenyl-7-propyl-6-benz-[4,5]-isoxazoloxy)butyloxy))phenoxyacetic acid

EXAMPLE 68

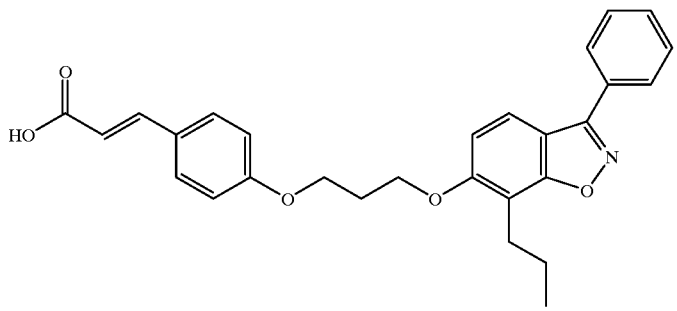

E-(4-(3-(3-phenyl-7-propyl-6-benz-[4, 5]-isoxazole)oxy)propyloxy) cinnamic acid

Step 1

Commercially available 4-hydroxycinnamic acid (2 g) was esterified as described in Example 23 Step 1. The ester was used without purification further.

Characteristic NMR Resonances; $^1$H NMR 400 MHz (CDCl$_3$); 7.62 (d, 1H, J=16 Hz), 7.41 (d, 2H, J=8.6 Hz with fine splitting), 6.82 (d, 2H, J=8.6 Hz with fine splitting), 6.28 (d, 1H, J=16 Hz), 5.32 (s, 1H), 3.78 (s, 3H). MS ESI M+1=179.1. MW=178.2

Step 2

The 6-(3-bromoprop-1-oxy)-3-phenyl-7-propylbenzisoxazole of Example 61 Step 1 (35.3 mg, 1.05 Eq, 0.85 mmol) and methyl 4-hydroxycinnamate of Example 68 Step 1 (16.3 mg, 1.6 Eq, 0.092 mmol) were condensed as described in Example 16 Step 4. The product was purified by elution from a silica gel column (2 g E. Merck 40–63μ) with toluene: hexanes: EtOAc 60:35:5.

Characteristic NMR Resonances; $^1$H NMR 400 MHz (CDCl$_3$); 7.92 (m, 2H), 7.63 7.66 (ovelapping d's, 2H), 7.53 (m, 3H), 7.47 (d, 1H, J=8.8 Hz), 7.2 (m, 1H), 7.0 (d, 1H, J=8.8 Hz), 6.92 (d, 1H, J=8.8 Hz), 6.30 (d, 1H, J=16 Hz), 4.29 (t, 2H, J=6.0 Hz), 4.25 (t, 2H, J=6.1 Hz), 3.79 (s, 3H), 2.92 (dd, 2H, J unresolved), 2.35 (m, 2H), 1.71 sext, 2H, J=7.5 Hz), 0.96 (t, 3H, J=7.5 Hz). MS ESI M+1=472.3. MW=471.2

Step 3

The ester of Example 68 Step 2 (25.9 mg, 1.0 Eq, 0.055 mmol) was hydrolyzed with LiOH (60 μL, 1.5 N, 2.2 Eq, 0.120 mmol) as described in Example 16 Step 5.

Characteristic NMR Resonances; $^1$H NMR 400 MHz (CDCl$_3$); 7.91 (m, 2H), 7.71 (d, 1H J=16 Hz), 7.64 (d, 1H, J=8.7 Hz), 7.51 (m, 3H), 7.0 (d, 1H, J=8.8 Hz), 6.92 (d, 1H, J=8.9 Hz plus fine coupling), 6.92 (d, 1H, J=16 Hz), 4.28 (t, 2H, J=5.9 Hz), 4.24 (t, 2H, J=6.2 Hz), 2.91 (t, 2H, J=7.4 Hz), 2.34 (m, 2H), 1.69 (sext, 2H, J=7.5 Hz), 0.95 (t, 3H, J=7.4 Hz). Analytical HPLC 75:25 CH$_3$CN:H$_2$O 0.1% TFA, E. Merck RP-8 5μ 4×250 mm, 1 ml/min. UV 210, RT 6.63 min. MS ESI M+1=458.4. MW=457.2

EXAMPLE 69

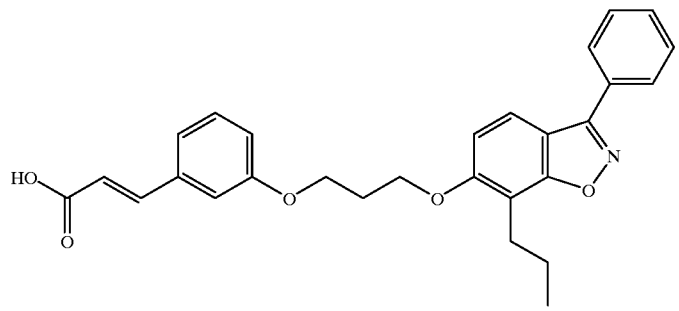

E-(3-(3-(3-phenyl-7-propyl-6-benz-[4, 5]isoxazole)oxy)propyloxy) cinnamic acid

Step 1

Commercially available 3-hydroxycinnamic acid (2 g) was esterified as described in Example 23 Step 1. The ester was used without purification further.

Characteristic NMR Resonances; $^1$H NMR 400 MHz (CDCl$_3$); 7.62 (d, 1H, J=16 Hz), 7.24 (m, 1H), 7.70 (d, 1H, J=7.7 Hz), 6.99 (m, 1H), 6.85 (dd, 1H, J=8.1, 2.1 Hz), 6.39 (d, 1H, J=16 Hz), 5.40 (s, 1H), 3.79 (s, 3H). MS ESI M+1=179.1. MW=178.1

Step 2

The 6-(3-bromoprop-1-oxy)-3-phenyl-7-propylbenzisoxazole of Example 61 Step 1 (31.4 mg, 1.0 Eq, 0.084 mmol) and methyl 3-hydroxycinnamate of Example 69Step 1 (30 mg, 2.0 Eq, 0.169 mmol) were condensed as described in Example 16 Step 4. The product was purified by elution from a silica gel column (2 g E. Merck 40–63μ) with toluene: hexanes: EtOAc 60:35:5.

Characteristic NMR Resonances; $^1$H NMR 400 MHz (CDCl$_3$); 7.92 (m, 2H), 7.66 (d, 1H J=16 Hz), 7.67 (d, 1H, J=8.0 Hz), 7.52 (m, 3H), 7.30 (t, 1H, J=7.8 Hz), 7.11 (m, 1H), 7.05 (brd s, 1H), 7.01 (d, 1H, J=8.7 Hz), 6.95 (dd, 1H), 6.42 (d, 1H, J=16 Hz), 4.29 (t, 2H, J=6.0 Hz), 4.24 (t, 2H, J=6.0 Hz), 3.80 (s, 3H), 2.93 (t, 2H, J=7.2 Hz), 2.35 (pent, 2H, J=5.8 Hz), 1.71 (sext, 2H, J=7.4 Hz), 0.96 (t, 3H, J=7.4 Hz). MS ESI M+1=472.3. MW=471.2

Step 3

The ester of Example 69 Step 2 (27.7 mg, 1.0 Eq, 0.055 mmol) was hydrolyzed with LiOH (65 μL, 1.5 N, 2.2 Eq, 0.131 mmol) as described in Example 16 Step 5.

Characteristic NMR Resonances; $^1$H NMR 400 MHz (CDCl$_3$); 7.92 (m, 2H), 7.72 (d, 1H, J=16 Hz), 7.64 (d, 1H, J=8.7 Hz), 7.52 (m, 3H), 7.30 (t, 1H, J=8.0 Hz), 7.13 (m, 1H), 7.08 (brd s, 1H), 7.00 (d, 1H, J=8.8 Hz), 6.96 (dd, 1H), 6.41 (d, 1H, J=16 Hz), 4.29 (t, 2H, J=6.0 Hz), 4.23 (t, 2H, J=6.0 Hz), 2.91 (t, 2H, J=7.5 Hz), 2.34 (pent, 2H), 1.69 (sext, 2H, J=7.5 Hz), 0.95 (t, 3H, J=7.3 Hz). Analytical HPLC 75:25 CH$_3$CN:H$_2$O 0.1% TFA, E. Merck RP-8 5μ 4×250 mm, 1 ml/min. UV 210, RT 6.89 min. MS ESI M+1=458.3. MW=457.2

EXAMPLE 70

Step 2

The 6-(3-bromoprop-1-oxy)-3-phenyl-7-propylbenzisoxazole of Example 61 Step 1 (38.4 mg, 1.0 Eq, 0.103 mmol) and methyl 3-(3-hydroxyphenyl)propionate of Example 70 Step 1 (20 mg, 2.0 Eq, 0.111 mmol) were condensed as described in Example 16 Step 4. The product was purified by elution from a silica gel column (2 g E. Merck 40–63μ) with toluene: hexanes: EtOAc 60:35:5.

Characteristic NMR Resonances; $^1$H NMR 400 MHz (CDCl$_3$); 7.92 (m, 2H), 7.66 (d, 1H, J=8.7 Hz), 7.53 (m, 3H), 7.20 (m, 1H), 7.01 (d, 1H, J=8.7 Hz), 6.78 (m, 3H), 4.29 (t, 2H, J=6.0 Hz), 4.20 (t, 2H, J=6.0 Hz), 3.66 (s, 3H), 2.92 (overlapping m's, 4H), 2.62 (t, 2H, J=7.5 Hz), 2.33 (pent, 2H, J=6.3 Hz), 1.71 (sext, 2H, J=7.5 Hz), 0.97 (t, 3H, J=7.5 Hz). MS ESI M+1=474.4. MW=473.2

Step 3

The ester of Example 70 Step 2 (32.7 mg, 1.0 Eq, 0.069 mmol) was hydrolyzed with LiOH (100 μL, 2.0 N, 2.9 Eq, 0.200 mmol) as described in Example 16 Step 5.

Characteristic NMR Resonances; $^1$H NMR 400 MHz (CDCl$_3$); 7.92 (m, 2H), 7.63 (d, 1H, J=8.7 Hz), 7.52 (m, 3H),

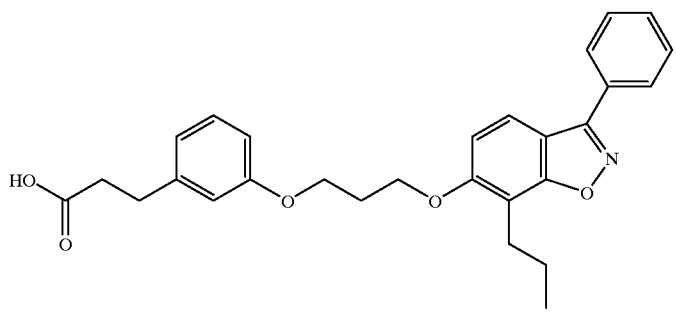

3-(3-(3-(3-phenyl-7-propyl-6-benz-[4,5]isoxazole)oxy)propyloxy) phenylpropionic acid Step 1

Methyl 3-hydroxycinnamate of Example 69 Step 1 (1.1 g, 1.0 Eq , 6.2 mmol) was hydrogenated at atmospheric pressure in EtOAc (45 ml) with 10% Pd on carbon (98 mg) as catalyst. After complete consumption of the starting cinnamate, the hydrogenation mixture was filtered through celite and reduced i. vac. The ester was used without purification.

Characteristic NMR Resonances; $^1$H NMR 400 MHz (CDCl$_3$); 7.14 (dd, 1H, J unresolved), 6.75 (d, 1H, J=7.8 Jz), 6.65 (m, 1H), 4.73 (s, 1H), 2.89 (t, 2H, J=7.5 Hz), 2.60 (t, 2H, J=7.5 Hz). MS EI M+=180.1. MW=180.1

7.19 (m, 1H), 6.99 (d, 1H, J=8.7 Hz), 6.78 (m, 3H), 4.27 (t, 2H, J=6.0 Hz), 4.18 (t, 2H, J=6.0 Hz), 2.91 (overlapping t's, 4H), 2.65 (t, 2H, J=8.1 Hz), 2.31 (pent, 2H, J=6.1 Hz), 1.71 (sext, 2H, J=7.3 Hz), 0.95 (t, 3H, J=7.4 Hz). Analytical HPLC 75:25 CH$_3$CN:H$_2$O 0.1% TFA, E. Merck RP-8 5μ 4×250 mm, 1 ml/min. UV 210, RT 6.55 min. MS ESI M+1=460.3. MW=459.2

EXAMPLE 71

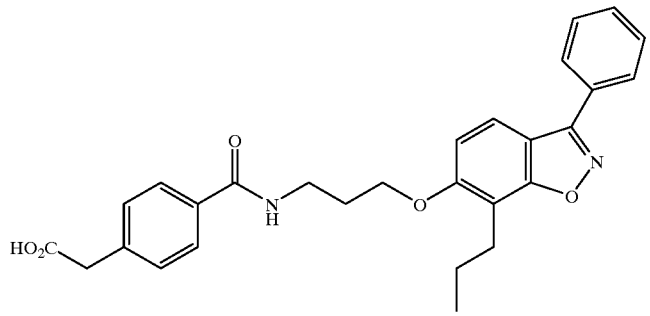

N-((4-carbomethoxymethyl)benzoyl)-3(3-phenyl-7-propyl-6-benz-[4,7]-isooxazolyloxy) propylamine Step A: Preparation of 3-phenyl-6-(3-aminopropyl)oxy-7-propyl benz-[4,7]-isoxazole hydrochloride: 506 mg (2.0 mmole, 1.0 eq.) of 3-phenyl-6-hydroxy-7-propyl benz-[4,7]-isoxazole (example 16, step 3) was dissolved in 20 ml of freshly distilled tetrahydrofuran, after which 525 mg (2.0 mmole, 1.0 eq.) triphenylphosphine and 0.34 ml (2.0 mmole, 1.0 eq.) of tert-butyl N-(3-hydroxypropyl)carbamate were added with stirring. The reaction vessel was cooled to 0° C. and 0.31 ml (2.0 mmole, 1.0 eq.) of diisopropyl azodicarboxylate was added dropwise. Once addition was complete the cooling bath was removed and the reaction was allowed to stir at room temperature for 24 hours. Saturated sodium bicarbonate solution was added to the stirring reaction mixture, which was then extracted with ethyl acetate. The ethyl acetate layer was washed with dilute HCl, dried over sodium sulfate, filtered and the filtrate evaporated. The residue was then treated with 10 ml of 4N HCl in dioxane (40 mmole, 20 eq.). After 20 minutes TLC shows Boc removal complete, so dioxane was evaporated and ether was added, upon which a precipitate formed. The suspension was stirred for 20 minutes, then filtered. The recovered solid was pumped on high vacuum to give 550 mg (79% yield) of the title compound.

$^1$H NMR (500 MHz, CD$_3$OD): δ 7.93 (m, 2H), 7.80 (d, 1H), 7.57 (m, 3H), 7.19 (d, 1I), 4.27 (t, 2H), 3.21 (t, 2H), 2.93 (t, 2H), 2.23 (m, 2H), 1.73 (m, 2H), 0.99 (t, 3H).

Step B: Preparation of N-((4-carbomethoxymethyl)benzoyl)-3(3-phenyl-7-propyl-6-benz-[4,7]-isooxazolyloxy) propylamine: 19.4 mg (0.10 mmole, 1.0 eq.) of the known compound methyl 4-carboxyphenyl acetate was dissolved in 1 ml dichloromethane, then treated with 21.1 mg (0.11 mmole, 1.1 eq.) of 1-(3-dimethylaminopropyl)-3-ethylcarbodiimide hydrochloride and 14.9 mg (0.11 mmole, 1.0 eq.) 1-hydroxybenzotriazole. After stirring together for 20 minutes, 34.7 mg (0.10 mmole, 1.0 eq) of 3-phenyl-6-(3-aminopropyl)oxy-7-propyl benz-[4,7]-isoxazole hydrochloride from Example 72 step A and 26 μl (0.15 mmole, 1.5 eq.) of diisopropylethylamine were added and the reaction stirred for 16 hours. The reaction mixture was then diluted with dichloromethane, washed twice each with 5% citric acid and 5% sodium bicarbonate solutions. The dichloromethane was then dried over sodium sulfate, filtered, evaporated and purified by silica gel chromatography to give 37 mg (76% yield) of the title compound.

$^1$H NMR (500 MHz, CDCl$_3$): δ 7.95 (dd, 2H), 7.74 (d, 2H), 7.68 (d, 1H), 7.55 (m, 3H), 7.35 (d, 2H), 7.01 (d, 1H), 6.45 (br t, 1H), 4.23 (t, 2H), 3.74 (q, 2H), 3.71 (s, 3H), 3.68 (s, 2H), 2.93 (t, 2H), 2.22 (m, 2H), 1.74 (m, 2H), 0.98 (t, 3H).

Step C: Preparation of N-((4-carboxymethyl)benzoyl)-3(3-phenyl-7-propyl-6-benz-[4,7]-isooxazolyloxy) propylamine: 10 mg (20.6 μmole, 1.0 eq.) of N-((4-carbomethoxymethyl)benzoyl)-3(3-phenyl-7-propyl-6-benz-[4,7]-isooxazolyloxy) propylamine from Example 72 step B was dissolved in 0.45 ml tetrahydrofuran and 0.25 ml of methanol. Then 0.15 ml of water and 0.10 ml of 0.25 N (25 μmole, 1.2 eq.) lithium hydroxide were added. The reaction was heated to 40° C. and after two hours diluted with water, acidified and extracted twice with dichloromethane. The dichloromethane was dried over sodium sulfate, filtered and the filtrate evaporated to give the title compound.

$^1$H NMR (500 MHz, CDCl$_3$): δ 7.94 (dd, 2H), 7.73 (d, 2H), 7.65 (d, 1H), 7.55 (m, 3H), 7.34 (d, 2H), 6.99 (d, 1H), 6.56 (br t, 1H), 4.20 (t, 2H), 3.72 (q, 2H), 3.69 (s, 2H), 2.91 (t, 2H), 2.20 (m, 2H), 1.74 (m, 2H), 0.95 (t, 3H). MS(ESI, TFA/HCOONH$_4$): m/e 473.3 [M+1].

EXAMPLE 72

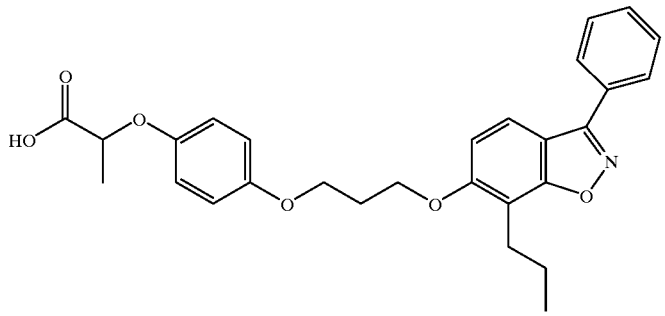

2-(4-(3-(3-phenyl-7-propyl-6-benz-[4,5]-isoxazoloxy)propyloxy))phenoxypropionic acid Step 1

The commercially available 2-(4-hydroxyphenoxy) propionic acid (2 g) was esterified as for Example 23 Step 1. The ester was used without purification.

Characteristic NMR Resonances; $^1$H NMR 400 MHz (CDCl$_3$); 6.75 (collapsed ABq, 4H), 4.66 (q, 1H, J=6.9 Hz), 3.75 (s, 3H), 1.58 (d, 3H, J=6.9 Hz). MS CI NH$_3$ M+NH$_4^+$= 214.1. MW=196

Step 2

The 6-(3-bromoprop-1-oxy)-3-phenyl-7-propylbenzisoxazole of Example 61 Step 1 (31.7 mg, 1.0 Eq, 0.85 mmol) and methyl 2-(4-hydroxyphenoxy)propionate of Example 72 Step (27 mg, 1.6 Eq, 0.138 mmol) were condensed as described in Example 16 Step 4. The product was purified by elution from a silica gel column (2 g E. Merck 40–63μ) with toluene: hexanes: EtOAc 60:35:5.

Characteristic NMR Resonances; $^1$H NMR 400 MHz (CDCl$_3$); 7.92 (m, 2H), 7.66 (d, 1H, J=8.7 Hz), 7.53 (m, 3H), 7.00 (d, 1H, J=8.9 Hz), 6.83 (s, 4H), 4.67 (q, 1H, J=6.8 Hz), 4.28 (t, 2H, J=6.0 Hz), 4.16 (t, 2H, J=6.0 Hz), 3.75 (s, 3H), 2.92 (dd, 2H, J=8.7, 7.4 Hz), 2.30 (pent, 2H, J=6.1 Hz), 1.71 (sext, 2H, J=7.6 Hz), 1.59 (d, 3H, J=6.8 Hz), 0.97 (t, 3H, J=7.4 Hz). MS ESI M+1=490.4. MW=489.2

Step 3

The ester of Example 72 Step 2 (29 mg, 1.0 Eq, 0.059 mmol) was hydrolyzed with LiOH (80 μL, 2.0 N, 2.7 Eq, 0.16 mmol) as described in Example 16 Step 5.

Characteristic NMR Resonances; $^1$H NMR 400 MHz (CDCl$_3$); 7.92 (m, 2H), 7.63 (d, 1H, J=8.8 Hz), 7.51 (m, 3H), 6.98 (d, 1H, J=8.7 Hz), 6.84 (s, 4H), 4.68 (q, 1H, J=6.9 Hz), 4.26 (t, 2H, J=5.9 Hz), 4.14 (t, 2H, J=6.0 Hz), 2.89 (dd, 2H, J unresolved), 2.29 (pent, 2H, J=6.0 Hz), 1.69 (sext, 2H, J=7.5 Hz), 1.60 (d, 3H, J=6.8 Hz), 0.94 (t, 3H, J=7.4 Hz). Analytical HPLC 75:25 CH₃CN:H₂O 0.1% TFA, E. Merck RP-8 5µ 4×250 mm, 1 ml/min. UV 210, RT 6.09 min. MS ESI M+1=476.3. MW=475.2

EXAMPLE 73

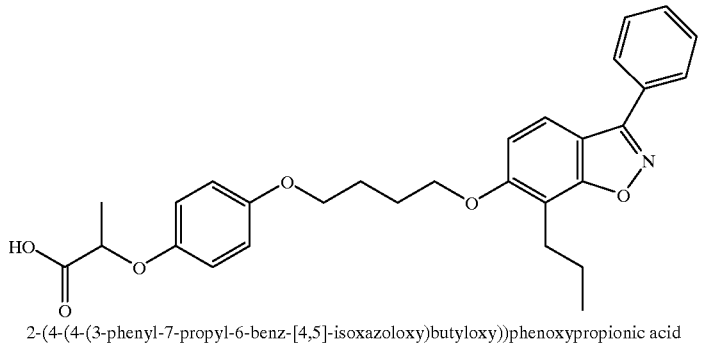

2-(4-(4-(3-phenyl-7-propyl-6-benz-[4,5]-isoxazoloxy)butyloxy))phenoxypropionic acid Step 1

The 6-(3-bromobut-1-oxy)-3-phenyl-7-propylbenzisoxazole of Example 62 Step 1 (37 mg, 1.2 Eq, 0.095 mmol) and methyl 2-(4-hydroxyphenoxy)propionate of Example 72 Step 1 (16 mg, 1.0 Eq, 0.082 mmol) were condensed as described in Example 16 Step 4. The product was purified by elution from a silica gel column (2 g E. Merck 40–63µ) with toluene: hexanes: EtOAc 60:35:5.

Characteristic NMR Resonances; ¹H NMR 400 MHz (CDCl₃); 7.92 (m, 2H), 7.65 (d, 1H, J=8.7 Hz), 7.53 (m, 3H), 6.98 (d, 1H, J=8.7 Hz), 6.83 (s, 4H), 4.67 (q, 1H, J=6.8 Hz), 4.10 (t, 2H), 4.01 (t, 2H), 3.75 (s, 3H), 2.93 (dd, 2H, J=8.6, 7.4 Hz), 2.02 (m, 4H), 1.73 (sext, 2H, J=7.5 Hz), 1.59 (d, 3H, J=6.8 Hz), 0.99 (t, 3H, J=7.4 Hz). MS ESI M+1=504.5. MW=503.2

Step 2

The ester of Example 73 Step 1 (35 mg, 1.0 Eq, 0.069 mmol) was hydrolyzed with LiOH (90 µL, 2.0 N, 2.6 Eq, 0.18 mmol) as described in Example 16 Step 5.

Characteristic NMR Resonances; ¹H NMR 400 MHz (CDCl₃); 7.92 (m, 2H), 7.63 (d, 1H, J=8.7 Hz), 7.53 (m, 3H), 6.96 (d, 1H, J=8.7 Hz), 6.83 (collapsed ABq, 4H), 4.69 (q, 1H, J=6.9 Hz), 4.14 (t, 2H, J=6.0 Hz), 4.00 (t, 2H, J=6.0 Hz), 2.90 (dd, 2H, J=8.7, 7.5 Hz), 2.00 (m, 4H), 1.71 (sext, 2H, J=7.4 Hz), 1.61 (d, 3H, J=6.8 Hz), 0.96 (t, 3H, J=7.4 Hz). Analytical HPLC 75:25 CH₃CN:H₂O 0.1% TFA, E. Merck RP-8 5µ 4×250 mm, 1 ml/min. UV 210, RT 6.84 min. MS ESI M+1=490.5. MW=489.2

EXAMPLE 74

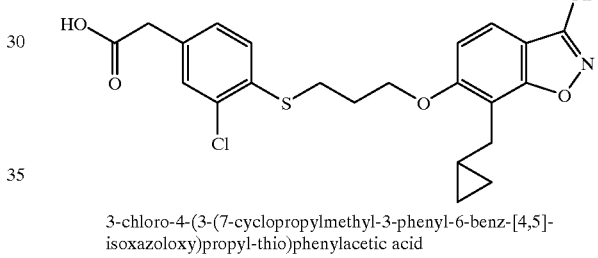

3-chloro-4-(3-(7-cyclopropylmethyl-3-phenyl-6-benz-[4,5]-isoxazoloxy)propyl-thio)phenylacetic acid STEP A: Preparation of 7-cyclopropylmethyl-3-phenyl-6-hydroxybenz-[4,5]-isoxazole
Using the method and materials in example 24 the titled compound was obtained.
STEP B: Preparation of Methyl 3-chloro-4-(3-(7-cyclopropylmethyl-3-phenyl-6-benz-[4,5]-isoxazoloxy)propyl-thio)phenylacetate
Using the method in example 20 step C (19632PV2), substituting 7-cyclopropylmethyl-3-phenyl-6-hydroxybenz-[4,5]-isoxazole, the titled compound was obtained.
NMR (CDCl₃) δ 7.92 (m, 2H); 7.66 (d, 1H); 7.51 (m, 3H); 7.29 (m, 2H); 7.13 (d, 1H); 6.98 (d, 1H, J=8.75 Hz); 4.22 (t, 2H, J=5.78 Hz); 3.67 (s, 3H); 3.54 (s, 2H); 3.17 (t, 2H, J=7.12 Hz); 2.86 (d, 2H, J=6.87 Hz); 2.15 (m, 2H); 0.43 (m, 1H); 0.34 (m, 1H).
STEP C: Preparation of 3-chloro-4-(3-(7-cyclopropylmethyl-3-phenyl-6-benz-[4,5]-isoxazoloxy)propyl-thio)phenylacetic acid
Using the method in example 2 step A THERE IS NO STEP A IN 19630PV2 OR 19632PV2, substituting Methyl 3-chloro-4-(3-(7-cyclopropylmethyl-3-phenyl-6-benz-[4,5]-isoxazoloxy)propylthio)phenylacetate, the titled compound was obtained.
NMR (CDCl₃) δ 7.91 (m, 2H); 7.66 (d, 1H, J=8.70 Hz); 7.52 (m, 3H); 7.29 (m, 2H); 7.14 (d, 1H, J=1.89 Hz); 6.98 (d, 1H, J=8.77 Hz); 4.22 (t, 2H, J=5.78 Hz); 3.57 (s, 2H); 3.18 (t, 2H, J=7.16 Hz); 2.86 (d, 2H, J=6.75 Hz); 2.20 (m, 2H); 0.42 (m, 1H); 0.31 (m, 1H). ESI: Mass spec: m/e=508 (M+1).

EXAMPLE 75

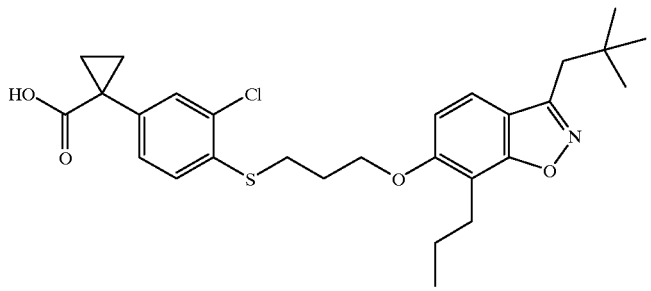

1-(3-chloro-4-(3-(3-(2,2-dimethylpropyl)-7-propyl-6-benz[4,5]isoxazole)oxy)propylthio) phenyl cyclopropane carboxylic acid

1. 3-(2,2-dimethylpropyl)-6-(3-bromopropyloxy)-7-propylbenz[4,5]isoxazole

A solution of 3-(2,2-dimethylpropyl)-6-hydroxy-7-propylbenz[4,5]isoxazole (2.000 grams; 8.090 mmol) in dry DMF (20 mL) was treated with 1,3-dibromopropane (4.29 mL; 42.263 mmol). Cesium carbonate (2.900 grams; 8.901 mmol) was added and the mixture stirred at 20° for 8 hours. The reaction mixture was partitioned between isopropyl acetate and pH 4 buffer. The organic was washed with water, then dried over magnesium sulfate. Filtration and evaporation afforded an oil which was chromatographed over silica gel, giving the title compound.

NMR (CDCl$_3$): 7.37 (d, 1H, J=8.8 Hz); 6.91 (d, 1H, J=8.7 Hz); 4.19 (t, 2H, J=5.6 Hz); 3.63 (t, 2H, J=7.0 Hz); 2.86 (bt, 2H, J=7.4 Hz); 2.80 (s, 2H); 1.03 (s, 9H).

2. 1-(3-chloro-4-(3-(3-(2,2-dimethylpropyl)-7-propyl-6-benz[4,5]isoxazole)oxy)propylthio)phenyl-1-cyclopropane carboxylic acid methyl ester A solution of 1-(3-chloro-4-dimethylcarbamoylthio) phenyl-1-cyclopropane carboxylic acid methyl ester (0.059 grams; 0.188 mmol) in dry methanol (1 mL) was treated with a solution of sodium methoxide in methanol (4.37 M; 0.060 mL; 0.263 mmol). The solution was stirred at 60° C. for 4 hours. The reaction was allowed to cool to 50° C. and treated with 3-(2,2-dimethylpropyl)-6-(3-bromopropyloxy)-7-propylbenz[4,5]-isoxazole (0.083 grams; 0.226 mmol). The reaction was stirred for 2 hours more, then partitioned between isopropyl acetate and pH 4 buffer. The organic was dried over magnesium sulfate, filtered and evaporated to a residue which was chromatographed to afford the title compound.

NMR (CDCl$_3$): 7.34 (d, 1H, J=8.4 Hz); 7.33 (d, 1H, J=1.8 Hz); 7.24 (d, 1H, J=8.1 Hz); 7.16 (dd, 1H, J=8.1, 1.9 Hz); 6.88 (d, 1H, J=8.6 Hz); 4.17 (t, 2H, J=5.8 Hz); 3.61 (s, 3H); 3.16 (t, 2H, J=7.1 Hz); 2.86 (bt, 2H, J=7.6 Hz); 2.79 (s, 2H); 1.59 (apparent quart, 2H, J=3.7 Hz); 1.13 (apparent quart, 2H, J=3.7 Hz); 1.03 (s, 9H).

3. 1-(3-chloro-4-(3-(3-(2,2-dimethylpropyl)-7-propyl-6-benz[4,5]isoxazole)oxy)propylthio)phenyl-1-cyclopropane carboxylic acid A solution of 1-(3-chloro-4-(3-(3-(2,2-dimethylpropyl)-7-propyl-6-benz[4,5]isoxazole)oxy)propylthio)phenyl-1-cyclopropane carboxylic acid methyl ester (0.051 grams; 0.096 mmol) in isopropanol (2 mL) was refluxed. The solution was treated with a solution of KOH in water (1.00 M; 0.192 mL; 0.192 mmol). Refluxing was continued for 1 hour. The reaction was partitioned between isopropyl acetate and 0.1 N HCl. The organic was dried over magnesium sulfate, filtered and concentrated to the title compound as a solid.

NMR (CDCl$_3$): 7.34 (d, 1H, J=8.4 Hz); 7.33 (d, 1H, J=1.8 Hz); 7.24 (d, 1H, J=8.1 Hz); 7.16 (dd, 1H, J=8.1, 1.9 Hz); 6.88 (d, 1H, J=8.6 Hz); 4.17 (t, 2H, J=5.8 Hz); 3.61 (s, 3H); 3.16 (t, 2H, J=7.1 Hz); 2.86 (bt, 2H, J=7.6 Hz); 2.79 (s, 2H); 1.65 (apparent quart, 2H, J=3.1 Hz); 1.20 (apparent quart, 2H, J=3.3 Hz); 1.03 (s, 9H).

EXAMPLE 76

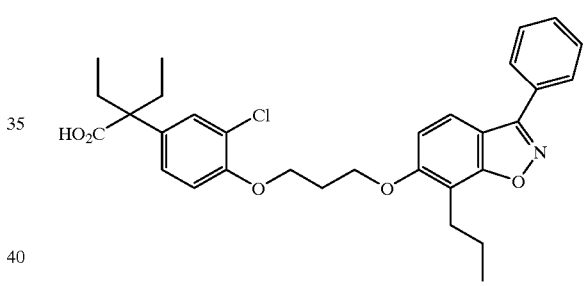

4-(3-(3-(Ethyl)-7-(phenyl)-6-benz-[4,5]-isoxazoloxy)propyloxy)-3-chloro-α, α-dimethyl-phenyl propionic acid Step A: Preparation of 3-chloro-(4-hydroxyphenyl) propionate:

In a 0° C. ice bath, 3-chloro-(4-hydroxyphenyl)acetic acid (2.06 g; 11.0 mmol), was dissolved in 3 ml of ether. Added to this solution was about 35 mL of diazomethane dissolved in ether (0.32 mmoL/mL). Allowed to stir for 5 minutes, vented the excess diazomethane to a cololess solution and concentrated in vacuo to afford a light yellow oil. Isolated 2.34 g of the title compound and used without further purification. NMR: δ 7.27 (m,1H); 7.10 (m,1H); 6.97 (d,1H) 3.71 (s,3H); 3.56 (s,2H)

Step B: Preparation of 3-phenyl-7-propyl-6-(3-bromopropyl)oxy-benz-[4,5]-isoxazole To a mixture of 3-phenyl-7-propyl-6-hydroxy-benz-[4,5]-isoxazole (1.0 g; 3.95 mmol, Prepared in Example 16 Step C), 1,3-dibromopropane (3.98g, 19.5 mmol) and potassium carbonate (0.573g, 4.15 mmol) in 4.0 mL of methyl ethyl ketone was warmed to reflux for 16 hours. Filtered, concentrated and chromatographed (silica gel, 30% ethyl acetate in hexane) to yeild 1.025 g of the title compound as a white solid. NMR (CDCl$_3$): δ 7.95 (d,2H); 7.69 (d,1H); 7.55 (m,3H); 7.03 (d,1H); 4.25 (t,2H); 3.68 (t,2H); 2.95 (t,2H); 2.41 (m,2H); 1.76 (m,2H); 1.01 (t,3H)

Step C: Preparation of 4-(3-(3-(Ethyl)-7-(phenyl)-6-benz-[4,5]-isoxazoloxy)propyloxy)-3-chloro-phenyl propionate A mixture of 3-chloro-(4-hydroxyphenyl)propionate (301.9 mg; 1.51 mmol), 3-(3-(Ethyl)-7-(phenyl)-6-benz-[4,5]-isoxazoloxy)propyloxy bromide (540.2 mg; 1.66 mmol), cesium carbonate (514.0 mg; 1.58 mmol) in about 10.0 ml dry dimethyl-formamide was stirred and heated for 1.5 hours. Concentrated, diluted with water and extracted with ethyl acetate, dried (Na$_2$SO$_4$), concentrated in vacuo and chromatographed (silica gel, 30% ethyl acetate in hexane) to yield 633.4 mg of the title compound as a light yellow oil. NMR (CDCl$_3$): δ 7.95 (d,2H); 7.67 (d,1H); 7.54 (m,3H); 7.31 (s,1H); 7.14 (q,1H); 7.05 (d,1H); 6.93 (d,1H); 4.35 (t,2H); 4.27 (t,2H); 4.13 (t,2H); 3.70 (s,3H); 3.55 (s,2H); 2.93 (t,2H); 2.38 (m,2H)

Step D: Preparation of 4-(3-(3-(Ethyl)-7-(phenyl)-6-benz-[4,5]-isoxazoloxy)propyloxy)-3-chloro-α-methyl-phenyl propionate To a solution of 4-(3-(3-(Ethyl)-7-(phenyl)-6-benz-[4,5]-isoxazoloxy)propyloxy)-3-chloro-phenyl propionate (148.0 mg; 0.332 mmol) in ca. 2.0 ml of dry tetrahydrofuran in a −78° C. ice bath under nitrogen was added hexamethyldisilylazid (0.5 M solution in toluene, 730 μL; 0.365 mmol) and stirred for 30 minutes. To this solution was added iodoethane (53.1 μL; 0.664 mmol) and was allowed to warm to room temperature and stir for 1 hour. The solution was quenched with 1 M(aq) NH$_2$Cl and washed with water and extracted with ethyl acetate, dried (Na$_2$SO$_4$) and concentrated in vacuo and chromato-graphed (silica gel 30% ethyl acetate) to yeild 32.1 mg of the title compound as a colorless oil. NMR (CDCl$_3$): δ 7.95 (d,2H); 7.68 (d,1H); 7.55 (m,3H); 7.33 (s,1H); 7.16 (d,1H); 7.07 (d,1H); 6.93 (d,1H); 4.35 (t,2H); 4.28 (t,2H);

Step E: Preparation of 4-(3-(3-(Ethyl)-7-(phenyl)-6-benz-[4,5]-isoxazoloxy)propyloxy)-3-chloro-α, α-dimethyl-phenyl propionate The title compound was prepared by following the procedures in Example 1, step G affording 30.0 mg of viscous oil.

NMR (CDCl$_3$): δ 7.95 (d,2H); 7.67 (d,1H); 7.56 (m,4H); 7.41 (d,1H); 7.05 (d,1H); 6.94 (d,1H); 4.36 (t,2H); 4.30 (t,2H); 3.79 (s,3H);

Step F: Preparation of 4-(3-(3-(Ethyl)-7-(phenyl)-6-benz-[4,5]-isoxazoloxy)propyloxy)-3-chloro-α, α-dimethyl-phenyl propionic acid A solution of 29.0 mg (0.0526 mmol) 4-(3-(3-(Ethyl)-7-(phenyl)-6-benz-[4,5]-isoxazoloxy)propyloxy)-3-chloro-α, α-dimethylphenyl propionate ca. 2.0 ml of isopropyl alcohol and 1 M aqueous potassium hydroxide (210 μL; 4 eq) was heated at 60° C. for 36 hours. The mixture was diluted with ethyl acetate and acidified to pH 5–6 with 1 M HCl, washed with water (2 times), brine (1 time) and dried over sodium sulfate, concentrated concentrated in vacuo and preparatory plate chromatography (silica 30% ethyl acetate in hex) to afford 20.0 mg of the title compound. (Mass Spec=536.3, calc=535.2); NMR (CDCl$_3$): δ 7.92 (d,2H); 7.63 (d,1H); 7.51 (m,4H); 6.99 (d,1H); 6.80 (d,1H); 4.29 (t,2H); 4.29 (t,2H); 3.46 (s,1H); 2.90 (t,2H); 2.32 (t,2H)

EXAMPLE 77

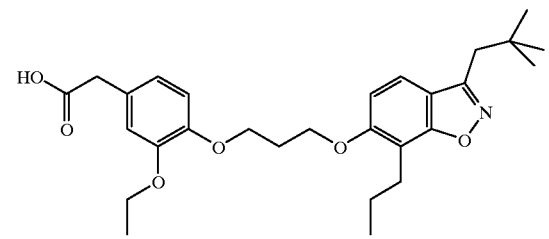

3-Ethoxy-4-(3-(3-(2,2-dimethylpropyl)-7-propyl-6-benz-[4,5]-isoxazoloxy)propyloxy)phenylacetate Step A: Preparation of methyl 3-ethoxy-4-(3-(3-(2,2-dimethylpropyl)-7-propyl-6-benz-[4,5]-isoxazoloxy)propyloxy)benzoate Using the method of Example 56, Step D, and substituting 3-(2,2-dimethylpropyl)-6-(3-bromopropyloxy)-7-propyl-6-benz-[4,5]-isoxazole (Example 65, Step A) and methyl 4-hydroxy-3-ethoxybenzoate as starting materials, the title compound was obtained as an oil. NMR (CDCl$_3$); δ 0.95 (t, 3H); 1.07 (s, 9H); 1.45 (t, 3H); 1.70 (m, 2H); 2.40 (m, 2H); 2.82 (s, 2H); 2.88 (t, 2H); 3.90 (s, 3H); 4.13 (q, 2H); 4.12 (t, 2H); 4.13 (t, 2H); 6.93 (d, 1H); 6.94 (d, 1H);7.37 (d, 1H); 7.56 (s, 1H); 7.66 (d 1H).

Step B: Preparation of 3-ethoxy-4-(3-(3-(2,2-dimethylpropyl)-7-propyl-6-benz-[4,5]-isoxazoloxy)propyloxy)benzoate Using the method of Example 37, Step E and substituting methyl 3-ethoxy-4-(3-(3-(2,2-dimethylpropyl)-7-propyl-6-benz-[4,5]-isoxazoloxy)propyloxy)benzoate, the title compound was obtained as an oil. NMR (CDCl$_3$); δ 0.96 (t, 3H); 1.07 (s, 9H); 1.46 (t, 3H);1.69 (m, 2H); 2.40 (m, 2H); 2.83 (s, 2H); 2.88 (t, 2H); 4.14 (q, 2H); 4.31 (t, 2H); 4.34 (t, 2H); 6.96 (d, 2H); 7.38 (d, 1H); 7.6 (s, 1H); 7.75 (d, 1H).

Step C: Preparation of methyl 3-ethoxy-4-(3-(3-(2,2-dimethylpropyl)-7-propyl-6-benz-[4,5]-isoxazoloxy)propyloxy)phenylacetate To a solution of 3-ethoxy-4-(3-(3-(2,2-dimethylpropyl)-7-propyl-6-benz-[4,5]-isoxazoloxy)propyloxy)benzoate (184 mg, 0.392 mmole) in methylene chloride (2 mL) and DMF (2 drops) at 0° C. was added oxalyl chloride (36 μL, 0.411 mmole). The mixture was stirred at room temperature for 30 minutes and then concentrated in vacuo. The residue was concentrated in vacuo 3× from methylene chloride The final residue was dissolved in ether (5 mL) and treated with excess diazomethane in ether until the yellow color persisted. The yellow solution was stirred at room temperature for 3 hours. Nitrogen was bubbled through the solution for 5 minutes before concentrating in vacuo. The residue was dissolved in ethyl acetate and washed with 1N sodium bicarbonate, water, brine, dried over magnesium sulfate and concentrated in vacuo to give a yellow oil. The oil was dissolved in methanol (4 mL) and triethylamine (850 μL) and stirred with silver benzoate (37 mg, 0.16 mmole) at room temperature for 18 hours. Celite and brine were added and the mixture was filtered, washing with methanol. The filtrate was concentrated in vacuo and the residue partitioned with ethyl acetate and 1N HCl. The organic phase was washed with water, brine, dried over magnesium sulfate and concentrated in vacuo to give an oil. Thin layer chromatography on silica gel eluting with hexane:2-propanol (9:1) provided the crude title compound (104 mg). A second thin layer chromatography on silica gel eluting with ethyl acetate:hexane (15:85) afforded the title compound (30 mg) as an oil. NMR (CDCl$_3$); δ 0.96 (t, 3H); 1.07 (s, 9H); 1.41

(t, 3H); 1.69 (m, 2H); 2.35 (m, 2H); 2.82 (s, 2H); 2.87 (t, 2H); 3.56 (s, 2H); 3.70 (s, 3H); 4.06 (q, 2H); 4.25 (t, 2H); 4.29 (t, 2H); 6.80 (d, 1H); 6.83 (d, 1H); 6.88 (d, 1H); 6.95 (d, 1H); 7.37 (d, 1H).

Step D: Preparation of 3-ethoxy-4-(3-(3-(2,2-dimethylpropyl)-7-propyl-6-benz-[4,5]-isoxazoloxy)propyloxy)phenylacetate Using the method of Example 37, Step E and substituting methyl 3-ethoxy-4-(3-(3-(2,2-dimethylpropyl)-7-propyl-6-benz-[4,5]-isoxazoloxy)propyloxy)phenylacetate, the title compound was obtained as a gum. NMR (CDCl$_3$) δ 0.95 (t, 3H); 1.07 (s, 9H); 1.41 (t, 3H);1.69 (m, 2H); 2.35 (m, 2H); 2.82 (s, 2H); 2.87 (t, 2H); 3.59 (s, 2H); 4.07 (q, 2H); 4.25 (t, 2H); 4.29 (t, 2H); 6.82 (d, 1H); 6.87 (d, 1H); 6.95 (d, 1H); 7.37 (d, 1H). Mass spec, m/e=484 (m +1).

EXAMPLE 78

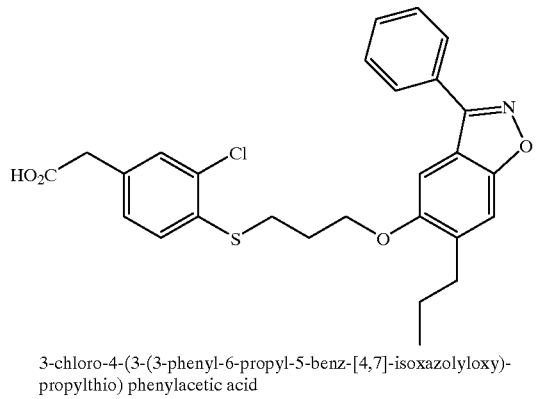

3-chloro-4-(3-(3-phenyl-6-propyl-5-benz-[4,7]-isoxazolyloxy)-propylthio) phenylacetic acid Step A: Preparation of 3-phenyl-5-hydroxy-6-propyl benz-[4,7]-isoxazole: 245 mg (0.90 mmole, 1.0 eq.) of 2,5-dihydroxy-4-propyl benzoxime from example 25, step G was dissolved in 5 ml acetic anhydride and allowed to stir 8 hours. The acetic anhydride was removed by high vacuum rotary evaporation and pumped on high vacuum for 16 hours. The crude material was then taken up in 3 ml pyridine and refluxed for 8 hours. Water and 2N HCl were added and the aqueous was extracted with ethyl acetate. The organic was dried over sodium sulfate, filtered and the filtrate evaporated. The residue was purified by silica gel chromatography to give 74.1 mg (32% yield) of the title compound, which was assigned after $^1$H NMR, NOE difference spectroscopy, and mass spectrometry.

$^1$H NMR (500 MHz, CDCl$_3$): δ 7.93 (m, 2H), 7.54 (m, 3H), 7.42 (s, 1H), 7.26 (s, 1H), 2.77 (t, 2H), 1.75 (m, 2H), 1.05 (t, 3H). MS (ESI, TFA/HCOONH$_4$): m/e 254.1 [M+1].

Step B: Preparation of methyl 4-(1-oxo-2-amino-5-(3-phenyl-7-propyl-6-benz-[4,7]-isoxazolyloxy)pentyl) phenyl acetate: 20 mg (79 μmole, 1.0 eq.) of 3-phenyl-5-hydroxy-6-propyl benz-[4,7]-isoxazole from Example 78 step A was dissolved in 0.75 ml of N,N-dimethylformamide. 27 mg (83 μmole, 1.05 eq.) of cesium carbonate and 26.7 mg (79 μmole, 1.0 eq.) of methyl 3-chloro-4-(3-bromopropylthio) phenyl acetate (example 25, step I) were then added and the reaction stirred at 60° C. for 200 minutes. The reaction was cooled to room temperature, diluted with water and ethyl acetate, then acidified with dilute aqueous HCl. The organic layer was dried over sodium sulfate, filtered and the filtrate evaporated. The crude material was purified by preparative TLC to give the title compound.

$^1$H NMR (400 MHz, CDCl$_3$): δ 7.89 (m, 2H), 7.53 (m, 3H), 7.40 (s, 1H), 7.29 (d, 1H), 7.27 (d, 1H), 7.13 (s, 1H), 7.10 (dd, 1H), 4.14 (t, 2H), 3.68 (s, 3H), 3.52 (s, 2H), 3.18 (t, 2H), 2.74 (t, 2H), 2.21 (m, 2H), 1.66 (m, 2H), 0.98 (t, 3H).

Step C: Preparation of 4-(1-oxo-2-amino-5-(3-phenyl-7-propyl-6-benz-[4,7]-isoxazolyloxy)pentyl) phenylacetic acid: 14.2 mg (28 μmole, 1.0 eq.) of methyl 4-(1-oxo-2-amino-5-(3-phenyl-7-propyl-6-benz-[4,7]-isoxazol-yloxy)pentyl) phenyl acetate from step B was dissolved in 0.4 ml of 1:1 tetrahydrofuran:methanol and 0.14 ml of 0.25 N (35 μmole, 1.25 eq.) of lithium hydroxide and allowed to stir for 16 hours. The reaction mixture was then diluted with water, acidified with dilute aqueous HCl, and extracted with ethyl acetate. The organic layer was dried over sodium sulfate, filtered and the filtrate evaporated. The residue was purified by silica gel chromatography to give 10 mg (73% yield) of the title compound.

$^1$H NMR (500 MHz, CDCl$_3$): δ 7.93 (m, 2H), 7.57 (m, 3H), 7.43 (s, 1H), 7.33 (d, 1H), 7.29 (d, 1H), 7.15 (s, 1H), 7.13 (dd, 1H), 4.17 (t, 2H), 3.60 (s, 2H), 3.21 (t, 2H), 2.77 (t, 2H), 2.24 (m, 2H), 1.70 (m, 2H), 1.00 (t, 3H). MS (ESI, TFA/HCOONH$_4$): m/e 496.3 [M+1].

BIOLOGICAL ASSAYS

I. White Adipose Tissue in vitro Assay

The ability of compounds of the present invention to enhance the insulin activation of $^{14}$C-glucose incorporation into glycogen in white adipose tissue (WAT) was determined by the following assay.

This assay measures the efficacy of the instant compounds to enhance the insulin activation of $^{14}$C-glucose incorporation into glycogen in white adipose tissue (WAT) in a 5 hour completely in vitro system. All procedures are performed in medium 199 containing 1% bovine serum albumen, 5 mM HEPES, and antibiotic (100 units/ml penicillin, 100 μg/ml streptomycin sulfate, 0.25 μg/ml amphotericin B), hereafter called culture medium. Epididymol fat pads are minced with scissors into small fragments, approximately 1 mm in diameter. Minced WAT fragments (100 mg) are incubated in a total volume of 0.9 ml culture medium containing 1 mU/ml insulin and test compound in tissue culture incubator at 37° C. with 5% CO$_2$ with orbital shaking for 3 hours. $^{14}$C-labeled glucose is added and incubation continued for 2 hours. Tubes are centrifuged at low speed, infranatant is removed and 1 M NaOH is added. Incubation of alkali-treated WAT for 10 minutes at 60° C. solubilizes tissue. Resulting tissue hydrolyzate is applied to Whatman filter paper strips which are then rinsed in 66% ethanol followed by 100% acetone which removes unincorporated $^{14}$C-glucose from bound $^{14}$C-glycogen. The dried paper is then incubated in solution of amyloglucosidase to cleave glycogen into glucose. Scintillation fluid is added and samples are counted for $^{14}$C activity. Test compounds that resulted in $^{14}$C activity substantially above incubations with insulin alone are considered active insulin-enhancing agents. Active compounds were titrated to determine the compound concentration which resulted in 50% of maximum enhancement of insulin activation and were termed EC$_{50}$ values. EC$_{50}$ values for the instant compounds were found to be 50 μM or less, preferably 5.0 to 0.0001 μM or less.

II. PPAR Receptor Binding and/or Transactivation Assays

Compounds of the instant invention which are useful for the above discussed treatments can be identified and/or characterized by employing the PPAR δ, and γ binding assays and/or PPAR δ, PPAR α and PPARγ transactivation assays. The assays are useful in predicting or quantitating in vivo effects having to do with the control or modulation of glucose, free fatty acid, triglyceride, insulin or cholesterol. To evaluate $IC_{50}$ or $EC_{50}$, values the compounds were titrated in the appropriate assay using different concentrations of the compound to be tested. To obtain the appropriate values (% Inhibition-$IC_{50}$, or % Activation-$EC_{50}$), the data resulting from the assays were then analyzed by determining the best fit of a 4 parameter function to the data using the Levenberg-Marquardt non-linear fitting algorithm in Kaleidagraph (Synergy Software, Reading, Pa.). The human nuclear receptor cDNA for PPARδ (hPPARδ) has been cloned from a human osteosarcoma cell cDNA library and is fully described in A. Schmidt et al., Molecular Endocrinology, 6:1634–1641 (1992), herein incorporated by reference in its entirety. See A. Elbrecht et al., Biochem. and Biophy. Res. Comm. 224:431–437 (1996) and T. Sher et al., Biochem. 32:5598–5604 (1993) for a description of the human nuclear receptor gene PPARγ and α.

The hPPARδ binding assay comprises the steps of:

(a) preparing multiple test samples by incubating separate aliquots of the receptor hPPARδ with a test compound in TEGM containing 5–10% COS-1 cell cytoplasmic lysate and 2.5 nM labeled ([$^3H_2$]Compound D, 17 Ci/mmole) for a minimum of 12 hours, and preferably for about 16 hours, at 4° C., wherein the concentration of the test compound in each test sample is different, and preparing a control sample by incubating a further separate aliquot of the receptor hPPARδ under the same conditions but without the test compound; then (b) removing unbound ligand by adding dextran/gelatin-coated charcoal to each sample while maintaining the samples at 4° C. and allowing at least 10 minutes to pass, then (c) subjecting each of the test samples and the control sample from step (b) to centrifugation at 4° C. until the charcoal is pelleted; then (d) counting a portion of the supernatant fraction of each of the test samples and the control sample from step (c) in a liquid scintillation counter and analyzing the results to determine the $IC_{50}$ of the test compound.

In the hPPARδ binding assay, preferably at least four test samples of varying concentrations of a single test compound are prepared in order to determine the $IC_{50}$.

The hPPARδ transactivation assay comprises the steps of:

(a) seeding an hPPARδ/GR stable CHO-K1 cell line into alpha MEM containing 10% FCS, 10 mM HEPES, and 500 mg/ml G418 at 37° C. in an atmosphere of 10% $CO_2$ in air, (b) incubating the cells from step (a) for 16 to 48 hours, preferably about 20 hours, at 37° C. in an atmosphere of 10% $CO_2$ in air;

(c) washing the cells from step (b) with alpha MEM;

(d) preparing multiple test cell groups by incubating separate groups of the cells from step (c) with the test compound in alpha MEM containing 5% charcoal stripped FCS, 10 mM HEPES, and 500 mg/ml G418, for 24 to 48 hours, preferably about 24 hours, at 37° C. in an atmosphere of 10% $CO_2$ in air, wherein the concentration of the test compound in each test cell group is different, and preparing a control cell group by incubating a further separate group of the cells from step (c) under the same conditions but without the test compound; then (e) preparing cell lysates from each of the test cell groups and the control cell group of step (d) using an aqueous detergent lysis buffer, and (f) measuring the luciferase activity of the test cell groups and the control cell group of step (e) and analyzing the results to determine the $EC_{50}$ of the test compound.

In the hPPARδ transactivation assay, preferably at least four test cell groups of varying concentrations of a single test compound are prepared in order to determine the $EC_{50}$.

Particular terms and abbreviations used herein are defined as follows: gst is glutathione-S-transferase; EDTA is ethylenediaminetetraacetic acid; HEPES is N-[2-hydroxyethyl]-piperazine-N'-[2-ethanesulfonic acid]; FCS is fetal calf serum; Lipofectamine is a 3:1 (w/w) liposome formulation of the polycationic lipid 2,3-dioleyloxy-N-[2(spermine-carboxamido)ethyl]-N,N-dimethyl-1-propanaminiumtrifluoroacetate and the neutral lipid dioleoyl phosphatidylethanolamine in water; G418 is geneticin; MEM is Minimum Essential Medium; Opti MEM 1 Reduced-Serum Medium is an aqueous composition containing HEPES buffer, 2400 mg/L sodium bicarbonate, hypoxanthine, thymidine, sodium pyruvate, L-glutamine, trace elements, growth factors, and phenol red reduced to 1.1 mg/L; Luciferase Assay Reagent (in re-constituted form) is an aqueous composition containing 20 mM tricine, 1.07 mM $(MgCO_3)_4Mg(OH)_2.5H_2O$, 2.67 mM $MgSO_4$, 0.1 mM EDTA, 33.3 mM DTT, 270 μM coenzyme A, 470 μM luciferin, 530 μM ATP, having a final pH of 7.8.

AD-5075 has the following structure:

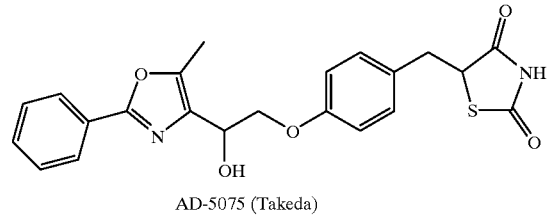

AD-5075 (Takeda)

Opti MEM 1 Reduced-Serum Medium, alpha MEM, G418, and Lipofectamine are commercially available from GibcoBRL Life Technologies, Gaithersburg, Md. Alpha MEM is an aqueous composition having the following components:

|  | mg/L |
|---|---|
| Component: Inorganic Salts | |
| $CaCl_2$ (anhyd.) | 200.00 |
| $CaCl_2.2H_2O$ | — |
| KCl | 400.00 |
| $MgSO_4$ (anhyd.) | 97.67 |
| $MgSO_4.7H_2O$ | — |
| NaCl | 6800.00 |
| $NaHCO_3$ | 2200.00 |
| $NaH_2PO_4.H_2O$ | 140.00 |
| $NaH_2PO_4.2H_2O$ | — |
| Other Components: | |
| D-Glucose | 1000.00 |
| Lipoic Acid | 0.20 |
| Phenol Red | 10.00 |
| Sodium Pyruvate | 110.00 |
| Amino Acids: | |
| L-Alanine | 25.00 |
| L-Arginine.HCl | 126.00 |
| L-Asparagine.$H_2O$ | 50.00 |
| L-Aspartic Acid | 30.00 |
| L-Cystine | — |

-continued

| | mg/L |
|---|---|
| L-Cystine.2HCl | 31.00 |
| L-Cysteine HCl | — |
| L-Cysteine HCl.H$_2$O | 100.00 |
| L-Glutamic Acid | 75.00 |
| L-Glutamine | 292.00 |
| L-Alanyl-L-Glutamine | — |
| Glycine | 50.00 |
| L-Histidine HCl.H$_2$O | 42.00 |
| L-Isoleucine | 52.00 |
| L-Leucine | 52.00 |
| L-Lysine.HCl | 73.00 |
| L-Methionine | 15.00 |
| L-Phenylalanine | 32.00 |
| L-Proline | 40.00 |
| L-Serine | 25.00 |
| L-Threonine | 48.00 |
| L-Tryptophan | 10.00 |
| L-Tyrosine | — |
| L-Tyrosine (disodium salt) | 52.00 |
| L-Valine | 46.00 |
| Vitamins: | |
| L-Ascorbic acid | 50.00 |
| Biotin | 0.10 |
| D-Ca Pantothenate | 1.00 |
| Choline Chloride | 1.00 |
| Folic acid | 1.00 |
| i-Inositol | 2.00 |
| Niacinamide | 1.00 |
| Pyridoxal HCl | 1.00 |
| Riboflavin | 0.10 |
| Thiamine HCl | 1.00 |
| Vitamin B$_{12}$ | 1.40 |
| Ribonucleosides | |
| Adenosine | 10.00 |
| Cytidine | 10.00 |
| Guanosine | 10.00 |
| Uridine | 10.00 |
| Deoxyribonucleosides | |
| 2' Deoxyadenosine | 10.00 |
| 2' Deoxycytidine HCl | 11.00 |
| 2' Deoxyguanosine | 10.00 |
| Thymidine | 10.00 |

The instant compounds, which are useful for treating the above discussed disease states, will preferably have IC$_{50}$ values at one, two or all of the PPAR (PPARγ, PPARδ or PPARα) receptor cites of equal to or less than 10 μM binding assay, and an EC$_{50}$ equal to or less than 10 μM in the transactivation assay. Preferably, an IC$_{50}$ of 100 nM in the binding assay, and an EC$_{50}$ equal to or less than 100 nM in the transactivation assay. More preferably, the instant compounds have an IC$_{50}$ equal to or less than 50 nM in the binding assay, and an EC$_{50}$ equal to or less than 50 nM in the transactivation assay. Most preferably, the instant compounds have an IC$_{50}$ equal to or less than 10 nM in the binding assay, and an EC$_{50}$ equal to or less than 10 nM in the transactivation assay.

PPAR Receptor Binding Assay

A. Preparation of Human PPARγ2 and δ

Human PPARγ2 and PPARδ, independently, were prepared as gst-fusion proteins in *E. coli*. The full length human cDNA for PPARγ2 and PPARδ were subcloned into the PGEX-2T and PGEX-KT, respectively, expression vector (Pharmacia). *E. coli* containing the plasmid were grown, induced, and then harvested by centrifugation. The resuspended pellet was broken in a French press and debris was removed by centrifugation at 12,000×g. Receptors were purified from the supernatant by affinity chromatography on glutathione sepharose. After application to the column, and 1 wash, receptor was eluted with glutathione. Glycerol was added to stabilize the receptor and aliquots were frozen at −80° C. for later use.

B. [$^3$H]AD-5075 and Example 11 Displacement Assay for PPARγ2 and PPARδ, Respectively For each assay, an aliquot of receptor (1:1000–1:3000 dilution) was incubated in TEGM (10 mM Tris, pH 7.2, 1 mM EDTA, 10% glycerol, 7 μl/100 ml 13-mercaptoethanol, 10 mM Na molybdate, 1 mM dithiothreitol, 5 μg/ml aprotinin, 2 μg/ml leupeptin, 2 μg/ml benzamide and 0.5 mM PMSF) containing 5–10% COS-1 cell cytoplasmic lysate and 10 nM labeled thiazolidinedione ([$^3$H$_2$]AD-5075, 21 Ci/mmole), ±test compound compound, [$^3$H$_2$]Example 11, 17 Ci/mmole), ±test compound, respectively. Assays were incubated for ~16 h at 4° C. in a final volume of 300 μl. Unbound ligand was removed by addition of 200 μl dextran/gelatin-coated charcoal, on ice, for ~10 minutes. After centrifugation at 3000 rpm for 10 min at 4° C., 200 μl of the supernatant fraction was counted in a liquid scintillation counter. In this assay the KD for AD-5075 and Example 11 is 1 nM, respectively.

PPAR Receptor Transactivation Assay

A. Activation of hPPARγ and hPPARδMethods

1. Plasmids

The chimeric receptor expression constructs, pSG5-hPPARγ2/GR and pSG5-hPPARδ/GR, were prepared by inserting the DNA binding domain of the murine glucocorticoid receptor adjacent to the ligand binding domain of hPPARγ2 or hPPARδ. These vectors were kindly provided by Dr. Azriel Schmidt (MRL). The glucocorticoid receptor-responsive reporter vector, pMMTV/luc/neo, contains the murine mammary tumour virus (MMTV) promoter adjacent to the luciferase gene (luc) and the neomycin resistance gene (neo). It was constructed from pMMTV/luc which was provided by Dr. Azriel Schmidt (Merck Research Laboratories). Prior to transfection into CHO-K1 cells, pSG5-hPPARγ2/GR and pSG5-hPPARδ/GR were linearized with Xba I. pMMTV/luc/neo DNA was cut with Pvu I. Wild type receptor constructs, pSG5-hPPARγ2, pSG5-hPPARδ and pSG5-hPPARα were prepared by inserting the full-length hPPARγ2, hPPARδ and PPARα cDNAs adjacent to the SV40 promoter in pSG5. The PPAR-responsive reporter construct, pPPRE-luc, contained 3 copies of a generic PPRE placed adjacent to the thymidine kinase minimal promoter and the luciferase reporter gene. The transfection control vector, pCMV-lacZ, contains the galactosidase Z gene under the regulation of the cytomegalovirus promoter.

2. Production of stable cell lines

CHO-K1 cells were seeded overnight at 6×10$^5$ cells/60 mm dish in alpha Minimum Essential Medium (MEM) containing 10% fetal calf serum (FCS), 10 mM HEPES, 100 units/ml PenicillinG and 100 μg/ml Streptomycin sulfate at 37° C. in an atmosphere of 10% CO$_2$ in air. The cells were washed once with OptiMEM 1 Reduced-Serum Medium and then cotransfected with 4.5 μg of pSG5-hPPARγ2/GR or pSG5-hPPARδ/GR expression vector and 0.5 μg of pMMTV/luc/neo in the presence of 100 μg Lipofectamine (GIBCO BRL) according to the instructions of the manufacturer. Transfection medium was removed 2 h later and replaced with growth medium. After being incubated for 3 days, cells were subcultured by diluting the cell suspension 1/1250 and 1/6250 and placing the cells in a 100 mm culture dish. Selection of the stable cell lines was initiated the next day by adding 500 μg/ml G418 to the medium. Cells were routinely fed with the selection media for 1 month at which time 120 colonies were picked and transferred to 24 well culture plates. Ten days later, confluent colonies were transferred to 6 well plates to maintain stocks and to 96 well plates to assay for luciferase activity. Positive clones were characterized and validated by titrating 4 known agonists on each clone. Two clones, g2B2P2D9 and d2A5P2G3, were selected for screening purposes.

B. hPPAR/GR Transactivation Screens in Stably Transfected CHO-K1 Cells

The hPPARγ2/GR and hPPARδ/GR stable CHO-K1 cell lines were seeded at $1 \times 10^4$ cells/well in 96 well cell culture plates in alpha MEM containing 10% FCS, 10 mM HEPES, and 500 mg/ml G418 at 37° C. in an atmosphere of 10% $CO_2$ in air. After a 20 hour incubation, cells were washed once with alpha MEM and then incubated in an atmosphere of 10% $CO_2$ in air in alpha MEM containing 5% charcoal stripped FCS, 10 mM HEPES, and 500 mg/ml G418. The cells were incubated for 24 hours in the absence of test compound or in the presence of a range of concentrations of test compound. Cell lysates were prepared from washed cells using Reporter Lysis Buffer (Promega) according to the manufacturer's directions. Luciferase activity in cell extracts was determined using Luciferase Assay Reagent buffer (Promega) in a ML3000 luminometer (Dynatech Laboratories).

Transactivation Wild-Type Assay

A. Characterization of Ligand Activity on Wild-type hPPARγ, hPPARδ and hPPARα.

COS-1 cells were seeded at $0.5 \times 10^5$ cells/dish into 24 well plates in Dulbecco's modified Eagle medium (high glucose) containing 10% charcoal stripped fetal calf serum, nonessential amino acids, 100 units/ml Penicillin G and 100 μg/ml Streptomycin sulfate at 37° C. in a humidified atmosphere of 10% $CO_2$. After 24 hours, transfections were performed with Lipofectamine (Gibco-BRL, Gaithersburg, Md.) according to the instructions of the manufacturer. In general, for transactivation experiments, transfection mixes contained 0.15 mg of hPPARγ2 hPPARα or hPPARδ expression vector, 0.15 mg of reporter vector pPPRE-luc and 0.001 mg of pCMV-lacZ as an internal control of transfection efficiency. Compounds demonstrating significant agonist activity in the above primary screen were further characterized by incubation with transfected cells for 48 h across a range of concentrations. Luciferase activity was determined as described above.

In a similar manner, hPPARγ1 cDNA can be used in place of hPPARγ2 cDNA in the methods described in Example 5 to make the wild type receptor construct, pSG5-hPPARγ1.

III. In Vivo Studies

Methods db/db Mice are obese, highly insulin resistant animals. The db locus has been shown to code for the leptin receptor. These animals are substantially hypertriglyceridemic and hyperglycemic.

Male db/db mice (10–11 week old C57B1/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, Cholesterol and triglyceride concentrations were determined from blood obtained by tail bleeds at 3–5 day intervals during the study period. Glucose, cholesterol and triglyceride, determinations were performed on a Boehringer Mannheim Hitachi 911 automatic analyzer (Boehringer Mannheim, Indianapolis, Ind.) using heparinized plasma diluted 1:5, or 1:6 (v/v) with normal saline. Lean animals were age-matched heterozygous mice maintained in the same manner. The instant compounds were found to lower triglyceride and glucose levels at a dose of about 100 mg/kg, preferably a dose of about 10–50 mg/kg, when administered by oral gavage daily for a period of at least 5 days.

Lipoprotein analysis was performed on either serum, or EDTA treated plasma obtained by heart puncture from anesthetized animals at the end of the study. Apolipoprotein concentrations were determined by ELISA, and cholesterol particles were analyzed by FPLC, precipitation, or ultracentrifugation. Total liver RNA was prepared from tissue that had been frozen on liquid nitrogen at the time of euthanasia. Apolipoprotein mRNA was analyzed on Northern Blots using specific probes for mouse or rat proteins.

What is claimed is:

1. A compound having the formula I:

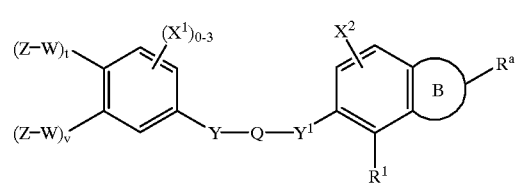

or a pharmaceutically acceptable salt thereof, wherein:

R is selected from the group consisting of H, $C_{1-6}$ alkyl, $C_{5-10}$ aryl, and benzisoxazolyl, said alkyl, aryl and benzisoxazolyl optionally substituted with 1 to 3 groups of $R^a$;

$R^1$ is selected from a group consisting of: H, $C_{1-15}$ alkyl, $C_{2-15}$ alkenyl, $C_{2-15}$ alkynyl and $C_{3-10}$ cycloalkyl, said alkyl, alkenyl, alkynyl, and cycloalkyl optionally substituted with 1 to 3 groups of $R^a$;

$R^3$ is selected from a group consisting of: H, $NHR^1$, NHacyl, $C_{1-15}$ alkyl, $C_{3-10}$ cycloalkyl, $C_{2-15}$ alkenyl, $C_{1-15}$ alkoxy, $CO_2$alkyl, OH, $C_{2-15}$ alkynyl, $C_{5-10}$ aryl, and benzisoxazolyl, said alkyl, cycloalkyl, alkenyl, alkynyl, aryl and benzisoxazolyl optionally substituted with 1 to 3 groups of $R^a$;

(Z—W—) is Z—$CR^6R^7$—, Z—CH═CH—, or

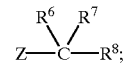

$R^8$ is selected from the group consisting of $CR^6R^7$, O, $NR^6$, and $S(O)_p$;

$R^6$ and $R^7$ are independently selected from the group consisting of H and $C_{1-6}$ alkyl;

B is an isoxazole, optionally unsubstituted or substituted with 1 group of $R^a$;

$X^1$ and $X^2$ are independently selected from a group consisting of: H, OH, $C_{1-15}$ alkyl, $C_{2-15}$ alkenyl, $C_{2-15}$ alkynyl, halo, $OR^3$, $ORCF_3$, $C_{5-10}$ aryl, $C_{5-10}$ aralkyl, benzisoxazolyl and $C_{1-10}$ acyl, said alkyl, alkenyl, alkynyl, aryl and benzisoxazolyl optionally substituted with 1 to 3 groups of $R^a$;

$R^a$ represents a member selected from the group consisting of: halo, acyl, aryl, benzisoxazolyl, $CF_3$, $OCF_3$, CN, $NO_2$, $R^3$, $OR^3$; $SR^3$, $S(O)R^3$, ═N(OR), $SO_2R^3$, $NR^3R^3$, $NR^3COR^3$, $NR^3CO_2R^3$, $NR^3CON(R^3)_2$, $NR^3SO_2R^3$, $COR^3$, $CO_2R^3$, $CON(R^3)_2$, $SO_2N(R^3)_2$, and $OCON(R^3)_2$, said aryl and benzisoxazolyl optionally substituted with 1 to 3 groups of halo or C1–6 alkyl;

Y is selected from the group consisting of: $S(O)_p$, —$CH_2$—, —C(O)—, —C(O)NH—, —NR—, —O—, —$SO_2$NH, and —$NHSO_2$;

$Y^1$ is O;

Z is selected from the group consisting of: $CO_2R^3$, $CONHSO_2R$, $CONH_2$ and 5-(1H-tetrazole);

t and v are independently 0 or 1 such that t+v=1;

Q is a saturated or unsaturated straight chain hydrocarbon containing 2–4 carbon atoms and p is 0–2.

2. A compound of claim 1 where $X^1$ and $X^2$ are independently H or halo.

3. A compound of claim 1 where Y is O.

4. A compound of claim 1 where Y is $S(O)_p$, wherein p is 0–2.

5. A compound of claim 1 where Y is —$CH_2$—.

6. A compound of claim 1 where Y is —CO—.

7. A compound of claim 1 where Y is —NH—.

8. A compound of claim 1 where Y is —$NHSO_2$ or —$SO_2NH$.

9. A compound of claim 1 where Y is —C(O)NH—.

10. A compound of claim 1 where (Z—W—)

is Z—$CR^6R^7$— or 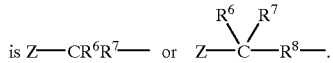

11. A compound of claim 1 wherein:

R is $C_{1-6}$ alkyl or $C_{5-10}$ aryl, said alkyl or aryl optionally substituted with 1 to 3 groups of $R^a$ $R^1$ is $C_{1-15}$ alkyl;

$X^1$ and $X^2$ are independently H, C1–6 alkyl or halo;

Y is O, NH or S;

$Y^1$ is O;

(Z—W—) is Z—$CR^6R^7$— or 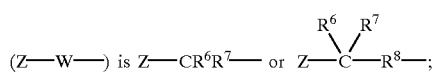;

$R^a$ is a member selected from the group consisting of: halo, acyl, aryl, benzisoxazolyl, $CF_3$, $OCF_3$, CN, $NO_2$, $R^3$, $OR^3$; $SR^3$, $S(O)R^3$, $SO_2R^3$, $NR^3COR^3$, $COR^3$, $CON(R^3)_2$, and $SO_2N(R^3)_2$, said aryl and benzisoxazolyl optionally substituted with 1 to 3 groups of halo or C1–6 alkyl; and Z is $CO_2R^3$, $CONHSO_2R$, $CONH_2$ or 5-(1H-tetrazole).

12. A compound of claim 1 selected from the group consisting of:

Methyl 3-chloro-4-(3-(3-ethyl-7-propyl-6-benz-[4,5]-isoxazoloxy)propylthio)phenylacetate;

3-chloro-4-(3-(3-ethyl-7-propyl-6-benz-[4,5]-isoxazoloxy)propylthio)phenylacetic acid;

Methyl 3-chloro-4-(3-(3-methoxy-7-propyl-6-benz-[4,5]-isoxazoloxy)propylthio)phenylacetate;

3-chloro-4-(3-(3-methoxy-7-propyl-6-benz-[4,5]-isoxazoloxy) propylthio)-phenylacetic acid;

Methyl 3-chloro-4-(3-(3-methyl-7-propyl-6-benz-[4,5]-isoxazoloxy)propylthio)phenylacetate;

3-chloro-4-(3-(3-methyl-7-propyl-6-benz-[4,5]-isoxazoloxy)propylthio)phenylacetic acid;

Methyl 3-chloro-4-(3-(3,7-dipropyl-6-benz-[4,5]-isoxazoloxy) propylthio)-phenylacetate;

3-chloro-4-(3-(3,7-dipropyl-6-benz-[4,5]-isoxazoloxy) propylthio) phenyl-acetic acid;

Methyl 3-chloro-4-(3-(3-ethyl-7-propyl-6-benz-[4,5]-isoxazoloxy)propylthio)phenylacetate S-oxide;

3-chloro-4-(3-(3-ethyl-7-propyl-6-benz-[4,5]-isoxazoloxy)propylthio)phenylacetic acid S-oxide;

Methyl 3-chloro-4-(3-(3-ethyl-7-propyl-6-benz-[4,5]-isoxazoloxy) propyl-thio)phenylacetate S,S-dioxide;

3-Chloro-4-(3-(3-ethyl-7-propyl-6-benz-[4,5]-isoxazole)oxy)-propylthio phenylacetic acid S,S-dioxide;

tert-Butyl 3-chloro-4-(3-(3-ethyl-7-propyl-6-benz-[4,5]-isoxazoloxy)propylthio)phenyl acetate;

2-methyl-2-(3-chloro-4-(3-(3-phenyl-7-propylbenz[4,5]isoxazol-6-oxy)propyl)thio)phenyl propionic acid;

Methyl 3-chloro-4-(3-(3-(2,2-dimethylpropyl)-7-propyl-6-benz-[4,5]-isoxazoloxy)-propylamino) phenylacetate;

3-Chloro-4-(3-(3-(2,2-dimethylpropyl)-7-propyl-6-benz-[4,5]-isoxazoloxy)-propylamino)phenylacetic acid;

Methyl 3-propyl-4-(3-(3-trifluoromethyl-7-propyl-6-benz-[4,5]-isoxazoloxy)-propylthio)phenylacetate;

3-propyl-4-(3-(3-trifluoromethyl-7-propyl-6-benz-[4,5]-isoxazoloxy)propylthio)phenylacetic acid;

3-chloro-4-(3-(2-propyl-3-trifluoromethyl-6-benz-[4,5]-isoxazoloxy)propylthio)phenylacetic acid;

3-chloro-4-(3-(3-phenyl-7-cyclopropylmethyl-6-benz-[4,5]-isoxazoloxy)butyloxy)phenylacetic acid;

4-(3-(3-Phenyl-7-propylbenzisoxazol-6-yloxy)propylthio)-phenyl(2,2-dimethyl)acetic acid;

4-(3-(3-Phenyl-7-propylbenzisoxazol-6-yloxy)propyloxy)-phenylpropan-3-oic acid;

3-(3-(3-Phenyl-7-propylbenzisoxazol-6-yloxy)propylthio)-phenoxyacetic acid;

4-(3-(3-Phenyl-7-propylbenzisoxazol-6-yloxy)propylthio)-phenoxyacetic acid;

N-[4-(3-(3-Phenyl-7-propylbenzisoxazol-6-yloxy)propylamino)phenyl]glycine;

4-(3-(3-Phenyl-7-propylbenzisoxazol-6-yloxy)propylamino)-phenylacetic acid;

3-(3-(2-Phenyl-5-propylbenzisoxazol-6-yloxy)propylamino)-3-chlorophenylacetic acid;

4-(3-(3-Phenyl-7-propylbenzisoxazol-6-yloxy)propylamino)-3-chlorophenylacetic acid;

4-(4-(3-Phenyl-7-prop-2-enylbenzisoxazol-6-yloxy)butyloxy)-3-chlorophenylacetic acid;

4-(3-(3-Phenyl-7-propylbenzisoxazol-6-yloxy)propylamino)-phenoxyacetic acid;

3-(3-(3-Phenyl-7-butylbenzisoxazol-6-yloxy)propylthio)-phenylpropan-3-oic acid;

4-(3-(3-Phenyl-7-butylbenzisoxazol-6-yloxy)propylthio)-phenylpropan-3-oic acid;

4-(3-(3-Phenyl-7-propylbenzisoxazol-6-yloxy)propyloxy)-2-phenyl-2,2-dimethylacetic acid;

4-(4-(3-Phenyl-7-(cyclopropylmethyl)benzisoxazol-6-yloxy)butylamino)phenoxy-2,2-dimethylacetic acid;

3-(3-(3-Neopentyl-7-propylbenzisoxazol-6-yloxy)propylthio)-3-methylphenylacetic acid 4-(3-(3-(2-Phenyl-2,2-dimethyl)-7-propylbenzisoxazol-6-yloxy)propyloxy)-3-butylphenylacetic acid;

4-(3-(3-Chloro-7-propylbenzisoxazol-6-yloxy)propylamino)-2-propylphenylacetic acid;

3-(3-(3-Chloro-7-propylbenzisoxazol-6-yloxy) propylamino)-2-propylphenylacetic acid;

4-(4-(3-Butoxy-7-propylbenzisoxazol-6-yloxy) butylthio)-2-fluorophenylacetic acid;

4-(3-(3-Phenyl-7-propylbenzisoxazol-6-yloxy) propylamino)phenoxyacetic acid;

3-(3-(3-Butylphenyl)-7-butylbenzisoxazol-6-yloxy) propylthio)phenylpropan-3-oic acid;

4-(3-(3-(2-Tolyl)-7-butylbenzisoxazol-6-yloxy) propylthio)-phenylpropan-3-oic acid;

4-(3-(3-(4-Fluorophenyl)-7-propylbenzisoxazol-6-yloxy) propyloxy)-2-phenyl-2,2-dimethylacetic acid;

4-(3-(3-Phenyl-7-propylbenzisoxazol-6-yloxy) propyloxy)-phenoxy-2-spiro-cyclopropylacetic acid;

3-(3-(3-Phenyl-7-propylbenzisoxazol-6-yloxy) propyloxy)-phenoxy-2-spiro-cyclopropylacetic acid;

5-(4-(3-(3-Phenyl-7-propylbenzisoxazol-6-yloxy) propyloxy)phenyl-3-propyl)-tetrazole;

5-(3-(3-(3-Phenyl-7-propylbenzisoxazol-6-yloxy) propylthio)phenoxy-2-ethyl)-tetrazole;

5-(4-(3-(3-Phenyl-7-propylbenzisoxazol-6-yloxy) propylthio)phenoxy-2-ethyl)-tetrazole;

3-chloro-4-(3-(3-ethyl-7-propyl-6-benz-[4,5]-isoxazoloxy)-but-2-en-thio)phenylacetic acid;

4-(3-(3-ethyl-7-propyl-6-benz[4,5]isoxazole)oxy) propyloxy phenoxy acetic acid;

N-Methylsulfonyl 3-chloro-4-(3-(3-ethyl-7-propyl-6-benz[4,5]isoxazole)oxy)propylthio phenyl acetamide;

3,5-dimethoxy-4-(3-(3-(Ethyl)-7-(propyl)-6-benz-[4,5]-isoxazoloxy)propyloxy)phenyl acetic acid;

3,5-dichloro-4-(3-(3-(Ethyl)-7-(propyl)-6-benz-[4,5]-isoxazoloxy)propyloxy)phenyl acetic acid;

3,5-dimethyl-4-(3-(3-(Ethyl)-7-(propyl)-6-benz-[4,5]-isoxazoloxy)propyloxy)phenyl acetic acid;

4-(3-(3-(Ethyl)-7-(propyl)-6-benz-[4,5]-isoxazoloxy)-propyloxy)-phenyl propionic acid;

3-chloro-4-(3-phenyimethyl-7-(n-propyl)-6-benz[4,5] isoxazoloxy)propylthio)phenylacetic acid;

3-chloro-4-(3-(2,2-dimethylpropyl)-7-(n-propyl)-6-benz[4,5]isoxazoloxy)propylthio)phenylacetic acid;

2-methyl-4-(3-(3-(Ethyl)-7-(propyl)-6-benz-[4,5]-isoxazoloxy)propyloxy)phenyl propionic acid;

3-Propyl-4-(3-(3-ethyl-7-propyl-6-benz-[4,5]-isoxazoloxy)propyloxy)phenylacetic acid;

4-(3-(3-(Ethyl)-7-propyl-6-benz-[4,5]-isoxazoloxy)butyl) phenylacetate;

3-chloro-4-(7-(n-propyl)-3-(3,3,3-trifluoropropyl)-6-benz[4,5]isoxazoloxy)propylthio)phenylacetic acid;

3-chloro-4-(3-(4-chlorophenylmethyl)-7-(n-propyl)-6-benz[4,5]isoxazoloxy)propylthio)phenylacetic acid;

3-Chloro-4-(3-(3-(2,2-dimethylpropyl)-7-propyl-6-benz-[4,5]-isoxazoloxy)propyl-N-methyl amino)phenyl acetate;

3,5-Dipropyl-4-(3-(3-ethyl-7-propyl-6-benz-[4,5]-isoxazoloxy)propyloxy)phenylacetic acid;

3-fluoro-4-(3-(7-propyl-3-trifluoromethyl-6-benz-[4,5] isoxazoloxy)propyloxy)phenylacetic acid;

3-chloro-4-(3-(3-trifluoromethyl-7-propyl-6-benz-[4,5]-isoxazoloxy)propylamino)phenylacetic acid;

3-Isobutyl-4-(3-(3-neo-pental-7-propyl-6-benz-[4,5]-isoxazoloxy)propyloxy)phenylacetic acid;

3-Propyl-4-(3-(3-neo-pental-7-propyl-6-benz-[4,5]-isoxazoloxy)propylthio)phenylacetic acid S,S-dioxide;

3-Chloro-4-(3-(3-phenyl-7-propyl-6-benz-[4,5]-isoxazoloxy)propylsulfoxy)phenylacetic acid;

3-fluoro-4-(4-(3-phenyl-7-propyl-6-benz-[4,5]-isoxazoloxy)butyloxy)phenylacetic acid;

3-chloro-4-(3-(7-propyl-3-trifluoromethyl-6-benz-[4,5]-isoxazoloxy)propyl-thio)phenylacetic acid S,S-dioxide;

3-chloro-4-(3-(7-propyl-3-trifluoromethyl-6-benz-[4,5]-isoxazoloxy)propyl-thio)phenylacetic acid S-oxide;

3-chloro-4-(3-(2-phenylethyl)-7-propyl-6-benz[4,5] isoxazoloxy)propylthio)phenylacetic acid;

3-Chloro-4-(3-(3-(4-fluorophenyl)-7-propyl-6-benz-[4,5]-isoxazoloxy)propylthio)phenylacetic acid;

3-Chloro-4-(3-(3-(4-fluorophenyl)-7-propyl-6-benz-[4,5]-isoxazoloxy)propylsulfinyl)phenylacetic acid;

3-Chloro-4-(3-(3-(4-fluorophenyl)-7-propyl-6-benz-[4,5]-isoxazoloxy)propylsulfonyl)) phenylacetic acid;

2,3-Dichloro-4-(3-(3-neo-pental-7-propyl-6-benz-[4,5]-isoxazoloxy)propylthio)phenylacetic acid;

2-Trifloroethoxy-4-(3-(3-neo-pental-7-propyl-6-benz-[4,5]-isoxazoloxy)propyloxy)phenylacetic acid;

3-Chloro-4-(3-(3-cyclopropyl)-7-propyl-6-benz-[4,5]-isoxazoloxy)propylamino)phenylacetate;

2-(3-chloro-4-(3-(3-ethyl-7-propyl-6-benz-[4,5]-isoxazoloxy)propylthio)) phenylpropionic acid;

3-(4-(3-(3-phenyl-7-propyl-6-benz-[4,5]-isoxazoloxy) propyloxy)) phenylpropionic acid;

3-Chloro-4-(3-(3-(3-fluorophenyl)-7-propyl-6-benz-[4,5]-isoxazoloxy)propylthio)phenylacetic acid;

3-Chloro-4-(3-(3-neo-pental-7-propyl-6-benz-[4,5]-isoxazoloxy)propyloxy)phenoxylacetic acid;

4-(3-(3-phenyl-7-propyl-6-benz[4,5]isoxazole)oxy) propyloxy phenoxy acetic acid;

(3-(4-(3-phenyl-7-propyl-6-benz-[4,5]-isoxazoloxy) butyloxy)) phenylacetic acid;

3-(4-(4-(3-phenyl-7-propyl-6-benz-[4,5]-isoxazoloxy) butyloxy)) phenylpropionic acid;

3-chloro-4-(3-(2-methyl-2-phenylpropyl)-7-(n-propyl)-6-benz[4,5]isoxazoloxy)propylthio)phenylacetic acid;

3-Methoxy-4-(3-(3-(2,2-dimethylpropyl)-7-propyl-6-benz-[4,5]-isoxazoloxy)propyloxy)phenylacetate;

3-(4-(2-(3-phenyl-7-propyl-6-benz-[4,5]-isoxazoloxy) ethyloxy)) phenylpropionic acid;

(3-(4-(3-phenyl-7-propyl-6-benz-[4,5]-isoxazoloxy) butyloxy)) phenoxyacetic acid;

E-(4-(3-(3-phenyl-7-propyl-6-benz[4,5]isoxazole)oxy) propyloxy) cinnamic acid;

E-(3-(3-(3-phenyl-7-propyl-6-benz[4,5]isoxazole)oxy) propyloxy) cinnamic acid;

3-(3-(3-phenyl-7-propyl-6-benz[4,5]isoxazole)oxy) propyloxy) phenylpropionic acid;

N-((4-carbomethoxymethyl)benzoyl)-3(3-phenyl-7-propyl-6-benz-[4,7]-isooxazolyloxy) propylamine;

2-(4-(3-(3-phenyl-7-propyl-6-benz-[4,5]-isoxazoloxy) propyloxy)) phenoxypropionic acid;

2-(4-(4-(3-phenyl-7-propyl-6-benz-[4,5]-isoxazoloxy) butyloxy)) phenoxypropionic acid;

3-chloro-4-(3-(7-cyclopropylmethyl-3-phenyl-6-benz-[4,5]-isoxazoloxy)propyl-thio)phenylacetic acid;

1-(3-chloro-4-(3-(3-(2,2-dimethylpropyl)-7-propyl-6-benz[4,5]isoxazole)oxy)propylthio) phenyl cyclopropane carboxylic acid;

4-(3-(3-(Ethyl)-7-(phenyl)-6-benz-[4,5]-isoxazoloxy) propyloxy)-3-chloro-α, α-dimethyl-phenyl propionic acid;

3-Ethoxy-4-(3-(3-(2,2-dimethylpropyl)-7-propyl-6-benz-[4,5]-isoxazoloxy)propyloxy)phenylacetate; and 3-chloro-4-(3-(3-phenyl-6-propyl-5-benz-[4,7]-isoxazolyloxy)-propylthio) phenylacetic acid.

13. A compound of claim 11 selected from the group consisting of:

Methyl 3-chloro-4-(3-(3-ethyl-7-propyl-6-benz-[4,5]-isoxazoloxy)propylthio)phenylacetate;

3-chloro-4-(3-(3-ethyl-7-propyl-6-benz-[4,5]-isoxazoloxy)propylthio)phenylacetic acid;

Methyl 3-chloro-4-(3-(3-methoxy-7-propyl-6-benz-[4,5]-isoxazoloxy)propylthio)phenylacetate;

3-chloro-4-(3-(3-methoxy-7-propyl-6-benz-[4,5]-isoxazoloxy)propylthio)-phenylacetic acid;

Methyl 3-chloro-4-(3-(3-ethyl-7-propyl-6-benz-[4,5]-isothiazoloxy)propylthio)phenyl acetate;

Methyl 3-chloro-4-(3-(3-methyl-7-propyl-6-benz-[4,5]-isoxazoloxy)propylthio)phenylacetate;

3-chloro-4-(3-(3-methyl-7-propyl-6-benz-[4,5]-isoxazoloxy)propylthio)phenylacetic acid;

Methyl 3-chloro-4-(3-(3,7-dipropyl-6-benz-[4,5]-isoxazoloxy) propylthio)-phenylacetate;

3-chloro-4-(3-(3 ,7-dipropyl-6-benz-[4,5]-isoxazoloxy) propylthio) phenyl-acetic acid;

Methyl 3-chloro-4-(3-(3-ethyl-7-propyl-6-benz-[4,5]-isoxazoloxy)propylthio)phenylacetate S-oxide;

3-chloro-4-(3-(3-ethyl-7-propyl-6-benz-[4,5]-isoxazoloxy)propylthio)phenylacetic acid S-oxide;

Methyl 3-chloro-4-(3-(3-ethyl-7-propyl-6-benz-[4,5]-isoxazoloxy) propyl-thio)phenylacetate S,S-dioxide;

3-Chloro-4-(3-(3-ethyl-7-propyl-6-benz-[4,5]-isoxazole) oxy)-propylthio phenylacetic acid S,S-dioxide;

tert-Butyl 3-chloro-4-(3-(3-ethyl-7-propyl-6-benz-[4,5]-isoxazoloxy)propylthio)phenyl acetate;

2-methyl-2-(3-chloro-4-(3-(3-phenyl-7-propylbenz[4,5]isoxazol-6-oxy)propyl)thio)phenyl propionic acid;

Methyl 3-chloro-4-(3-(3-(2,2-dimethylpropyl)-7-propyl-6-benz-[4,5]-isoxazoloxy)-propylamino) phenylacetate;

3-Chloro-4-(3-(3-(2,2-dimethylpropyl)-7-propyl-6-benz-[4,5]-isoxazoloxy)-propylamino)phenylacetic acid;

Methyl 3-propyl-4-(3-(3-trifluoromethyl-7-propyl-6-benz-[4,5]-isoxazoloxy)-propylthio)phenylacetate;

3-propyl-4-(3-(3-trifluoromethyl-7-propyl-6-benz-[4,5]-isoxazoloxy)propylthio)phenylacetic acid;

3-chloro-4-(3-(2-propyl-3-trifluoromethyl-6-benz-[4,5]-isoxazoloxy)propylthio)phenylacetic acid;

3-chloro-4-(3-(3-phenyl-7-cyclopropylmethyl-6-benz-[4, 5]-isoxazoloxy)butyloxy)phenylacetic acid;

4-(3-(3-Phenyl-7-propylbenzisoxazol-6-yloxy) propyloxy)-phenylacetic acid;

3-(4-(3-Phenyl-7-propylbenzisoxazol-6-yloxy)butyloxy)-phenylacetic acid;

4-(3-(3-Phenyl-7-propylbenzisoxazol-6-yloxy) propyloxy)-phenoxyacetic acid;

4-(3-(3-Phenyl-7-propylbenzisoxazol-6-yloxy) propylthio)-3-propylphenylacetic acid;

4-(3-(3-Phenyl-7-propylbenzisoxazol-6-yloxy) propylsulfono)-3-propylphenylacetic acid;

4-(4-(3-Phenyl-7-propylbenzisoxazol-6-yloxy)butylthio)-3-propylbenzyltetrazole;

4-(3-(3-Phenyl-7-propylbenzisoxazol-6-yloxy) propylamino)-phenylacetic acid;

3-(4-(4-(3-Phenyl-7-propylbenzisoxazol-6-yloxy) butyloxy)-phenylacetic acid;

3-chloro-4-(3-(2,2-dimethylpropyl)-7-(n-propyl)-6-benz [4,5]isoxazoloxy)propylthio)phenylacetic acid;

3-Propyl-4-(3-(3-ethyl-7-propyl-6-benz-[4,5]-isoxazoloxy)propyloxy)phenylacetic acid;

4-(3-(3-(Ethyl)-7-propyl-6-benz-[4,5]-isoxazoloxy)butyl) phenylacetate;

3-chloro-4-(7-(n-propyl)-3-(3,3,3-trifluoropropyl)-6-benz [4,5]isoxazoloxy)propylthio)phenylacetic acid;

3-chloro-4-(3-(3-trifluoromethyl-7-propyl-6-benz-[4,5]-isoxazoloxy)propylamino)phenylacetic acid;

3-Chloro-4-(3-(3-phenyl-7-propyl-6-benz-[4,5]-isoxazoloxy)propylsulfoxy)phenylacetic acid;

3-fluoro-4-(4-(3-phenyl-7-propyl-6-benz-[4,5]-isoxazoloxy)butyloxy)phenylacetic acid;

3-chloro-4-(3-(2-phenylethyl)-7-propyl-6-benz[4,5] isoxazoloxy)propylthio)phenylacetic acid;

3-Chloro-4-(3-(3-(4-fluorophenyl)-7-propyl-6-benz-[4, 5]-isoxazoloxy)propylthio)phenylacetic acid;

3-Chloro-4-(3-(3-(4-fluorophenyl)-7-propyl-6-benz-[4, 5]-isoxazoloxy)propylsulfonyl)) phenylacetic acid;

2,3-Dichloro-4-(3-(3-neo-pental-7-propyl-6-benz-[4,5]-isoxazoloxy)propylthio)phenylacetic acid;

2-(3-chloro-4-(3-(3-ethyl-7-propyl-6-benz-[4,5]-isoxazoloxy)propylthio)) phenylpropionic acid;

3-(4-(3-(3-phenyl-7-propyl-6-benz-[4,5]-isoxazoloxy) propyloxy)) phenylpropionic acid;

3-Chloro-4-(3-(3-(3-fluorophenyl)-7-propyl-6-benz-[4, 5]-isoxazoloxy)propylthio)phenylacetic acid;

4-(3-(3-phenyl-7-propyl-6-benz[4,5]isoxazole)oxy) propyloxy phenoxy acetic acid;

(3-(4-(3-phenyl-7-propyl-6-benz-[4,5]-isoxazoloxy) butyloxy)) phenylacetic acid;

3-(4-(4-(3-phenyl-7-propyl-6-benz-[4,5]-isoxazoloxy) butyloxy)) phenylpropionic acid;

3-chloro-4-(3-(2-methyl-2-phenylpropyl)-7-(n-propyl)-6-benz[4,5]isoxazoloxy)propylthio)phenylacetic acid;

3-(4-(2-(3-phenyl-7-propyl-6-benz-[4,5]-isoxazoloxy) ethyloxy)) phenylpropionic acid;

(3-(4-(3-phenyl-7-propyl-6-benz-[4,5]-isoxazoloxy) butyloxy)) phenoxyacetic acid;

E-(4-(3-(3-phenyl-7-propyl-6-benz[4,5]isoxazole)oxy) propyloxy) cinnamic acid;

3-(3-(3-(3-phenyl-7-propyl-6-benz[4,5]isoxazole)oxy) propyloxy) phenylpropionic acid;

2-(4-(3-(3-phenyl-7-propyl-6-benz-[4,5]-isoxazoloxy) propyloxy)) phenoxypropionic acid;

2-(4-(4-(3-phenyl-7-propyl-6-benz-[4,5]-isoxazoloxy) butyloxy)) phenoxypropionic acid;

3-chloro-4-(3-(7-cyclopropylmethyl-3-phenyl-6-benz-[4, 5]-isoxazoloxy)propyl-thio)phenylacetic acid;

1-(3-chloro-4-(3-(3-(2,2-dimethylpropyl)-7-propyl-6-benz[4,5]isoxazole)oxy)propylthio) phenyl cyclopropane carboxylic acid; and 4-(3-(3-(Ethyl)-7-(phenyl)-6-benz-[4,5]-isoxazoloxy) propyloxy)-3-chloro-α, α-dimethyl-phenyl propionic acid.

14. A composition for the treatment of diabetes or for lowering triglyceride levels or for halting, preventing or reducing the risk of developing atherosclerosis and related disease events, or for raising high densisty lipoprotein plasma levels, which comprises an inert carrier and an effective amount of a compound of claim 1.

15. A composition for the treatment of diabetes which comprises an inert carrier and an effective amount of a compound of claim 1, in combination with a sulfonylurea, fibrate, HMG-CoA reductase inhibitor, beta-sitosterol inhibitor, cholesterol acyltransferase inhibitor, biguanides, cholestyramine, angiotensin II antagonist, melinamide, nicotinic acid, fibrinogen receptor antagonists, aspirin, α-glucosidase inhibitors, insulin secretogogue or insulin.

16. A composition for halting, preventing or reducing the risk of developing atherosclerosis and related disease events, or for raising high density lipoprotein plasma levels, which comprises an inert carrier and an effective amount of a compound of claim 1, in combination with a sulfonylurca, fibrate, HMG-CoA reductase inhibitor, beta-sitosterol inhibitor, cholesterol acyltransferase inhibitor, biguanides, cholestyramine, angiotensin II antagonist, melinamide, nicotinic acid, fibrinogen receptor antagonists, aspirin, α-glucosidase inhibitors, insulin secretogogue or insulin.

* * * * *